US010259821B2

(12) United States Patent
Sato et al.

(10) Patent No.: US 10,259,821 B2
(45) Date of Patent: Apr. 16, 2019

(54) TETRAHYDROISOQUINOLINE DERIVATIVES

(71) Applicants: Astellas Pharma Inc., Tokyo (JP); Cytokinetics, Incorporated, South San Francisco, CA (US)

(72) Inventors: Ippei Sato, Tokyo (JP); Takashi Kamikubo, Tokyo (JP); Masanori Miura, Tokyo (JP); Yuji Matsushima, Tokyo (JP); Hiroaki Tanaka, Tokyo (JP); Yasuhiro Shiina, Tokyo (JP); Susumu Yamaki, Tokyo (JP); Tomoyuki Saito, Tokyo (JP); Hiroshi Kiyohara, Tokyo (JP); Munemichi Ohe, Tokyo (JP); Kayoko Mihara, Tokyo (JP); Bradley Paul Morgan, Moraga, CA (US); Fady Malik, Burlingame, CA (US); Scott Emile Collibee, San Carlos, CA (US); Luke Ashcraft, San Francisco, CA (US); Pu-Ping Lu, Foster City, CA (US); Jeffrey Michael Warrington, San Mateo, CA (US); Marc Garard, San Leandro, CA (US)

(73) Assignees: Astellas Pharma Inc., Tokyo (JP); Cytokinetics, Incorporated, South San Francisco, CA (US)

(*) Notice: Subject to any disclaimer, the term of this patent is extended or adjusted under 35 U.S.C. 154(b) by 0 days.

(21) Appl. No.: 15/873,571

(22) Filed: Jan. 17, 2018

(65) Prior Publication Data

US 2018/0148458 A1 May 31, 2018

Related U.S. Application Data

(62) Division of application No. 15/429,738, filed on Feb. 10, 2017, now Pat. No. 9,914,741.

(60) Provisional application No. 62/285,039, filed on Feb. 12, 2016.

(51) Int. Cl.
| | | |
|---|---|---|
| *C07D 491/20* | (2006.01) | |
| *C07D 491/107* | (2006.01) | |
| *C07D 471/04* | (2006.01) | |
| *C07D 471/10* | (2006.01) | |
| *C07D 217/24* | (2006.01) | |
| *C07D 217/26* | (2006.01) | |

(52) U.S. Cl.
CPC ......... *C07D 491/20* (2013.01); *C07D 217/24* (2013.01); *C07D 217/26* (2013.01); *C07D 471/04* (2013.01); *C07D 471/10* (2013.01); *C07D 491/107* (2013.01)

(58) Field of Classification Search
CPC .............. C07D 491/20; C07D 491/107; C07D 217/24; C07D 217/26; C07D 471/04; C07D 471/10

USPC ........................................................ 514/249
See application file for complete search history.

(56) References Cited

U.S. PATENT DOCUMENTS

| 3,301,857 A | 1/1967 | Berger et al. |
| 3,947,451 A | 3/1976 | Jönsson et al. |
| 6,492,520 B1 | 12/2002 | Chen |
| 2007/0027147 A1 | 2/2007 | Hayama et al. |
| 2008/0039452 A1 | 2/2008 | Kajino et al. |
| 2008/0085890 A1 | 4/2008 | Tsou et al. |
| 2013/0060025 A1 | 3/2013 | Ashcraft et al. |
| 2015/0203505 A1 | 7/2015 | Kanayama et al. |

FOREIGN PATENT DOCUMENTS

| WO | WO 2008/016669 A2 | 2/2008 |
| WO | WO 2011/133882 A1 | 10/2011 |
| WO | WO 2011/133888 A1 | 10/2011 |
| WO | WO 2011/133920 A1 | 10/2011 |
| WO | WO 2012/153154 A1 | 11/2012 |
| WO | WO 2013/151938 A1 | 10/2013 |
| WO | WO 2013/155262 A2 | 10/2013 |
| WO | WO 2015/168064 A1 | 11/2015 |

OTHER PUBLICATIONS

Jiang et al. Handb Exp Pharmacol (2011), 202, p. 45-67.*
Kim et al. Tetrahedron Letters, (2009), 50(47), p. 6476-6479.*
Invitation to pay additional fees and, where applicable, protest fee issued May 8, 2017 in PCT/US17/17295.
D. Ben-Ishai, et al., Cyclic Acylimines and Cyclic Carbinolamides II. Isoquinolones, Journal of Heterocyclic Chemistry, Technion-Israel Institute of Technology, vol. 7 No. 3, Jun. 1970, pp. 615-622.
Didier Barbry, et al., "A Convenient Synthesis of 1-Substituted 1,4-Dihydroisoquinolin-3-ones"Synthetic Communications, vol. 32 No. 12, 2002, pp. 1787-1790.

(Continued)

*Primary Examiner* — Yong L Chu
(74) *Attorney, Agent, or Firm* — Oblon, McClelland, Maier & Neustadt, L.L.P.

(57) ABSTRACT

Novel tetrahydroisoquinoline derivative compounds are disclosed herein that may be used as an active ingredient for a pharmaceutical composition, and in particular, for a pharmaceutical composition useful for preventing or treating a disease or condition responsive to modulation of the contractility of the skeletal sarcomere. This may be accomplished, for example, by modulation of the troponin complex of the fast skeletal muscle sarcomere through one or more of fast skeletal myosin, actin, tropomyosin, troponin C, troponin I, and troponin T, and fragments and isoforms thereof. The tetrahydroisoquinoline derivative compounds can thus be used as an agent for preventing or treating 1) neuromuscular disorders, 2) disorders of voluntary muscle, 3) CNS disorders in which muscle weakness, atrophy, and fatigue are prominent symptoms, 4) muscle symptoms stemming from systemic disorders, and 5) dysfunctions of pelvic floor and urethral/anal sphincter muscle.

14 Claims, 7 Drawing Sheets

(56) References Cited

OTHER PUBLICATIONS

Sung Hwan Kim, et al., "An expedient synthesis of poly-substituted 1-arylisoquinolines from δ-ketonitriles via indium-mediated Barbier reaction protocol", Tetrahedron Letters, vol. 50 No. 47, 2009, pp. 6476-6479.
International Search Report and Written Opinion with Search History dated Jul. 3, 2017 in PCT/US17/17295.

* cited by examiner

Example 20

N=9/group
mean ± SEM
*p<0.05,
vs. vehicle
paired t-test

Example 22b

N=16/group
mean ± SEM
*p<0.05,
paired t-test

BBB score change (BBB postdose − BBB predose) was calculated for each Example 52 and vehicle dosing.
Differences in BBB score change between groups of Example 52 and vehicle dosing were compared at three time slots.

TETRAHYDROISOQUINOLINE DERIVATIVES

CROSS-REFERENCE TO RELATED APPLICATIONS

This application is a division of U.S. patent application Ser. No. 15/429,738, filed on Feb. 10, 2017, now U.S. Pat. No. 9,914,741, and claims priority to U.S. Provisional Applications No. 62/285,039, filed Feb. 12, 2016, the contents of which are hereby incorporated by reference herein in their entirety.

BACKGROUND OF THE INVENTION

Field of the Invention

The present invention relates to tetrahydroisoquinoline derivatives or salts thereof which are useful as an active ingredient for a pharmaceutical composition, in particular, a pharmaceutical composition for treating a disease or condition responsive to modulation of the contractility of the skeletal sarcomere.

Discussion of the Background

The cytoskeleton of skeletal and cardiac muscle cells is unique compared to that of all other cells. It consists of a nearly crystalline array of closely packed cytoskeletal proteins called the sarcomere. The sarcomere is elegantly organized as an interdigitating array of thin and thick filaments. The thick filaments are composed of myosin, the motor protein responsible for transducing the chemical energy of ATP hydrolysis into force and directed movement. The thin filaments are composed of actin monomers arranged in a helical array. There are four regulatory proteins bound to the actin filaments, which allows the contraction to be modulated by calcium ions. An influx of intracellular calcium initiates muscle contraction; thick and thin filaments slide past each other driven by repetitive interactions of the myosin motor domains with the thin actin filaments.

Of the thirteen distinct classes of myosin in human cells, the myosin-II class is responsible for contraction of skeletal, cardiac, and smooth muscle. This class of myosin is significantly different in amino acid composition and in overall structure from myosin in the other twelve distinct classes. Myosin-II forms homo-dimers resulting in two globular head domains linked together by a long alpha-helical coiled-coiled tail to form the core of the sarcomere's thick filament. The globular heads have a catalytic domain where the actin binding and ATPase functions of myosin take place. Once bound to an actin filament, the release of phosphate (cf. ADP-Pi to ADP) signals a change in structural conformation of the catalytic domain that in turn alters the orientation of the light-chain binding lever arm domain that extends from the globular head; this movement is termed the power stroke. This change in orientation of the myosin head in relationship to actin causes the thick filament of which it is a part to move with respect to the thin actin filament to which it is bound. Un-binding of the globular head from the actin filament ($Ca^{2+}$ regulated) coupled with return of the catalytic domain and light chain to their starting conformation/orientation completes the catalytic cycle, responsible for intracellular movement and muscle contraction.

Tropomyosin and troponin mediate the calcium effect on the interaction on actin and myosin. The troponin complex is comprised of three polypeptide chains: troponin C, which binds calcium ions; troponin I, which binds to actin; and troponin T, which binds to tropomyosin. The skeletal troponin-tropomyosin complex regulates the myosin binding sites extending over several actin units at once.

Troponin, a complex of the three polypeptides described above, is an accessory protein that is closely associated with actin filaments in vertebrate muscle. The troponin complex acts in conjunction with the muscle form of tropomyosin to mediate the $Ca^{2+}$ dependency of myosin ATPase activity and thereby regulate muscle contraction. The troponin polypeptides T, I, and C, are named for their tropomyosin binding, inhibitory, and calcium binding activities, respectively. Troponin T binds to tropomyosin and is believed to be responsible for positioning the troponin complex on the muscle thin filament. Troponin I binds to actin, and the complex formed by troponins I and T, and tropomyosin inhibits the interaction of actin and myosin. Skeletal troponin C is capable of binding up to four calcium molecules. Studies suggest that when the level of calcium in the muscle is raised, troponin C exposes a binding site for troponin I, recruiting it away from actin. This causes the tropomyosin molecule to shift its position as well, thereby exposing the myosin binding sites on actin and stimulating myosin ATPase activity.

Human skeletal muscle is composed of different types of contractile fibers, classified by their myosin type and termed either slow or fast fibers. Table 1 summarizes the different proteins that make up these types of muscle.

TABLE 1

| | Muscle Fiber Type | |
| --- | --- | --- |
| | Fast Skeletal | Slow Skeletal |
| Myosin Heavy Chain (MHC) | IIa, (IIb*), IIx/d | Cardiac β |
| Troponin I (TnI) | TnI fast Skeletal | TnI slow Skeletal |
| Troponin T (TnT) | TnT fast Skeletal | TnT slow Skeletal |
| Troponin C (TnC) | TnC fast Skeletal | TnC slow/cardiac |
| Tropomyosin (TM) | TM-β/TM-α/TPM3** | TM-β/TM-αs |

*MHC IIb is not expressed in human muscle but is present in rodents and other mammals.
**TPM3 represents tropomyosin 3

In healthy humans, most skeletal muscles are composed of both fast and slow fibers, although the proportions of each vary with muscle type. Slow skeletal fibers, often called type I fibers, have more structural similarity with cardiac muscle and tend to be used more for fine and postural control. They usually have a greater oxidative capacity and are more resistant to fatigue with continued use. Fast skeletal muscle fibers, often called type II fibers, are classified into fast oxidative (IIa) and fast glycolytic (type IIx/d) fibers. While these muscle fibers have different myosin types, they share many components including the troponin and tropomyosin regulatory proteins. Fast skeletal muscle fibers tend to exert greater force but fatigue faster than slow skeletal muscle fibers and are functionally useful for acute, large scale movements such as rising from a chair or correcting falls.

Muscle contraction and force generation is controlled through nervous stimulation by innervating motor neurons. Each motor neuron may innervate many (approximately 100 to 380) muscle fibers as a contractile whole, termed a motor unit. When a muscle is required to contract, motor neurons send stimuli as nerve impulses (action potentials) from the brain stem or spinal cord to each fiber within the motor unit. The contact region between nerve and muscle fibers is a specialized synapse called the neuromuscular junction (NMJ). Here, membrane depolarizing action potentials in the nerve are translated into an impulse in the muscle fiber through release of the neurotransmitter acetylcholine (ACh). ACh triggers a second action potential in the muscle that spreads rapidly along the fiber and into invaginations in the membrane, termed t-tubules. T-tubules are physically connected to $Ca^{2+}$ stores within the sarcoplasmic reticulum (SR) of muscle via the dihydropyridine receptor (DHPR). Stimulation of the DHPR activates a second $Ca^{2+}$ channel in the SR, the ryanodine receptor, to trigger the release of $Ca^{2+}$ from stores in the SR to the muscle cytoplasm where it can interact with the troponin complex to initiate muscle contraction. If muscle stimulation stops, calcium is rapidly taken back up into the SR through the ATP dependent $Ca^{2+}$ pump, sarco/endoplasmic reticulum $Ca^{2+}$-ATPase (SERCA).

Muscle function can become compromised in disease by many mechanisms. Examples include the frailty associated with old age (termed sarcopenia) and cachexia syndromes associated with diseases such as cancer, heart failure, chronic obstructive pulmonary disease (COPD), and chronic kidney disease/dialysis. Severe muscular dysfunction can arise from neuromuscular diseases (such as amyotrophic lateral sclerosis (ALS), spinal muscular atrophy (SMA), and myasthenia gravis) or muscular myopathies (such as muscular dystrophies). Additionally, muscle function may become compromised due to rehabilitation-related deficits, such as those associated with recovery from surgery (e.g., post-surgical muscle weakness), prolonged bed rest, or stroke rehabilitation. Additional examples of diseases or conditions where muscle function becomes compromised include peripheral vascular disease (e.g., claudication), chronic fatigue syndrome, metabolic syndrome, obesity, dysfunctions of pelvic floor and urethral/anal sphincter muscles (e.g., urinary incontinence such as stress urinary incontinence (SUI) and mixed urinary incontinence (MUI), and fecal incontinence), post-spinal cord injury (SCI) muscle dysfunction, and ventilator-induced muscle weakness.

Currently, there is limited treatment or no cure for most neuromuscular diseases. WO2008/016669 discloses a compound represented by the following general formula (A) for treating a patient having a disease responsive to modulation of skeletal troponin C, etc.

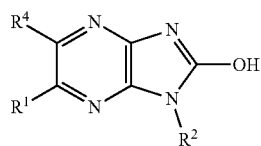

formula (A)

For the symbols, refer to this publication.

WO2011/0133888 discloses a compound represented by the following general formula (B) for treating a patient having a disease responsive to modulation of skeletal troponin C, etc.

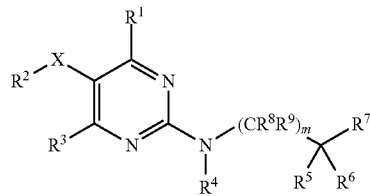

formula (B)

For the symbols, refer to this publication.

WO2011/0133882, WO2011/133920, and US2013-0060025 disclose another compound for treating a patient having a disease responsive to modulation of skeletal troponin C, etc.

WO2013/151938, WO2013/155262, and WO2015/168064 disclose treatment methods such as improving diaphragm function, improving resistance to skeletal muscle fatigue, reducing decline in vital capacity by using a skeletal muscle troponin activator.

U.S. Pat. Nos. 3,947,451 and 3,301,857 along with Journal of Heterocyclic Chemistry, 7 (3) p 615-22, (1970) and Synthetic Communications, 32 (12) p 1787-90, (2002) disclose compounds having 1,4-dihydroisoquinolin-3(2H) structure, but fail to disclose any pharmacological activities of the compounds described therein.

Tetrahedron Letters, 50 (47) p 6476-6479, (2009) discloses 1,1-diallyl-3-oxo-2,4-dihydroisoquinoline-4-carboxylate, but fail to disclose any pharmacological activities of the compounds described therein.

Accordingly, there is a need for the development of new compounds that modulate skeletal muscle contractility. There remains a need for agents that exploit new mechanisms of action and which may have better outcomes in terms of relief of symptoms, safety, and patient mortality, both short-term and long-teen and an improved therapeutic index.

SUMMARY OF THE INVENTION

Accordingly, it is one object of the present invention to provide novel tetrahydroisoquinoline compounds and salts thereof which are useful as an active ingredient for pharmaceutical compositions, in particular, pharmaceutical compositions for treating a disease or condition responsive to modulation of the contractility of the skeletal sarcomere.

It is another object of the present invention to provide novel pharmaceutical compositions which contain such a compound.

It is another object of the present invention to provide novel methods of preparing such a compound.

It is another object of the present invention to provide novel methods for preventing or treating a disease or condition responsive to modulation of the contractility of the skeletal sarcomere.

These and other objects, which will become apparent during the following detailed description, have been achieved by the inventors' discovery compounds of formula (I) and (I') described below.

The present invention provides novel compounds which are expected to be used as an active ingredient in a pharmaceutical composition, and in particular, in a pharmaceutical composition for preventing or treating a disease or condition responsive to modulation of the contractility of the skeletal sarcomere. Modulation of the skeletal sarcomere may be modulation, for example, by modulation of the troponin complex of the fast skeletal muscle sarcomere through one or more of fast skeletal myosin, actin, tropomyosin, troponin C, troponin I, and troponin T, and fragments and isoforms thereof.

Compounds of formula (I), (I'), and embodiments thereof are provided herein, as well as pharmaceutical compositions containing such compounds, methods of preparing such compounds, and methods of using such compounds in therapy. It is intended that any of the pharmaceutical compositions, methods of preparation, and methods of use provided herein encompass any of the compounds of formula (I), (I') and any embodiments thereof provided herein, including, without limitation, Embodiments 1-1 through 8-4 and Embodiments (1)-(57).

The present invention relates to a compound of the formula (I) or a salt thereof, and a pharmaceutical composition comprising a compound of the formula (I) or a salt thereof and an excipient.

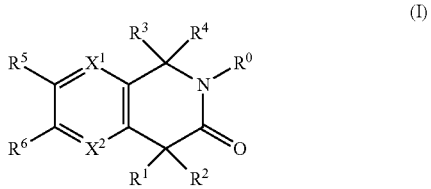

(I)

wherein,
$X^1$: $C-R^{11}$ or N;
$X^2$: $C-R^{12}$ or N;
$R^{11}$: i) H, ii) halogen, iii) —CN, or iv) —O—$C_{1-6}$ alkyl;
$R^{12}$: H or halogen;
$R^1$: i) H, ii) $C_{1-6}$ alkyl which may be substituted with one or more substituent(s) selected from the group consisting of halogen(s), and pyrazolyl(s), iii) $C_{2-6}$ alkenyl, or iv) —$OR^0$;
$R^2$: i) $C_{1-6}$ alkyl which may be substituted with one or more substituent(s) selected from the group consisting of —$OR^0$(s), halogen(s), —$COOR^0$(s), —$CONR^{21}R^{22}$(s), phenyl(s) which may be substituted with one or more substituent(s) selected from the $G^1$ group, and heteroaryl(s) which is selected from the group consisting of pyridyl, pyrazolyl, imidazolyl, thiazolyl, thiadiazolyl, thienyl, oxazolyl, isoxazolyl, and triazolyl, wherein the heteroaryl may be substituted with one or more substituent(s) selected from the $G^2$ group, ii) $C_{2-6}$ alkenyl, iii) $C_{2-6}$ alkynyl, iv) —$OR^0$, v) —$NR^{23}R^{24}$, vi) —$COOR^0$, or vii) phenyl;
$R^{21}$: H or $C_{1-6}$ alkyl;
$R^{22}$: i) $C_{1-6}$ alkyl which may be substituted with one or more phenyl(s), or ii) phenyl;
$R^{23}$: i) H, or ii) $C_{1-6}$ alkyl which may be substituted with one or more —OH(s);
$R^{24}$: i) $C_{1-6}$ alkyl which may be substituted with one or more phenyl(s), ii) $C_{3-8}$ cycloalkyl which may be substituted with one or more $C_{1-6}$ alkyl(s), iii) phenyl which may be substituted with one or more halogen(s), or iv) tetrahydropyranyl; or
$R^1$, $R^2$, and a carbon atom bounded by $R^1$ and $R^2$ may interact to form a 4-piperidine ring or 4-tetrahydropyran ring, and the carbon atom bounded by $R^1$ and $R^2$ is a spiro atom and the 4-piperidine ring may be substituted with one or more substituent(s) selected from the group consisting of —$SO_2$—($C_{1-6}$ alkyl) and —$COOR^0$;

$R^3$, $R^4$: the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and heteroaryl(s) which is selected from the group consisting of pyrazolyl and thienyl, wherein the heteroaryl may be substituted with one or more $C_{1-6}$ alkyl(s), or,
$R^3$, $R^4$, and a carbon atom bounded by $R^3$ and $R^4$ may interact to form a 3-oxetane ring and the carbon atom bounded by $R^3$ and $R^4$ is a spiro atom;
$R^5$: i) H, ii) $C_{1-6}$ alkyl which may be substituted with one or more —O—($C_{1-6}$ alkyl)(s), iii) —O—($C_{1-6}$ alkyl), iv) halogen, v) —COO—($C_{1-6}$ alkyl), or vi) $C_{3-8}$ cycloalkyl;
$R^6$: i) H, ii) $C_{1-6}$ alkyl which may be substituted with one or more substituent(s) s elected from the group consisting of —O—($C_{1-6}$ alkyl(s) which may be substituted with one or more halogen(s)) and halogen(s), iii) —OH, iv) —O—($C_{1-6}$ alkyl which may be substituted with one or more halogen(s)), v) halogen, vi) —CN, vii) —S—($C_{1-6}$ alkyl), viii) $C_{3-8}$ cycloalkyl, ix) —$NR^0R^0$, or x) $C_{2-6}$ alkenyl;
$G^1$ group: i) halogen, ii) —$COOR^0$, iii) —$CONR^0R^0$, iv) —OH, v) $C_{1-6}$ alkyl which may be substituted with one or more substituent(s) selected from the group consisting of —OH(s) and halogen, or vi) —O—($C_{1-6}$ alkyl which may be substituted with one or more substituent(s) selected from the group consisting of —OH(s) and halogen(s));
$G^2$ group: i) halogen, ii) $C_{1-6}$ alkyl which may be substituted with one or more substituent(s) selected from the group consisting of —OH(s) and halogen(s) or iii) —$CONR^0R^0$;
$R^0$: the same or different each other, H or $C_{1-6}$ alkyl.

In one embodiment, the present invention relates to a compound of the formula (I) or a salt thereof, and a pharmaceutical composition comprising a compound of the formula (I) or a salt thereof and an excipient.

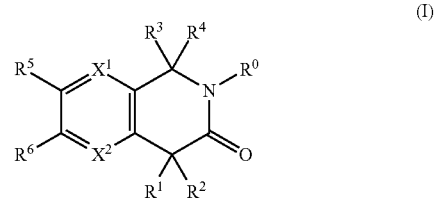

(I)

wherein,
$X^1$: $C-R^{11}$ or N;
$X^2$: $C-R^{12}$ or N;
$R^{11}$: i) H, ii) halogen, iii) —CN, or iv) —O—$C_{1-6}$ alkyl;
$R^{12}$: H or halogen;
$R^1$: i) H, ii) $C_{1-6}$ alkyl which may be substituted with one or more substituent(s) selected from the group consisting of halogen(s), and pyrazolyl(s), iii) $C_{2-6}$ alkenyl, or iv) —$OR^0$;
$R^2$: i) $C_{1-6}$ alkyl which may be substituted with one or more substituent(s) selected from the group consisting of —$OR^0$(s), halogen(s), —$COOR^0$(s), —$CONR^{21}R^{22}$(s), phenyl(s) which may be substituted with one or more substituent(s) selected from the $G^1$ group, and heteroaryl(s) which is selected from the group consisting of pyridyl, pyrazolyl, imidazolyl, thiazolyl, thiadiazolyl, thienyl, oxazolyl, isoxazolyl, and triazolyl, wherein the heteroaryl may be substituted with one or more substituent(s) selected from the $G^2$ group, ii) $C_{2-6}$ alkenyl, iii) $C_{2-6}$ alkynyl, iv) —$OR^0$, v) —$NR^{23}R^{24}$, vi) —$COOR^0$, or vii) phenyl;

$R^{21}$: H or $C_{1-6}$ alkyl;

$R^{22}$: $C_{1-6}$ alkyl which may be substituted with one or more phenyl(s), or ii) phenyl;

$R^{23}$: i) H, or ii) $C_{1-6}$ alkyl which may be substituted with one or more —OH(s);

$R^{24}$: i) $C_{1-6}$ alkyl which may be substituted with one or more phenyl(s) which may be substituted with one or more halogen(s), ii) $C_{3-8}$ cycloalkyl which may be substituted with one or more $C_{1-6}$ alkyl(s), iii) phenyl which may be substituted with one or more halogen(s), or iv) tetrahydropyranyl; or $R^1$, $R^2$, and a carbon atom bounded by $R^1$ and $R^2$ may interact to form a 4-piperidine ring or 4-tetrahydropyran ring, and the carbon atom bounded by $R^1$ and $R^2$ is a spiro atom and the 4-piperidine ring may be substituted with one or more substituent(s) selected from the group consisting of —SO$_2$—(C$_{1-6}$ alkyl) and —COOR$^0$;

$R^3$, $R^4$; the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and heteroaryl(s) which is selected from the group consisting of pyrazolyl and thienyl, wherein the heteroaryl may be substituted with one or more $C_{1-6}$ alkyl(s), or, $R^3$, $R^4$, and a carbon atom bounded by $R^3$ and $R^4$ may interact to form a 3-oxetane ring and the carbon atom bounded by $R^3$ and $R^4$ is a Spiro atom;

$R^5$: i) H, ii) $C_{1-6}$ alkyl which may be substituted with one or more —O—($C_{1-6}$ alkyl)(s), iii) —O—($C_{1-6}$ alkyl), iv) halogen, v) —COO—($C_{1-6}$ alkyl), or vi) $C_{3-8}$ cycloalkyl;

$R^6$: i) H, ii) $C_{1-6}$ alkyl which may be substituted with one or more substituent(s) selected from the group consisting of —O—($C_{1-6}$ alkyl(s) which may be substituted with one or more halogen(s)) and halogen(s), iii) —OH, iv) —O—($C_{1-6}$ alkyl which may be substituted with one or more halogen(s)), v) halogen, vi) —CN, vii) —S—($C_{1-6}$ alkyl), viii) $C_{3-8}$ cycloalkyl, ix) —NR$^0$R$^0$, or x) $C_{2-6}$ alkenyl;

$G^1$ group: i) halogen, ii) —COOR$^0$, iii) —CONR$^0$R$^0$, iv) —OH, v) $C_{1-6}$ alkyl which may be substituted with one or more substituent(s) selected from the group consisting of —OH(s) and halogen, or vi) —O—($C_{1-6}$ alkyl which may be substituted with one or more substituent(s) selected from the group consisting of —OH(s) and halogen(s));

$G^2$ group: i) halogen, ii) $C_{1-6}$ alkyl which may be substituted with one or more substituent(s) selected from the group consisting of —OH(s) and halogen(s) or iii) —CONR$^0$R$^0$;

$R^0$: the same or different each other, H or $C_{1-6}$ alkyl, provided that said compound is not methyl 1,1-diallyl-3-oxo-2,4-dihydroisoquinoline-4-carboxylate or a salt thereof.

Unless specifically described otherwise, when symbols in one formula in the specification are also used in other formulae, same symbols denote same meanings. When the same symbol is used more than once in a given formula, it is to be understood that each instance of that symbol in the formula represents an independently selected chemical moiety and that all instances of the symbol in the formula need not necessarily represent identical chemical moieties.

Further, the present invention relates to a pharmaceutical composition comprising the compound of the formula (I) or a salt thereof, and a pharmaceutically acceptable excipient. Furthermore, the invention relates to a pharmaceutical composition for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof, comprising the compound of the formula (I) or a salt thereof. Furthermore, the invention relates to an agent for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof, comprising the compound of the formula (I) or a salt thereof.

Moreover, the present invention relates to use of the compound of the formula (I) or a salt thereof for the manufacture of a pharmaceutical composition for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof; use of the compound of the formula (I) or a salt thereof for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof; the compound of the formula (I) or a salt thereof for use in preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof; and a method for preventing or treating a disease or condition responsive to modulation of the contractility of the skeletal sarcomere, for example, modulation of the troponin complex of the fast skeletal muscle sarcomere through one or more of fast skeletal myosin, actin, tropomyosin, troponin C, troponin I, and troponin T, and fragments and isoforms thereof, comprising administering to a subject an effective amount of the compound of the formula (I) or a salt thereof. Further, the "subject" is a human or a non-human animal in need of the prevention or treatment, and in one embodiment, a human in need of the prevention or treatment.

In one aspect, the compound of the formula (I) or a salt thereof modulates the contractility of the skeletal sarcomere. Specifically, the compounds modulate the troponin complex of the fast skeletal muscle sarcomere through one or more of fast skeletal myosin, actin, tropomyosin, troponin C, troponin I, and troponin T, and fragments and isoforms thereof. As used in this context, "modulate" means either increasing or decreasing activity. In some instances, the compounds described and/or disclosed herein potentiate (i.e., increase activity) of one or more of fast skeletal myosin, actin, tropomyosin, troponin C, troponin I, and troponin T, and fragments and isoforms thereof. In other instances, the compounds described and/or disclosed herein inhibit (i.e., decrease activity) of one or more of fast skeletal myosin, actin, tropomyosin, troponin C, troponin I, and troponin T, and fragments and isoforms thereof. As used in this context, "activation of the fast skeletal muscle fiber such as myofibril" means to amplify the response of fast skeletal muscle fiber (such as myofibril) to stimulation/Ca$^{2+}$.

In a further aspect, the compounds and pharmaceutical compositions described and/or disclosed herein are capable of modulating the contractility of the fast skeletal sarcomere in vivo, and can have application in both human and animal disease. Modulation would be desirable in a number of conditions or diseases, including, but not limited to, 1) neuromuscular disorders, such as Amyotrophic Lateral Sclerosis (ALS), Spinal Muscular Atrophy (SMA), peripheral neuropathies, and myasthenia gravis; 2) disorders of voluntary muscle, including muscular dystrophies, myopathies and conditions of muscle wasting, such as sarcopenia and cachexia syndromes (e.g., cachexia syndromes caused by diseases such as cancer, heart failure, chronic obstructive pulmonary disease (COPD), and chronic kidney disease/dialysis), rehabilitation-related deficits, such as those associated with recovery from surgery (e.g., post-surgical muscle weakness), prolonged bed rest or stroke rehabilitation, and ventilator-induced muscle weakness; 3) central nervous system (CNS) disorders in which muscle weakness, atrophy, and fatigue are prominent symptoms, such as multiple sclerosis, Parkinson's disease, stroke, and spinal cord injury; 4) muscle symptoms stemming from systemic disorders, including Peripheral Vascular Disease (PVD) or Peripheral Arterial Disease (PAD) (e.g., claudication), metabolic syndrome, chronic fatigue syndrome, obesity, and frailty due to aging; and 5) dysfunctions of pelvic floor and urethral/anal sphincter muscles such as stress urinary incontinence, mixed urinary incontinence and fecal incontinence.

In a further aspect, the present invention relates to a pharmaceutical composition for preventing or treating a disease or condition selected from the group consisting of stress urinary incontinence (SUI), mixed urinary incontinence (MUI) and fecal incontinence comprising a compound of the formula (I), or a salt thereof. In a further aspect, the invention relates to a pharmaceutical composition for preventing or treating a disease or condition selected from the group consisting of frailty and sarcopenia comprising a compound of the formula (1), or a salt thereof. In a further aspect, the invention relates to a pharmaceutical composition for preventing or treating chronic obstructive pulmonary disease (COPD) comprising a compound of the formula (I), or a salt thereof. In a further aspect, the invention relates to a pharmaceutical composition for preventing or treating cachexia syndrome and/or muscle wasting caused by heart failure, cancer, or chronic kidney disease/dialysis comprising a compound of the formula (I), or a salt thereof. In a further aspect, the invention relates to a pharmaceutical composition for preventing or treating a disease or condition selected from the group consisting of amyotrophic lateral sclerosis (ALS), spinal muscular atrophy (SMA), myasthenia gravis and muscular myopathies comprising a compound of the formula (I), or a salt thereof. In a further aspect, the invention relates to a pharmaceutical composition for preventing or treating a disease or condition selected from the group consisting of post-spinal cord injury (SCI) muscle dysfunction and post-stroke muscle dysfunction comprising a compound of the formula (I), or a salt thereof. In a further aspect, the invention relates to a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome comprising a compound of the formula (I), or a salt thereof.

In a further aspect, the present invention relates to use of a compound of the formula (I), or a salt thereof for the manufacture of a pharmaceutical composition for preventing or treating a disease or condition selected from the group consisting of stress urinary incontinence (SUI), mixed urinary incontinence (MUI) and fecal incontinence. In a further aspect, the invention relates to use of a compound of the formula (I), or a salt thereof for the manufacture of a pharmaceutical composition for preventing or treating a disease or condition selected from the group consisting of frailty and sarcopenia. In a further aspect, the present invention relates to use of a compound of the formula (I), or a salt thereof for the manufacture of a pharmaceutical composition for preventing or treating chronic obstructive pulmonary disease (COPD). In a further aspect, the invention relates to a use of a compound of the formula (I), or a salt thereof for the manufacture of a pharmaceutical composition for preventing or treating cachexia syndrome and/or muscle wasting caused by heart failure, cancer, or chronic kidney disease/dialysis. In a further aspect, the invention relates to use of a compound of the formula (I), or a salt thereof for the manufacture of a pharmaceutical composition for preventing or treating a disease or condition selected from the group consisting of amyotrophic lateral sclerosis (ALS), spinal muscular atrophy (SMA) and myasthenia gravis, muscular myopathies. In a further aspect, the invention relates to use of a compound of the formula (I), or a salt thereof for the manufacture of a pharmaceutical composition for preventing or treating a disease or condition selected from the group consisting of post-spinal cord injury (SCI) muscle dysfunction and post-stroke muscle dysfunction. In a further aspect, the invention relates to use of a compound of the formula (I), or a salt thereof for the manufacture of a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to use of a compound of the formula (I), or a salt thereof for preventing or treating a disease or condition selected from the group consisting of stress urinary incontinence (SUI), mixed urinary incontinence (MUI) and fecal incontinence. In a further aspect, the present invention relates to use of a compound of the formula (I), or a salt thereof for preventing or treating a disease or condition selected from the group consisting of frailty and sarcopenia. In a further aspect, the invention relates to use of a compound of the formula (I), or a salt thereof for preventing or treating chronic obstructive pulmonary disease (COPD). In a further aspect, the invention relates to use of a compound of the formula (I), or a salt thereof for preventing or treating cachexia syndrome and/or muscle wasting caused by heart failure, cancer, or chronic kidney disease/dialysis. In a further aspect, the invention relates to use of a compound of the formula (I), or a salt thereof for preventing or treating a disease or condition selected from the group consisting of amyotrophic lateral sclerosis (ALS), spinal muscular atrophy (SMA), myasthenia gravis and muscular myopathies. In a further aspect, the invention relates to use of a compound of the formula (T), or a salt thereof for preventing or treating a disease or condition selected from the group consisting of post-spinal cord injury (SCI) muscle dysfunction and post-stroke muscle dysfunction. In a further aspect, the invention relates to use of a compound of the formula (I), or a salt thereof for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to a method for preventing or treating a disease or condition selected from the group consisting of stress urinary incontinence (SUI), mixed urinary incontinence (MUI) and fecal incontinence, comprising administering to a subject an effective amount of the compound of the formula (I), or a salt thereof. In a further aspect, the present invention relates to a method for preventing or treating a disease or condition selected from the group consisting of frailty and sarcopenia, comprising administering to a subject an effective amount of the compound of the formula (I), or a salt thereof. In a further aspect, the invention relates to a method for preventing or treating chronic obstructive pulmonary disease (COPD), comprising administering to a subject an effective amount of the compound of the formula (I), or a salt thereof. In a further aspect, the invention relates to a method for preventing or treating cachexia syndrome and/or muscle wasting caused by heart failure, cancer, or chronic kidney disease/dialysis, comprising administering to a subject an effective amount of the compound of the formula (I), or a salt thereof. In a further aspect, the invention relates to a method for preventing or treating a disease or condition selected from the group consisting of amyotrophic lateral sclerosis (ALS), spinal muscular atrophy (SMA), myasthenia gravis and muscular myopathies, comprising administering to a subject an effective amount of the compound of the formula (I), or a salt thereof. In a further aspect, the invention relates to a method for preventing or treating a disease or condition selected from the group consisting of post-spinal cord injury (SCI) muscle dysfunction and post-stroke muscle dysfunction, comprising administering to a subject an effective amount of the compound of the formula (I), or a salt thereof. In a further aspect, the invention relates to a method for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome, comprising administering to a subject an effective amount of the compound of the formula (I), or a salt thereof. In any variation described herein, the subject is a human or a non-human animal in need of the prevention or treatment, and in one embodiment, a human in need of the prevention or treatment.

In a further aspect, the present invention relates to a compound of the formula (I), or a salt thereof, for use in the prevention or treatment of a disease or condition selected from the group consisting of stress urinary incontinence (SUI), mixed urinary incontinence (MUI) and fecal incontinence. In a further aspect, the present invention relates to a compound of the formula (I), or a salt thereof, for use in the prevention or treatment of a disease or condition selected from the group consisting of frailty and sarcopenia. In a further aspect, the invention relates to a compound of the formula (I), or a salt thereof, for use in the prevention or treatment of chronic obstructive pulmonary disease (COPD). In a further aspect, the invention relates to a compound of the formula (I), or a salt thereof, for use in the prevention or treatment of cachexia syndrome and/or muscle wasting caused by heart failure, cancer, or chronic kidney disease/dialysis. In a further aspect, the invention relates to a compound of the formula (I), or a salt thereof, for use in the prevention or treatment of a disease or condition selected from the group consisting of amyotrophic lateral sclerosis (ALS), spinal muscular atrophy (SMA), myasthenia gravis and muscular myopathies. In a further aspect, the invention relates to a compound of the formula (I), or a salt thereof, for use in the prevention or treatment of a disease or condition selected from the group consisting of post-spinal cord injury (SCI) muscle dysfunction and post-stroke muscle dysfunction. In a further aspect, the invention relates to a compound of the formula (I), or a salt thereof, for use in the prevention or treatment of a disease or condition selected from the group consisting of peripheral vascular disease, peripheral arterial disease, rehabilitation-related deficits, metabolic syndrome, obesity, ventilator-induced muscle weakness and chronic fatigue syndrome.

BRIEF DESCRIPTION OF DRAWINGS

A more complete appreciation of the invention and many of the attendant advantages thereof will be readily obtained as the same become better understood by reference to the following detailed description when considered in connection with the accompanying drawings, wherein:

In FIG. 1, Example 20 means Example Compound 20, and Example 22b means Example Compound 22b.

In FIG. 2, Example 20 means Example Compound 20.

In FIG. 3, Example 22b means Example Compound 22b.

In FIG. 4, Example 20 means Example Compound 20, and Example 22b means Example Compound 22b.

In FIG. 5, Example 20 means Example Compound 20.

In FIG. 6, Example 22b means Example Compound 22b.

In FIG. 7, Example 52 means Example Compound 52.

In FIG. 8, Example 52 means Example Compound 52.

In FIG. 9, Example 20 means Example Compound 20.

In FIG. 10, Example 20 means Example Compound 20.

DETAILED DESCRIPTION

Figure 1:
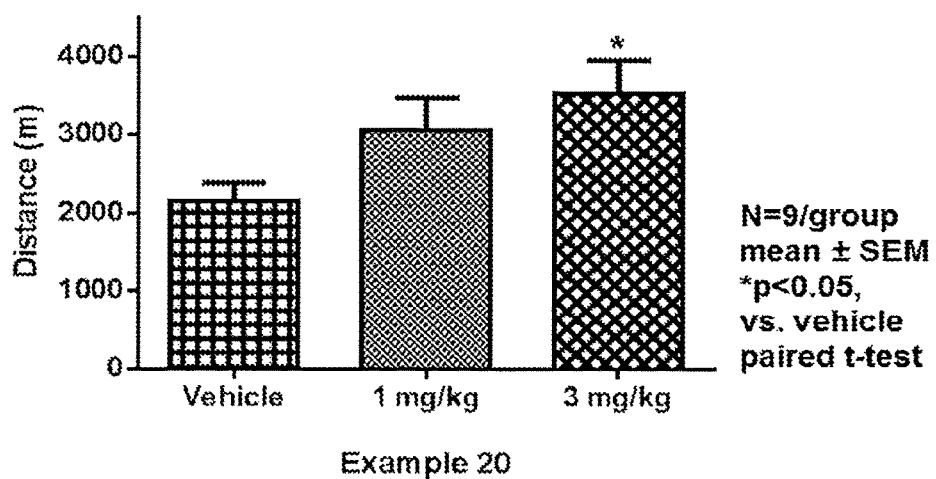
FIG. 1 is graphs showing results obtained by an assay of rat treadmill running performance. Significance is defined as *p<0.05 vs. vehicle treatment.
Figure 1:
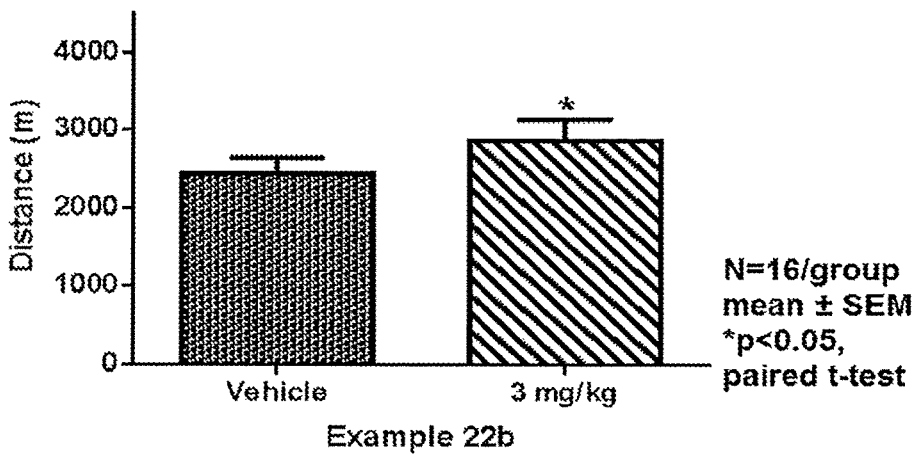

Hereinafter, the invention will be described in detail.

The term "alkyl" refers to linear or branched alkyl. Accordingly, the "$C_{1-6}$ alkyl" is linear or branched alkyl having 1 to 6 carbon atoms, and specific examples thereof include methyl, ethyl, n-propyl, isopropyl, n-butyl, isobutyl, sec-butyl, tert-butyl, n-pentyl, or n-hexyl; in one embodiment, methyl, ethyl, n-propyl, isopropyl, n-butyl, isobutyl, sec-butyl, or tert-butyl; in one embodiment, a group selected from the group consisting of methyl, ethyl, and isopropyl; and in one embodiment, a group selected from the group consisting of methyl and ethyl. It is understood that the linear or branched alkyl refers to a linear or branched saturated hydrocarbon.

The term "alkenyl" refers to an unsaturated linear or branched alkyl group having the indicated number of carbon atoms (e.g., 2 to 8, or 2 to 6 carbon atoms) and at least one carbon-carbon double bond derived by the removal of one molecule of hydrogen from adjacent carbon atoms of the corresponding alkyl. The group may be in either the cis or trans configuration (Z or E configuration) about the double bond(s). Alkenyl groups include, but are not limited to ethenyl, propenyl (e.g., prop-1-en-1-yl, prop-1-en-2-yl, prop-2-en-1-yl (allyl)), and butenyl (e.g., but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl). Alkenyl groups may be prepared by any method known in the art.

The term "alkynyl" refers to an unsaturated linear or branched alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl or prop-2-yn-1-yl) and butynyl (e.g., but-1-yn-1-yl, but-1-yn-3-yl or but-3-yn-1-yl). Alkynyl groups may be prepared by any method known in the art.

The term "cycloalkyl" refers to a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic or tricyclic). Examples of cycloalkyl groups include cyclopropyl, cyclobutyl, cyclopentyl and cyclohexyl, as well as bridged and caged ring groups (e.g., norbornane or bicyclo[2.2.2]octane).

The term "heteroaryl" refers to a monocyclic aromatic hetero ring or a bicyclic aromatic hetero ring. The "monocyclic aromatic hetero ring" includes a monocyclic aromatic hetero ring group having 5 to 7 ring members, which has 1 to 4 hetero atoms selected from the group consisting of a nitrogen atom, an oxygen atom, and a sulfur atom as a ring-constituting atom, and specific examples thereof include pyrrolyl, pyrazolyl, imidazolyl, triazolyl, furyl, thienyl, oxazolyl, isoxazolyl, oxadiazolyl, thiazolyl, thiadiazolyl, pyridyl, pyridazinyl, pyrimidinyl or pyrazinyl; in one embodiment, pyrazolyl, imidazolyl, triazolyl, thienyl, oxazolyl, isoxazolyl, thiazolyl, thiadiazolyl or pyridyl.

The term "bicyclic aromatic hetero ring" refers to a bicyclic aromatic hetero ring group in which the monocyclic aromatic hetero ring is fused with a benzene ring or monocyclic aromatic hetero ring and includes a partially hydrogenated ring group thereof, and specific examples thereof include indolyl, isoindolyl, indazolyl, benzotriazolyl, benzofuranyl, benzothienyl, benzooxazolyl, benzothiazolyl, quinolyl, isoquinolyl, cinnolinyl, quinazolinyl, quinoxalinyl, naphthyridinyl, propyridyl, thienopyridyl, indolinyl, di hydrobenzofuranyl, dihydrobenzothienyl, dihydroquinolyl, tetrahydroquinolyl, dihydroisoquinolyl, tetrahydroisoquinolyl, dihydropropyridyl or dihydrothienopyridyl; and in one embodiment, benzothienyl.

The term "saturated hetero ring" includes 3 to 8 membered saturated ring group, which has 1 to 4 hetero atoms selected from the group consisting of a nitrogen atom, an oxygen atom, and a sulfur atom as a ring-constituting atom, and may be bridged with $C_{1-6}$ alkylene, in which a sulfur atom as the ring-constituting atom may be oxidized. Specific examples thereof include azepanyl, diazepanyl, oxazepanyl, thiazepanyl, aziridinyl, azetidinyl, pyrrolidinyl, imidazolidi-nyl, piperidinyl, pyrazolidinyl, piperazinyl, azocanyl, thiomorpholinyl, thiazolindinyl, isothiazolindinyl, oxazolindinyl, morpholinyl, thiomorpholinyl, tetrahydrothiopyranyl, oxathioranyl, oxiranyl, oxetanyl, dioxiranyl, tetrahydrofuranyl, tetrahydropyranyl or 1,4-dioxanyl.

The term "halogen" means fluoro, chloro, bromo or iodo; in one specific embodiment, fluoro, chloro or bromo; in another specific embodiment, fluoro; in a further specific embodiment, chloro, and in another specific embodiment, bromo.

The term "$R^3$, $R^4$, and a carbon atom bounded by $R^3$ and $R^4$ interact to form a 3-oxetane ring and the carbon atom bounded by $R^3$ and $R^4$ is a spiro atom" means, as clear from the description, $R^3$ and $R^4$, together with the carbon to which they are attached, form a 3-oxetane ring as described below;

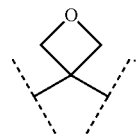

The term "$R^1$, $R^2$, and a carbon atom bounded by $R^1$ and $R^2$ interact to form a 4-piperidine ring or 4-tetrahydropyran ring, and the carbon atom bounded by $R^1$ and $R^2$ is a spiro atom" means, as clear from the description, $R^1$ and $R^2$, together with the carbon to which they are attached, form a 4-piperidine ring or 4-tetrahydropyran ring as described below;

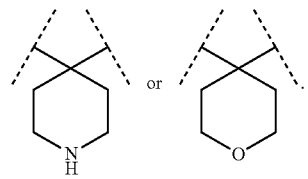

In the specification, the expression "which may be substituted" means "which is not substituted" or "which is substituted with about 1 to about 5 substituents." Further, if it has a plurality of substituents, the substituents may be the same as or different from each other.

In powder X-ray diffraction pattern described in the present specification, the spacing of the crystal lattice and the overall pattern are important in identifying crystals on the nature of the powder X-ray diffraction data, and the diffraction angle and diffraction intensity should not be strictly interpreted, since they can include some errors according to the crystal growth direction, the particle size and the measurement conditions. The diffraction angles (2θ(°)) of powder X-ray diffraction pattern in the present specification can include a measurement error of ±0.2° as an embodiment in consideration of error margin commonly accepted in the measurement method. Moreover, for example, a peak which is nearby a peak derived from pharmaceutical excipients and on a tilted baseline of the peak can visually shift by ±0.3° in the case that powder X-ray measurement is performed in the state of a mixture with pharmaceutical excipients.

In both preclinical and clinical settings, activators of the fast skeletal troponin complex have been shown to amplify the response of fast skeletal muscle to nerve stimulation, resulting in an increase in muscle force development at sub-maximal muscle activation (see, e.g., Russell et al., "The Fast Skeletal Troponin Activator, CK-2017357, Increases Skeletal Muscle Force in vitro and in situ", 2009 Experimental Biology Conference, New Orleans, La., April 2009). Activators of the fast skeletal troponin complex have been shown to increase the sensitivity of skinned skeletal muscle fibers to calcium, and in living muscle to the frequency of stimulation, each of which results in an increase in muscle force development at sub-maximal muscle activation. Such activators have also been shown to reduce muscle fatigue and/or to increase the overall time to fatigue in normal and low oxygenated conditions (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009; Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010). The increase in muscle force in response to nerve input has been demonstrated in healthy human volunteers as well (see, e.g., Hansen et al., "CK-2017357, a Novel Activator of Fast Skeletal Muscle, Increases Isometric Force Evoked by Electrical Stimulation of the Anterior Tibialis Muscle in Healthy Male Subjects", Society for Neuroscience 40th Annual Meeting: Neuroscience 2010, November 2010). Work in additional preclinical models of muscle function suggests that activators of the fast skeletal troponin complex also cause an increase in muscle power and/or endurance. These pharmacological properties suggest this mechanism of action could have application in conditions, for example, where neuromuscular function is impaired.

Provided are methods for enhancing fast skeletal muscle efficiency in a patient in need thereof, comprising administering to said patient an effective amount of a compound or composition described and/or disclosed herein that selectively binds the troponin complex of fast skeletal muscle fiber or sarcomere. In some embodiments, the compound disclosed and/or described herein activates fast skeletal muscle fibers or sarcomeres. In some embodiments, administration of a compound disclosed and/or described herein results in an increase in fast skeletal muscle power output. In some embodiments, administration of a compound disclosed and/or described herein results in increased sensitivity of fast skeletal muscle fibers or sarcomeres to calcium ion, as compared to fast skeletal muscle fibers or sarcomeres untreated with the compound. In some embodiments, administration of a compound disclosed and/or described herein results in a lower concentration of calcium ions causing fast skeletal muscle myosin to bind to actin. In some embodiments, administration of a compound disclosed and/or described herein results in the fast skeletal muscle fiber generating force to a greater extent at submaximal levels of muscle activation.

Also provided is a method for sensitizing a fast skeletal muscle fiber to produce force in response to a lower concentration of calcium ion, comprising contacting the fast skeletal muscle fiber with a compound or composition described and/or disclosed herein that selectively binds to troponin complexes in the fast skeletal muscle sarcomere. In some embodiments, contacting the fast skeletal muscle fiber with the compound results in activation of the fast skeletal muscle fiber at a lower calcium ion concentration than in an untreated fast skeletal muscle fiber. In some embodiments, contacting the fast skeletal muscle fiber with the compound results in the production of increased force at a lower calcium ion concentration in comparison with an untreated fast skeletal muscle fiber.

Also provided is a method for increasing time to fast skeletal muscle fatigue in a patient in need thereof, comprising contacting fast skeletal muscle fibers with a compound or composition described and/or disclosed herein that selectively binds to the troponin complexes of the fast skeletal muscle fibers. In some embodiments, the compound binds to form ligand-troponin-calcium ion complexes that activate the fast skeletal muscle fibers. In some embodiments, formation of the complexes and/or activation of the fast skeletal muscle fibers results in enhanced force and/or increase time to fatigue as compared to untreated fast skeletal muscle fibers contacted with a similar calcium ion concentration.

Some embodiments of the present invention are described below.

Embodiment 1-1

The compound of the formula (I) or a salt thereof, in which
$X^1$ is C—$R^{11}$ or N;
$X^2$ is C—$R^{12}$ or N;
$R^{11}$ is i) H, ii) halogen, iii) —CN, or iv) —O—$C_{1-6}$ alkyl; and
$R^{12}$ is H or halogen.

Embodiment 1-2

The compound of the formula (I) or a salt thereof, in which
$X^1$ is C—$R^{11}$ or N;
$X^2$ is C—$R^{12}$ or N;
$R^{11}$ is i) H, ii) halogen, iii) —CN, or iv) —O—$C_{1-6}$ alkyl; and
$R^{12}$ is H.

Embodiment 1-3

The compound of the formula (I) or a salt thereof, in which
$X^1$ is C—$R^{11}$;
$X^2$ is C—$R^{12}$;
$R^{11}$ is i) H, ii) halogen, iii) —CN, or iv) —O—$C_{1-6}$ alkyl; and
$R^{12}$ is H.

Embodiment 1-4

The compound of the formula (I) or a salt thereof, in which
$X^1$ is C—$R^{11}$;
$X^2$ is N; and
$R^{11}$ i) H, ii) halogen, iii) —CN, or iv) —O—$C_{1-6}$ alkyl.

Embodiment 1-5

The compound of the formula (I) or a salt thereof, in which
$X^1$ is N; and
$X^2$ is N.

Embodiment 2-1

The compound of the formula (I) or a salt thereof, in which
$R^1$ is i) H, ii) $C_{1-6}$ alkyl which may be substituted with one or more substituent(s) selected from the group consisting of halogen(s) and pyrazolyl(s), iii) $C_{2-6}$ alkenyl, or iv) —$OR^0$;
$R^2$ is i) $C_{1-6}$ alkyl which may be substituted with one or more substituent(s) selected from the group consisting or —OR⁰, halogen, —COOR⁰, —CONR²¹R²², phenyl which may be substituted with one or more substituent(s) selected from the $G^1$ group and heteroaryl is selected from the group consisting of pyridyl, pyrazolyl, imidazolyl, thiazolyl, thiadiazolyl, thienyl, oxazolyl, isoxazolyl, and triazolyl, wherein the heteroaryl which may be substituted with one or more substituent(s) selected from the $G^2$ group, ii) $C_{2-6}$ alkenyl, iii) $C_{2-6}$ alkynyl, iv) —OR⁰, v) —NR²³R²⁴, vi) —COOR⁰, or vii) phenyl;

$R^{21}$ is H or $C_{1-6}$ alkyl;

$R^{22}$ is i) $C_{1-6}$ alkyl which may be substituted with one or more phenyl(s), or ii) phenyl;

$R^{23}$ is i) H, or ii) $C_{1-6}$ alkyl which may be substituted with one or more —OH(s); and $R^{24}$ is i) $C_{1-6}$ alkyl which may be substituted with one or more phenyl(s) which may be substituted with one or more halogen(s), ii) $C_{3-8}$ cycloalkyl which may be substituted with one or more $C_{1-6}$ alkyl(s), iii) phenyl which may be substituted with one or more halogen(s), or iv) tetrahydropyranyl; or $R^1$, $R^2$, and a carbon atom bounded by $R^1$ and $R^2$ may interact to form a 4-piperidine ring or 4-tetrahydropyran ring, and the carbon atom bounded by $R^1$ and $R^2$ is a Spiro atom and the 4-piperidine ring may be substituted with one or more substituent(s) selected from the group consisting of —SO₂—$C_{1-6}$ alkyl and —COOR⁰;

$G^1$ group is selected from group consisting of i) halogen, ii) —COOR⁰, iii) —CONR⁰R⁰, iv) —OH, v) $C_{1-6}$ alkyl which may be substituted with one or more substituent(s) selected from the group consisting of —OH(s) and halogen(s), and vi) —O—$C_{1-6}$ alkyl which may be substituted with one or more substituent(s) selected from the group consisting of —OH(s) and halogen(s);

$G^2$ group is selected from the group consisting of i) halogen, ii) $C_{1-6}$ alkyl which may be substituted with one or more substituent(s) selected from the group consisting of —OH(s) and halogen(s) and iii) —CONR⁰R⁰; and $R^0$ is the same or different each other, H or $C_{1-6}$ alkyl.

Embodiment 2-2

The compound of the formula (I) or a salt thereof, in which
$R^1$ is i) H, or ii) $C_{1-6}$ alkyl;

$R^2$ is i) $C_{1-6}$ alkyl which may be substituted with one or more substituent(s) selected from the group consisting of —OR⁰ (s), halogen(s), —CONR²¹R²²(s), phenyl(s) which may be substituted with one or more substituent(s) selected from the group consisting of halogen(s) and —COOR⁰(s), and heteroaryl(s) which is selected from the group consisting of pyrazolyl, and triazolyl, ii) $C_{2-6}$ alkenyl, iii) $C_{2-6}$ alkynyl, iv) —NR²³R²⁴, or v) —COOR⁰;

$R^{21}$ is $C_{1-6}$ alkyl;

$R^{22}$ is $C_{1-6}$ alkyl;

$R^{23}$ is $C_{1-6}$ alkyl; and $R^{24}$ is i) $C_{3-8}$ cycloalkyl, or ii) phenyl; or $R^1$, $R^2$, and a carbon atom bounded by $R^1$ and $R^2$ may interact to form a 4-tetrahydropyran ring, and the carbon atom bounded by $R^1$ and $R^2$ is a Spiro atom; and $R^0$ is the same or different each other, H or $C_{1-6}$ alkyl.

Embodiment 2-3

The compound of the formula (I) or a salt thereof, in which
$R^1$ is $C_{1-6}$ alkyl;

$R^2$ is $C_{1-6}$ alkyl which may be substituted with a —OR⁰; and $R^0$ is the same or different each other, H or $C_{1-6}$ alkyl.

Embodiment 2-4

The compound of the formula (I) or a salt thereof, in which
$R^1$ is i) H, ii) $C_{1-6}$ alkyl which may be substituted with one or more substituents selected from the group consisting of halogen and pyrazolyl, iii) $C_{2-6}$ alkenyl, or iv) —OR⁰;

$R^2$ is i) $C_{1-6}$ alkyl which may be substituted with one or more substituents selected from the group consisting or —OR⁰, halogen, —COOR⁰, —CONR²¹R²², phenyl which may be substituted with one or more substituents selected from the $G^1$ group, and heteroaryl which is selected from the group consisting of pyridyl, pyrazolyl, imidazolyl, thiazolyl, thiadiazolyl, thienyl, oxazolyl, isoxazolyl, and triazolyl, wherein the heteroaryl may be substituted with one or more substituents selected from the $G^2$ group, ii) $C_{2-6}$ alkenyl, iii) $C_{2-6}$ alkynyl, iv) —OR⁰, v) —NR²³R²⁴, or vi) phenyl;

$R^{21}$ is H or $C_{1-6}$ alkyl;

$R^{22}$ is i) $C_{1-6}$ alkyl which may be substituted with one or more phenyl substituents, or ii) phenyl;

$R^{23}$ is i) H or ii) $C_{1-6}$ alkyl which may be substituted with one or more —OH substituents;

$R^{24}$ is i) $C_{1-6}$ alkyl which may be substituted with one or more phenyl substituents which may be substituted with one or more halogen substituents, ii) $C_{3-8}$ cycloalkyl which may be substituted with one or more $C_{1-6}$ alkyl substituents, iii) phenyl which may be substituted with one or more halogen substituents, or iv) tetrahydropyranyl;

$G^1$ group is i) halogen, ii) —COOR⁰, iii) —CONR⁰R⁰, iv) —OH, v) $C_{1-6}$ alkyl which may be substituted with one or more substituents selected from the group consisting of —OH and halogen, or vi) —O—($C_{1-6}$ alkyl which may be substituted with one or more substituents selected from the group consisting of —OH and halogen);

$G^2$ group is i) halogen, ii) $C_{1-6}$ alkyl which may be substituted with one or more substituents selected from the group consisting of —OH and halogen or iii) —CONR⁰R⁰; and each $R^0$ is independently H or $C_{1-6}$ alkyl.

Embodiment 3-1

The compound of the formula (I) or a salt thereof, in which
$R^3$ and $R^4$ are the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and heteroaryl(s) which is selected from the group consisting of pyrazolyl and thienyl, wherein the heteroaryl(s) may be substituted with one or more $C_{1-6}$ alkyl(s), or, $R^3$, $R^4$, and a carbon atom bounded by $R^3$ and $R^4$ may interact to form a 3-oxetane ring and the carbon atom bounded by $R^3$ and $R^4$ is a spiro atom.

Embodiment 3-2

The compound of the formula (I) or a salt thereof, in which
$R^3$ and $R^4$ are the same or different each other, i) $C_{1-3}$alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and pyrazolyl(s) which may be substituted with one or more $C_{1-6}$ alkyl(s), or, $R^3$, $R^4$, and a carbon atom bounded by $R^3$ and $R^4$ may interact to form a 3-oxetane ring and the carbon atom bounded by $R^3$ and $R^4$ is a spiro atom.

Embodiment 3-3

The compound of the formula (I) or a salt thereof, in which $R^3$ and $R^4$ are the same or different each other, $C_{1-3}$ alkyl.

Embodiment 3-4

The compound of the formula (I) or a salt thereof, in which $R^3$, $R^4$, and a carbon atom bounded by $R^3$ and $R^4$ may interact to form a 3-oxetane ring and the carbon atom bounded by $R^3$ and $R^4$ is a spiro atom as represented by formula (II) below;

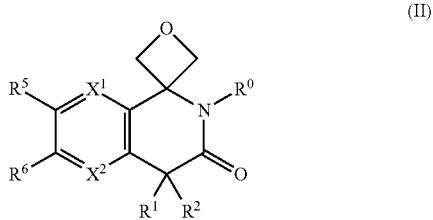

(II)

Embodiment 3-5

The compound of the formula (I) or a salt thereof, in which $R^3$ and $R^4$ are independently i) $C_{1-3}$ alkyl which may be substituted with one or more substituents selected from the group consisting of halogen and —OH, or
$R^3$ and $R^4$, together with the carbon to which they are attached, form a 3-oxetane ring.

Embodiment 4-1

The compound of the formula (I) or a salt thereof, in which
$R^5$ is i) H, ii) $C_{1-6}$ alkyl which may be substituted with one or more —O—$C_{1-6}$ alkyl(s), iii) —O—$C_{1-6}$ alkyl, iv) halogen, v) —COO—$C_{1-6}$ alkyl, or vi) $C_{3-8}$ cycloalkyl;
$R^6$ is i) H, ii) $C_{1-6}$ alkyl which may be substituted with one or more substituent(s) selected from the group consisting of —O—($C_{1-6}$ alkyl(s) which may be substituted with one or more halogen(s)) and halogen(s), iii) —OH, iv) —O—($C_{1-6}$ alkyl which may be substituted with one or more halogen(s)), v) halogen, vi) —CN, vii) —S—$C_{1-6}$ alkyl, viii) $C_{3-8}$ cycloalkyl, ix) —NR°R°, or x) $C_{2-6}$ alkenyl; and
$R^0$ is the same or different each other, H or $C_{1-6}$ alkyl.

Embodiment 4-2

The compound of the formula (I) or a salt thereof, in which
$R^5$ is i) H, ii) $C_{1-6}$ alkyl, iii) —O—$C_{1-6}$ alkyl, iv) halogen, or v) $C_{3-8}$ cycloalkyl;
$R^6$ is i) H, ii) $C_{1-6}$ alkyl which may be substituted with one or more substituent(s) selected from the group consisting of —O—($C_{1-6}$ alkyl)(s) and halogen(s), iii) —OH, iv) —O—($C_{1-6}$ alkyl which may be substituted with one or more halogen(s)), v) halogen, vi) —CN, vii) —S—$C_{1-6}$ alkyl, viii) —NR°R°, or ix) $C_{2-6}$ alkenyl; and
$R^0$ is the same or different each other, H or $C_{1-6}$ alkyl.

Embodiment 4-3

The compound of the formula (I) or a salt thereof, in which
$R^5$ is H; and
$R^6$ is i) $C_{1-6}$ alkyl, ii) —O—($C_{1-6}$ alkyl which is substituted with one to three halogen(s)), iii) halogen, or iv) —CN.

The invention includes the compounds which are a combination of two or more of the embodiments described in 1-1 to 4-3 above, which are not inconsistent with each other. The specific examples include the following embodiments.

Embodiment 5-1

The compound of the formula (I) or a salt thereof, in which
$X^1$ is C—$R^{11}$ or N;
$X^2$ is C—$R^{12}$ or N;
$R^{11}$ is H, ii) halogen, iii) —CN, or iv) —O—$C_{1-6}$ alkyl;
$R^{12}$ is H,
$R^1$ is i) H, or ii) $C_{1-6}$ alkyl;
$R^2$ is i) $C_{1-6}$ alkyl which may be substituted with one or more substituent(s) selected from the group consisting of —OR°(s), halogen(s), —CONR$^{21}$R$^{22}$(s), phenyl(s) which may be substituted with one or more substituent(s) selected from the group consisting of halogen(s) and —COOR°(s), and heteroaryl(s) which is selected from the group consisting of pyrazolyl, and triazolyl, ii) $C_{2-6}$ alkenyl, iii) $C_{2-6}$ alkynyl, iv) —NR$^{23}$R$^{24}$, or v) —COOR°;
$R^{21}$ is $C_{1-6}$ alkyl;
$R^{22}$ is $C_{1-6}$ alkyl;
$R^{23}$ is $C_{1-6}$ alkyl;
$R^{24}$ is i) $C_{3-8}$ cycloalkyl, or ii) phenyl; or
$R^1$, $R^2$, and a carbon atom bounded by $R^1$ and $R^2$ may interact to form a 4-tetrahydropyran ring, and the carbon atom bounded by $R^1$ and $R^2$ is a spiro atom;
$R^3$ and $R^4$ are the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and pyrazolyl(s) which may be substituted with one or more $C_{1-6}$ alkyl(s), or,
$R^3$, $R^4$, and a carbon atom bounded by $R^3$ and $R^4$ may interact to form a 3-oxetane ring and the carbon atom bounded by $R^3$ and $R^4$ is a Spiro atom;
$R^5$ is i) H, ii) $C_{1-6}$ alkyl, iii) —O—$C_{1-6}$ alkyl, iv) halogen, or v) $C_{3-8}$ cycloalkyl;
$R^6$ is i) H, ii) $C_{1-6}$ alkyl which may be substituted with one or more substituent(s) selected from the group consisting of —O—$C_{1-6}$ alkyl and halogen, iii) —OH, iv) —O—$C_{1-6}$ alkyl which may be substituted with one or more halogen(s)), v) halogen, vi) —CN, vii) —S—$C_{1-6}$ alkyl, viii) —NR°R°, or ix) $C_{2-6}$ alkenyl;
$R^0$ is the same or different each other, H or $C_{1-6}$ alkyl.

Embodiment 5-2

The compound or a salt thereof as described in embodiment 5-1 above, in which
$R^1$ is $C_{1-6}$ alkyl;
$R^2$ is $C_{1-6}$ alkyl which may be substituted with a —OR°;
$R^3$, $R^4$, and a carbon atom bounded by $R^3$ and $R^4$ interact to form a 3-oxetane ring and the carbon atom bounded by $R^3$ and $R^4$ is a Spiro atom as represented by formula (II) below;

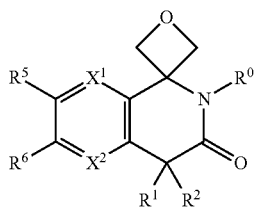

(II)

$R^5$ is H; and
$R^6$ is i) $C_{1-6}$ alkyl, ii) —O—$C_{1-6}$ alkyl which is substituted with one to three halogen(s), iii) halogen, or iv) —CN.

Embodiment 5-3

The compound or a salt thereof as described in embodiment 5-2 above, in which $X^1$ and $X^2$ are as described in Embodiment 1-3.

Embodiment 6-1

The compound of the formula (I) or a salt thereof, in which $R^1$ and $R^2$ are as described in Embodiment 2-1, and
$X^1$: C—$R^{11}$ or N;
$X^2$: C—$R^{12}$ or N;
$R^{11}$: i) H, ii) halogen, iii) —CN, or iv) —O—$C_{1-6}$ alkyl;
$R^{12}$: H or halogen;
$R^3$, $R^4$: the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and heteroaryl(s) which is selected from the group consisting of pyrazolyl, and thienyl wherein the heteroaryl may be substituted with one or more $C_{1-6}$ alkyl(s), or,
$R^3$, $R^4$, and a carbon atom bounded by $R^3$ and $R^4$ may interact to form a 3-oxetane ring and the carbon atom bounded by $R^3$ and $R^4$ is a Spiro atom;
$R^5$: i) H, ii) $C_{1-6}$ alkyl which may be substituted with one or more —O—($C_{1-6}$ alkyl)(s), iii) —O—($C_{1-6}$ alkyl), iv) halogen, v) —COO—($C_{1-6}$ alkyl), or vi) $C_{3-8}$ cycloalkyl;
$R^6$: i) H, ii) $C_{1-6}$ alkyl which may be substituted with one or more substituent(s) s elected from the group consisting of —O—($C_{1-6}$ alkyl(s) which may be substituted with one or more halogen(s)) and halogen(s), iii) —OH, iv) —O—$C_{1-6}$ alkyl which may be substituted with one or more halogen(s)), v) halogen, vi) —CN, vii) —S—($C_{1-6}$ alkyl), viii) $C_{3-8}$ cycloalkyl, ix) —NR$^0$R$^0$, or x) $C_{2-6}$ alkenyl;
$G^1$ group: i) halogen, ii) —COOR$^0$, iii) —CONR$^0$R$^0$, iv) —OH, v) $C_{1-6}$ alkyl which may be substituted with one or more substituent(s) selected from the group consisting of —OH(s) and halogen, or vi) —O—($C_{1-6}$ alkyl which may be substituted with one or more substituent(s) selected from the group consisting of —OH(s) and halogen(s));
$G^2$ group: i) halogen, ii) $C_{1-6}$ alkyl which may be substituted with one or more substituent(s) selected from the group consisting of —OH(s) and halogen(s) or iii) —CONR$^0$R$^0$.

Embodiment 6-2

The compound or a salt thereof as described in embodiment 6-1 above, in which $R^3$ and $R^4$ are as described in Embodiment 3-1.

Embodiment 6-3

The compound or a salt thereof as described in embodiment 6-2 above, in which $R^3$ and $R^4$ are as described in Embodiment 4-1.

Embodiment 7-1

A compound, or a salt thereof, which is selected from the group consisting of
(−)-2-(difluoromethyl)-8-ethyl-8-(2-hydroxyethyl)-6H-spiro[1,6-naphthyridine-5,3'-oxetan]-7(8H)-one,
4,4-diethyl-1,1-dimethyl-3-oxo-1,2,3,4-tetrahydroisoquinoline-6-carbonitrile,
8,8-diethyl-5,5-dimethyl-7-oxo-5,6,7,8-tetrahydro-1,6-naphthyridine-2-carbonitrile,
(−)-6-bromo-4-ethyl-4-(2-hydroxyethyl)-1,1-dimethyl-1,4-dihydroisoquinolin-3(2H)-one,
(+)-6-bromo-4-ethyl-4-(2-hydroxyethyl)-1,1-dimethyl-1,4-dihydroisoquinolin-3(2H)-one,
8,8-diethyl-7-oxo-7,8-dihydro-6H-spiro[1,6-naphthyridine-5,3'-oxetane]-2-carbonitrile,
8',8'-diethyl-7'-oxo-7',8'-dihydro-6'H-spiro[oxetane-3,5'-pyrido[3,4-b]pyrazine]-2'-carbonitrile,
4,4-di ethyl-3-oxo-3,4-dihydro-2H-spiro[isoquinoline-1,3'-oxetane]-6-carbonitrile,
6-chloro-4,4-dimethyl-2H-spiro[isoquinoline-1,3'-oxetan]-3(4H)-one,
4,4-dimethyl-3-oxo-3,4-dihydro-2H-spiro[isoquinoline-1,3'-oxetane]-6-carbonitrile,
2-(difluoromethoxy)-8,8-dimethyl-6H-spiro[1,6-naphthyridine-5,3'-oxetan]-7(8H)-one,
(+)-6-chloro-4-(2-hydroxyethyl)-4-methyl-2H-spiro[isoquinoline-1,3'-oxetan]-3 (4H)-one,
(−)-6-chloro-4-(2-hydroxyethyl)-4-methyl-2H-spiro[isoquinoline-1,3'-oxetan]-3(4H)-one, and
(−)-2-(difluoromethoxy)-8-ethyl-8-(2-hydroxyethyl)-6H-spiro[1,6-naphthyridine-5,3'-oxetan]-7(8H)-one.

Embodiment 7-2

A compound, or a salt thereof, which is selected from the group consisting of
(−)-2-(difluoromethyl)-8-ethyl-8-(2-hydroxyethyl)-6H-spiro[1,6-naphthyridine-5,3'-oxetan]-7(8H)-one,
4,4-diethyl-1,1-dimethyl-3-oxo-1,2,3,4-tetrahydroisoquinoline-6-carbonitrile,
8,8-diethyl-5,5-dimethyl-7-oxo-5,6,7,8-tetrahydro-1,6-naphthyridine-2-carbonitrile,
(−)-6-bromo-4-ethyl-4-(2-hydroxyethyl)-1,1-dimethyl-1,4-dihydroisoquinolin-3(2H)-one,
(+)-6-bromo-4-ethyl-4-(2-hydroxyethyl)-1,1-dimethyl-1,4-dihydroisoquinolin-3(2H)-one,
8,8-diethyl-7-oxo-7,8-dihydro-6H-spiro[1,6-naphthyridine-5,3'-oxetane]-2-carbonitrile,
8',8'-diethyl-7'-oxo-7',8'-dihydro-6'H-spiro[oxetane-3,5'-pyrido[3,4-b]pyrazine]-2'-carbonitrile,
4,4-diethyl-3-oxo-3,4-dihydro-2H-spiro[isoquinoline-1,3'-oxetane]-6-carbonitrile,
6-chloro-4,4-dimethyl-2H-spiro[isoquinoline-1,3'-oxetan]-3(4H)-one,
4,4-dimethyl-3-oxo-3,4-dihydro-2H-spiro[isoquinoline-1,3'-oxetane]-6-carbonitrile,
2-(difluoromethoxy)-8,8-dimethyl-6H-spiro[1,6-naphthyridine-5,3'-oxetan]-7(8H)-one,
(−)-6-chloro-4-(2-hydroxyethyl)-4-methyl-2H-spiro[isoquinoline-1,3'-oxetan]-3 (4H)-one, and (−)-2-(difluoromethoxy)-8-ethyl-8-(2-hydroxyethyl)-6H-spiro[1,6-naphthyridine-5,3'-oxetan]-7(8H)-one.

Embodiment 7-3

A compound, or a salt thereof, which is selected from the group consisting of
4,4-diethyl-3-oxo-3,4-dihydro-2H-spiro[isoquinoline-1,3'-oxetane]-6-carbonitrile,
6-chloro-4,4-dimethyl-2H-spiro[isoquinoline-1,3'-oxetan]-3(4H)-one,
4,4-dimethyl-3-oxo-3,4-dihydro-2H-spiro[isoquinoline-1,3'-oxetane]-6-carbonitrile,
(+)-6-chloro-4-(2-hydroxyethyl)-4-methyl-2H-spiro[isoquinoline-1,3'-oxetan]3(4H)-one, and
(−)-6-chloro-4-(2-hydroxyethyl)-4-methyl-2H-spiro[isoquinoline-1,3'-oxetan]-3(4H)-one.

Embodiment 7-4

A compound, or a salt thereof, which is
4,4-diethyl-3-oxo-3,4-dihydro-2H-spiro[isoquinoline-1,3'-oxetane]-6-carbonitrile.

Embodiment 7-5

A compound, or a salt thereof, which is
6-chloro-4,4-dimethyl-2H-spiro[isoquinoline-1,3'-oxetan]-3(4H)-one.

Embodiment 7-6

A compound, or a salt thereof, which is
4,4-dimethyl-3-oxo-3,4-dihydro-2H-spiro[isoquinoline-1,3'-oxetane]-6-carbonitrile.

Embodiment 7-7

A compound, or a salt thereof, which is
(+)-6-chloro-4-(2-hydroxyethyl)-4-methyl-2H-spiro[isoquinoline-1,3'-oxetan]-3(4H)-one.

Embodiment 7-8

A compound, or a salt thereof, which is
(−)-6-chloro-4-(2-hydroxyethyl)-4-methyl-2H-spiro[isoquinoline-1,3'-oxetan]-3(4H)-one.

One embodiment of the present invention includes, but are not limited to, the following Embodiment 8-1 to 8-4:

Embodiment 8-1

A crystalline form of 4,4-dimethyl-3-oxo-3,4-dihydro-2H-spiro[isoquinoline-1,3'-oxetane]-6-carbonitrile, having an X-ray powder diffraction spectrum, comprising at the following angles 2θ(°): 12.1, 15.6, 16.6, 21.4 and 23.4, measured with Cu-Kα irradiation (1.54184 Å).

Embodiment 8-2

A crystalline form of 4,4-dimethyl-3-oxo-3,4-dihydro-2H-spiro[isoquinoline-1,3'-oxetane]-6-carbonitrile, having an X-ray powder diffraction spectrum, comprising at the following angles 2θ(°): 8.3, 12.1, 15.6, 16.6, 17.3, 20.5, 21.4, 23.4, 24.0 and 25.7, measured with Cu-Kα irradiation (1.54184 Å).

Embodiment 8-3

A crystalline form of (−)-6-chloro-4-(2-hydroxyethyl)-4-methyl-2H-spiro[isoquinoline-1,3'-oxetan]-3(4H)-one, having an X-ray powder diffraction spectrum, comprising at the following angles 2θ(°): 12.2, 15.5, 18.3, 21.7 and 22.7, measured with Cu-Kα irradiation (1.54184 Å).

Embodiment 8-4

A crystalline form of (−)-6-chloro-4-(2-hydroxyethyl)-4-methyl-2H-spiro[isoquinoline-1,3'-oxetan]-3(4H)-one, having an X-ray powder diffraction spectrum, comprising at the following angles 2θ(°): 6.7, 11.1, 12.2, 13.7, 15.5, 16.2, 17.0, 18.3, 21.7 and 22.7, measured with Cu-Kα irradiation (1.54184 Å).

In a further embodiment of the present invention includes a pharmaceutical composition comprising a compound according to any one of Embodiment 1-1 to Embodiment 7-8 above, or a salt thereof and a pharmaceutically acceptable excipient. In a further embodiment of the present invention includes a pharmaceutical composition comprising a crystalline form according to any one of Embodiment 8-1 to Embodiment 8-4 above, and a pharmaceutically acceptable excipient.

In a further aspect, the present invention relates to a pharmaceutical composition for preventing or treating a disease or condition selected from the group consisting of stress urinary incontinence (SUI), mixed urinary incontinence (MUI) and fecal incontinence comprising a compound according to any one of Embodiment 1-1 to Embodiment 7-8 above, or a salt thereof. In a further aspect, the invention relates to a pharmaceutical composition for preventing or treating a disease or condition selected from the group consisting of frailty and sarcopenia comprising a compound according to any one of Embodiment 1-1 to Embodiment 7-8 above, or a salt thereof. In a further aspect, the invention relates to a pharmaceutical composition for preventing or treating chronic obstructive pulmonary disease (COPD) comprising a compound according to any one of Embodiment 1-1 to Embodiment 7-8 above, or a salt thereof. In a further aspect, the invention relates to a pharmaceutical composition for preventing or treating cachexia syndrome and/or muscle wasting caused by heart failure, cancer, or chronic kidney disease/dialysis comprising a compound according to any one of Embodiment 1-1 to Embodiment 7-8 above, or a salt thereof. In a further aspect, the invention relates to a pharmaceutical composition for preventing or treating a disease or condition selected from the group consisting of amyotrophic lateral sclerosis (ALS), spinal muscular atrophy (SMA), myasthenia gravis and muscular myopathies comprising a compound according to any one of Embodiment 1-1 to Embodiment 7-8 above, or a salt thereof. In a further aspect, the invention relates to a pharmaceutical composition for preventing or treating a disease or condition selected from the group consisting of post-spinal cord injury (SCI) muscle dysfunction and post-stroke muscle dysfunction comprising a compound according to any one of Embodiment 1-1 to Embodiment 7-8 above, or a salt thereof. In a further aspect, the invention relates to a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome comprising a compound according to any one of Embodiment 1-1 to Embodiment 7-8 above, or a salt thereof.

In a further aspect, the present invention relates to a pharmaceutical composition for preventing or treating a disease or condition selected from the group consisting of stress urinary incontinence (SUI), mixed urinary incontinence (MUI) and fecal incontinence comprising a crystalline form according to any one of Embodiment 8-1 to Embodiment 8-4 above. In a further aspect, the invention relates to a pharmaceutical composition for preventing or treating a disease or condition selected from the group consisting of frailty and sarcopenia comprising a crystalline form according to any one of Embodiment 8-1 to Embodiment 8-4 above. In a further aspect, the invention relates to a pharmaceutical composition for preventing or treating chronic obstructive pulmonary disease (COPD) comprising a crystalline form according to any one of Embodiment 8-1 to Embodiment 8-4 above. In a further aspect, the invention relates to a pharmaceutical composition for preventing or treating cachexia syndrome and/or muscle wasting caused by heart failure, cancer, or chronic kidney disease/dialysis comprising a crystalline form according to any one of Embodiment 8-1 to Embodiment 8-4 above. In a further aspect, the invention relates to a pharmaceutical composition for preventing or treating a disease or condition selected from the group consisting of amyotrophic lateral sclerosis (ALS), spinal muscular atrophy (SMA), myasthenia gravis and muscular myopathies comprising a crystalline form according to any one of Embodiment 8-1 to Embodiment 8-4 above. In a further aspect, the invention relates to a pharmaceutical composition for preventing or treating a disease or condition selected from the group consisting of post-spinal cord injury (SCI) muscle dysfunction and post-stroke muscle dysfunction comprising a crystalline form according to any one of Embodiment 8-1 to Embodiment 8-4 above. In a further aspect, the invention relates to a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome comprising a crystalline form according to any one of Embodiment 8-1 to Embodiment 8-4 above.

In a further aspect, the present invention relates to use of a compound according to any one of Embodiment 1-1 to Embodiment 7-8 above, or a salt thereof for the manufacture of a pharmaceutical composition for preventing or treating a disease or condition selected from the group consisting of stress urinary incontinence (SUI), mixed urinary incontinence (MUI) and fecal incontinence. In a further aspect, the invention relates to use of a compound according to any one of Embodiment 1-1 to Embodiment 7-8 above, or a salt thereof for the manufacture of a pharmaceutical composition for preventing or treating a disease or condition selected from the group consisting of frailty and sarcopenia. In a further aspect, the invention relates to use of a compound according to any one of Embodiment 1-1 to Embodiment 7-8 above, or a salt thereof for the manufacture of a pharmaceutical composition for preventing or treating chronic obstructive pulmonary disease (COPD). In a further aspect, the invention relates to a use of a compound according to any one of Embodiment 1-1 to Embodiment 7-8 above, or a salt thereof for the manufacture of a pharmaceutical composition for preventing or treating cachexia syndrome and/or muscle wasting caused by heart failure, cancer, or chronic kidney disease/dialysis. In a further aspect, the invention relates to use of a compound according to any one of Embodiment 1-1 to Embodiment 7-8 above, or a salt thereof for the manufacture of a pharmaceutical composition for preventing or treating a disease or condition selected from the group consisting of amyotrophic lateral sclerosis (ALS), spinal muscular atrophy (SMA) and myasthenia gravis, muscular myopathies. In a further aspect, the invention relates to use of a compound according to any one of Embodiment 1-1 to Embodiment 7-8 above, or a salt thereof for the manufacture of a pharmaceutical composition for preventing or treating a disease or condition selected from the group consisting of post-spinal cord injury (SCI) muscle dysfunction and post-stroke muscle dysfunction. In a further aspect, the invention relates to use of a compound according to any one of Embodiment 1-1 to Embodiment 7-8 above, or a salt thereof for the manufacture of a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to use of a crystalline form according to any one of Embodiment 8-1 to Embodiment 8-4 above for the manufacture of a pharmaceutical composition for preventing or treating a disease or condition selected from the group consisting of stress urinary incontinence (SUI), mixed urinary incontinence (MUI) and fecal incontinence. In a further aspect, the invention relates to use of a crystalline form according to any one of Embodiment 8-1 to Embodiment 8-4 above for the manufacture of a pharmaceutical composition for preventing or treating a disease or condition selected from the group consisting of frailty and sarcopenia. In a further aspect, the invention relates to use of a crystalline form according to any one of Embodiment 8-1 to Embodiment 8-4 above for the manufacture of a pharmaceutical composition for preventing or treating chronic obstructive pulmonary disease (COPD). In a further aspect, the invention relates to a use of a crystalline form according to any one of Embodiment 8-1 to Embodiment 8-4 above for the manufacture of a pharmaceutical composition for preventing or treating cachexia syndrome and/or muscle wasting caused by heart failure, cancer, or chronic kidney disease/dialysis. In a further aspect, the invention relates to use of a crystalline form according to any one of Embodiment 8-1 to Embodiment 8-4 above for the manufacture of a pharmaceutical composition for preventing or treating a disease or condition selected from the group consisting of amyotrophic lateral sclerosis (ALS), spinal muscular atrophy (SMA) and myasthenia gravis, muscular myopathies. In a further aspect, the invention relates to use of a crystalline form according to any one of Embodiment 8-1 to Embodiment 8-4 above for the manufacture of a pharmaceutical composition for preventing or treating a disease or condition selected from the group consisting of post-spinal cord injury (SCI) muscle dysfunction and post-stroke muscle dysfunction. In a further aspect, the invention relates to use of a crystalline form according to any one of Embodiment 8-1 to Embodiment 8-4 above for the manufacture of a pharmaceutical composition for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to use of a compound according to any one of Embodiment 1-1 to Embodiment 7-8 above, or a salt thereof for preventing or treating a disease or condition selected from the group consisting of stress urinary incontinence (SUI), mixed urinary incontinence (MUI) and fecal incontinence. In a further aspect, the invention relates to use of a compound according to any one of Embodiment 1-1 to Embodiment 7-8 above, or a salt thereof for preventing or treating a disease or condition selected from the group consisting of frailty and sarcopenia. In a further aspect, the invention relates to use of a compound according to any one of Embodiment 1-1 to Embodiment 7-8 above, or a salt thereof for preventing or treating chronic obstructive pulmonary disease (COPD). In a further aspect, the invention relates to use of a compound according to any one of Embodiment 1-1 to Embodiment 7-8 above, or a salt thereof for preventing or treating cachexia syndrome and/or muscle wasting caused by heart failure, cancer, or chronic kidney disease/dialysis. In a further aspect, the invention relates to use of a compound according to any one of Embodiment 1-1 to Embodiment 7-8 above, or a salt thereof for preventing or treating a disease or condition selected from the group consisting of amyotrophic lateral sclerosis (ALS), spinal muscular atrophy (SMA), myasthenia gravis and muscular myopathies. In a further aspect, the invention relates to use of a compound according to any one of Embodiment 1-1 to Embodiment 7-8 above, or a salt thereof for preventing or treating a disease or condition selected from the group consisting of post-spinal cord injury (SCI) muscle dysfunction and post-stroke muscle dysfunction. In a further aspect, the invention relates to use of a compound according to any one of Embodiment 1-1 to Embodiment 7-8 above, or a salt thereof for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to use of a crystalline form according to any one of Embodiment 8-1 to Embodiment 8-4 above for preventing or treating a disease or condition selected from the group consisting of stress urinary incontinence (SUI), mixed urinary incontinence (MUI) and fecal incontinence. In a further aspect, the invention relates to use of a crystalline form according to any one of Embodiment 8-1 to Embodiment 8-4 above for preventing or treating a disease or condition selected from the group consisting of frailty and sarcopenia. In a further aspect, the invention relates to use of a crystalline form according to any one of Embodiment 8-1 to Embodiment 8-4 above for preventing or treating chronic obstructive pulmonary disease (COPD). In a further aspect, the invention relates to use of a crystalline form according to any one of Embodiment 8-1 to Embodiment 8-4 above for preventing or treating cachexia syndrome and/or muscle wasting caused by heart failure, cancer, or chronic kidney disease/dialysis. In a further aspect, the invention relates to use of a crystalline form according to any one of Embodiment 8-1 to Embodiment 8-4 above for preventing or treating a disease or condition selected from the group consisting of amyotrophic lateral sclerosis (ALS), spinal muscular atrophy (SMA), myasthenia gravis and muscular myopathies. In a further aspect, the invention relates to use of a crystalline form according to any one of Embodiment 8-1 to Embodiment 8-4 above for preventing or treating a disease or condition selected from the group consisting of post-spinal cord injury (SCI) muscle dysfunction and post-stroke muscle dysfunction. In a further aspect, the invention relates to use of a crystalline form according to any one of Embodiment 8-1 to Embodiment 8-4 above for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to a method for preventing or treating a disease or condition selected from the group consisting of stress urinary incontinence (SUI), mixed urinary incontinence (MUI) and fecal incontinence, comprising administering to a subject an effective amount of the compound according to any one of Embodiment 1-1 to Embodiment 7-8 above, or a salt thereof. In a further aspect, the invention relates to a method for preventing or treating a disease or condition selected from the group consisting of frailty and sarcopenia, comprising administering to a subject an effective amount of the compound according to any one of Embodiment 1-1 to Embodiment 7-8 above, or a salt thereof. In a further aspect, the invention relates to a method for preventing or treating chronic obstructive pulmonary disease (COPD), comprising administering to a subject an effective amount of the compound according to any one of Embodiment 1-1 to Embodiment 7-8 above, or a salt thereof. In a further aspect, the invention relates to a method for preventing or treating cachexia syndrome and/or muscle wasting caused by heart failure, cancer, or chronic kidney disease/dialysis, comprising administering to a subject an effective amount of the compound of the formula (I), or a salt thereof. In a further aspect, the invention relates to a method for preventing or treating a disease or condition selected from the group consisting of amyotrophic lateral sclerosis (ALS), spinal muscular atrophy (SMA), myasthenia gravis and muscular myopathies, comprising administering to a subject an effective amount of the compound according to any one of Embodiment 1-1 to Embodiment 7-8 above, or a salt thereof. In a further aspect, the invention relates to a method for preventing or treating a disease or condition selected from the group consisting of post-spinal cord injury (SCI) muscle dysfunction and post-stroke muscle dysfunction, comprising administering to a subject an effective amount of the compound according to any one of Embodiment 1-1 to Embodiment 7-8 above, or a salt thereof. In a further aspect, the invention relates to a method for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome, comprising administering to a subject an effective amount of the compound according to any one of Embodiment 1-1 to Embodiment 7-8 above, or a salt thereof.

In a further aspect, the present invention relates to a method for preventing or treating a disease or condition selected from the group consisting of stress urinary incontinence (SUI), mixed urinary incontinence (MUI) and fecal incontinence, comprising administering to a subject an effective amount of the crystalline form according to any one of Embodiment 8-1 to Embodiment 8-4 above. In a further aspect, the invention relates to a method for preventing or treating a disease or condition selected from the group consisting of frailty and sarcopenia, comprising administering to a subject an effective amount of the crystalline form according to any one of Embodiment 8-1 to Embodiment 8-4 above. In a further aspect, the invention relates to a method for preventing or treating chronic obstructive pulmonary disease (COPD), comprising administering to a subject an effective amount of the crystalline form according to any one of Embodiment 8-1 to Embodiment 8-4 above. In a further aspect, the invention relates to a method for preventing or treating cachexia syndrome and/or muscle wasting caused by heart failure, cancer, or chronic kidney disease/dialysis, comprising administering to a subject an effective amount of the crystalline form according to any one of Embodiment 8-1 to Embodiment 8-4 above. In a further aspect, the invention relates to a method for preventing or treating a disease or condition selected from the group consisting of amyotrophic lateral sclerosis (ALS), spinal muscular atrophy (SMA), myasthenia gravis and muscular myopathies, comprising administering to a subject an effective amount of the crystalline form according to any one of Embodiment 8-1 to Embodiment 8-4 above. In a further aspect, the invention relates to a method for preventing or treating a disease or condition selected from the group consisting of post-spinal cord injury (SCI) muscle dysfunction and post-stroke muscle dysfunction, comprising administering to a subject an effective amount of the crystalline form according to any one of Embodiment 8-1 to Embodiment 8-4 above. In a further aspect, the invention relates to a method for preventing or treating a disease or condition selected from the group consisting of peripheral vascular disease, peripheral arterial disease, rehabilitation-related deficits, metabolic syndrome, obesity, ventilator-induced muscle weakness and chronic fatigue syndrome, comprising administering to a subject an effective amount of the crystalline form according to any one of Embodiment 8-1 to Embodiment 8-4 above.

In a further aspect, the present invention relates to a compound according to any one of Embodiment 1-1 to Embodiment 7-8 above, or a salt thereof, for use in the prevention or treatment of a disease or condition selected from the group consisting of stress urinary incontinence (SUI), mixed urinary incontinence (MUI) and fecal incontinence. In a further aspect, the invention relates to a compound according to any one of Embodiment 1-1 to Embodiment 7-8 above, or a salt thereof, for use in the prevention or treatment of a disease or condition selected from the group consisting of frailty and sarcopenia. In a further aspect, the invention relates to a compound according to any one of Embodiment 1-1 to Embodiment 7-8 above, or a salt thereof, for use in the prevention or treatment of chronic obstructive pulmonary disease (COPD). In a further aspect, the invention relates to a compound according to any one of Embodiment 1-1 to Embodiment 7-8 above, or a salt thereof, for use in the prevention or treatment of cachexia syndrome and/or muscle wasting caused by heart failure, cancer, or chronic kidney disease/dialysis. In a further aspect, the invention relates to a compound according to any one of Embodiment 1-1 to Embodiment 7-8 above, or a salt thereof, for use in the prevention or treatment of a disease or condition selected from the group consisting of amyotrophic lateral sclerosis (ALS), spinal muscular atrophy (SMA), myasthenia gravis and muscular myopathies. In a further aspect, the invention relates to a compound according to any one of Embodiment 1-1 to Embodiment 7-8 above, or a salt thereof, for use in the prevention or treatment of a disease or condition selected from the group consisting of post-spinal cord injury (SCI) muscle dysfunction and post-stroke muscle dysfunction. In a further aspect, the invention relates to a compound according to any one of Embodiment 1-1 to Embodiment 7-8 above, or a salt thereof, for use in the prevention or treatment of a disease or condition selected from the group consisting of peripheral vascular disease, peripheral arterial disease, rehabilitation-related deficits, metabolic syndrome, obesity, ventilator-induced muscle weakness and chronic fatigue syndrome.

In a further aspect, the present invention relates to a crystalline form according to any one of Embodiment 8-1 to Embodiment 8-4 above, for use in the prevention or treatment of a disease or condition selected from the group consisting of stress urinary incontinence (SUI), mixed urinary incontinence (MUI) and fecal incontinence. In a further aspect, the invention relates to a crystalline form according to any one of Embodiment 8-1 to Embodiment 8-4 above, for use in the prevention or treatment of a disease or condition selected from the group consisting of frailty and sarcopenia. In a further aspect, the invention relates to a crystalline form according to any one of Embodiment 8-1 to Embodiment 8-4 above, for use in the prevention or treatment of chronic obstructive pulmonary disease (COPD). In a further aspect, the invention relates to a crystalline form according to any one of Embodiment 8-1 to Embodiment 8-4 above, for use in the prevention or treatment of cachexia syndrome and/or muscle wasting caused by heart failure, cancer, or chronic kidney disease/dialysis. In a further aspect, the invention relates to a crystalline form according to any one of Embodiment 8-1 to Embodiment 8-4 above, for use in the prevention or treatment of a disease or condition selected from the group consisting of amyotrophic lateral sclerosis (ALS), spinal muscular atrophy (SMA), myasthenia gravis and muscular myopathies. In a further aspect, the invention relates to a crystalline form according to any one of Embodiment 8-1 to Embodiment 8-4 above, for use in the prevention or treatment of a disease or condition selected from the group consisting of post-spinal cord injury (SCI) muscle dysfunction and post-stroke muscle dysfunction. In a further aspect, the invention relates to a crystalline form according to any one of Embodiment 8-1 to Embodiment 8-4 above, for use in the prevention or treatment of a disease or condition selected from the group consisting of peripheral vascular disease, peripheral arterial disease, rehabilitation-related deficits, metabolic syndrome, obesity, ventilator-induced muscle weakness and chronic fatigue syndrome.

Moreover, one embodiment of the present invention is described below.

Embodiment (1) A compound of the formula (I') or a salt thereof

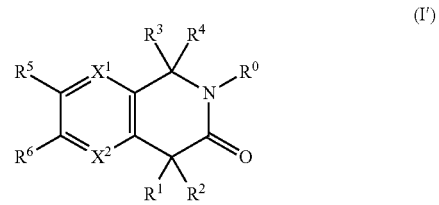

wherein, $X^1$: C—$R^{11}$ or N;

$X^2$: C—$R^{12}$ or N;

$R^{11}$: i) H, ii) halogen, iii) —CN, or iv) —O—$C_{1-6}$ alkyl;

$R^{12}$: H or halogen;

$R^1$: is i) H, ii) $C_{1-6}$ alkyl optionally substituted with one or more substituents independently selected from the group consisting of halogen and pyrazolyl, iii) $C_{2-6}$ alkenyl, or iv) —$OR^0$;

$R^2$ is i) $C_{1-6}$ alkyl optionally substituted with one or more substituents independently selected from the group consisting or —$OR^0$, halogen, —$COOR^0$, —$CONR^{21}R^{22}$, phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from $G^2$, ii) $C_{2-6}$ alkenyl, iii) $C_{2-6}$ alkynyl, iv) —$OR^O$, v) —$NR^{23}R^{24}$, vi) —$COOR^O$, or vii) phenyl;

each $R^{21}$ is independently H or $C_{1-6}$ alkyl;

each $R^{22}$ is independently i) $C_{1-6}$ alkyl optionally substituted with one or more phenyl substituents, or ii) phenyl;

$R^{23}$ is i) H or ii) $C_{1-6}$ alkyl optionally substituted with one or more —OH substituents;

$R^{24}$ is i) $C_{1-6}$ alkyl optionally substituted with one or more phenyl substituents, wherein the phenyl substituents are independently optionally substituted with one or more halogen substituents, ii) $C_{3-8}$ cycloalkyl optionally substituted with one or more $C_{1-6}$ alkyl substituents, iii) phenyl optionally substituted with one or more halogen substituents, or iv) tetrahydropyranyl; or $R^1$ and $R^2$, together with the carbon to which they are attached, form a 4-piperidine ring or 4-tetrahydropyran ring, wherein the 4-piperidine ring is optionally substituted with one or more substituents selected from the group consisting of —$SO_2$—($C_{1-6}$ alkyl) and —$COOR^O$;

$R^3$ and $R^4$ are independently i) $C_{1-3}$ alkyl optionally substituted with one or more substituents independently selected from the group consisting of halogen and —OH, or ii) $C_{2-6}$ alkenyl optionally substituted with one or more substituents independently selected from the group consisting of —OH and heteroaryl, wherein each heteroaryl is independently selected from the group consisting of pyrazolyl and thienyl, and wherein each heteroaryl is independently optionally substituted with one or more $C_{1-6}$ alkyl substituents; or $R^3$ and $R^4$, together with the carbon to which they are attached, form a 3-oxetane ring;

$R^5$ is i) H, ii) $C_{1-6}$ alkyl optionally substituted with one or more —O—($C_{1-6}$ alkyl) substituents, iii) —O—($C_{1-6}$ alkyl), iv) halogen, v) —COO—($C_{1-6}$ alkyl), or vi) $C_{3-8}$ cycloalkyl;

$R^6$ is i) H, ii) $C_{1-6}$ alkyl optionally substituted with one or more substituents independently selected from the group consisting of —O—($C_{1-6}$ alkyl optionally substituted with one or more halogen substituents) and halogen, iii) —OH, iv) —O—($C_{1-6}$ alkyl optionally substituted with one or more halogen substituents), v) halogen, vi) —CN, vii) —S—($C_{1-6}$ alkyl), viii) $C_{3-8}$ cycloalkyl, ix) —$NR^OR^O$, or x) $C_{2-6}$ alkenyl;

each $G^1$ is independently i) halogen, ii) —$COOR^O$, iii) —$CONR^OR^O$, iv) —OH, v) $C_{1-6}$ alkyl optionally substituted with one or more substituents selected from the group consisting of —OH and halogen, or vi) —O—($C_{1-6}$ alkyl optionally substituted with one or more substituents selected from the group consisting of —OH and halogen);

each $G^2$ is independently i) halogen, ii) $C_{1-6}$ alkyl optionally substituted with one or more substituents selected from the group consisting of —OH and halogen or iii) —$CONR^OR^O$; and each $R^O$ is independently H or $C_{1-6}$ alkyl, provided that said compound is not methyl 1,1-diallyl-3-oxo-2,4-dihydroisoquinoline-4-carboxylate or a salt thereof.

Embodiment (2) The compound of embodiment (1), or a salt thereof, wherein $X^1$ is C—$R^{11}$.

Embodiment (3) The compound of embodiment (1) or (2), or a salt thereof, wherein $R^{11}$ is H.

Embodiment (4) The compound of embodiment (1), or a salt thereof, wherein $X^1$ is N.

Embodiment (5) The compound of any one of embodiments (1)-(4), or a salt thereof, wherein $X^2$ is C—$R^{12}$.

Embodiment (6) The compound of embodiment (5), or a salt thereof, wherein $R^{12}$ is H.

Embodiment (7) The compound of any one of embodiments (1)-(4), or a salt thereof, wherein $X^2$ is N.

Embodiment (8) The compound of any one of embodiments (1)-(7), or a salt thereof, wherein $R^1$ is i) H or ii) $C_{1-6}$ alkyl optionally substituted with one or more halogen substituents.

Embodiment (9) The compound of any one of embodiments (1)-(7), or a salt thereof, wherein $R^1$ is $C_{1-6}$ alkyl.

Embodiment (10) The compound of any one of embodiments (1)-(9), or a salt thereof, wherein $R^2$ is i) $C_{1-6}$ alkyl optionally substituted with one or more substituents independently selected from the group consisting or —$OR^O$, halogen, —$COOR^O$, —$CONR^{21}R^{22}$, phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from $G^2$, ii) $C_{2-6}$ alkenyl, iii) $C_{2-6}$ alkynyl, iv) —$OR^O$, v) —$NR^{23}R^{24}$, or vi) phenyl;

each $R^{21}$ is independently H or $C_{1-6}$ alkyl;

each $R^{22}$ is independently i) $C_{1-6}$ alkyl optionally substituted with one or more phenyl substituents, or ii) phenyl;

$R^{23}$ is i) H or ii) $C_{1-6}$ alkyl optionally substituted with one or more —OH substituents;

$R^{24}$ is i) $C_{1-6}$ alkyl optionally substituted with one or more phenyl substituents, wherein the phenyl substituents are independently optionally substituted with one or more halogen substituents, ii) $C_{3-8}$ cycloalkyl optionally substituted with one or more $C_{1-6}$ alkyl substituents, iii) phenyl optionally substituted with one or more halogen substituents, or iv) tetrahydropyranyl;

each $G^1$ is independently i) halogen, ii) —$COOR^O$, iii) —$CONR^OR^O$, iv) —OH, v) $C_{1-6}$ alkyl optionally substituted with one or more substituents selected from the group consisting of —OH and halogen, or vi) —O—($C_{1-6}$ alkyl optionally substituted with one or more substituents selected from the group consisting of —OH and halogen);

each $G^2$ is independently i) halogen, ii) $C_{1-6}$ alkyl optionally substituted with one or more substituents selected from the group consisting of —OH and halogen or iii) —$CONR^OR^O$; and each $R^O$ is independently H or $C_{1-6}$ alkyl.

Embodiment (11) The compound of any one of embodiments (1)-(9), or a salt thereof, wherein $R^2$ is $C_{1-6}$ alkyl optionally substituted with one or more substituents independently selected from the group consisting or —$OR^O$, halogen, —$COOR^O$, —$CONR^{21}R^{22}$, phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from $G^2$;

each $R^{21}$ is independently $C_{1-6}$ alkyl;

each $R^{22}$ is independently $C_{1-6}$ alkyl optionally substituted with one or more phenyl substituents;

each $G^1$ is independently i) halogen or ii) —$COOR^O$;

each $G^2$ is independently $C_{1-6}$ alkyl; and each $R^O$ is independently H or $C_{1-6}$ alkyl.

Embodiment (12) The compound of any one of embodiments (1)-(9), or a salt thereof, wherein $R^2$ is $C_{1-6}$ alkyl optionally substituted with one or more substituents independently selected from the group consisting or —OR⁰, halogen, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from $G^2$;

each $G^2$ is independently $C_{1-6}$ alkyl; and each $R^O$ is independently H or $C_{1-6}$ alkyl.

Embodiment (13) The compound of any one of embodiments (10)-(12), or a salt thereof, wherein each heteroaryl is independently selected from the group consisting of pyrazolyl and triazolyl.

Embodiment (14) The compound of any one of embodiments (1)-(9), or a salt thereof, wherein $R^2$ is $C_{1-6}$ alkyl optionally substituted with one or more —OR⁰ substituents; and each $R^O$ is independently H or $C_{1-6}$ alkyl.

Embodiment (15) The compound of any one of embodiments (1)-(9), or a salt thereof, wherein $R^2$ is $C_{1-6}$ alkyl.

Embodiment (16) The compound of any one of embodiments (1)-(9), or a salt thereof, wherein $R^2$ is i) $C_{2-6}$ alkenyl, ii) $C_{2-6}$ alkynyl, iii) —NR²³R²⁴, iv) —COOR⁰, or v) phenyl; $R^{23}$ is $C_{1-6}$ alkyl; $R^{24}$ is $C_{1-6}$ alkyl, $C_{3-8}$ cycloalkyl, or phenyl; and each $R^O$ is independently H or $C_{1-6}$ alkyl.

Embodiment (17) The compound of any one of embodiments (1)-(7), or a salt thereof, wherein $R^1$ and $R^2$ are each methyl.

Embodiment (18) The compound of any one of embodiments (1)-(7), or a salt thereof, wherein $R^1$ is methyl, $R^2$ is $C_{1-6}$ alkyl optionally substituted with one or more —OR⁰ substituents, and each $R^O$ is independently H or $C_{1-6}$ alkyl.

Embodiment (19) The compound of any one of embodiments (1)-(7), or a salt thereof, wherein $R^1$ and $R^2$, together with the carbon to which they are attached, form a 4-piperidine ring or 4-tetrahydropyran ring, wherein the 4-piperidine ring is optionally substituted with one or more substituents selected from the group consisting of —SO₂—($C_{1-6}$ alkyl) and —COOR⁰.

Embodiment (20) The compound of any one of embodiments (1)-(19), or a salt thereof, wherein $R^3$ and $R^4$ are independently i) $C_{1-3}$ alkyl optionally substituted with one or more substituents independently selected from the group consisting of halogen and —OH; or $R^3$ and $R^4$, together with the carbon to which they are attached, form a 3-oxetane ring.

Embodiment (21) The compound of any one of embodiments (1)-(19), or a salt thereof, wherein $R^3$ and $R^4$ are independently i) $C_{1-3}$ alkyl optionally substituted with one or more substituents independently selected from the group consisting of halogen and —OH, or ii) $C_{2-6}$ alkenyl optionally substituted with one or more heteroaryl substituents, wherein each heteroaryl is independently selected from the group consisting of pyrazolyl and thienyl, and wherein each heteroaryl is independently optionally substituted with one or more $C_{1-6}$ alkyl substituents.

Embodiment (22) The compound of any one of embodiments (1)-(19), or a salt thereof, wherein $R^3$ and $R^4$ are independently $C_{1-3}$ alkyl optionally substituted with one or more substituents independently selected from the group consisting of halogen and —OH.

Embodiment (23) The compound of any one of embodiments (1)-(19), or a salt thereof, wherein $R^3$ and $R^4$, together with the carbon to which they are attached, form a 3-oxetane ring.

Embodiment (24) The compound of any one of embodiments (1)-(23), or a salt thereof, wherein $R^5$ is i) H, ii) $C_{1-6}$ alkyl, iii) —O—($C_{1-6}$ alkyl), iv) halogen, or v) $C_{3-8}$ cycloalkyl.

Embodiment (25) The compound of any one of embodiments (1)-(23), or a salt thereof, wherein $R^5$ is H.

Embodiment (26) The compound of any one of embodiments (1)-(25), or a salt thereof, wherein $R^6$ is i) H, ii) $C_{1-6}$ alkyl optionally substituted with one or more substituents independently selected from the group consisting of —O—($C_{1-6}$ alkyl optionally substituted with one or more halogen substituents) and halogen, iii) —O—($C_{1-6}$ alkyl optionally substituted with one or more halogen substituents), iv) halogen, v) —CN, vi) —S—($C_{1-6}$ alkyl), or vii) $C_{3-8}$ cycloalkyl.

Embodiment (27) The compound of any one of embodiments (1)-(25), or a salt thereof, wherein $R^6$ is i) H, ii) $C_{1-6}$ alkyl optionally substituted with one or more halogen substituents, iii) —OH, iv) —O—($C_{1-6}$ alkyl optionally substituted with one or more halogen substituents), v) halogen, vi) —CN, or vii) $C_{2-6}$ alkenyl.

Embodiment (28) The compound of any one of embodiments (1)-(25), or a salt thereof, wherein $R^6$ is i) H, ii) $C_{1-6}$ alkyl, iii) —O—($C_{1-6}$ alkyl optionally substituted with one or more halogen substituents), iv) halogen, v) —CN, vi) —NR⁰R⁰, or vii) $C_{2-6}$ alkenyl.

Embodiment (29) The compound of any one of embodiments (1)-(25), or a salt thereof, wherein $R^6$ is i) halogen or ii) —CN.

Embodiment (30) The compound of any one of embodiments (1)-(29), or a salt thereof, wherein each $R^O$ is H.

Embodiment (31) The compound of any one of embodiments (1)-(29), or a salt thereof, wherein each $R^O$ is independently $C_{1-6}$ alkyl.

Embodiment (32) The compound of any one of embodiments (1)-(7), or a salt thereof, wherein $R^1$ is i) H or ii) $C_{1-6}$ alkyl optionally substituted with one or more halogen substituents;

$R^2$ is i) $C_{1-6}$ alkyl optionally substituted with one or more substituents independently selected from the group consisting or —OR⁰, halogen, —COOR⁰, —CONR²¹R²², phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from $G^2$, ii) $C_{2-6}$ alkenyl, iii) $C_{2-6}$ alkynyl, iv) —NR²³R²⁴, v) —COOR⁰, or vi) phenyl;

each $R^{21}$, $R^{22}$, and $R^{23}$ is independently is $C_{1-6}$ alkyl;

$R^{24}$ is i) $C_{1-6}$ alkyl, ii) $C_{3-8}$ cycloalkyl, or iii) phenyl; or $R^1$ and $R^2$, together with the carbon to which they are attached, form a 4-piperidine ring or 4-tetrahydropyran ring, wherein the 4-piperidine ring is optionally substituted with one or more substituents selected from the group consisting of —SO₂—($C_{1-6}$ alkyl) and —COOR⁰;

$R^3$, $R^4$ are independently i) $C_{1-3}$ alkyl optionally substituted with one or more substituents independently selected from the group consisting of halogen and —OH, or ii) $C_{2-6}$ alkenyl optionally substituted with one or more heteroaryl substituents, wherein each heteroaryl is independently selected from the group consisting of pyrazolyl and thienyl, and wherein each heteroaryl is independently optionally substituted with one or more $C_{1-6}$ alkyl substituents, or $R^3$ and $R^4$, together with the carbon to which they are attached, form a 3-oxetane ring $R^5$ is i) H, ii) $C_{1-6}$ alkyl, iii) —O—($C_{1-6}$ alkyl), iv) halogen, or v) $C_{3-8}$ cycloalkyl;

$R^6$ is i) H, ii) $C_{1-6}$ alkyl optionally substituted with one or more substituents independently selected from the group consisting of —O—($C_{1-6}$ alkyl optionally substituted with one or more halogen substituents) and halogen, iii) —OH, iv) —O—($C_{1-6}$ alkyl optionally substituted with one or more halogen substituents), v) halogen, vi) —CN, vii) —S—($C_{1-6}$ alkyl), viii) $C_{3-8}$ cycloalkyl, ix) —NR$^O$R$^O$, or x) $C_{2-6}$ alkenyl;

each $G^1$ is independently i) halogen or ii) —COOR$^O$;

each $G^2$ is independently ii) $C_{1-6}$ alkyl; and each $R^O$ is independently H or $C_{1-6}$ alkyl.

Embodiment (33) The compound of embodiment (1), or a salt thereof, wherein $X^1$ is C—$R^{11}$;

$X^2$ is C—$R^{12}$;

$R^{11}$ is i) H, ii) halogen, iii) —CN, or iv) —O—$C_{1-6}$ alkyl;

$R^{12}$ is H or halogen;

$R^1$ is i) H or ii) $C_{1-6}$ alkyl optionally substituted with one or more halogen substituents;

$R^2$ is i) $C_{1-6}$ alkyl optionally substituted with one or more substituents independently selected from the group consisting or —OR$^O$, halogen, —COOR$^O$, —CONR$^{21}$R$^{22}$, phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, ii) —NR$^{23}$R$^{24}$, or iii) phenyl;

each $R^{21}$ is independently $C_{1-6}$ alkyl;

each $R^{22}$ is independently $C_{1-6}$ alkyl optionally substituted with one or more phenyl substituents;

$R^{23}$ is $C_{1-6}$ alkyl;

$R^{24}$ is i) $C_{1-6}$ alkyl, ii) $C_{3-8}$ cycloalkyl, or iii) phenyl; or $R^1$ and $R^2$, together with the carbon to which they are attached, form a 4-piperidine ring or 4-tetrahydropyran ring, wherein the 4-piperidine ring is optionally substituted with one or more substituents selected from the group consisting of —SO$_2$—($C_{1-6}$ alkyl) and —COOR$^O$;

$R^3$ and $R^4$ are independently $C_{1-3}$ alkyl optionally substituted with one or more halogen substituents, or $R^3$ and $R^4$, together with the carbon to which they are attached, formula 3-oxetane ring;

$R^5$ is i) H, ii) $C_{1-6}$ alkyl, iii) —O—($C_{1-6}$ alkyl), iv) halogen, or v) $C_{3-8}$ cycloalkyl;

$R^6$ is i) H, ii) $C_{1-6}$ alkyl optionally substituted with one or more halogen substituents, iii) —OH, iv) —O—($C_{1-6}$ alkyl optionally substituted with one or more halogen substituents), iv) halogen, v) —CN, or v) $C_{2-6}$ alkenyl;

each $G^1$ is independently i) halogen or ii) —COOR$^O$; and each $R^O$ is independently H or $C_{1-6}$ alkyl.

Embodiment (34) The compound of embodiment (1), or a salt thereof, wherein $X^1$ is C—$R^{11}$ or N;

$X^2$ is C—$R^{12}$ or N;

$R^{11}$ is i) H, ii) halogen, iii) —CN, or iv) —O—$C_{1-6}$ alkyl;

$R^{12}$ is H;

$R^1$ is i) H, or ii) $C_{1-6}$ alkyl;

$R^2$ is i) $C_{1-6}$ alkyl optionally substituted with one or more substituents independently selected from the group consisting or —OR$^O$, halogen, —CONR$^{21}$R$^{22}$, phenyl optionally substituted with one or more substituent independently selected from the group consisting of halogen and —COOR$^O$, and heteroaryl, wherein each heteroaryl is independently selected from the group consisting of pyrazolyl and triazolyl, ii) $C_{2-6}$ alkenyl, iii) $C_{2-6}$ alkynyl, iv) —NR$^{23}$R$^{24}$, or v) —COOR$^O$;

$R^{21}$ is $C_{1-6}$ alkyl;

$R^{22}$ is $C_{1-6}$ alkyl;

$R^{23}$ is $C_{1-6}$ alkyl;

$R^{24}$ is i) $C_{3-8}$ cycloalkyl, or ii) phenyl; or $R^1$, $R^2$, together with the carbon to which they are attached, form a 4-tetrahydropyran ring;

$R^3$ and $R^4$ are independently i) $C_{1-3}$ alkyl optionally substituted with one or more substituents independently selected from the group consisting of halogen and —OH, or ii) $C_{2-6}$ alkenyl optionally substituted with one or more substituents independently selected from the group consisting of —OH and pyrazolyl, wherein each pyrazolyl is independently optionally substituted with one or more $C_{1-6}$ alkyl substituents; or $R^3$ and $R^4$, together with the carbon to which they are attached, form a 3-oxetane ring;

$R^5$ is i) H, ii) $C_{1-6}$ alkyl, iii) —O—($C_{1-6}$ alkyl), iv) halogen, or v) $C_{3-8}$ cycloalkyl;

$R^6$ is i) H, ii) $C_{1-6}$ alkyl optionally substituted with one or more substituents selected from the group consisting of —O—($C_{1-6}$ alkyl) and halogen, iii) —OH, iv) —O—($C_{1-6}$ alkyl optionally substituted with one or more halogen substituents), v) halogen, vi) —CN, vii) —S—($C_{1-6}$ alkyl), viii) —NR$^O$R$^O$, or ix) $C_{2-6}$ alkenyl; and each $R^O$ is independently H or $C_{1-6}$ alkyl.

Embodiment (35) The compound of embodiment (34), or a salt thereof, wherein $R^1$ is $C_{1-6}$ alkyl;

$R^2$ is $C_{1-6}$ alkyl optionally substituted with —OR$^O$;

$R^3$ and $R^4$, together with the carbon to which they are attached, form a 3-oxetane ring;

$R^5$ is H; and $R^6$ is i) $C_{1-6}$ alkyl, ii) —O—($C_{1-6}$ alkyl optionally substituted with one to three halogen substituents), iii) halogen, or iv) —CN.

Embodiment (36) The compound of embodiment (34) or (35), or a salt thereof, wherein $X^1$ is C—$R^{11}$;

$X^2$ is C—$R^{12}$;

$R^{11}$ is i) H, ii) halogen, iii) —CN, or iv) —O—$C_{1-6}$ alkyl; and $R^{12}$ is H.

Embodiment (37) The compound of (1), or a salt thereof, wherein $X^1$ is C—$R^{11}$;

$X^2$ is C—$R^{12}$;

$R^{11}$ is i) H, ii) halogen, iii) —CN, or iv) —O—$C_{1-6}$ alkyl;

$R^{12}$ is H or halogen;

$R^1$ is i) H or ii) $C_{1-6}$ alkyl optionally substituted with one or more halogen substituents;

$R^2$ is i) $C_{1-6}$ alkyl optionally substituted with one or more substituents independently selected from the group consisting or —OR$^O$, halogen, —COOR$^O$, —CONR$^{21}$R$^{22}$, phenyl optionally substituted with one or more substituents independently selected from $G^1$, and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, ii) —NR$^{23}$R$^{24}$, or iii) phenyl;

each $R^{21}$ is independently $C_{1-6}$ alkyl;

each $R^{22}$ is independently $C_{1-6}$ alkyl optionally substituted with one or more phenyl substituents;

$R^{23}$ is $C_{1-6}$ alkyl;

$R^{24}$ is i) $C_{1-6}$ alkyl, ii) $C_{3-8}$ cycloalkyl, or iii) phenyl; or

R$^1$ and R$^2$, together with the carbon to which they are attached, form a 4-piperidine ring or 4-tetrahydropyran ring, wherein the 4-piperidine ring is optionally substituted with one or more substituents selected from the group consisting of —SO$_2$—(C$_{1-6}$ alkyl) and —COOR$^0$;

R$^3$ and R$^4$ are independently C$_{1-3}$ alkyl optionally substituted with one or more halogen substituents, or R$^3$ and R$^4$, together with the carbon to which they are attached, form a 3-oxetane ring;

R$^5$ is i) H, ii) C$_{1-6}$ alkyl, iii) —O—(C$_{1-6}$ alkyl), iv) halogen, or v) C$_{3-8}$ cycloalkyl;

R$^6$ is i) H, ii) C$_{1-6}$ alkyl optionally substituted with one or more halogen substituents, iii) —OH, iv) —O—(C$_{1-6}$ alkyl optionally substituted with one or more halogen substituents), iv) halogen, v) —CN, or v) C$_{2-6}$ alkenyl;

each G$^1$ is independently i) halogen or ii) —COOR$^0$; and
each R$^0$ is independently H or C$_{1-6}$ alkyl.

Embodiment (38) The compound of embodiment (1), or a salt thereof, wherein

X$^1$ is C—R$^{11}$;
X$^2$ is N;
R$^{11}$ is H;
R$^1$ is i) H or ii) C$_{1-6}$ alkyl;
R$^2$ is i) C$_{1-6}$ alkyl optionally substituted with one or more substituents independently selected from the group consisting or —OR$^0$, halogen and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from G$^2$, ii) C$_{2-6}$ alkenyl, iii) C$_{2-6}$ alkynyl, or vi) —COOR$^0$;

R$^3$ and R$^4$ are independently i) C$_{1-3}$ alkyl or ii) C$_{2-6}$ alkenyl optionally substituted with one or more heteroaryl substituents, wherein each heteroaryl is independently selected from the group consisting of pyrazolyl and thienyl, and wherein each heteroaryl is independently optionally substituted with one or more C$_{1-6}$ alkyl substituents, or R$^3$ and R$^4$, together with the carbon to which they are attached, form a 3-oxetane ring;

R$^5$ is H;
R$^6$ is i) H, ii) C$_{1-6}$ alkyl optionally substituted with one or more substituents independently selected from the group consisting of —O—(C$_{1-6}$ alkyl optionally substituted with one or more halogen substituents) and halogen, iii) —O—(C$_{1-6}$ alkyl optionally substituted with one or more halogen substituents), iv) halogen, v) —CN, or vi) —S—(C$_{1-6}$ alkyl);
each G$^2$ is independently C$_{1-6}$ alkyl; and
each R$^0$ is independently H or C$_{1-6}$ alkyl.

Embodiment (39) The compound of embodiment (1), or a salt thereof, wherein

X$^1$ is C—R$^{11}$;
X$^2$ is N;
R$^{11}$ is H;
R$^1$ is i) H or ii) C$_{1-6}$ alkyl;
R$^2$ is i) C$_{1-6}$ alkyl optionally substituted with one or more substituents independently selected from the group consisting or —OR$^0$, halogen and heteroaryl, wherein each heteroaryl is independently selected from the group consisting of pyridyl, pyrazolyl, imidazolyl, thiazolyl, thiadiazolyl, thienyl, oxazolyl, isoxazolyl, and triazolyl, and wherein each heteroaryl is optionally substituted with one or more substituents independently selected from G$^2$, ii) C$_{2-6}$ alkenyl, iii) C$_{2-6}$ alkynyl, or vi) —COOR$^0$;

R$^3$ and R$^4$ are independently i) C$_{1-3}$ alkyl or ii) C$_{2-6}$ alkenyl optionally substituted with one or more heteroaryl substituents, wherein each heteroaryl is independently selected from the group consisting of pyrazolyl and thienyl, and wherein each heteroaryl is independently optionally substituted with one or more C$_{1-6}$ alkyl substituents, or R$^3$ and R$^4$, together with the carbon to which they are attached, form a 3-oxetane ring;

R$^5$ is H;
R$^6$ is i) H, ii) C$_{1-6}$ alkyl optionally substituted with one or more substituents independently selected from the group consisting of —O—(C$_{1-6}$ alkyl optionally substituted with one or more halogen substituents) and halogen, iii) —O—(C$_{1-6}$ alkyl optionally substituted with one or more halogen substituents), iv) halogen, v) —CN, or vi) —S—(C$_{1-6}$ alkyl);
each G$^2$ is independently C$_{1-6}$ alkyl; and
each R$^0$ is independently H or C$_{1-6}$ alkyl.

Embodiment (40) The compound of embodiment (1), or a salt thereof, wherein

X$^1$ is N;
X$^2$ is C—R$^{12}$;
R$^{12}$ is H;
R$^1$ is i) H, ii) C$_{1-6}$ alkyl;
R$^2$ is i) C$_{1-6}$ alkyl optionally substituted with one or more —OR$^0$ substituents or ii) —COOR$^0$;
R$^3$ and R$^4$ are independently C$_{1-3}$ alkyl, or
R$^3$ and R$^4$, together with the carbon to which they are attached, form a 3-oxetane ring;
R$^5$ is H;
R$^6$ is i) halogen or ii) —CN; and
each R$^0$ is independently H or C$_{1-6}$ alkyl.

Embodiment (41) The compound of embodiment (1), or a salt thereof, wherein

X$^1$ and X$^2$ are each N;
R$^1$ is i) H or ii) C$_{1-6}$ alkyl;
R$^2$ is i) C$_{1-6}$ alkyl or ii) —COOR$^0$;
R$^3$ and R$^4$ are independently C$_{1-3}$ alkyl optionally substituted with one or more —OH, or
R$^3$ and R$^4$, together with the carbon to which they are attached, form a 3-oxetane ring;
R$^5$ is H;
R$^6$ is i) H, ii) C$_{1-6}$ alkyl, iii) —O—(C$_{1-6}$ alkyl optionally substituted with one or more halogen substituents), iv) halogen, v) —CN, iv) —NR$^0$R$^0$, or vii) C$_{2-6}$ alkenyl; and
each R$^0$ is independently H or C$_{1-6}$ alkyl.

Embodiment (42) The compound of embodiment (1), or a salt thereof, wherein

X$^1$ is CH;
X$^2$ is CH or N;
R$^1$ is H or C$_{1-6}$ alkyl;
R$^2$ is C$_{1-6}$ alkyl optionally substituted with one or more substituents selected from the group consisting of —OR$^0$ and halogen;
R$^3$ and R$^4$ are independently C$_{1-3}$ alkyl, or
R$^3$ and R$^4$, together with the carbon to which they are attached, form a 3-oxetane ring;
R$^5$ is H;
R$^6$ is H, C$_{1-6}$ alkyl, halogen, or —CN; and
each R$^0$ is independently H or C$_{1-6}$ alkyl.

Embodiment (43) The compound of embodiment (1), or a salt thereof, wherein

X$^1$ and X$^2$ are each CH;
R$^1$ is H, methyl, or ethyl;
R$^2$ is methyl or ethyl, each of which is optionally substituted with one or more substituents selected from the group consisting of —OH and halogen;
R$^3$ and R$^4$, together with the carbon to which they are attached, form a 3-oxetane ring;
R$^5$ is H; and
R$^6$ is H, methyl, halogen, or —CN.

Embodiment (44) The compound of any one of embodiments (1)-(16), and (18)-(43), or a salt thereof, wherein the carbon bearing $R^1$ and $R^2$ is in the S configuration in case that $R^1$ is not the same as $R^2$.

Embodiment (45) The compound of any one of embodiments (1)-(16), and (18)-(43), or a salt thereof, wherein the carbon bearing $R^1$ and $R^2$ is in the R configuration in case that $R^1$ is not the same as $R^2$.

Embodiment (46) The compound of any one of embodiments (1)-(22) and (24)-(45), or a salt thereof, wherein the carbon bearing $R^3$ and $R^4$ is in the S configuration in case that $R^3$ is not the same as $R^4$.

Embodiment (47) The compound of any one of embodiments (1)-(22) and (24)-(45), or a salt thereof, wherein the carbon bearing $R^3$ and $R^4$ is in the R configuration in case that $R^3$ is not the same as $R^4$.

Embodiment (48) The compound of embodiment (1), or a salt thereof, wherein $X^1$ is C—$R^{11}$ and $X^2$ is C—$R^{12}$, and wherein the compound is selected from the group consisting of:

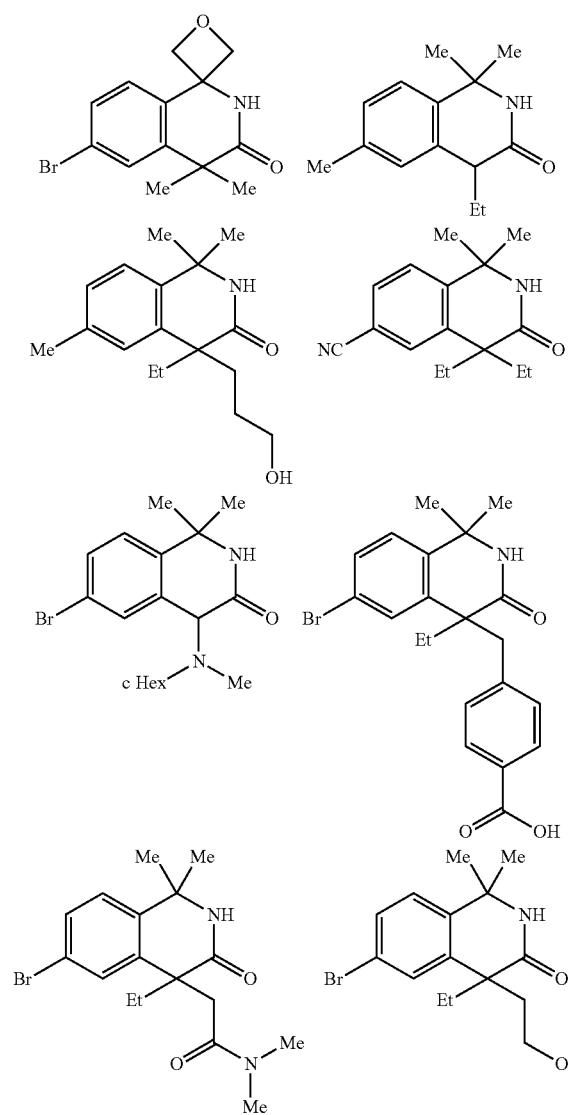

-continued

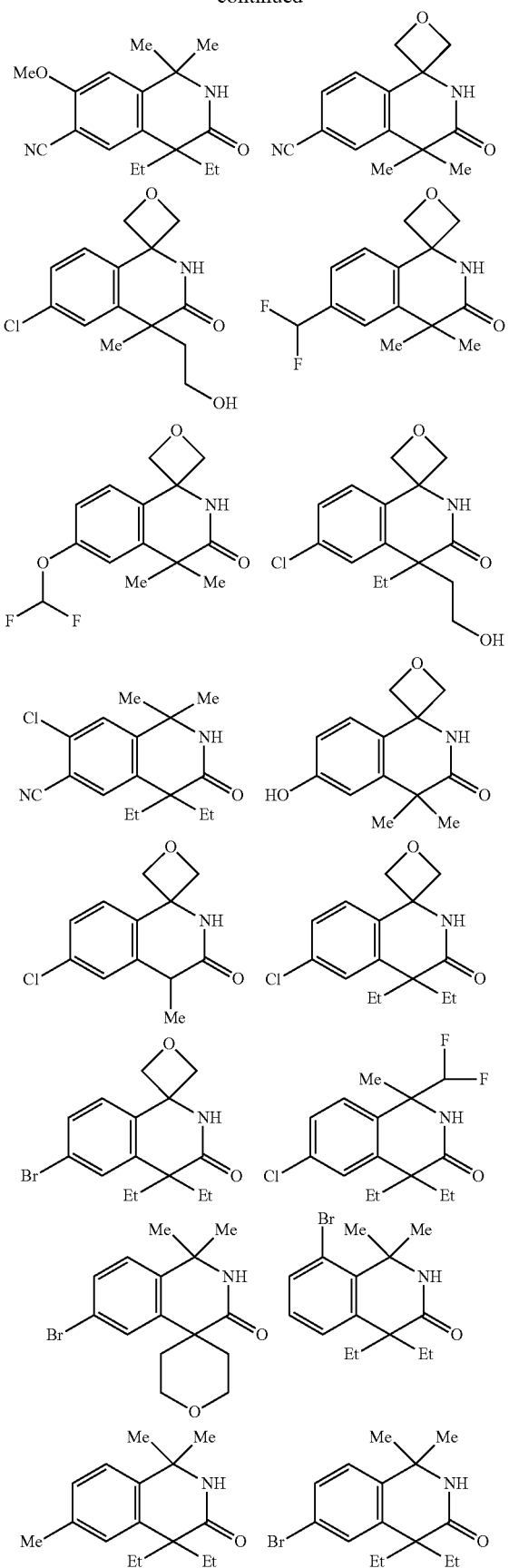

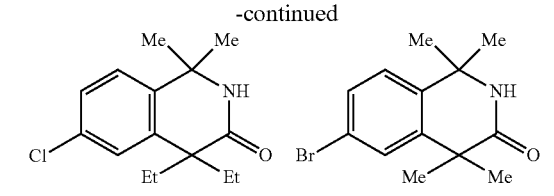
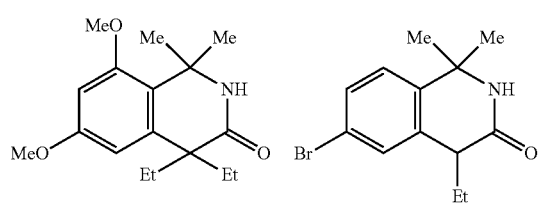
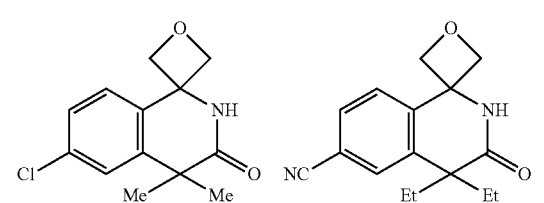
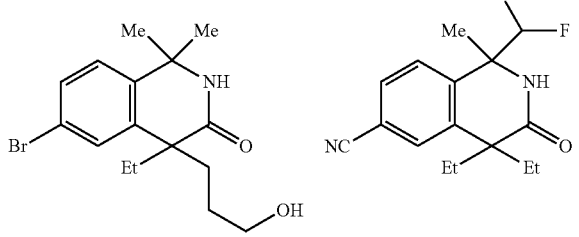
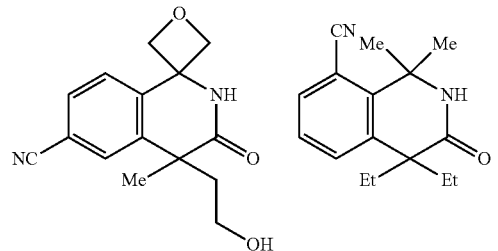
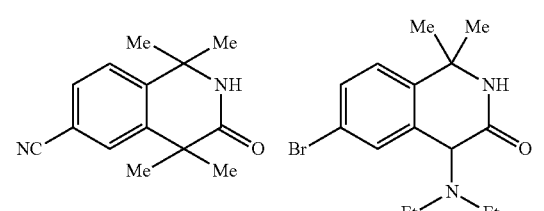
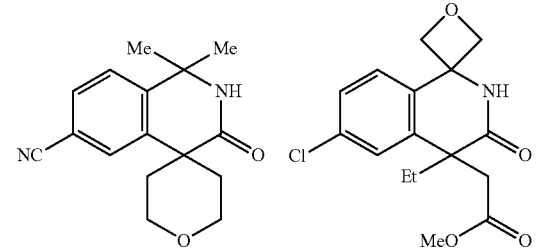
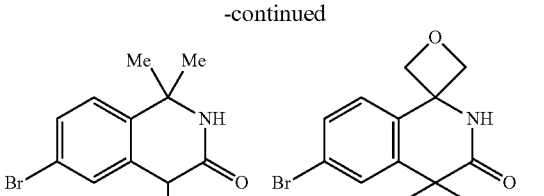
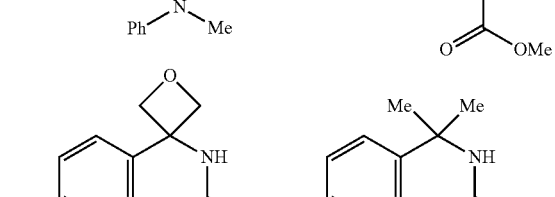
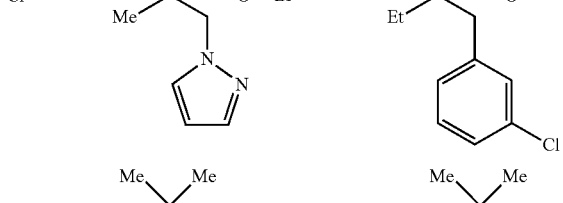
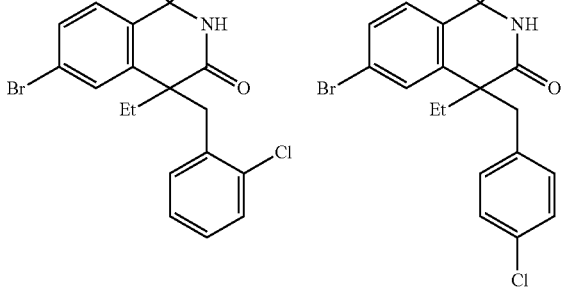
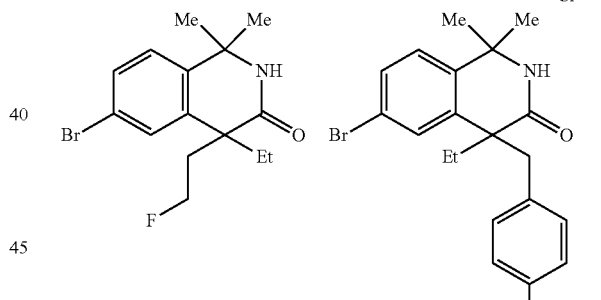
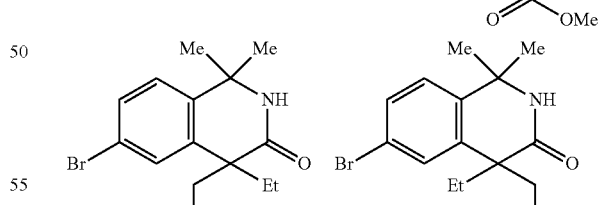
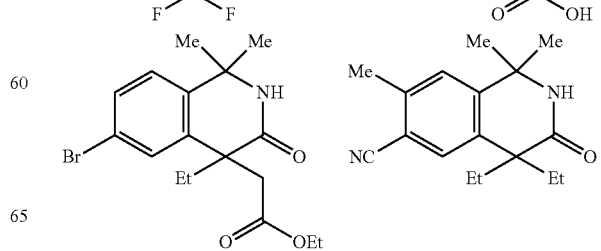

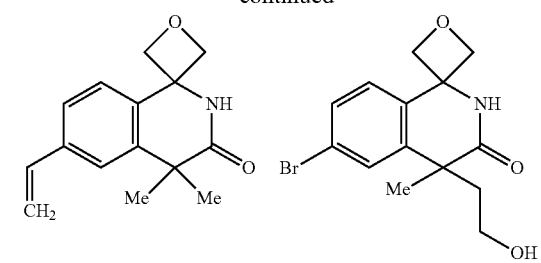
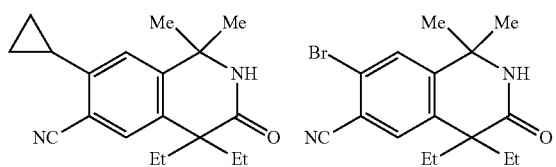
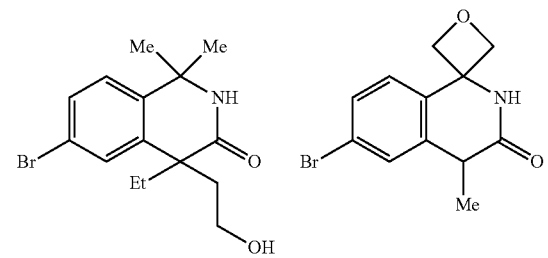
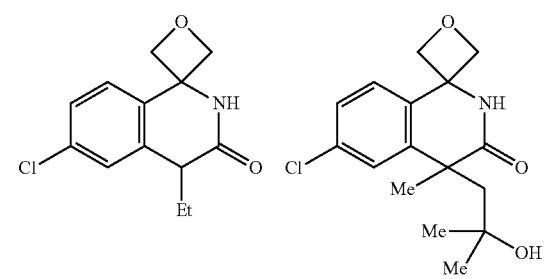
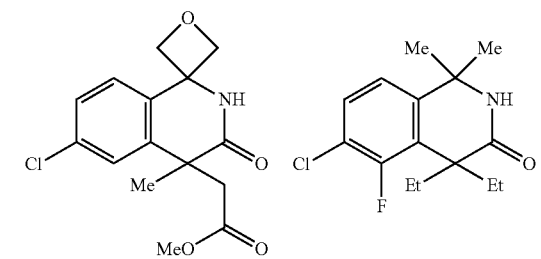
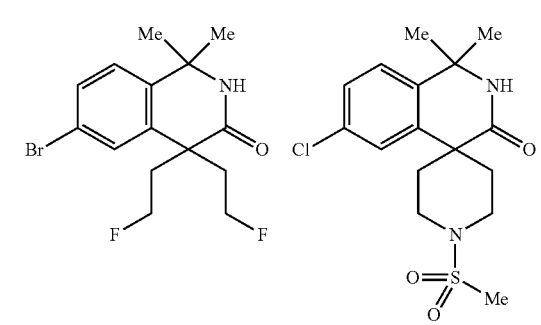
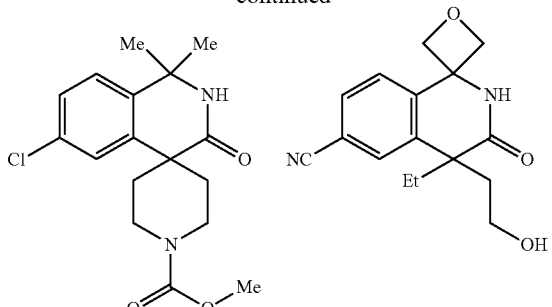
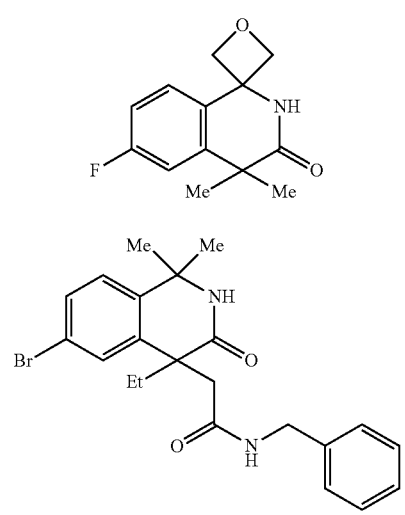
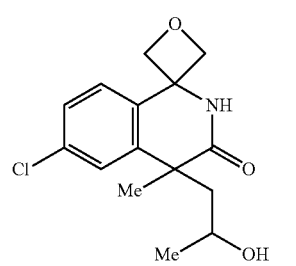
Embodiment (49) The compound of embodiment (1), or a salt thereof, wherein $X^1$ is C—$R^{11}$ and $X^2$ is N, and wherein the compound is selected from the group consisting of:
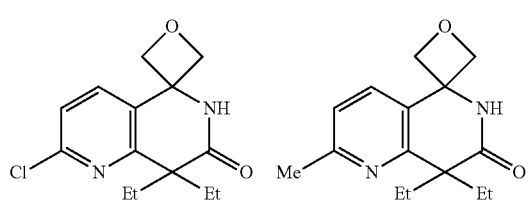
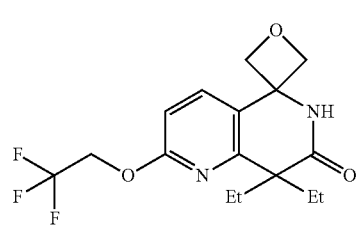

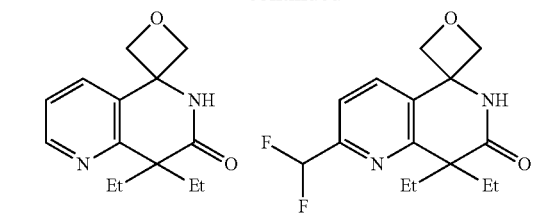
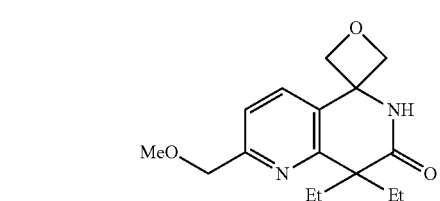
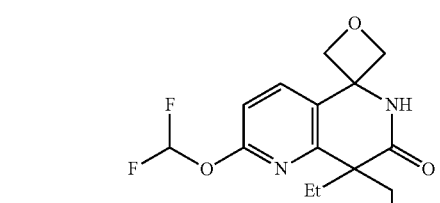
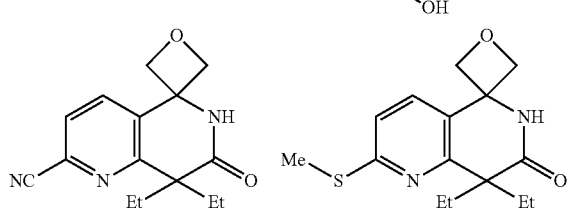
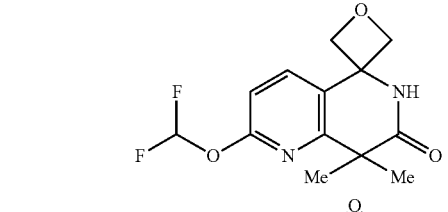
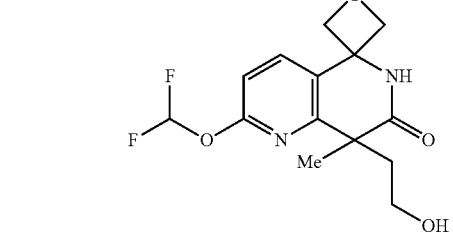
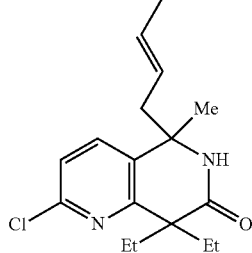
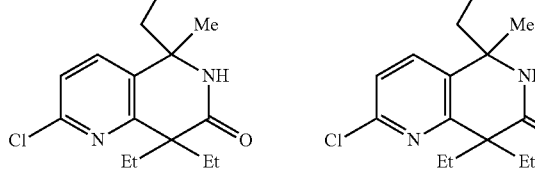
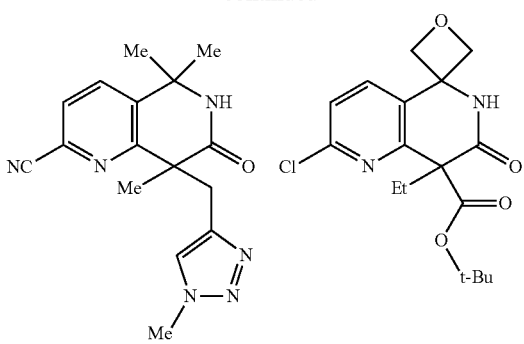
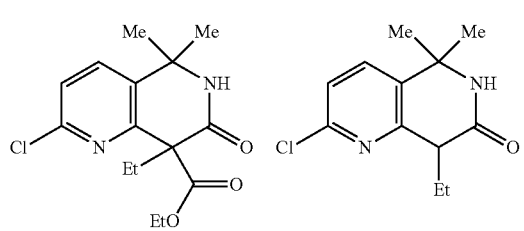
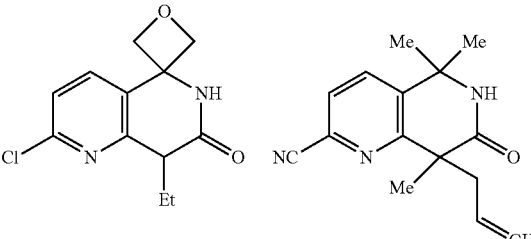
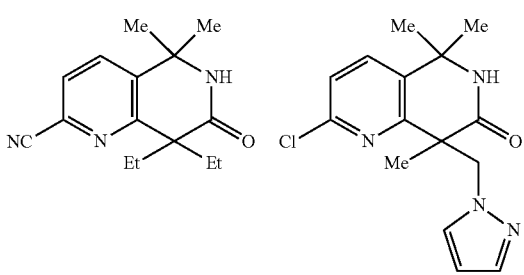
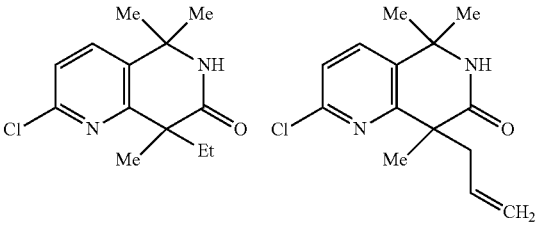
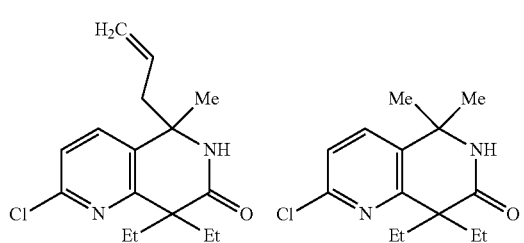

-continued
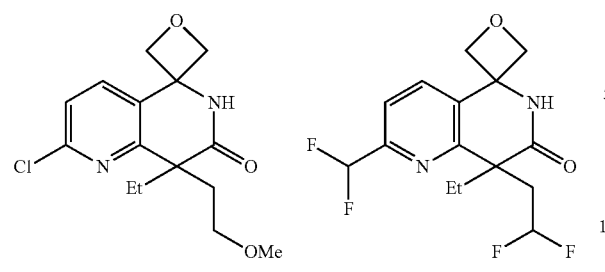
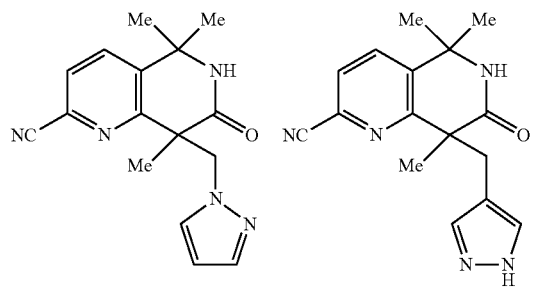
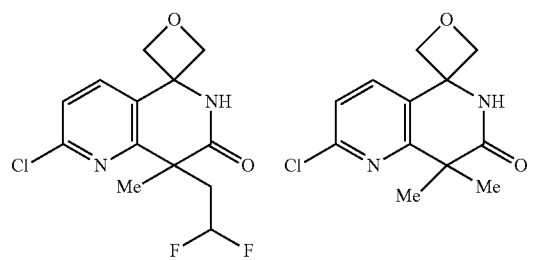
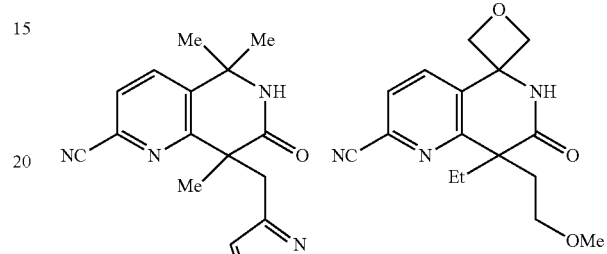
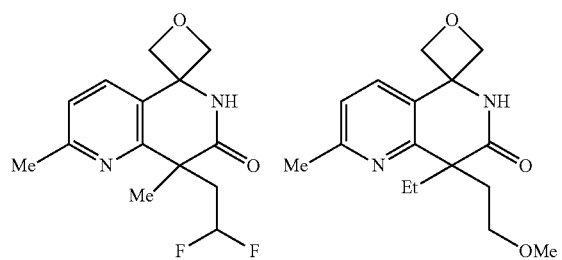
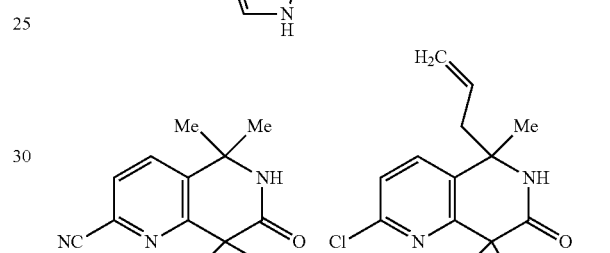
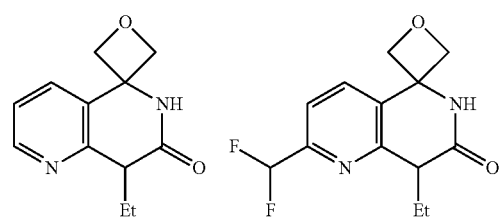
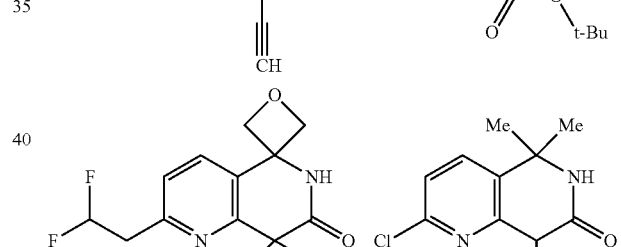
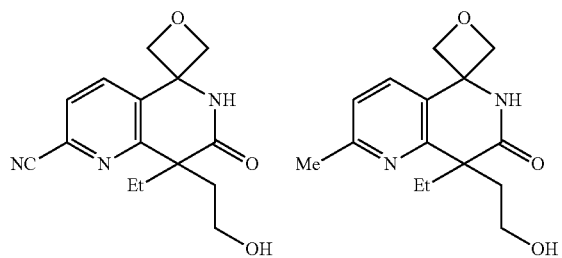
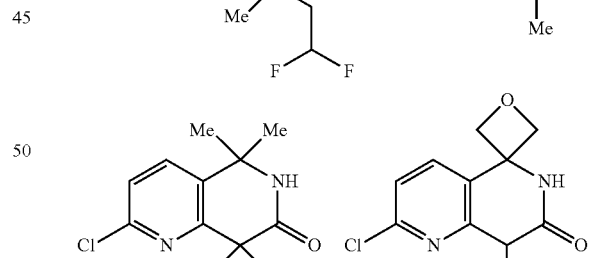
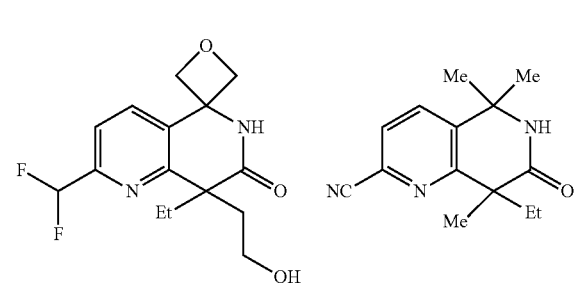
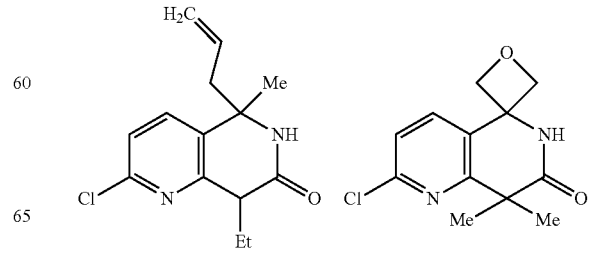

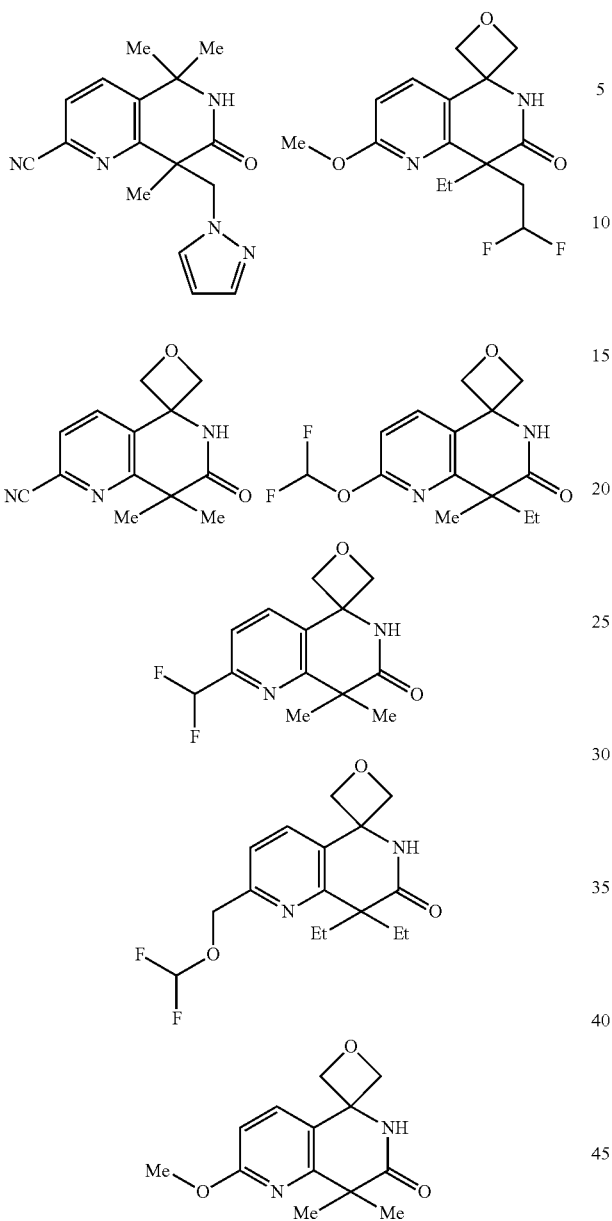
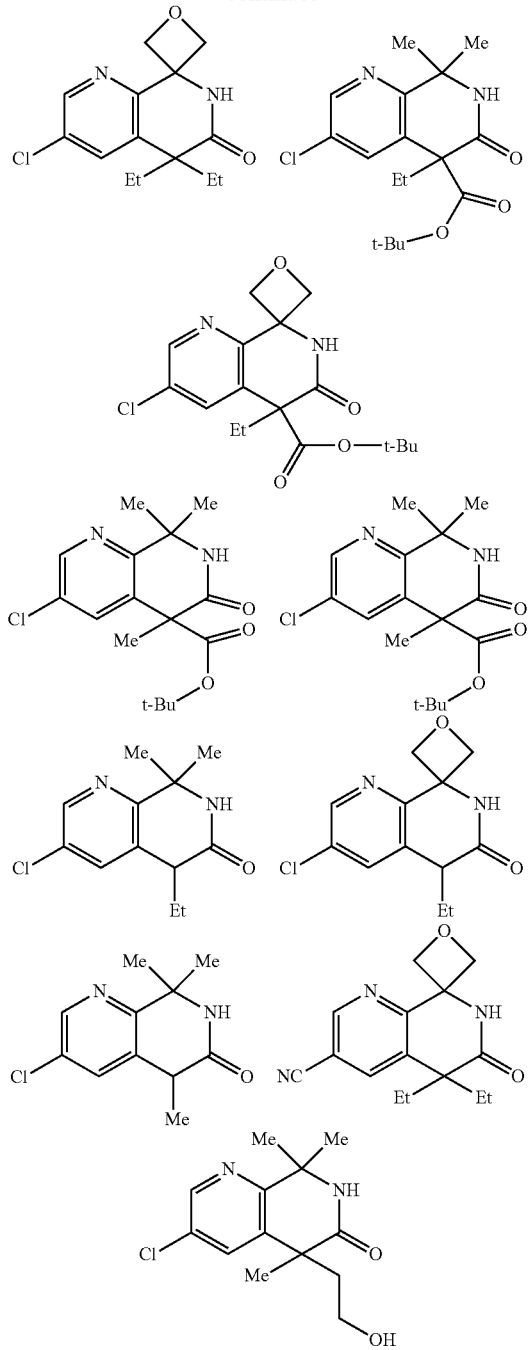
Embodiment (50) The compound of embodiment (1), or a salt thereof, wherein $X^1$ is N and $X^2$ is C—$R^{12}$, and wherein the compound is selected from the group consisting of:
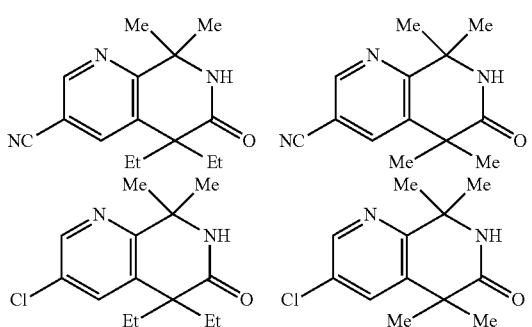
Embodiment (51) The compound of embodiment (1), or a salt thereof, wherein $X^1$ is N and $X^2$ is N, and wherein the compound is selected from the group consisting of:
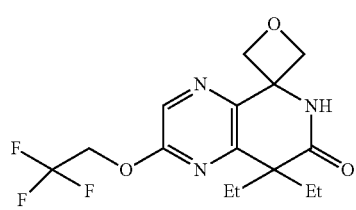

-continued

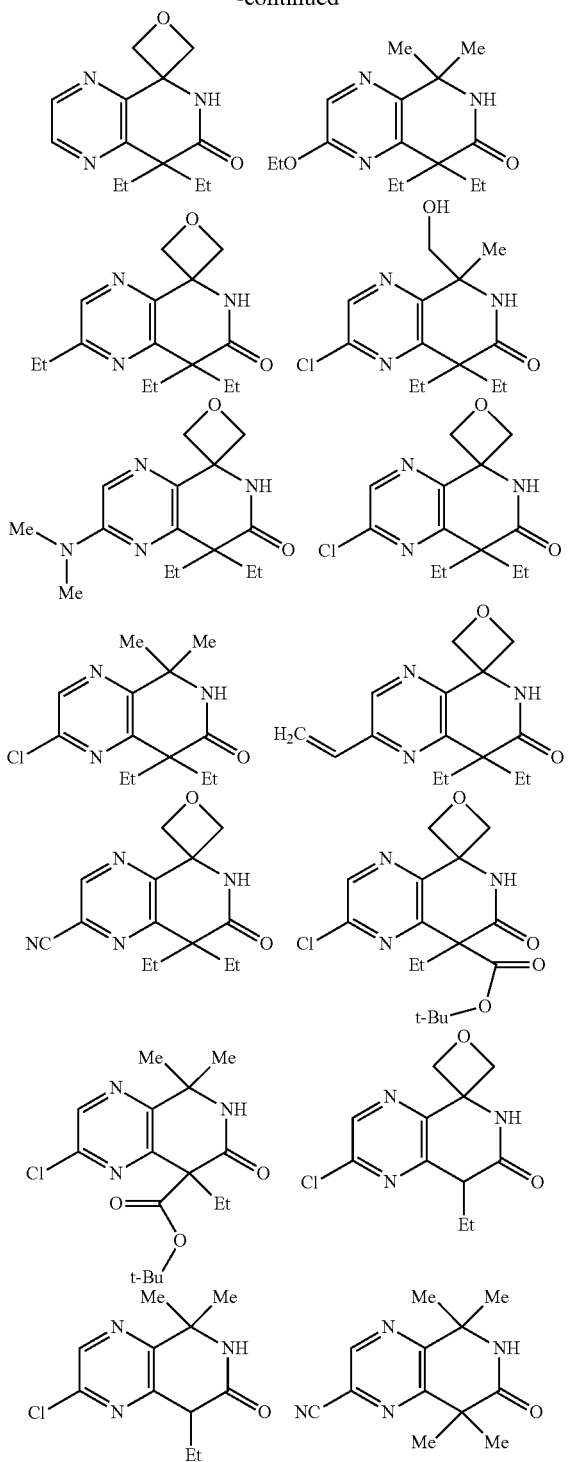

Embodiment (52) A compound, or a salt thereof, which is selected from the group consisting of
4,4-diethyl-3-oxo-3,4-dihydro-2H-spiro[isoquinoline-1,3'-oxetane]-6-carbonitrile,
6-chloro-4,4-dimethyl-2H-spiro[isoquinoline-1,3'-oxetan]-3 (4H)-one,
4,4-dimethyl-3-oxo-3,4-dihydro-2H-spiro[isoquinoline-1,3'-oxetane]-6-carbonitrile,
(+)-6-chloro-4-(2-hydroxy ethyl)-4-methyl-2H-spiro[isoquinoline-1,3'-oxetan]-3(4H)-one, and (−)-6-chloro-4-(2-hydroxyethyl)-4-methyl-2H-spiro[isoquinoline-1,3'-oxetan]-3(4H)-one.

Embodiment (53) The compound of embodiment (52), or a salt thereof, which is 4,4-diethyl-3-oxo-3,4-dihydro-2H-spiro[isoquinoline-1,3'-oxetane]-6-carbonitrile.

Embodiment (54) The compound of embodiment (52), or a salt thereof, which is 6-chloro-4,4-dimethyl-2H-spiro[isoquinoline-1,3'-oxetan]-3(4H)-one.

Embodiment (55) The compound of embodiment (52), or a salt thereof, which is 4,4-dimethyl-3-oxo-3,4-dihydro-2H-spiro[isoquinoline-1,3'-oxoetane]-6-carbonitrile.

Embodiment (56) The compound of embodiment (52), or a salt thereof, which is (+)-6-chloro-4-(2-hydroxyethyl)-4-methyl-2H-spiro[isoquinoline-1,3'-oxetan]-3 (4H)-one.

Embodiment (57) The compound of embodiment (52), or a salt thereof, which is (−)-6-chloro-4-(2-hydroxyethyl)-4-methyl-2H-spiro[isoquinoline-1,3'-oxetan]-3 (4H)-one.

Embodiment (58) A pharmaceutical composition comprising a compound of any one of embodiments (1)-(57), or a pharmaceutically acceptable salt thereof, and a pharmaceutically acceptable excipient.

Embodiment (59) A pharmaceutical composition for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome, comprising a compound of any one of embodiments (1)-(57), or a pharmaceutically acceptable salt thereof.

Embodiment (60) Use of a compound of any one of embodiments (1)-(57), or a pharmaceutically acceptable salt thereof, for the manufacture of a pharmaceutical composition for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome.

Embodiment (61) Use of a compound of any one of embodiments (1)-(57), or a pharmaceutically acceptable salt thereof, for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome.

Embodiment (62) A method for treating a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome, comprising administering to a subject an effective amount of a compound of any one of embodiments (1)-(57), or a pharmaceutically acceptable salt thereof.

Embodiment (63) A compound of any one of embodiments (1)-(57), or a pharmaceutically acceptable salt thereof, for use in the prevention or treatment of a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome.

Embodiment (64) A kit comprising a compound of any one of embodiments (1)-(57), or a pharmaceutically acceptable salt thereof, and instructions for use in the treatment of a disease or condition selected from the group consisting of stress urinary incontinence (SUI), mixed urinary incontinence (MUI), fecal incontinence, frailty, sarcopenia, chronic obstructive pulmonary disease (COPD), cachexia syndrome and/or muscle wasting caused by heart failure, cancer, or chronic kidney disease/dialysis, amyotrophic lateral sclerosis (ALS), spinal muscular atrophy (SMA), myasthenia gravis, a muscular myopathy, post-spinal cord injury (SCI) muscle dysfunction, post-stroke muscle dysfunction, peripheral vascular disease, peripheral arterial disease, rehabilitation-related deficits, metabolic syndrome, obesity, ventilator-induced muscle weakness, and chronic fatigue syndrome.

Embodiment (65) An article of manufacture comprising a compound of any one of embodiments (1)-(57), or a pharmaceutically acceptable salt thereof.

Any variation described herein with reference to formula (I) can also be applied to formula (I') as if each and every such variation had been specifically described for formula (I'). Similarly, any variation described herein with reference to formula (I') can also be applied to formula (I) as if each and every such variation had been specifically described for formula (I). Furthermore, each variation of $X^1$, $X^2$, $R^1$, $R^2$, $R^3$, $R^4$, $R^5$, $R^6$, and $R^0$ described herein can be combined with one another as if each combination had been specifically and separately described.

With regard to the compound of the formula (I) or the formula (I'), tautomers or geometrical isomers thereof may exist, depending on the kinds of the substituents. In the specification, the compound of the formula (I) or the formula (I') may be described in only one form of isomers in some cases, but the invention includes other isomers, isolated forms of the isomers, or a mixture thereof.

Furthermore, some of the compounds of the formula (I) or the formula (I') may have asymmetric carbon atoms or asymmetries in some cases, and correspondingly, the optical isomers thereof can exist. The invention includes the isolated form of the optical isomer of the compound of the formula (I) or the formula (I'), or a mixture of optical isomers in any ratio.

In addition, a pharmaceutically acceptable prodrug of the compound represented by the formula (I) or the formula (I') is also included in the invention. The pharmaceutically acceptable prodrug refers to a compound having a group which can be converted into an amino group, a hydroxyl group, a carboxyl group, or the like, by solvolysis or under a physiological condition. Examples of the groups forming the prodrug include those as described in Prog. Med., 5, 2157-2161 (1985) or "Pharmaceutical Research and Development" (Hirokawa Publishing Company, 1990), vol. 7, Drug Design, 163-198.

Moreover, the salt of the compound of the formula (I) or the formula (I') is a pharmaceutically acceptable salt of the compound of the formula (I) or the formula (I'), and the compounds of the formula (I) or the formula (I') may form an acid addition salt or a salt with a base, depending on the kinds of the substituents in some cases. Specifically, examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propanoic acid, oxalic acid, malonic acid, succinic acid, fumaric acid, maleic acid, lactic acid, malic acid, mandelic acid, tartaric acid, dibenzoyl tartaric acid, ditolyl tartaric acid, citric acid, methanesulfonic acid, ethanesulfonic acid, benzenesulfonic acid, p-toluenesulfonic acid, aspartic acid, and glutamic acid, and salts with metal anions such as sodium, potassium, magnesium, calcium, and aluminum, and with organic bases such as methylamine, ethylamine, and ethanolamine, salts with various amino acids such as acetyl leucine, lysine, and ornithine, or derivatives of amino acids, ammonium salts, and others.

In addition, the present invention also includes various hydrates or solvates, and crystal polymorph substances of the compound of the formula (I) or the formula (I') and a salt thereof. In addition, the invention also includes the compounds labeled with various radioactive or non-radioactive isotopes.

The compound of the formula (I) or the formula (I'), or a salt thereof can be prepared by applying various known synthetic methods, using the characteristics based on their basic structures or the kinds of the substituents. Depending on the types of the functional groups, it is in some cases advantageous to protect the functional group with an appropriate protective group (a group which is capable of being easily converted into the functional group), during the steps from starting materials to intermediates. Examples of the protective group include the protective groups as described in "Greene's Protective Groups in Organic Synthesis (5th edition, John Wiley & Sons, Inc., 2014)", edited by P. G. M. Wuts, and the like, which may be appropriately selected and used depending on the reaction conditions. In these methods, a desired compound can be obtained by introducing the protective group to carry out the reaction, and then, if desired, removing the protective group.

In addition, the prodrug of the compound of the formula (I) or the formula (I') can be prepared by introducing a specific group during the steps from starting materials to intermediates, in the same manner as for the above protective groups, or by further carrying out the reaction using the obtained compound of the formula (I) or the formula (I'). The reaction can be carried out by applying a method known to a person skilled in the art, such as common esterification, amidation, and dehydration.

Herein below, typical preparation methods of the compound of the formula (I) or the formula (I') and the compound of the formula (a) which is the starting compound will be described. Each of the production processes can also be carried out with reference to the documents appended to the description herein. Further, the preparation methods of the invention are not limited to the examples as shown below.

Production Process 1

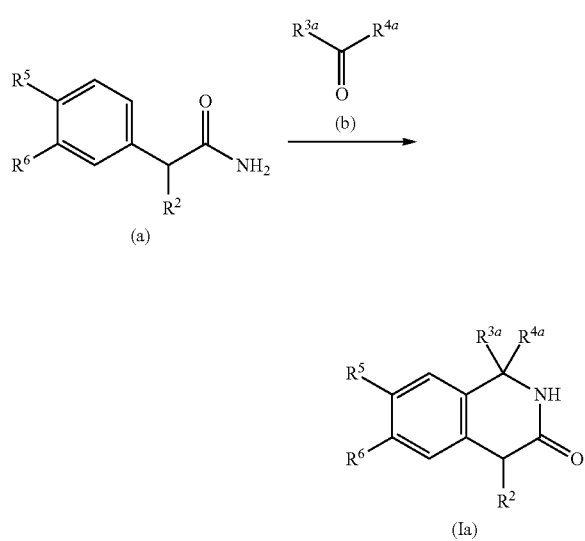

(in which, $R^{3a}$, $R^{4a}$ represents the same or different each other, $C_{1-3}$ alkyl which may be substituted with one or more substituent(s) selected from the group consisting of halogen(s) and —OH(s) or $C_{2-6}$ alkenyl which may be substituted with one or more substituent(s) selected from the group consisting of —OH(s) and heteroaryl(s) which is selected from the group consisting of pyrazolyl and thienyl, wherein the heteroaryl(s) may be substituted with one or more $C_{1-6}$ alkyl(s), which shall apply hereinafter).

This reaction is a method for producing a compound of the formula (Ia) which is a compound of the invention, by cyclization reaction known as Pictet-Spengler reaction.

This reaction is carried out using the compound of the formula (a) and (b) in equivalent amounts, or either thereof in an excess amount, by stirring the mixture under the temperature condition ranging from under cooling to heating to reflux in acidic condition, usually for 0.1 hours to 5 days, in a solvent which is inert to the reaction or without a solvent. Examples of the acid used herein are not particularly limited, but include hydrochloric acid, hydrobromic acid, hydroiodic acid, acetic acid, trifluoroacetic acid, sulfuric acid, nitric acid, phosphoric acid, polyphosphoric acid, methansulfonic acid, and Eaton's reagent. See also, for example, Synthetic Communications, 32(12), 1787-1790 (2002).

Production Process 2

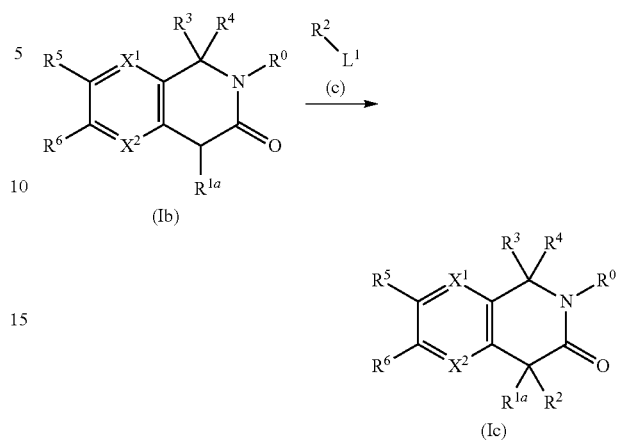

(in which, $R^{1a}$ represents $C_{1-6}$ alkyl which may be substituted with one or more substituent(s) selected from the group consisting of halogen(s), and pyrazolyl(s), ii) $C_{2-6}$ alkenyl, or iii) —$OR^O$, which shall apply hereinafter).

This production process is a method for producing the compound of the formula (Ic) which is included in the compound of the formula (I) or the formula (I') from the compound of the formula (Ib) which is also included in the formula (I) or the formula (I') and compound of the formula (c). Examples of $L^1$ may include chloro and the like.

The reaction is carried out using the compound of the formula (Ib) and the compound of the formula (c) in equivalent amounts, or either thereof in an excess amount, by stirring the mixture under the temperature condition ranging from under cooling to under heating, preferably at −20° C. to 60° C., usually for 0.1 hours to 5 days, in a solvent which is inert to the reaction, in the presence of a base. Examples of the base used herein are not particularly limited, but include sodium hydride, potassium tert-butoxide, potassium carbonate, and cesium carbonate. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran, dioxane, 1,2-dimethoxyethane, cyclopentylmethyl ether and the like, N,N-dimethylformamide, 1,3-dimethylimidazolidin-2-one, 1-methylpyrrolidin-2-one, dimethylsulfoxide, ethyl acetate, acetonitrile, water, and a mixture thereof. See also, for example, WO2011/159760 A1 and WO2005/26120.

Production Process 3

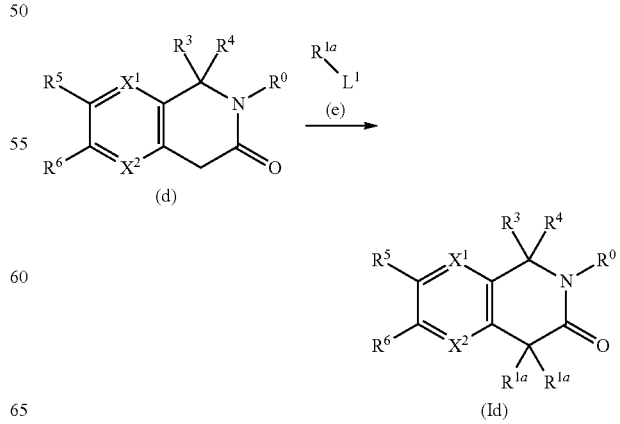

This production process is a method for producing the compound of the formula (Id) from the compound of the formula (d) and the compound (e).

The reaction is carried out using the compound of the formula (d) and the compound of the formula (e) in an 2 mole equivalent or more amount of, the compound of the formula (e) by stirring the mixture under the temperature condition ranging from under cooling to under heating, preferably at −40° C. to 60° C., more preferably at −20° C. to 60° C., usually for 0.1 hours to 5 days, in a solvent which is inert to the reaction, in the presence of 2 mole equivalent or more amount of a base. Examples of the base used herein are not particularly limited, but include sodium hydride, potassium tert-butoxide, potassium carbonate, and cesium carbonate. Examples of the solvent used herein are not particularly limited, but include aromatic hydrocarbons such as benzene, toluene, xylene and the like, halogenated hydrocarbons such as dichloromethane, 1,2-dichloroethane, chloroform and the like, ethers such as diethyl ether, tetrahydrofuran, dioxane, 1,2-dimethoxyethane, cyclopentylmethyl ether and the like, N,N-dimethylformamide, 1,3-dimethylimidazolidin-2-one, 1-methylpyrrolidin-2-one, dimethylsulfoxide, ethyl acetate, acetonitrile, water, and a mixture thereof. See also, for example, WO2011/159760.

Production Process 4

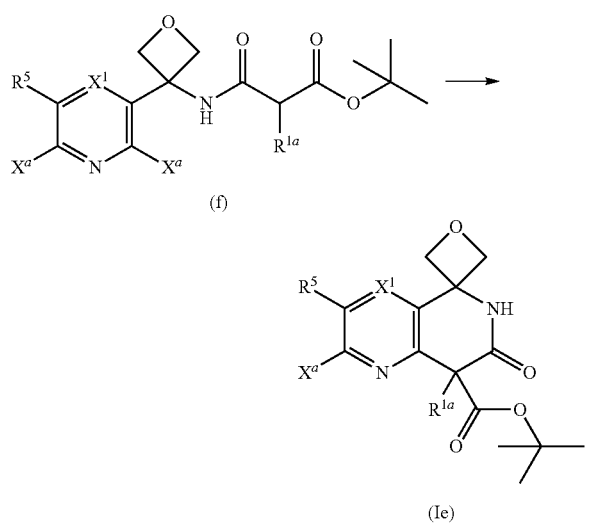

(in which, $X^a$ represents halogen).

This reaction is a method for producing a compound of the formula (Ie) which is a compound of the invention, by cyclization reaction.

This reaction is carried out using the compound of the formula (f), in the presence of equivalent or more amount of a base, by stirring the mixture under the temperature condition ranging from under cooling to room temperature, usually for 0.1 hours to 5 days, in a solvent which is inert to the reaction or without a solvent. Examples of the base used herein are not particularly limited, but include sodium bis(trimethylsilyl)amide, sodium hydride, and potassium tert-butoxide. Examples of the solvent used herein are not particularly limited, but include ethers such as diethyl ether, tetrahydrofuran, dioxane, 1,2-dimethoxyethane, cyclopentylmethyl ether and the like, N,N-dimethylformamide, 1,3-dimethylimidazolidin-2-one, 1-methylpyrrolidin-2-one, and the like. Further, there are some cases where a mixed solvent of the solvent and water is highly suitable for the reaction. See also, for example, WO2008/82009.

Production Process 5

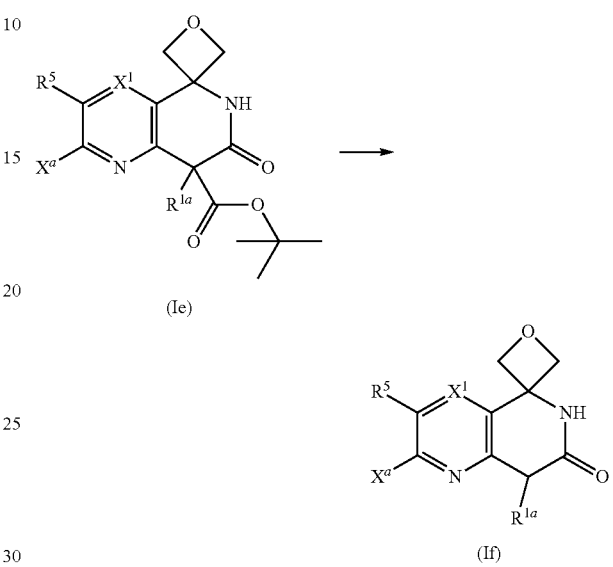

This reaction is a method for producing a compound of the formula (If) which is a compound of the invention, by a decarboxylation reaction.

This reaction is carried out using the compound of the formula (Ie), in the presence of equivalent or more amount of an acid, by stirring the mixture under the temperature condition ranging from under cooling to heating to reflux in acidic condition, usually for 0.1 hours to 5 days, in a solvent which is inert to the reaction or without a solvent. Examples of the acid used herein are not particularly limited, but include hydrochloric acid, hydrobromic acid, hydroiodic acid, formic acid, acetic acid, trifluoroacetic acid, and sulfuric acid. Examples of the solvent used herein are not particularly limited, but include halogenated hydrocarbons such as dichloromethane, 1,2-dichloroethane, chloroform and the like, N,N-dimethylformamide, tetrahydrofuran, and the like. Further, there are some cases where a mixed solvent of the solvent and water is highly suitable for the reaction. See also, for example, J. Org. Chem., 1983, 48 (6), pp 791-796, Org. Lett., 2011, Vol. 13, p 5560-5563.

Production Process 6

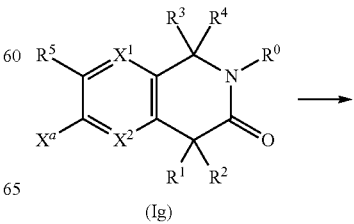

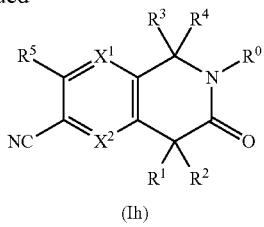

(Ih)

This reaction is a method for producing a compound of the formula (Ih) which is a compound of the invention, by cyanation using Pd-catalyst from a compound of the formula (Ig).

This reaction is carried out using the compound of the formula (Ig) and cyanation reagent by stirring the mixture under the temperature condition ranging from under cooling to heating to reflux or using microwave irradiation, usually for 0.1 hours to 5 days, in a solvent which is inert to the reaction or without a solvent. Examples of the cyanation reagent used herein are not particularly limited, but may include CuCN, $Zn(CN)_2$, KCN. Further, there are some cases where existence of Palladium catalyst such as palladium(II) diacetate, $Pd_2(dba)_3$, $Pd(TFA)_2$ or [1,1'-bis(diphenylphosphino)ferrocene]dichloropalladium(II) is highly suitable for the reaction. Further, there are some cases where existence of di-tert-butyl(2',4',6'-triisopropylbiphenyl-2-yl)phosphine (tBuXphos), 2',4',6'-diisopropyl-1,1'-biphenyl-2-yldicyclohexylphosphine (Xphos), or, 1,1'-bis(diphenylphosphino)ferrocene (dppf) is suitable for the reaction. Further, there are some cases where existence of Zn is suitable for the reaction. Examples of the solvent used herein are not particularly limited, but include halogenated hydrocarbons such as dichloromethane, 1,2-dichloroethane, chloroform and the like, N,N-dimethylformamide, N,N-dimethylacetamide, tetrahydrofuran, and the like. Further, there are some cases where a mixed solvent of the solvent and water is highly suitable for the reaction. See, for example, Org. Lett., 2007, 9 (9), pp. 1711-1714, Med. Chem. Lett., 2013, 4 (2), pp. 211-215, Journal of Medicinal Chemistry, 2005, vol. 48, p. 3953-3979.

Some compounds of the formula (I) or the formula (I') can be prepared by known reaction such as Suzuki coupling, ipso substitution, etc., from the compound (If). See also, for example, WO2010/131145; WO2008/147547; and U.S. Pat. No. 6,809,097.

Some compounds of the formula (I) or the formula (I') can be prepared by known reaction such as halogenation, reduction, hydroxylation, amido-condensation etc., from the compounds of the formula (I) or the formula (I'). See also, for example, Bioorganic and Medicinal Chemistry, 2011, vol. 19, p. 1666-1673; Journal of Organic Chemistry, 1980, vol. 45, p. 4391-4398; and WO2010/51373.

The compound of the formula (d) can be prepared by the same method of Production Process 1. Some synthetic intermediates for preparation of the compound of the formula (I) or the formula (I') can be prepared by known synthetic methods or synthetic methods described in this specification from known compounds. See also, for example, WO2008/3690; Org. Lett., 2007, 9 (9), pp. 1711-1714; Med. Chem. Lett., 2013, 4 (2), pp. 211-215; J. Org. Chem. 2013, 78, 2661-2669; Bioorganic and Medicinal Chemistry Letters, 2010, vol. 20, p. 1890-1894; and J. Org. Chem. 2013, 78, 2786-2791.

Production Process of Synthetic Intermediates 1

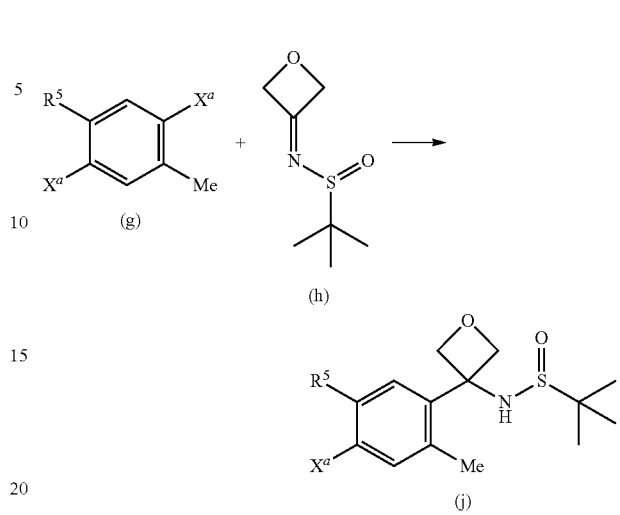

This reaction is carried out using the compound of the formula (g) and the compound of the formula (h) under basic condition by stirring the mixture under the temperature condition ranging from under cooling to room temperature, usually for 0.1 hours to 5 days, in a solvent which is inert to the reaction or without a solvent. Examples of the basic reagent used herein are not particularly limited, but include n-butyllithium, sec-butyllithium, tert-butyllithium. Examples of the solvent used herein are not particularly limited, but include ethers such as diethyl ether, tetrahydrofuran, dioxane, 1,2-dimethoxyethane, cyclopentylmethyl ether and the like, hydrocarbons such as n-hexane, n-pentane, and the like, aromatic hydrocarbons such as benzene, toluene, xylene and the like.

Production Process of Synthetic Intermediates 2

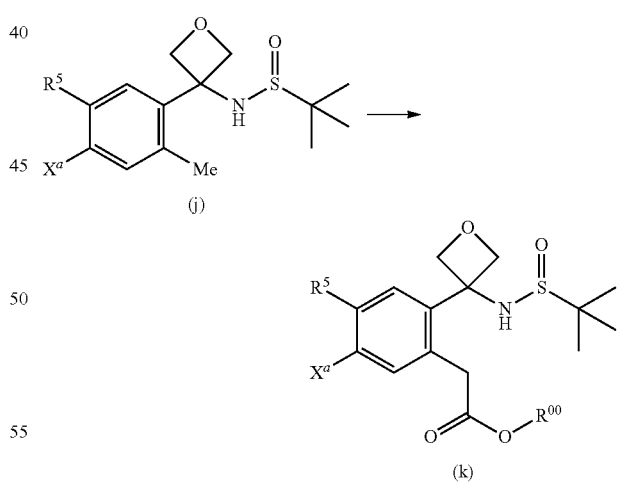

(where $R^{00}$ represents $C_{1-6}$ alkyl, which shall apply hereinafter).

This reaction is carried out using the compound of the formula (j) and $R^{00}$—OCO-Lv (Lv represents O—($C_{1-6}$ alkyl) or halogen) by stirring the mixture under the temperature condition ranging from under cooling to room temperature, usually for 0.1 hours to 5 days, in a solvent which is inert to the reaction or without a solvent under basic condition. Examples of the basic reagent used herein are not particularly limited, but include n-butyllithium, sec-butyllithium, tert-butyllithium, lithium diisopropylamide, and lithium 2,2,6,6-tetramethylpiperidide. Examples of the solvent used herein are not particularly limited, but include ethers such as diethyl ether, tetrahydrofuran, dioxane, 1,2-dimethoxyethane, cyclopentylmethyl ether and the like, hydrocarbons such as n-hexane, n-pentane, and the like.

Production Process of Synthetic Intermediates 3

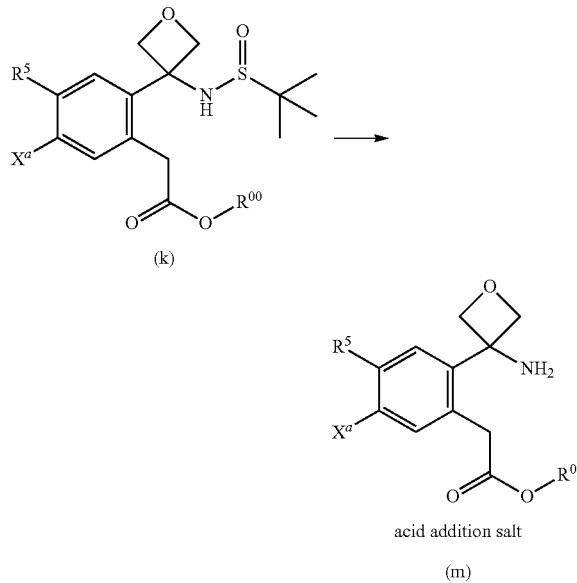

This reaction is carried out using the compound of the formula (k) under acidic condition in a solvent which is inert to the reaction or without a solvent by stirring the mixture under the temperature condition ranging from under cooling to room temperature, usually for 0.1 hours to 5 days. Examples of the acid used herein are not particularly limited, but include hydrochloric acid, hydrobromic acid, hydroiodic acid, acetic acid, trifluoroacetic acid, sulfuric acid, nitric acid, and thionyl chloride. Examples of the solvent used herein are not particularly limited, but include ethyl acetate, acetonitrile, ethers such as diethyl ether, tetrahydrofuran, dioxane, 1,2-dimethoxyethane, cyclopentylmethyl ether and the like, hydrocarbons such as n-hexane, n-pentane, and the like, alcohols such as methanol, ethanol, and the like.

Production Process of Synthetic Intermediates 4

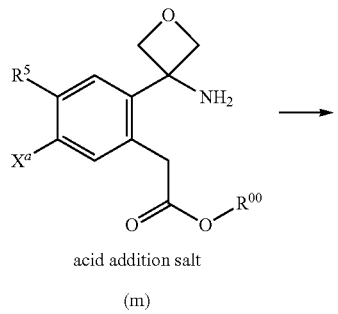

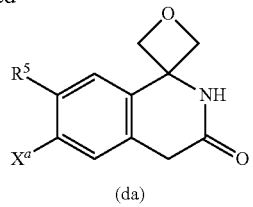

This reaction is carried out using the compound of the formula (m) in a solvent which is inert to the reaction or without a solvent under basic condition by stirring the mixture under the temperature condition ranging from under cooling to room temperature, usually for 0.1 hours to 5 days. Examples of the basic reagent used herein are not particularly limited, but include sodium hydrogen carbonate, sodium hydroxide, potassium hydroxide, potassium carbonate, sodium carbonate, potassium hydrogen carbonate, triethylamine, and N,N-diisopropylethylamine. Examples of the solvent used herein are not particularly limited, but include water, alcohols such as methanol, ethanol, and the like, ethers such as diethyl ether, tetrahydrofuran, dioxane, 1,2-dimethoxyethane, cyclopentylmethyl ether and the like.

Production Process of Synthetic Intermediates 5 pentamethylcyclopentadienyliridium(III) dichloride dimer

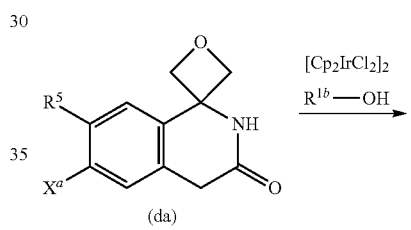

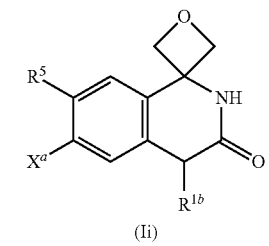

(in which, $R^{1b}$ represents $C_{1-6}$ alkyl which may be substituted with one or more substituent(s) selected from the group consisting of halogen(s)).

This reaction is carried out using the compound of the formula (da), pentamethylcyclopentadienyliridium(III) dichloride dimer, and $R^{1b}$—OH by stirring the mixture under the temperature condition ranging from room temperature to heating to reflux or using microwave irradiation, usually for 0.1 hours to 5 days, in a solvent which is inert to the reaction or without a solvent under basic condition. Examples of the base used herein are not particularly limited, but may include potassium hydroxide, sodium hydroxide, potassium tert-butoxide, potassium carbonate, and cesium carbonate. Examples of the solvent used herein are not particularly limited, but include alcohol such as $R^{1b}$—OH, aromatic hydrocarbons such as benzene, toluene, xylene and the like. In case that alcohol is used as solvent, the alcohol needs to be the same as $R^{1b}$—OH. See also, for example, Tetrahedron, 65 (2009), 4375-4383.

The compound of the formula (I) or the formula (I') is isolated and purified as its free compound, or a salt, a hydrate, a solvate, or crystal polymorph substance thereof. The salt of the compound of the formula (I) or the formula (I') can also be prepared by a conventional method.

Isolation and purification are carried out by employing general chemical operations such as extraction, fractional crystallization, and various types of fractional chromatography.

Various isomers can be prepared by selecting appropriate starting compound, or separated by separation using differences in the physicochemical properties among the isomers. For example, the optical isomers can be obtained by means of general optical resolution methods of racemic compounds (for example, fractional crystallization introducing the compound into a diastereomer salt with an optically active base or acid; chromatography using a chiral column or the like; and others), or can also be prepared from appropriate optically active starting compound.

The pharmacological activity of certain compounds of the formula (I) or the formula (I') was confirmed by the following assay.

Assay Example 1: Preparation and Assay of Fast Skeletal Myofibrils

Preparation of fast skeletal myofibrils: Rabbit skeletal myofibrils were prepared based upon the method of Herrmann et al. (Biochem. 32(28):7255-7263(1993). Myofibrils were prepared from rabbit psoas muscle purchased from Pel-Freez Biologicals (Arkansas) within 2 days of ordering, stored on ice. Minced muscle was homogenized in volumes of ice-cold "standard" buffer (50 mM Tris, pH 7.4, 0.1 M KOAc, 5 mM KCl, 2 mM dithiothreitol (DTT), 0.2 mM phenylmethylsulfonyl fluoride (PMSF), 10 µM leupeptin, 5 µM pepstatin, and 0.5 mM sodium azide) containing 5 mM ethylenediaminetetraacetic acid (EDTA) and 0.5% Triton X-100 using an Omni-Macro homogenizer. Myofibrils were recovered by low speed centrifugation (3000 rpm for 10 minutes) and washed 2 times in the Triton X-100 containing buffer to ensure removal of cellular membrane. Following the Triton washes, myofibrils were washed 3 times in "standard" buffer containing 2 mM magnesium acetate. A final wash in assay buffer (12 mM piperazine-1,4-bis(2-ethanesulfonic acid) (PIPES), pH 6.8, 60 mM KCl, 1 mM DTT) was performed and brought to 10% sucrose for flash freezing in liquid nitrogen and storage at −80° C.

Activation of Fast Skeletal Myofibrils: Fast fiber activators were identified by measuring the enzymatic activity of muscle myofibril preparations using the proprietary PUMA (trademark) (see, e.g., U.S. Pat. Nos. 6,410,254, 6,743,599, 7,202,051, and 7,378,254) assay system. Myofibril preparations consisted of rabbit skeletal muscle (approximately 90% fast fibers) that had been mechanically homogenized and washed with a detergent (Triton X-100) to remove cellular membranes. This preparation retained all of the sarcomeric components in a native conformation and the enzymatic activity was still regulated by calcium. Compounds were tested using a myofibril suspension and a level of calcium sufficient to increase enzymatic activity of the myofibrils to 25% of their maximal rate (termed pCa25). Enzymatic activity was tracked via a pyruvate kinase and lactate dehydrogenase-coupled enzyme system. This assay regenerates myosin-produced ADP into ATP by oxidizing NADH, producing an absorbance change at 340 nm. The buffering system was 12 mM PIPES, 2 mM $MgCl_2$, 1 mM DTT at pH 6.8 (PM12 buffer). Data was reported as AC1.4, which is the concentration at which the compound increased the enzymatic activity by 40%. The results are summarized in Table 2 below. In Table 2, "Ex. Cmpd." denotes the Example Compound with reference to the structures provided in Table 4 below.

TABLE 2

| Ex. Cmpd. | AC1.4 (µM) |
| --- | --- |
| 2 | 1.569 |
| 3 | 1.778 |
| 4 | 0.159 |
| 5 | 1.400 |
| 6 | 0.255 |
| 7 | 0.694 |
| 8 | >39.200 |
| 9a | 0.626 |
| 9b | 0.349 |
| 10 | 0.829 |
| 11 | 0.616 |
| 12 | 12.602 |
| 13 | 0.277 |
| 14 | 11.985 |
| 15 | 1.064 |
| 16 | 0.168 |
| 17 | 1.708 |
| 18 | 0.536 |
| 19 | 3.144 |
| 20 | 1.109 |
| 21 | 1.132 |
| 22a | 2.317 |
| 22b | 0.473 |
| 23 | 1.717 |
| 24 | 1.664 |
| 25 | 8.216 |
| 26 | 34.268 |
| 27 | 1.581 |
| 28 | 8.625 |
| 29 | 15.846 |
| 30 | 12.465 |
| 31a | 3.073 |
| 31b | >39.200 |
| 32 | 0.384 |
| 33 | 12.478 |
| 34 | 0.229 |
| 35 | 0.565 |
| 43 | 0.051 |
| 44 | 5.982 |
| 46 | 0.106 |
| 48 | <0.077 |
| 49 | <0.077 |
| 50 | 0.763 |
| 51 | 0.093 |
| 52 | 0.326 |
| 53 | 0.711 |
| 54 | 0.596 |
| 55 | 0.141 |
| 56 | 2.067 |
| 57 | 0.976 |
| 58 | 5.040 |
| 59 | 0.381 |
| 60 | 0.252 |
| 61 | 0.537 |
| 62 | >39.200 |
| 63 | 3.707 |
| 64 | 0.390 |
| 65 | 1.052 |
| 66 | 2.502 |
| 68 | 0.830 |
| 69 | 0.485 |
| 70 | 0.522 |
| 71 | 0.367 |
| 72 | 0.420 |
| 73 | 1.571 |
| 74 | 0.902 |
| 75 | 1.174 |
| 76 | 0.223 |
| 77 | 7.898 |
| 79 | <0.077 |
| 80 | 0.112 |

TABLE 2-continued

| Ex. Cmpd. | AC1.4 (μM) |
|---|---|
| 81 | 0.098 |
| 82 | 0.084 |
| 83 | <0.077 |
| 84 | 0.401 |
| 88 | 0.203 |
| 90 | 2.555 |
| 91 | 20.240 |
| 92a | 1.318 |
| 92b | 0.400 |
| 94 | 8.994 |
| 95 | 0.720 |
| 96 | 5.393 |
| 97 | 0.332 |
| 98 | 2.085 |
| 101 | 2.228 |
| 102 | 8.474 |
| 103 | 1.247 |
| 104 | 5.017 |
| 105 | 4.313 |
| 106 | 0.494 |
| 107 | 1.080 |
| 108 | 0.450 |
| 109 | 1.919 |
| 110 | 3.478 |
| 111 | 0.321 |
| 112 | 1.437 |
| 113 | 0.271 |
| 115 | 0.474 |
| 116 | 0.274 |
| 134a | 0.626 |
| 134b | 4.986 |
| 137 | 2.365 |
| 138 | 7.955 |
| 139 | 30.805 |
| 140 | 0.199 |
| 141 | <0.077 |
| 142 | 2.377 |
| 143 | 2.830 |
| 145 | 0.581 |
| 146 | 0.283 |
| 147 | 2.346 |
| 153 | 1.590 |
| 155 | 8.340 |
| 156 | 5.881 |
| 157 | 2.566 |
| 159 | 11.374 |
| 161 | 1.987 |
| 165 | 1.202 |
| 167a | 3.293 |
| 167b | 0.869 |
| 169 | 1.730 |

Assay Example 2: Preparation and Assay of Rat Isometric Ankle Plantarflexor Muscle Force Female Sprague Dawley rats were placed under a stable anesthesic plane with inhaled isoflurane (1-5%). One incision was made on the mid-thigh region of the right leg to expose the sciatic nerve. To prevent co-contraction of the ankle dorsiflexors, an additional incision was made lateral to the patella to isolate and sever the peroneal nerve. Rats were then placed on a temperature-maintained in situ muscle analysis rig (Aurora Scientific, Model 806C). The knee was immobilized in a clamp between two sharpened screws and the foot was taped to a footplate attached to a force transducer (Aurora Scientific, Ontario, Canada). Stainless steel needle electrodes (0.10 mm) were hooked around the exposed sciatic nerve. Isometric ankle plantarflexor muscle contractile force was assessed with the ankle joint at 90° flexion. A 30 Hz electrical stimulation (under supramaximal voltage conditions) was applied to the nerve and the resulting muscle force was recorded via a servomotor. A pre-dose 30 Hz force response was established as the baseline force. A pre-dose 150 Hz force response was established as the maximum isometric force. Compounds were formulated in 50% polyethylene glycol (PEG): 16% Cavitron: 10% dimethylacetamide (DMA) and administered by continuous intravenous infusion over a sixty minute period. The muscle force response to compound was measured every two minutes over the dosing period. Data was reported as an estimated $EC_{50}$ value, which is the concentration at which muscle force is 50% of the pre-dose maximum tension. The $EC_{50}$ results are summarized in Table 3 below. In Table 3, "Ex. Cmpd." denotes the Example Compound with reference to the structures provided in Table 4 below.

TABLE 3

| Ex. Cmpd. | PLANTARFLEXOR $EC_{50}$ (μM) |
|---|---|
| 11 | 17 |
| 12 | 34 |
| 13 | 19.5 |
| 15 | 16.4 |
| 16 | 13 |
| 18 | 16 |
| 19 | 35 |
| 20 | 30 |
| 35 | 23 |
| 49 | 8.2 |
| 52 | 25.6 |
| 55 | 7.6 |
| 56 | 30 |
| 57 | 28 |
| 61 | 10.3 |
| 64 | 10 |
| 72 | 15.4 |
| 73 | 50 |
| 74 | 15.4 |
| 101 | 24 |
| 103 | 23 |
| 104 | 30 |
| 106 | 15 |
| 108 | 23 |
| 109 | 39.7 |
| 113 | 8 |
| 22b | 9.99 |

Assay Example 3: Preparation and Assay of Rat Treadmill Running Performance

Female Sprague Dawley rats were acclimated to a treadmill (Columbus Instruments). Rats were trained to run on a treadmill for 5 days at a speed of 25 meters per minute (m/min) for ten minutes at a 5° incline. An experimenter-blinded cross-over treadmill study was performed to assess the effect of compounds on treadmill running performance. Rats were dosed with vehicle (0.5% hydroxypropyl methylcellulose (HPMC)/0.2% Tween-80) or compound at a pre-treatment time based on each respective compounds' pharmacokinetic properties prior to treadmill testing. Rats then ran until they reached exhaustion at a constant 35 m/min or a graded speed ranging from 25-45 m/min for up to 150 minutes. Treadmill time was recorded. Two days after the first treadmill test, the opposite treatment was administered to rats and the treadmill test protocol was repeated. Terminal blood was collected for plasma compound analysis. Treadmill running distance data is summarized in FIG. 1.

Increase of treadmill running distance: As shown in FIG. 1, Example Compound and Example Compound 22b increased treadmill running distance.

Assay Example 4: Preparation and Assay of Electrical Field Stimulation (EFS)-Induced Contraction of Isolated External Anal Sphincter (EAS)

Preparation of EFS-induced contraction of isolated EAS from the rats. EAS was isolated from the female SD rats (10-11 week old) euthanized using exsanguination under anesthesia. The isolated circular EAS was cut and divided into two strips. One end of each strip was hanged on a tension transducer (TB-611T; Nihon Kohden) attached to an amplifier (AP-621G; Nihon Kohden) and an interface (Power Lab; Ad Instrument), and the hanged strip was set in a tissue bath filled with Krebs buffer. The Krebs buffer was aerated with 95% $O_2$ and 5% $CO_2$, and kept warm at 37° C. Another end of the strip was hanged on an electrode of an EFS system (SEN-7203 and SEN-8203; Nihon Kohden) attached to a drive amplifier (SEG-3104; Nihon Kohden). The hanged strip was washed with Krebs buffer and rested with 0.5 g tension for 30 minutes to stabilize resting tension. This step (washing and 30 minutes resting of the strip) was repeated three times for complete stabilization of resting tension. The stabilized strip was stimulated with a single pulse (20 V and 30 μsec pulse width) and the strip which showed more than 60 mg contraction was selected and used for the further EFS contraction. After selected strip was washed with Krebs buffer, the strip underwent the EFS whose conditions are 20 V stimulus voltage, 30 μsec pulse width, 20 Hz frequency, and 1 sec duration. The EFS was repeated three times at 30 sec. interval. Contraction power was defined as the difference of the strip tension between pre- and post-EFS contraction. Pre-contraction was defined as the average contraction power of the three times EFS without any compound. After pre-contraction measurement, Example Compound 20, Example Compound 22b, or DMSO was added to the Krebs buffer with the strip. Fifteen minutes after the addition, the strip underwent the EFS three times at 30 sec. interval. Post-contraction was defined as the average contraction power of the three times EFS with each compound and calculated as % of pre-contraction. The effect of Example Compound 20 or Example Compound 22b was analyzed using Dunnett's multiple comparison test (a probability value of less than 0.05 was considered as a significant difference). Data were expressed as the mean±standard error of the mean (SEM).

Figure 2:
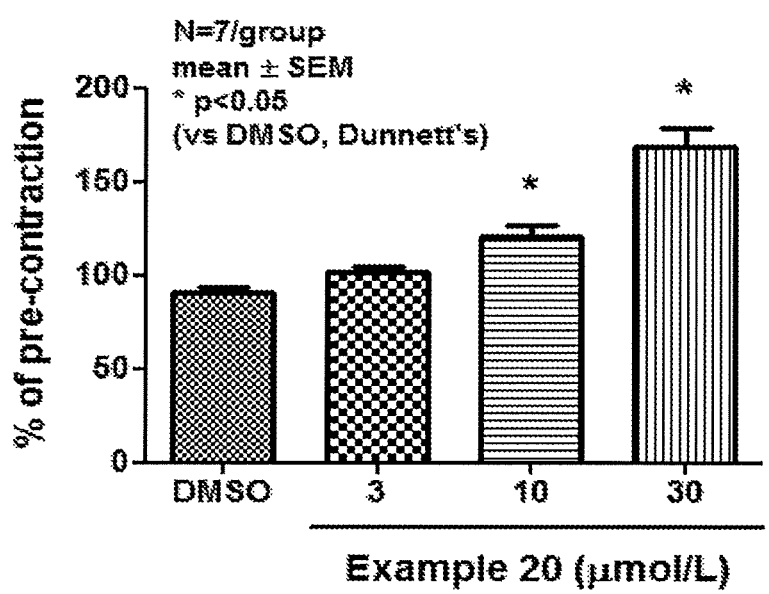
FIG. 2 is a graph showing results obtained by an assay of Electrical Field Stimulation (EFS)-induced concentration of isolated External Anal Sphincter (EAS).
Figure 3:
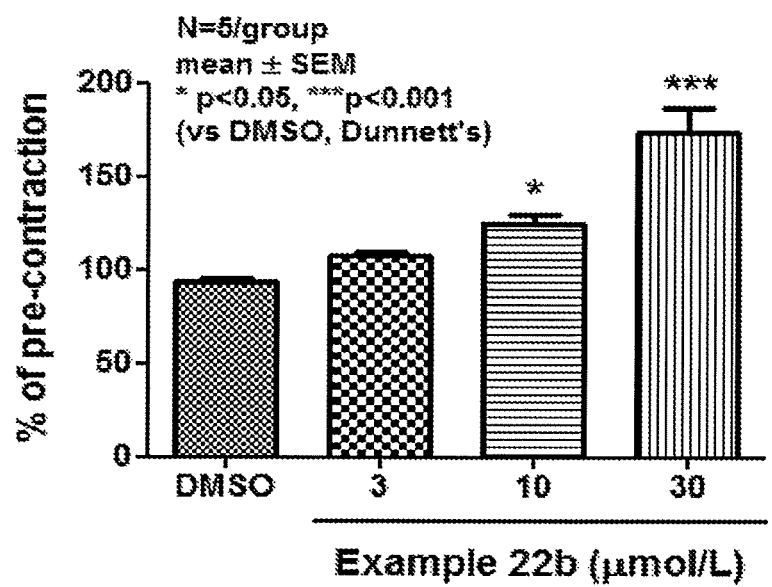
FIG. 3 is a graph showing results obtained by an assay of EFS-induced concentration of isolated EAS.

Increase of EFS-induced contraction of isolated EAS: As shown in FIGS. 2 and 3, Example Compound 20 and Example Compound 22b increased EFS-induced contraction of isolated EAS from the rats.

Assay Example 5: Preparation and Assay of Anal Pressure Induced by Electrical Stimulation of Pudendal Nerve Preparation of the rat anal pressure induced by electrical stimulation of pudendal nerve. Female SD rats (11-12 weeks old) were fasted for 12-16 h and anesthetized with urethane (1.2 g/kg, sc). A cannula (PE 50) for test substance administration was inserted into the jugular vein. A lower back incision was made and electrodes for electrical stimulation were placed under unilateral pudendal nerves. An UniTip catheter (Unisensor AG) for measurement of anal pressure attached to an amplifier (AP-621G, Nihon Kohden) and an interface (Power Lab, ADInstrument) was inserted into the anus through the anal orifice. Pudendal nerve stimulation (PudNS, frequency: 10 Hz, pulse width: 50 μsec, duration: 400 msec, voltage: 1 V) was applied by an electric stimulator (SEN-3401, Nihon Kohden) and the position of catheter was fixed at the point where PudNS-induced elevation of anal pressure could be elicited stably. Voltage was adjusted to elicit about 30-90% elevation of maximal anal pressure elicited at 1-10 V. For evaluation of test substance, PudNS (frequency: 10 Hz, pulse width: 50 μsec, duration: 400 msec, voltage: adjusted above) was repeated at 1 minute intervals. Before the test substance administration, at least 3 times of elevations of anal pressure were elicited and confirmed to be approximately equivalent. Vehicle, Example Compound 20 (3 mg/mL/kg) or Example Compound 22b (3 mg/mL/kg) was administered intravenously. The average pressure calculated from the last three elevations of anal pressure before the administration and the average pressure calculated from the three elevations of anal pressure between 1 to 4 min after the administration were defined as pre- and post-pressure, respectively. Data were expressed as a percentage of pre-pressure and the effect of vehicle, Example Compound 20 or Example Compound 22b was analyzed using Dunnett's multiple comparison test (a probability value of less than 0.05 was considered as a significant difference). Data were expressed as the mean±SEM of 4 animals.

Figure 4:
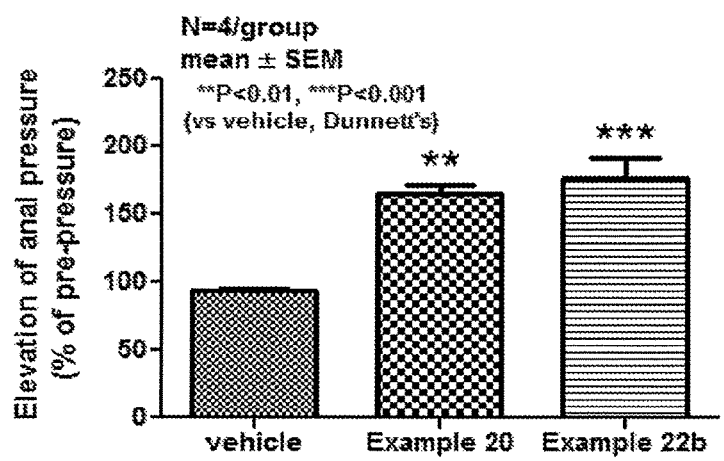
FIG. 4 is a graph showing results obtained by an assay of anal pressure induced by electrical stimulation of pudenal nerve.

PudNS-induced elevation of anal pressure. As shown in FIG. 4, Example Compound 20 and Example Compound 22b significantly potentiated the PudNS-induced elevation of anal pressure.

Assay Example 6: Preparation and Assay of Urine Leak Point Pressure (LPP) Under Abdominal Pressure Preparation of the rat model of urine leakage under abdominal pressure. The rat model was prepared based on the method of Conway et. al. (Int Urogynecol J 16:359-363, 2005). Female SD rats (10-14 week old) were anesthetized with pentobarbital. After laparotomy, an incision was made to the bladder dome, and a cannula (PE 100; Becton, Dickinson and Company) was inserted into the bladder and sutured with thread. In addition, another cannula (PE 100; Becton, Dickinson and Company) was inserted into the duodenum and sutured with thread. After abdominal closure, urine within the bladder was drained and physiological saline was injected via the bladder cannula. The volume of physiological saline in the bladder was kept at 75% of the maximum bladder capacity (the maximum capacity was set as the volume that leakage of physiological saline from urethral orifice starts). Subsequently, physiological saline was infused at 0.6 mL/h via the bladder cannula with infusion pumps (TE-331S and STC-525; Terumo), and the bladder pressure was recorded using the following instruments: a pressure transducer (DX-100; Nihon Kohden), pressure amplifiers (AP-601G, AP-621G, and AP630G; Nihon Kohden), and an interface (Power Lab; ADInstruments). In parallel with physiological saline infusion, abdomen of the rats was manually compressed with the lidside of a plastic 50 mL centrifuge tube, and the bladder pressure at the time when leakage from urethral orifice starts was defined as LPP. Abdominal compression was repeated more than five times at 1 minute interval. Pre-LPP was set as the average of three LPP scores immediately before compound dosing. 5 ml/kg of Example Compound 20, Example Compound 22b, or Vehicle (13.3% DMSO, 13.3% PEG400, 13.3% Tween20, and 60% distilled water) was dosed via the duodenal cannula, and LPP was measured three times at the following each time point: 5, 15, 30, 45, and 60 minutes after the dosing. Delta LPP was calculated based on the difference from Pre-LPP.

Figure 5:
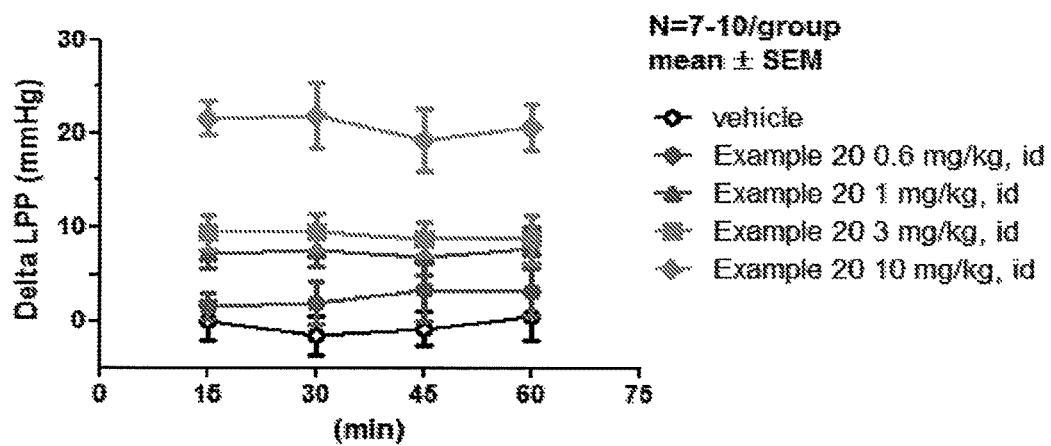
FIG. 5 is a graph showing results obtained by an assay of urine Leak Point Pressure (LPP) under abdominal pressure.
Figure 6:
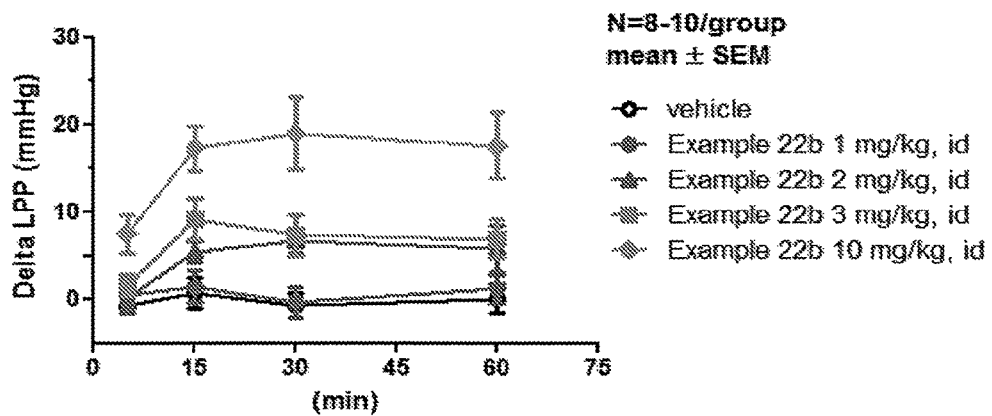
FIG. 6 is a graph showing results obtained by an assay of urine LPP under abdominal pressure.

Increase of LPP. As shown in FIGS. 5 and 6, Example Compound 20 and Example Compound 22b increased LPP in the rat model of urine leakage under abdominal pressure.

Assay Example 7: Preparation and Assay of Basso, Beattie, and Bresnahan (BBB) Score of Post-Spinal Cord Injury (SCI)

Figure 7:
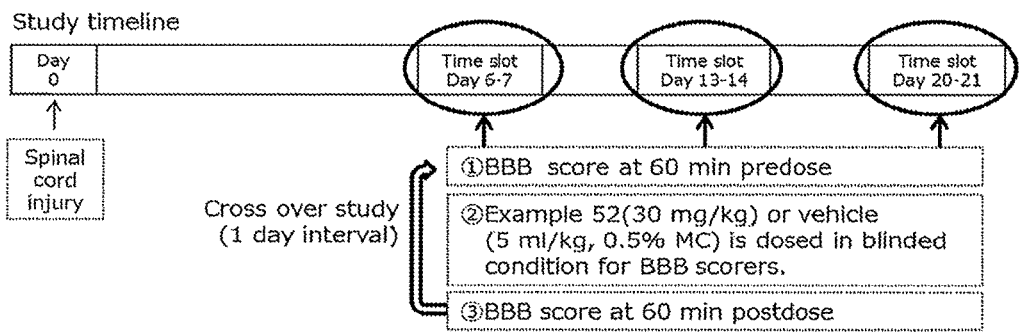
FIG. 7 is a diagram showing study timeline of an assay of Basso, Beattie, and Bresnahan (BBB) score of post-spinal cord injury (SCI).

Preparation of the rat model of post-SCI: The rat model was prepared based on the method of Scheff et. al. (J Neurotrauma. 2003 February; 20(2):179-93.) which uses Infinite Horizon impactor (IH-0400; Precision Systems and Instrumentation). Female SD rats (10 week old) were anesthetized with a mixture of 0.3 mg/kg medetomidine, 4 mg/kg midazoram, and 5 mg/kg butorphanol (s.c.). The dorsal region of the rats was incised and the thoracic spine from T8 to T12 was exposed. Subsequently, laminectomy was performed on T9 and T10. On the stage of IH-0400, the exposed spinal column of the rats was stabilized by clamping with two forceps attached to the joints of IH-0400. Each of the joint and the forceps was tightly locked. Injury of T9 and T10 was induced with a rod impact of 210 kdyn. After dorsal closure, the rats were housed one per cage under the postoperative care which includes the injections of 5 mL saline s.c. and 50 mg/kg Cefamezin s.c twice a day for a week after the SCI, and includes the manual expression of the bladder of the rats twice a day using Crede maneuver until the function of the bladder recovers. At three time slots (day 6-7, day 13-14, and day 20-21 after the SCI), test substance (Example Compound 52 or vehicle) dosing and BBB scoring were performed as shown in FIG. 7. The effect of Example Compound 52 or vehicle was analyzed using unpaired t test (a probability value of less than 0.05 was considered as a significant difference). Data were expressed as the mean±SEM.

Figure 8:
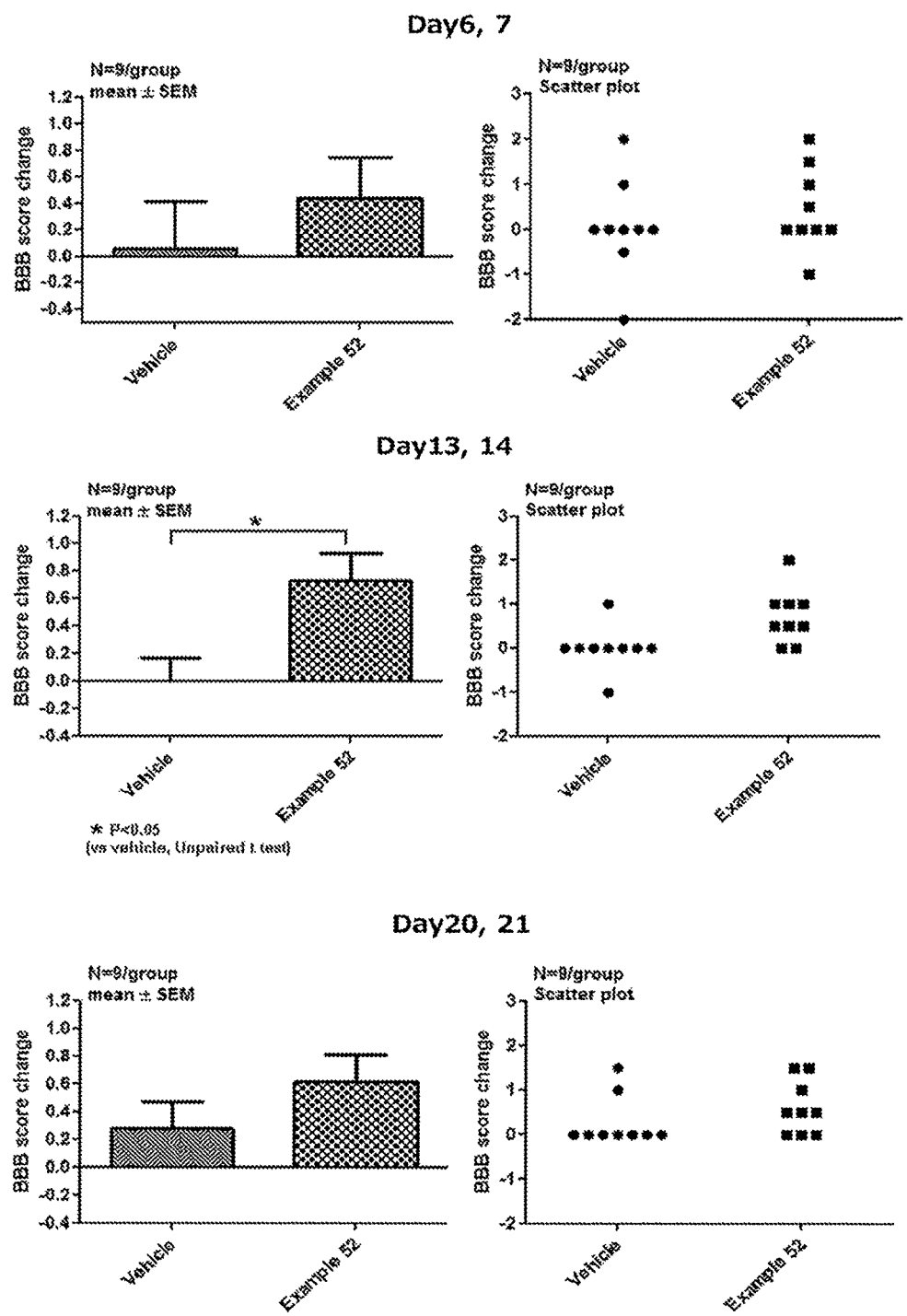
FIG. 8 is graphs showing results obtained by the assay of BBB score of post-SCI.

Increase of BBB score. As shown in FIG. 8, Example Compound 52 increased BBB score in the rat model of post-SCI.

Figure 9:
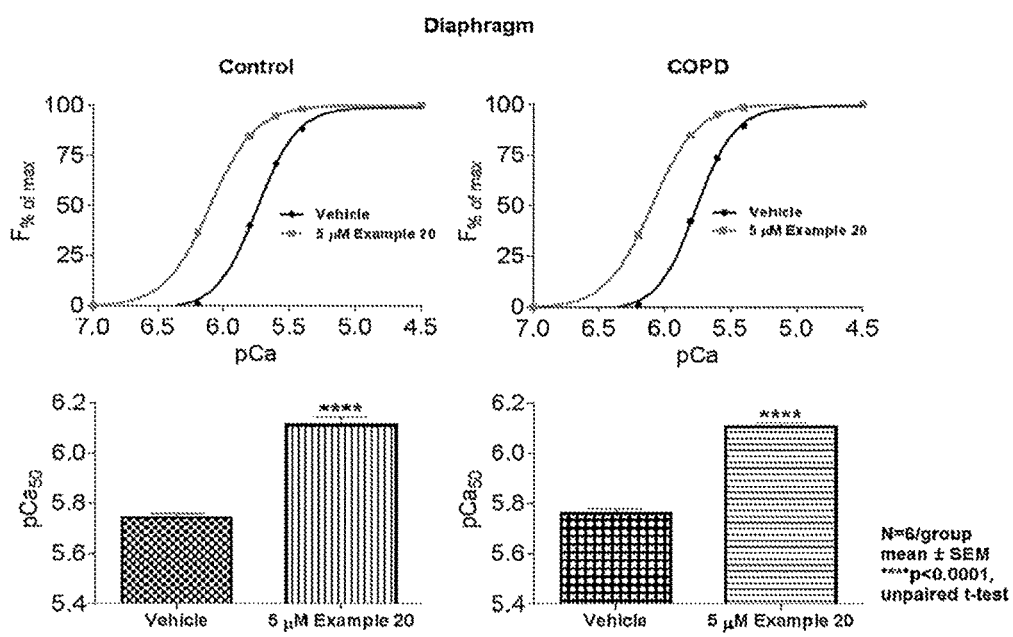
FIG. 9 is graphs showing results obtained by an assay of force-calcium relationship in choronic obstructive pulmonary disease (COPD) diaphragm muscle biopsies.
Figure 10:
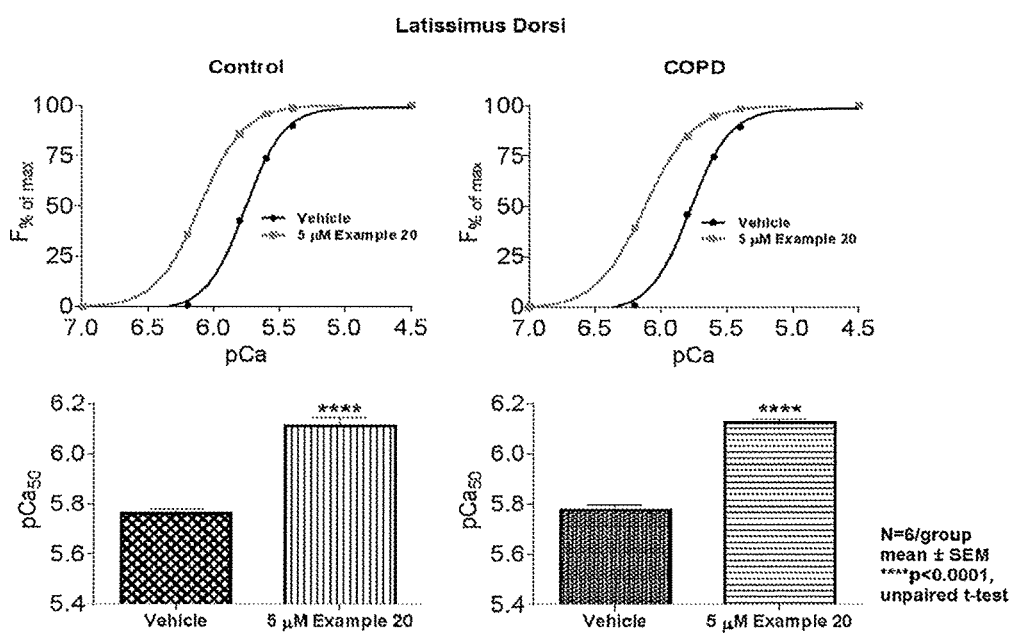
FIG. 10 is graphs showing results obtained by an assay of force-calcium relationship in choronic obstructive pulmonary disease (COPD) latissimus dorsi muscle biopsies.

Assay Example 8: Preparation and Assay of Force-Calcium Relationship in Chronic Obstructive Pulmonary Disease (COPD) Muscle Biopsies Diaphragm and latissimus dorsi biopsy specimens were obtained from control and COPD patients whom underwent a thoracotomy for removal of a primary lung tumor. All COPD patients were classified as having moderate or severe disease according to GOLD classification. A part of the fresh biopsy was placed for 24 hours at −20° C. In 4 mL relax-glycerol solution (5.89 mM $Na_2ATP$, 6.48 mM $MgCl_2$, 40.76 mM Kprop, 100 mM BES, 6.97 mM EGTA, 14.50 mM CrP) containing high concentrations of protease inhibitors (1.0 mM DTT, 0.24 mM PMSF, 0.4 mM leupeptin, 0.1 mM E64). Segments of single fibers of approximately 1-1.5 mm were subsequently isolated in a relaxing solution at 5° C. At both ends, two aluminium clips were attached. Myofibers were incubated for 10 minutes in cold (5° C.) skinning solution (relax solutions with 1% Triton X-100, 1.0 mM DTT, 0.24 mM PMSF, 0.04 mM leupeptin, 0.01 mM E64) to permeabilize the plasma membrane enabling activation of myofilaments with exogenous calcium. Subsequently, the myofibers were mounted horizontally on two stainless-steel hooks in a relax solution filled chamber (200 μL) with a glass coverslip bottom on the stage of an inverted microscope (Zeiss, The Netherlands). One hook was attached to a force transducer (model 403A Aurora Scientific Inc, Ontario, Canada) with a resonance frequency of 10 kHz, whereas the other end was attached to a servo-motor (model 315C, Aurora Scientific Inc.; Aurora, Ontario, Canada) with a step time of 250 μs. Fiber dimensions were measured by means of a camera device coupled to the objective. Fiber length was determined with 100× magnification, depth and width were measured at the widest part of the cell with 400× magnification (an elliptical cross section of the myofiber was assumed). Fibers were stretched to optimal length by setting sarcomere length at 2.5 μm with dedicated Aurora software. To ensure stable attachment of the fiber in the clips throughout the mechanical protocol, the myofiber was briefly maximally activated prior to the experiment, and when necessary restretched to a sarcomere length of 2.5 μm. Single myofibers were transferred from relax to pre-, sub- and maximal activating solutions (5.97 mM Na2ATP, 7.0 mM CaEGTA, 6.28 mM MgCl, 40.64 mM Kprop, 100 mM BES and 14.50 mM CrP with pCa ranging from 4.5 to 9) by means of an automated bath controller device. During the experiment, data were automatically collected by a data acquisition board (sampling rate 10000 Hz). All measurements were performed at 20° C. Fibers were activated with solutions containing incremental calcium concentrations with vehicle (1% DMSO) or 5 μM of Example Compound 20 and the resulting force was recorded. At least five fast-twitch fibers per subject were analysed. The obtained force-pCa data were fit to the Hill equation, providing the pCa50. 5 μM of Example Compound 20 increased the sensitivity of force to calcium in both control and COPD diaphragms (control: 5.74±0.02 vs 6.11±0.03; COPD: 5.76±0.02 vs. 6.11±0.02, mean±SEM, n=6/group, p<0.0001). 5 μM of Example Compound 20 increased the sensitivity of force to calcium in both control and COPD latissimus dorsi (control: 5.76±0.02 vs 6.11±0.03; COPD: 5.78±0.02 vs. 6.13±0.02, mean±SEM, n=6/group, p<0.0001). The force-pCA data are summarized in FIGS. 9 and 10. Significance is defined as *p<0.05 vs. vehicle treatment.

The compounds of the formula (I) or the formula (I'), or a salt thereof modulate the contractility of the skeletal sarcomere, and thus are expected to be used as an agent for preventing or treating 1) neuromuscular disorders, 2) disorders of voluntary muscle, 3) CNS disorders in which muscle weakness, atrophy, and fatigue are prominent symptoms, 4) muscle symptoms stemming from systemic disorders, and 5) dysfunctions of pelvic floor and urethral/anal sphincter muscle.

In an embodiment of the present invention, the compounds and compositions described and/or disclosed herein are expected to be used to treat neuromuscular diseases, i.e., diseases that affect any part of the nerve-muscle unit. Neuromuscular diseases include, for example: 1) diseases of the motor unit, including but not limited to Amyotrophic Lateral Sclerosis (ALS) including bulbar and primary lateral sclerosis (PLS) variants; Spinal Muscular Atrophy (SMA) types 1-4; Kennedy syndrome; post-polio syndrome; motor neuropathies including, for example, critical illness polyneuropathy; multifocal motor neuropathy with conduction block; Charcot-Marie-Tooth disease and other hereditary motor and sensory neuropathies; and Guillain-Barre syndrome, 2) disorders of the neuromuscular junction, including myasthenia gravis, Lambert-Eaton myasthenic syndrome, and prolonged neuromuscular blockade due to drugs or toxins; and 3) peripheral neuropathies, such as acute inflammatory demyelinating polyradiculoneuropathy, diabetic neuropathy, chronic inflammatory demyelinating polyradiculoneuropathy, traumatic peripheral nerve lesions, neuropathy of leprosy, vasculitic neuropathy, dermatomyositis/polymyositis, and neuropathy of Friedreich ataxia.

In another embodiment of the present invention, the compounds and compositions described and/or disclosed herein are expected to be used to treat disorders of voluntary muscle. Disorders of voluntary muscle include 1) muscular dystrophies (including, for example, Duchenne, Becker, Limb-Girdle, facioscapulohumeral, Emery-Dreyfus, oculopharyngeal, and congenital muscular dystrophies); and 2) myopathies, such as nemaline myopathy, central core disease, congenital myopathies, mitochondrial myopathies, acute myopathy; inflammatory myopathies (such as dermatomyositis/polymyositis and inclusion body myositis), endocrine myopathies (such as those associated with hyper- or hypothyroidism), Cushing's or Addison's syndrome or disease and pituitary gland disorders, metabolic myopathies (such as glycogen storage diseases, e.g., McArdle's disease, Pompe disease, etc.), drug-induced myopathy (statins, antretroviral drugs, and steroid myopathy) restrictive lung disease, sarcoidosis, Schwartz-Jampel Syndrome, focal muscular atrophies, and distal myopathies.

In a specific embodiment, the compounds and compositions described and/or disclosed herein are expected to be used to treat Amyotrophic Lateral Sclerosis (ALS). ALS is a disease that generally arises later in life (Age 50+) and has a rapid progression from initial limb weakness to paralysis and death. Common life expectancy after diagnosis is 3-5 years. The cause of disease for most ALS patients is unknown (termed the spontaneous form) while a small proportion of patients have an inherited form (familial) of disease. The condition causes progressive death of motor neurons through causes that are not clear. Surviving motor units attempt to compensate for dying ones by innervating more fibers (termed sprouting) but this can only partially correct muscle function, as muscles are subsequently more prone to problems of coordination and fatigue. Eventually, surviving motor neurons die, resulting in complete paralysis of the affected muscle. The disease is commonly fatal through the eventual loss of innervation to the diaphragm, resulting in respiratory failure. Current treatment options for ALS are limited.

In another specific embodiment, the compounds and compositions described and/or disclosed herein are expected to be used to treat Spinal Muscular Atrophy (SMA). SMA is a genetic disorder that arises through the mutation of a protein, survival motor neuron 1 (SMN1) that appears to be required for the survival and health of motor neurons. The disease is most common in children as the majority of patients only survive until 11-12 years of age. There is currently no available treatment for SMA.

In another specific embodiment, the compounds and compositions described and/or disclosed herein are expected to be used to treat myasthenia gravis. Myasthenia gravis is a chronic autoimmune neuromuscular disease wherein the body produces antibodies that block, alter, or destroy proteins involved in signaling at the neuromuscular junction, thus preventing muscle contraction from occurring. These proteins include nicotinic acetylcholine receptor (AChR) or, less frequently, a muscle-specific tyrosine kinase (MuSK) involved in AChR clustering (see, e.g., Drachman, N. Eng. J. of Med., 330:1797-1810, 1994). The disease is characterized by varying degrees of weakness of the skeletal (voluntary) muscles of the body. The hallmark of myasthenia gravis is muscle weakness that increases during periods of activity and improves after periods of rest. Although myasthenia gravis may affect any voluntary muscle, certain muscles, such as those that control eye and eyelid movement, facial expression, chewing, talking, and swallowing are often, but not always, involved in the disorder. The muscles that control breathing and neck and limb movements may also be affected. In most cases, the first noticeable symptom is weakness of the eye muscles. In others, difficulty in swallowing and slurred speech may be the first signs. The degree of muscle weakness involved in myasthenia gravis varies greatly among patients, ranging from a localized form, limited to eye muscles (ocular myasthenia), to a severe or generalized form in which many muscles—sometimes including those that control breathing—are affected. Symptoms, which vary in type and severity, may include a drooping of one or both eyelids (ptosis), blurred or double vision (diplopia) due to weakness of the muscles that control eye movements, unstable or waddling gait, weakness in arms, hands, fingers, legs, and neck, a change in facial expression, difficulty in swallowing and shortness of breath, and impaired speech (dysarthria). Generalized weakness develops in approximately 85% of patients.

In further embodiments, the compounds and compositions described and/or disclosed herein are expected to be used to treat sarcopenia, e.g., sarcopenia associated with aging or disease (e.g., HTV infection). Sarcopenia is characterized by a loss of skeletal muscle mass, quality, and strength. Clinically, a decline in skeletal muscle tissue mass (muscle atrophy) contributes to frailty in older individuals. In human males, muscle mass declines by one-third between the ages of 50 and 80. In older adults, extended hospitalization can result in further disuse atrophy leading to a potential loss of the ability for independent living and to a cascade of physical decline. Moreover, the physical aging process profoundly affects body composition, including significant reductions in lean body mass and increases in central adiposity. The changes in overall adiposity and fat distribution appear to be important factors in many common age-related diseases such as hypertension, glucose intolerance and diabetes, dyslipidemia, and atherosclerotic cardiovascular disease. In addition, it is possible that the age-associated decrement in muscle mass, and subsequently in strength and endurance, may be a critical determinant for functional loss, dependence and disability. Muscle weakness is also a major factor predisposing the elderly to falls and the resulting morbidity and mortality.

The compounds and compositions described and/or disclosed herein are expected to be used to treat cachexia. Cachexia is a state often associated with cancer or other serious diseases or conditions, (e.g., chronic obstructive pulmonary disease (COPD), heart failure, chronic kidney disease, and kidney dialysis), that is characterized by progressive weight loss, muscle atrophy and fatigue, due to the loss of adipose tissue and skeletal muscle.

The compounds and compositions described and/or disclosed herein are expected to be used to treat muscular dystrophies. Muscular dystrophy can be characterized by progressive muscle weakness, destruction and regeneration of the muscle fibers and eventual replacement of the muscle fibers by fibrous and fatty connective tissue.

The compounds and compositions described and/or disclosed herein are expected to be used to treat post-surgical muscle weakness, which is a reduction in the strength of one or more muscles following surgical procedure. Weakness may be generalized (i.e., total body weakness) or localized to a specific area, side of the body, limb, or muscle.

The compounds and compositions described and/or disclosed herein are expected to be used to treat post-traumatic muscle weakness, which is a reduction in the strength of one or more muscles following a traumatic episode (e.g., bodily injury). Weakness may be generalized (i.e., total body weakness) or localized to a specific area, side of the body, limb, or muscle.

The compounds and compositions described and/or disclosed herein are expected to be used to treat muscle weakness and fatigue produced by peripheral vascular disease (PVD) or peripheral artery disease (PAD). Peripheral vascular disease is a disease or disorder of the circulatory system outside of the brain and heart. Peripheral artery disease (PAD), also known as peripheral artery occlusive disease (PAOD), is a form of PVD in which there is partial or total blockage of an artery, usually one leading to a leg or arm. PVD and/or PAD can result from, for example, atherosclerosis, inflammatory processes leading to stenosis, embolus/thrombus formation, or damage to blood vessels due to disease (e.g., diabetes), infection or injury. PVD and/or PAD can cause either acute or chronic ischemia, typically of the legs. The symptoms of PVD and/or PAD include pain, weakness, numbness, or cramping in muscles due to decreased blood flow (claudication), muscle pain, ache, cramp, numbness or fatigue that occurs during exercise and is relieved by a short period of rest (intermittent claudication), pain while resting (rest pain) and biological tissue loss (gangrene). The symptoms of PVD and/or PAD often occur in calf muscles, but symptoms may also be observed in other muscles such as the thigh or hip. Risk factors for PVD and/or PAD include age, obesity, sedentary lifestyle, smoking, diabetes, high blood pressure, and high cholesterol (i.e., high LDL, and/or high triglycerides and/or low HDL). People who have coronary heart disease or a history of heart attack or stroke generally also have an increased frequency of having PVD and/or PAD. Activators of the fast skeletal troponin complex have been shown to reduce muscle fatigue and/or to increase the overall time to fatigue in in vitro and in situ models of vascular insufficiency (see, e.g., Russell et al., "The Fast Skeletal Troponin Activator, CK-2017357, Increases Skeletal Muscle Force and Reduces Muscle Fatigue in vitro and in situ", 5th Cachexia Conference, Barcelona, Spain, December 2009; Hinken et al., "The Fast Skeletal Troponin Activator, CK-2017357, Reduces Muscle Fatigue in an in situ Model of Vascular Insufficiency", Society for Vascular Medicine's 2010 Annual Meeting: 21st Annual Scientific Sessions, Cleveland, Ohio, April 2010).

The compounds and compositions described and/or disclosed herein are expected to be used to treat symptoms of frailty, e.g., frailty associated with aging which has been shown to affect motor unit depletion and muscle power (McComas, Journal of Electromyography and Kinesiology Vol. 8, 391-402, 1998). Frailty is characterized by one or more of unintentional weight loss, muscle weakness, slow walking speed, exhaustion, and low physical activity.

The compounds and compositions described and/or disclosed herein are expected to be used to treat muscle weakness and/or fatigue due to wasting syndrome, which is a condition characterized by involuntary weight loss associated with chronic fever and diarrhea. In some instances, patients with wasting syndrome lose 10% of baseline body weight within one month.

The compounds and compositions described and/or disclosed herein are expected to be used to treat muscular diseases and conditions caused by structural and/or functional abnormalities of skeletal muscle tissue, including muscular dystrophies, congenital muscular dystrophies, congenital myopathies, distal myopathies, other myopathies (e.g., myofibrillar, inclusion body), myotonic syndromes, ion channel muscle diseases, malignant hyperthermias, metabolic myopathies, congenital myasthenic syndromes, sarcopenia, muscle atrophy, and cachexia.

The compounds and compositions described and/or disclosed herein are also expected to be used to treat diseases and conditions caused by muscle dysfunction originating from neuronal dysfunction or transmission, including amyotrophic lateral sclerosis, spinal muscular atrophies, hereditary ataxias, hereditary motor and sensory neuropathies, hereditary paraplegias, stroke, multiple sclerosis, brain injuries with motor deficits, spinal cord injuries, Alzheimer's disease, Parkinson's disease with motor deficits, myasthenia gravis, and Lambert-Eaton syndrome.

The compounds and compositions described and/or disclosed herein are also expected to be used to treat diseases and conditions caused by CNS, spinal cord or muscle dysfunction originating from endocrine and/or metabolic dysregulation, including claudication secondary to peripheral artery disease, hypothyroidism, hyper- or hypo-parathyroidism, diabetes, adrenal dysfunction, pituitary dysfunction, and acid/base imbalances.

The compounds and compositions described and/or disclosed herein are also expected to be used to treat diseases and conditions caused by dysfunctions of pelvic floor and urethral/anal sphincter muscles including urinary incontinence such as stress urinary incontinence (SIM) and mixed urinary incontinence (WI), and fecal incontinence (Bharucha et. al., Am. J. Gastroenterol., Vol. 110, 127-36 (2015)).

The compounds and compositions described and/or disclosed herein are also expected to be used in combination with one or more electrical muscle stimulation (EMS) devices to treat Stress urinary incontinence, Mixed urinary incontinence, and Fecal incontinence. Examples of EMS devices include InterStim II® (Sacral nerve stimulator; Medtronic; sacral nerve controls urethral sphincter, anal sphincter, and pelvic floor muscle) and Uromaster® (Interferential low-frequency stimulation to urethral sphincter, anal sphincter, and pelvic floor muscle; Nihon Medix Co.). The combined effect of the compounds of the present invention and EMS to urethral sphincter, anal sphincter, and pelvic floor muscle is relieved by the results of Example 2 of WO2016/039367 or Assay Example 5 of this specification (Preparation and assay of anal pressure induced by electrical stimulation of pudendal nerve).

The compounds and compositions described and/or disclosed herein are also expected to be used in combination with one or more electrical muscle stimulation (EMS) devices to treat post-stroke muscle dysfunction, post-spinal cord injury (SCI) muscle dysfunction, and rehabilitation-related deficits. Examples of EMS devices include NESS L300® (Limb muscle stimulator; Bioness Inc.), NESS L300® Plus (Limb muscle stimulator; Bioness Inc.), NESS H200® (Limb muscle stimulator; Bioness Inc.), IVES® (Limb muscle stimulator; OG Wellness Technologies Co., Ltd), WalkAide® (Limb muscle stimulator; Innovative Neurotronics, Inc.), and NM-F1, (Limb muscle stimulator; ITO PHYSIOTHERAPY&REHABILITATION). The combined effect of the compounds of the present invention and EMS to limb muscle is relieved by the results of Assay Example 2 of this specification (Preparation and assay of rat isometric ankle plantarflexor muscle force) or from the findings of the study described in Muscle Nerve. 2014 December; 50(6): 925-31.

The compounds and compositions described and/or disclosed herein are also expected to be used in combination with one or more electrical muscle stimulation (EMS) devices to treat diaphragm dysfunctions of Amyotrophic lateral sclerosis (ALS) and post-spinal cord injury (SCI).

Examples of EMS devices include NeuRx Diaphragm Pacing System (DPS)® (Diaphragm muscle stimulator; SYNAPSE Biomedical Inc.). The combined effect of the compounds of the present invention and EMS to the diaphragm is relieved from the findings of the study described in PLoS One. 2014; 9(5): e96921.

The compounds and compositions described and/or disclosed herein may be administered alone or in combination with other therapies and/or therapeutic agents useful in the treatment of the aforementioned disorders.

A pharmaceutical composition including one or two or more kinds of the compound of the formula (I) or the formula (I') as an active ingredient can be prepared using an excipient which is usually used in the art, that is, an excipient for a pharmaceutical preparation, a carrier for a pharmaceutical preparation, and the like, according to a method usually used.

A pharmaceutical composition provided herein may comprise one or more of the compounds of the formula (I) or the formula (I') or any embodiment thereof, including, without limitation, any of Embodiments 1-1 through 8-4 and any of Embodiments (1)-(57). A pharmaceutical composition may comprise a single enantiomer of any of the compounds of the formula (I) or the formula (I') contained thereof, or a single diastereomer of any of the compounds of the formula (I) or the formula (I') contained thereof, or a mixture of enantiomers or diastereomers of any of the compounds of the formula (T) or the formula (I') contained thereof in any ratio.

Administration can be accomplished either by oral administration via tablets, pills, capsules, granules, powders, solutions, and the like, or parenteral administration via injections, such as intra-articular, intravenous, and intramuscular injections, suppositories, transdermal liquid preparations, ointments, transdermal patches, transmucosal liquid preparations, transmucosal patches, inhalers, and the like.

As a solid composition for oral administration, tablets, powders, granules, and the like are used. In such a solid composition, one kind or two or more kinds of the active ingredients are mixed with at least one inactive excipient. In a conventional method, the composition may contain inactive additives such as a lubricant, a disintegrating agent, a stabilizer, or a solubilization assisting agent. If necessary, tablets or pills may be coated with a sugar or with a film of a gastric or enteric coating substance.

The liquid composition for oral administration includes pharmaceutically acceptable emulsions, solutions, suspensions, syrups, elixirs, or the like, and also includes generally used inert diluents, for example, purified water or ethanol. The liquid composition may also include auxiliary agents such as a solubilization assisting agent, a moistening agent, and a suspending agent, sweeteners, flavors, aromatics, and antiseptics, in addition to the inert diluent.

The injections for parenteral administration include sterile aqueous or non-aqueous solution preparations, suspensions, or emulsions. The aqueous solvent includes, for example, distilled water for injection and saline. Examples of the non-aqueous solvent include alcohols such as ethanol. Such a composition may further include a tonicity agent, an antiseptic, a moistening agent, an emulsifying agent, a dispersing agent, a stabilizing agent, or a solubilizing assisting agent. These are sterilized, for example, by filtration through a bacteria retaining filter, blending of a bactericide, or irradiation. In addition, these can also be used by preparing a sterile solid composition, and dissolving or suspending it in sterile water or a sterile solvent for injection prior to its use.

Examples of the agent for external use include ointments, hard plasters, creams, jellies, cataplasms, sprays, and lotions. The agent further contains generally used ointment bases, lotion bases, aqueous or non-aqueous liquid preparations, suspensions, emulsions, or the like.

As the transmucosal agents such as an inhaler and a transnasal agent, those in the form of a solid, liquid, or semi-solid state are used, and can be prepared in accordance with a method known in the related art. For example, a known excipient, and also a pH adjusting agent, an antiseptic, a surfactant, a lubricant, a stabilizing agent, a thickening agent, or the like may be appropriately added thereto. For the administration, an appropriate device for inhalation or blowing can be used. For example, a compound may be administered alone or as a powder of formulated mixture, or as a solution or suspension in combination with a pharmaceutically acceptable carrier, using a known device or sprayer such as a metered administration inhalation device. A dry powder inhaler or the like may be for single or multiple administration use, and a dry powder or a powder-containing capsule may be used. Alternatively, this may be in a form such as a pressurized aerosol spray that uses an appropriate propellant agent, for example, a suitable gas such as chlorofluoroalkanes, and carbon dioxide, or other forms.

Usually, in the case of oral administration, the daily dose is from about 0.001 mg/kg to 100 mg/kg, preferably from 0.1 mg/kg to 30 mg/kg, and more preferably from 0.1 mg/kg to 10 mg/kg, per body weight, administered in one portion or in 2 to 4 divided portions. In the case of intravenous administration, the daily dose is suitably administered from about 0.0001 mg/kg to 10 mg/kg per body weight, once a day or two or more times a day. In addition, a transmucosal agent is administered at a dose from about 0.001 mg/kg to 100 mg/kg per body weight, once or plural times a day. The dose is appropriately decided in response to the individual case by taking the symptoms, the age, and the gender, and the like into consideration.

Although there are differences depending on a route of administration, a dosage form, an administration site, and a type of the excipient or additive, a pharmaceutical composition of the invention comprises 0.01% by weight to 100% by weight of, as an embodiment, 0.01% by weight to 50% by weight of, one or more of the compound of the formula (I) or the formula (I'), or a salt thereof which is the active ingredient.

The compound of the formula (I) or the formula (I') may be used in combination with various agents for treating or preventing diseases on which the compound of the formula (I) or the formula (I') is considered to show the effect. Such combined preparations may be administered simultaneously, or separately and continuously, or at a desired time interval. The preparations to be co-administered may be a blend, or may be prepared individually.

Other features of the invention will become apparent in the course of the following descriptions of exemplary embodiments which are given for illustration of the invention and are not intended to be limiting thereof.

EXAMPLES

Herein below, the production process for the compound of the formula (I) or the formula (I') will be described in more detail with reference to Examples. Further, the invention is not limited to the compounds described in the Examples below. Further, the production processes for the starting compounds will be described in Preparation Examples. In addition, the production processess for the compound of the formula (I) or the formula (I') are not limited to the production processes of the specific Examples shown below, but the compound of the formula (I) or the formula (I') can be prepared by a combination of these production processess or a method that is apparent to a person skilled in the art.

Further, in the specification, nomenclature software such as ACD/Name (registered trademark, Advanced Chemistry Development, Inc.) may be used for nomenclature of compounds in some cases.

Moreover, the following abbreviations may be used in Examples, Preparation Examples, and Tables below in some cases. For instance, "Str" means Structural chemical formula ("Me" represents methyl, "Et" represents ethyl, "Ac" represents acetyl, "n-Bu" represents n-butyl, "tBu" or "t-Bu" represents tert-butyl, "cHex" represents cyclohexyl, "Ph" represents phenyl, "Bz" represents benzyl, "SEM" represents [2-(trimethylsilyl)ethoxy]methyl, "TBDMS" represents tert-butyldimethylsilyl, "TMS" represents trimethylsilyl, "Boc" represents tert-butoxy carbonyl), "EtOAc" represents ethyl acetate, "DMAc" represents N,N-dimethylacetamide, "tBuOH" represents tert-butyl alcohol, "IPE" represents diisopropyl ether, "DMI" represents 1,3-dimethylimidazolidin-2-one, "DMF" represents N,N-dimethylformamide, "THF" represents tetrahydrofuran, "MeCN" represents acetonitrile, "NMP" represents 1-methylpyrrolidin-2-one, "DCE" represents 1,2-dichloroethane, "TFA" represents trifluoroacetic acid, "WSC/HCl" represents N-[3-(dimethylamino)propyl]-N'-ethylcarbodiimide hydrochloride, "HOBt" represents 1H-benzotriazol-1-ol, "TBAF" represents tetrabutylammonium fluoride, "$Pd_2(dba)_3$" represents tris(dibenzylideneacetone)dipalladium, "NaH-MDS" represents sodium bis(trimethylsilyl)amide, "n-BuLi" represents n-butyllithium, "KOtBu" represents potassium tert-butoxide, "EtOH" represents ethanol, "$Et_2O$" represents diethyl ether, "DMSO" represents dimethyl sulfoxide, "KOAc" represents potassium acetate, "Mer" represents methyl iodide and "DIPEA" represents N,N-diisopropylethylamine, "min" represents minutes, "sat.' represents saturated, "aq." represents aqueous, "Ar" represents Argon, "HPLC" means high performance liquid chromatography, "DAT" means physicochemical data, "NMR" means nuclear magnetic resonance, "ESI+" means m/z values in mass spectroscopy (electrospray ionization method ESI, representing $[M+H]^+$ unless otherwise specified), "APCI/ESI+" means APCI/ESI-MS (atmospheric pressure chemical ionization method APCI, representing $[M+H]^+$ unless otherwise specified; in which APCI/ESI means simultaneous measurement of APCI and ESI), "APCI" means m/z values in mass spectroscopy (atmospheric pressure chemical Ionization method APCI, representing $[M+H]^1$ unless otherwise specified), $^1$H-NMR (CDCl$_3$): δ (ppm) of peaks in $^1$H-NMR in CDCl$_3$, $^1$H-NMR (DMSO-d$_6$): δ (ppm) of peaks in $^1$H-NMR in DMSO-d$_6$, $^1$H NMR (CD$_3$OD): δ (ppm) of peaks in $^1$H-NMR in CD$_3$OD, s: singlet (spectrum), d: doublet (spectrum), t: triplet (spectrum), q: quartet (spectrum), br: broad line (spectrum) (e.g.: brs), m: multiplet (spectrum). SFC represents supercritical fluid chromatography. Aminosilica represents amino-functionalized silica gel, such as Chromatorex NH(trademark) and Hi-flash amino(trademark).

The symbol "*" in a chemical structural formula indicates that the corresponding compound is a single optical isomer. The symbol "#" indicates that the corresponding compound is a mixture of isomers which have (R) and (S) configurations, respectively, in an asymmetric atom with the steric configuration not indicated (racemate). The symbol "$" indicates that the corresponding compound is a mixture of 4 stereoisomers. Further, HCl in the structural formula indicates that the compound is a monohydrochloride; 2HCl indicates that the compound is a dihydrochloride.

In addition, for the sake of convenience, a concentration of mol/L is represented by M. For example, a 1 M aqueous sodium hydroxide solution means a 1 mol/L aqueous sodium hydroxide solution.

In the condition of chiral supercritical fluid chromatography (SFC) in Examples 92a and 92b, CHIRALCEL® OZ-H as a column, $CO_2$:MeOH=80:20 as a mobile phase, were used. In the condition of chiral supercritical fluid chromatography (SFC) in Examples 134a and 134b, ChromegaChiral CC4 as a column, $CO_2$:EtOH with 0.5% isopropylamine=85:15 as a mobile phase, were used.

The result of powder X-ray diffraction in the present invention was measured by using RINT-TTRII under the conditions of tube: Cu, tube current: 300 mA, tube voltage: 50 kV, sampling width: 0.020°, scanning speed: 4°/min, wavelength: 1.54184 Å, and measurement diffraction angle range (2θ): 2.5° to 40°.

Preparation Example 1 (1a and 1b)

To a solid of $P_2O_5$ (50.0 g) was added $H_3PO_4$ (50.6 g), and the mixture was stirred at 140° C. for 1.5 hours. To the mixture were added 2-(3-bromophenyl)acetamide (5.00 g) and acetone (3.5 mL) at 80° C., and then stirred at 140° C. for 2 hours. To the mixture was added acetone (2.0 mL) at 140° C., and stirred at the same temperature for 1 hour. And then, to the mixture was added acetone (2.0 mL) at 140° C. again, and stirred at the same temperature for additional 1 hour. The mixture was poured into iced water, and diluted with EtOAc, and the phases were separated. The organic layer was washed with sat. aq. NaHCO$_3$ and brine, and dried over Na$_2$SO$_4$, filtered, and concentrated under reduced pressure. The residue was purified by silica gel column chromatography (CHCl$_3$/MeOH). The obtained solid was washed with 50% EtOAc/hexanes to give 6-bromo-1,1-dimethyl-1,4-dihydroisoquinolin-3(2H)-one (2.01 g) as a solid. The mother liquid was concentrated under reduced pressure to give the 1:1 mixture of 6-bromo-1,1-dimethyl-1,4-dihydroisoquinolin-3(2H)-one and 8-bromo-1,1-dimethyl-1,4-dihydroisoquinolin-3(2H)-one (996 mg) as a solid.

Preparation Example 2

A mixture of 6-bromo-1,1-dimethyl-1,4-dihydroisoquinolin-3(2H)-one (100 mg), N-bromosuccinimide (72 mg), 3-chloroperbenzoic acid (7 mg), and CCl$_4$ (3 mL) was refluxed for 3 hours. And then, the mixture was cooled to room temperature, filtered, and concentrated under reduced pressure. The residue was purified by silica gel column chromatography (EtOAc/hexanes) to give 4,6-dibromo-1,1-dimethyl-1,4-dihydroisoquinolin-3(2H)-one (75 mg) as a solid.

Preparation Example 3

To a mixture of 2-(3-bromophenyl)butanoic acid (582 mg) and MeCN (10 mL) were added WSC/HCl (551 mg) and HOBt (389 mg) under Ar atmosphere, and the mixture was stirred at room temperature for 1 hour. To the mixture was added 28% aq. ammonia (0.8 mL) under ice bath cooling dropwise over 5 min. Then the mixture was stirred at room temperature for 13 hours. The mixture was concentrated under reduced pressure, diluted with H$_2$O and stirred under ice bath cooling for 1 hour. The precipitate was collected to give the crude product as a solid. The obtained solid was purified by silica gel column chromatography (EtOAc/CHCl$_3$) to give 2-(3-bromophenyl)butanamide (427 mg) as a solid.

Preparation Example 4

A mixture of 1-(2,6-dichloropyridin-3-yl)ethan-1-one (78.8 g), CH$_2$Cl$_2$ (300 mL), 2-methylpropane-2-sulfinamide (60.6 g), and titanium tetraethoxide (284.4 g) was stirred at 50° C. overnight. Additional titanium tetraethoxide (50.0 g) was added, and the mixture was stirred at 50° C. for 4 hours. The mixture was cooled to room temperature and then aq. NaHCO$_3$ was slowly added. The mixture was then filtered through a pad of Celite, and the Celite pad was washed with CH$_2$Cl$_2$. The filtrate was concentrated, suspended in EtOAc, and then washed with sat. aq. NaHCO$_3$. The organic layer was dried over Na$_2$SO$_4$, concentrated, and then purified by silica gel column chromatography (EtOAc/hexanes) to give N-[1-(2,6-dichloropyridin-3-yl)ethylidene]-2-methylpropane-2-sulfinamide (63.9 g) as an oil.

Preparation Example 5

To a mixture of N-[1-(2,6-dichloropyridin-3-yl)ethylidene]-2-methylpropane-2-sulfinamide (130.5 g) and THF (300 mL) was slowly added allyl magnesium bromide (1 M in Et$_2$O, 447 mL) at −78° C. The mixture was stirred at −78° C. for 2 hours, followed by the slow addition of a sat. aq. NaHCO$_3$ (600 mL). The mixture was warmed to room temperature and filtered through a pad of Celite. The Celite was washed with EtOAc. The filtrate was washed with sat. aq. NaHCO$_3$ (100 mL) three times. The organic layer was dried over Na$_2$SO$_4$ and then concentrated to give N-[2-(2,6-dichloropyridin-3-yl)pent-4-en-2-yl]-2-methylpropane-2-sulfinamide (134.8 g) as an oil.

Preparation Example 6

To a mixture of 5-chloro-2,3-difluoropyridine (9.0 g), isobutyronitrile (4.2 g), and toluene (120 mL) was added NaHMDS (2 M in THF, 30.6 mL) at −78° C. The mixture was then stirred for 1 hour. The mixture was diluted with sat. aq. NH$_4$Cl (50 mL) and warmed to room temperature. The mixture was then diluted with EtOAc (300 mL), washed with water (100 mL), brine (100 mL), dried over Na$_2$SO$_4$, concentrated, and then purified by silica gel column chromatography (EtOAc/hexanes) to give 2-(5-chloro-3-fluoropyridin-2-yl)-2-methylpropanenitrile (10.6 g) as a solid.

Preparation Example 7

A mixture of 2-(2,6-dichloropyridin-3-yl)-2-methylpropanenitrile (10.00 g) and sulfuric acid (100 mL) was stirred at room temperature for 12 hours. The mixture was poured into iced water and the mixture was basified with 28% aq. ammonia. EtOAc and H$_2$O were added to the mixture, and the phases were separated. Aqueous layer was extracted with EtOAc, and combined organic layers were washed with brine, and dried over Na$_2$SO$_4$, filtered, and concentrated under reduced pressure to give 2-(2,6-dichloropyridin-3-yl)-2-methylpropanamide (10.76 g) as a solid.

Preparation Example 8

To a mixture of 2-(2,6-dichloropyridin-3-yl)-2-methylpropanamide (10.76 g), MeCN (220 mL), and H$_2$O (110 ml) was added [bis(trifluoroacetoxy)iodo]benzene (22.00 g) at room temperature. Then the mixture was stirred at room temperature for 24 hours. The mixture was diluted with sat. aq. NaHCO$_3$. EtOAc and H$_2$O were added to the mixture, and the phases were separated. Aqueous layer was extracted with EtOAc, and combined organic layers were extracted with 1M aq. HCl. Aqueous layer was basified with aq. NaHCO$_3$, and extracted with EtOAc, and combined organic layers were washed with brine, and dried over Na$_2$SO$_4$, filtered, and concentrated under reduced pressure to give 2-(2,6-dichloropyridin-3-yl)propan-2-amine (9.40 g) as an oil.

Preparation Example 9

To a mixture of 2-(2,6-dichloropyridin-3-yl)propan-2-amine (4.40 g) and 2,4-dimethoxybenzaldehyde (3.92 g) and CH$_2$Cl$_2$ (100 mL) was added sodium triacetoxyborohydride (6.80 g) at room temperature. Then the mixture was stirred at the same temperature for 12 hours. CHCl$_3$ and sat. aq. NaHCO$_3$ were added to the mixture, and the phases were separated. Aqueous layer was extracted with CHCl$_3$, and combined organic layers were washed with brine, and dried over Na$_2$SO$_4$, filtered, and concentrated under reduced pressure. The residue was purified by amino-silica gel column chromatography (EtOAc/hexanes) to give 2-(2,6-dichloropyridin-3-yl)-N-(2,4-dimethoxybenzyl)propan-2-amine (7.62 g) as an oil.

Preparation Example 10

To a mixture of 2-(2,6-dichloropyridin-3-yl)-N-(2,4-dimethoxybenzyl)propan-2-amine (7.62 g), 2,6-dimethylpyridine (7.5 mL), and toluene (100 mL) was added a mixture of ethyl 2-(chlorocarbonyl)butanoate (5.55 g) and toluene (20 mL) with ice bath cooling under Ar atmosphere. Then the mixture was stirred at the same temperature for 30 min, and stirred at room temperature for 6 hours. EtOAc and sat. aq. NaHCO$_3$ were added to the mixture, and the phases were separated. Aqueous layer extracted with EtOAc, and combined organic layers were washed with brine, and dried over Na$_2$SO$_4$, filtered, and concentrated under reduced pressure. The residue was purified by amino-silica gel column chromatography (EtOAc/hexanes) to give ethyl 2-{[2-(2,6-dichloropyridin-3-yl)propan-2-yl](2,4-dimethoxybenzyl)carbamoyl}butanoate (9.65 g) as a solid.

Preparation Example 11

To a mixture of tert-butyl 2-{[1-{[tert-butyl(dimethyl)silyl]oxy}-2-(3,5-dichloropyrazin-2-yl)propan-2-yl]carbamoyl}butanoate (1.17 g, 1:1 mixture of all stereoisomers) and anhydrous toluene (10 mL) was added NaHMDS (1 M in toluene, 6.95 mL) dropwise under ice bath cooling. The mixture was stirred at the same temperature for 2 hours. The mixture was diluted with sat. aq. NH$_4$Cl (30 mL), and extracted with EtOAc (2×75 mL). The combined organic extracts were dried over Na$_2$SO$_4$, filtered, and concentrated. The residue was purified by silica gel chromatography (EtOAc/hexanes) to give tert-butyl 5-({[tert-butyl(dimethyl)silyl]oxy}methyl)-2-chloro-8-ethyl-5-methyl-7-oxo-5,6,7,8-tetrahydropyrido[3,4-b]pyrazine-8-carboxylate (457 mg, 3:2 mixture of all stereoisomers) as an oil.

Preparation Example 12

To a mixture of 5,5,8-trimethyl-7-oxo-8-(prop-2-yn-1-yl)-5,6,7,8-tetrahydro-1,6-naphthyridine-2-carbonitrile (40 mg)

and DMSO/H₂O mixture (5:1, 1 mL) were added trimethylsilymethylazide (100 mg), copper (I) sulfate (1 mg), and sodium ascorbate (3 mg). The mixture was stirred at room temperature for 18 hours followed by filtration through a syringe filter. The filtrate was then purified by HPLC (1 to 50% MeCN, 0.1% formic acid) to give 5,5,8-trimethyl-7-oxo-8-({1-[(trimethylsilyl)methyl]-1H-1,2,3-triazol-4-yl}methyl)-5,6,7,8-tetrahydro-1,6-naphthyridine-2-carbonitrile (29 mg) as a solid.

Preparation Example 13

A mixture of 2-(tert-butoxycarbonyl)butanoic acid (14.8 g), thionyl chloride (11.5 mL), CH₂Cl₂ (80 mL), and DMF (4 drops) was stirred at room temperature for 2 hours and then concentrated to give tert-butyl 2-(chlorocarbonyl)butanoate (16.1 g) as an oil.

Preparation Example 14

To a mixture of 2-(5-chloro-3-fluoropyridin-2-yl)-2-methylpropanenitrile (7.5 g), DMSO (75 mL), and K₂CO₃ (7.85 g) was slowly added H₂O₂ (30% aq. solution, 44 mL) under ice bath cooling. The reaction was warmed to room temperature and stirred for 1 hour. The reaction was then diluted with EtOAc (300 mL), washed with H₂O (100 mL), brine (100 mL), dried over Na₂SO₄, and concentrated to give 2-(5-chloro-3-fluoropyridin-2-yl)-2-methylpropanamide (8.2 g) as a solid.

Preparation Example 15

To a mixture of 2,2,6,6-tetramethylpiperidine (45 mL) and THF (350 mL) was added n-BuLi (1.55 M in hexane, 155 mL) with dry ice-acetone bath cooling under Ar atmosphere. Then the mixture was stirred under ice bath cooling for 10 min. To the mixture were added a mixture of 2,6-dichloropyridine (36.96 g) and THF (100 mL) under dry ice-acetone bath cooling over 20 min. Then the mixture was stirred at the same temperature for 1 hour. To the mixture was added a mixture of 2-methyl-N-(oxetan-3-ylidene)propane-2-sulfinamide (35.00 g) and THF (50 mL) at the same temperature over 30 min. Then the mixture was stirred at the same temperature for 1 hour. The mixture was diluted with sat. aq. NH₄Cl (200 mL) at the same temperature. To the mixture was added EtOAc (200 mL), and then organic layer was separated. Aqueous layer was extracted with EtOAc (200 mL), and combined organic layers were washed with brine (200 mL), dried over Na₂SO₄, filtered, and concentrated under reduced pressure. The residue was purified by silica gel column chromatography twice (CHCl₃/EtOAc and EtOAc/hexanes) to give N-[3-(2,6-dichloropyridin-3-yl)oxetan-3-yl]-2-methylpropane-2-sulfinamide (31.58 g) as a foam.

Preparation Example 16

To a mixture of N-[3-(2,6-dichloropyridin-3-yl)oxetan-3-yl]-2-methylpropane-2-sulfinamide (79.29 g) and EtOAc (1.2 L) was added HCl (4 M in EtOAc, 184 mL) at room temperature. Then the mixture was stirred at the same temperature for 1 hour. The precipitate was collected, and washed with EtOAc to give 3-(2,6-dichloropyridin-3-yl)oxetan-3-amine monohydrochloride (59.61 g) as a solid.

Preparation Example 17

A mixture of N-[3-(3,5-dichloropyrazin-2-yl)oxetan-3-yl]-2-methylpropane-2-sulfinamide (1.21 g), 2-(tert-butoxycarbonyl)butanoic acid (847 mg), 2-chloro-1-methyl pyridinium iodide (1.44 g), triethylamine (758 mg), and MeCN (20 mL) was refluxed for 4 hours and partially concentrated (ca 5 mL). The residue was dissolved in EtOAc (30 mL), washed with H₂O, brine, dried over Na₂SO₄, and concentrated. The residue was purified by silica gel chromatography (EtOAc/hexanes) to give tert-butyl 2-{[3-(3,5-dichloropyrazin-2-yl)oxetan-3-yl]carbamoyl}butanoate (951 mg) as a solid.

Preparation Example 18

To a mixture of 2-chloro-8,8-diethyl-6H-spiro[1,6-naphthyridine-5,3'-oxetan]-7(8H)-one (1.70 g) and DMF (45 mL) was added NaH (55% dispersion in mineral oil, 363 mg) under ice bath cooling. Then the mixture was stirred at the same temperature for 10 min. To the mixture was added [2-(chloromethoxy)ethyl](trimethyl)silane (1.20 mL) under ice bath cooling. Then the mixture was stirred at room temperature for 4 hours. Additional NaH (55% dispersion in mineral oil, 368 mg) and [2-(chloromethoxy)ethyl](trimethyl)silane (1.20 mL) were added under ice bath cooling, and the mixture was stirred at room temperature for 1 hour. The mixture was diluted with sat. aq. NH₄Cl. H₂O and EtOAc were added to the mixture, and the phases were separated. Aqueous layer was extracted with EtOAc, and combined organic layers were washed with brine, dried over Na₂SO₄, filtered, and concentrated under reduced pressure. The residue was purified by silica gel column chromatography (EtOAc/hexanes) to give 2-chloro-8,8-diethyl-6-{[2-(trimethylsilyl)ethoxy]methyl}-6H-spiro[1,6-naphthyridine-5,3'-oxetan]-7(8H)-one (1.73 g) as an oil.

Preparation Example 19

To a mixture of 2-chloro-8,8-diethyl-6-{[2-(trimethylsilyl)ethoxy]methyl}-6H-spiro[1,6-naphthyridine-5,3'-oxetan]-7(8H)-one (1.73 g), 1,4-dioxane (35 mL), and H₂O (3.5 mL) were added 2,4,6-trivinylcyclotriboroxane pyridine complex (2.08 g), [1,1'-bis(diphenylphosphino)ferrocene]dichloropalladium(II) (330 mg), and K₂CO₃ (1.76 g). Then the mixture was stirred at 110° C. for 4 hours. The mixture was filtered through a pad of Celite. The organic layer was separated, dried over Na₂SO₄, filtered, and concentrated under reduced pressure. The residue was purified by silica gel column chromatography (EtOAc/hexanes) to give 8,8-diethyl-6-{[2-(trimethylsilyl)ethoxy]methyl}-2-vinyl-6H-spiro[1,6-naphthyridine-5,3'-oxetan]-7(8H)-one (1.37 g) as a gum.

Preparation Example 20

To a mixture of 8,8-diethyl-6-{[2-(trimethylsilyl)ethoxy]methyl}-2-vinyl-6H-spiro[1,6-naphthyridine-5,3'-oxetan]-7(8H)-one (1.37 g), THF (72 mL), and H₂O (18 mL) was added OsO₄ (2.5 wt % in tBuOH, 3.50 mL) at room temperature. Then the mixture was stirred at room temperature for 10 min. To the mixture was added a mixture of sodium periodate (2.31 g) and H₂O (54 mL). Then the mixture was stirred at room temperature for 3 hours. The mixture was diluted with sat. aq. Na₂S₂O₃ (100 mL), and concentrated under reduced pressure. EtOAc was added to the mixture, and the phases were separated. The organic layer was dried over Na₂SO₄, filtered, and concentrated under reduced pressure. The residue was purified by silica gel column chromatography (EtOAc/hexanes) to give 8,8- diethyl-7-oxo-6-{[2-(trimethylsilyl)ethoxy]methyl}-7,8-dihydro-6H-spiro[1,6-naphthyridine-5,3'-oxetane]-2-carbaldehyde (524 mg) as a solid.

Preparation Example 21

To a mixture of 8,8-diethyl-7-oxo-6-{[2-(trimethylsilyl)ethoxy]methyl}-7,8-dihydro-6H-spiro[1,6-naphthyridine-5,3'-oxetane]-2-carbaldehyde (524 mg) and THF (15 mL) was added NaBH$_4$ (66 mg) with ice bath cooling under Ar atmosphere. Then the mixture was stirred at the same temperature for 2 hours. The mixture was diluted with sat. aq. NH$_4$Cl. EtOAc was added to the mixture, and the phases were separated. The organic layer was dried over Na$_2$SO$_4$, filtered, and concentrated under reduced pressure. The residue was purified by silica gel column chromatography (EtOAc/hexanes) to give 8,8-diethyl-2-(hydroxymethyl)-6-{[2-(trimethylsilyl)ethoxy]methyl}-6H-spiro[1,6-naphthyridine-5,3'-oxetan]-7(8H)-one (567 mg) as a solid.

Preparation Example 22

To a mixture of 8,8-diethyl-2-(hydroxymethyl)-6-{[2-(trimethylsilyl)ethoxy]methyl}-6H-spiro[1,6-naphthyridine-5,3'-oxetan]-7(8H)-one (283 mg) and DMF (6 mL) was added NaH (55% dispersion in mineral oil, 45 mg) under ice bath cooling. Then the mixture was stirred for 10 min. To the mixture was added MeI (65 µL). Then the mixture was stirred at room temperature for 1 hour. The mixture was diluted with sat. aq. NH$_4$Cl. EtOAc was added to the mixture, and the phases were separated. The organic layer was dried over Na$_2$SO$_4$, filtered, and concentrated under reduced pressure. The residue was purified by silica gel column chromatography (EtOAc/hexanes) to give 8,8-diethyl-2-(methoxymethyl)-6-{[2-(trimethylsilyl)ethoxy]methyl}-6H-spiro[1,6-naphthyridine-5,3'-oxetan]-7(8H)-one (299 mg) as an oil.

Preparation Example 23

A mixture of 8-(2-{[tert-butyl(dimethyl)silyl]oxy}ethyl)-2-chloro-8-ethyl-6H-spiro[1,6-naphthyridine-5,3'-oxetan]-7(8H)-one (456 mg), Zn(CN)$_2$ (398 mg), Zn (38 mg), palladium(II) bis(trifluoroacetate) (41 mg), di-tert-butyl(2',4',6'-triisopropylbiphenyl-2-yl)phosphine (tBuXphos, 106 mg) and DMAc (10 mL) (which was bubbled with Ar gas for 15 min prior to use) was heated in the microwave reactor at 130° C. for 1 hour. The mixture was diluted with EtOAc and H$_2$O, and filtered through a pad of Celite. The filtrate was extracted with EtOAc. The organic layer was washed with brine, dried over MgSO$_4$, and concentrated under reduced pressure. The residue was purified by silica gel chromatography (EtOAc/hexanes) to give 8-(2-{[tert-butyl(dimethyl)silyl]oxy}ethyl)-8-ethyl-7-oxo-7,8-dihydro-6H-spiro[1,6-naphthyridine-5,3'-oxetane]-2-carbonitrile (342 mg) as a solid.

Preparation Example 24

To a mixture of 6-chloro-4-methyl-2H-spiro[isoquinoline-1,3'-oxetan]-3(4H)-one (30.00 g) and DMI (150 mL) was added NaH (55% dispersion in mineral oil, 5.78 g) under ice bath cooling. After removal of ice bath, the mixture was stirred for 20 min. To the mixture was added a mixture of tert-butyl(2-iodoethoxy)dimethylsilane (39.74 g) and DMI (30 mL) dropwise over 5 min under ice bath cooling. After removal of ice bath, the mixture was stirred for 2 hours. The mixture was poured into iced water (500 mL), and then stirred at room temperature overnight. The precipitate was collected to give 4-(2-{[tert-butyl(dimethyl)silyl]oxy}ethyl)-6-chloro-4-methyl-2H-spiro[isoquinoline-1,3'-oxetan]-3(4H)-one (49.98 g) as a solid.

Preparation Example 25

To a mixture of tert-butyl 5-({[tert-butyl(dimethyl)silyl]oxy}methyl)-2-chloro-8-ethyl-5-methyl-7-oxo-5,6,7,8-tetrahydropyrido[3,4-b]pyrazine-8-carboxylate (457 mg, 3:2 mixture of all stereoisomers) and CH$_2$Cl$_2$ (3 mL) was added TFA (3 mL). The mixture was stirred at room temperature for 1.5 hours. The solvents were evaporated under reduced pressure, and the residue was partitioned between EtOAc (50 mL) and sat. aq. NaHCO$_3$ (20 mL). The layers were separated, and the organic phase was dried over Na$_2$SO$_4$ and concentrated. The residue was purified by silica gel chromatography (EtOAc/hexanes) to give 5-({[tert-butyl(dimethyl)silyl]oxy}methyl)-2-chloro-8-ethyl-5-methyl-5,8-dihydropyrido[3,4-b]pyrazin-7(6H)-one (140 mg, 3:2 mixture of all stereoisomers) as a solid.

Preparation Example 26

To a mixture of 6-bromo-4,4-dimethyl-2H-spiro[isoquinoline-1,3'-oxetan]-3(4H)-one (1.00 g), KOAc (497 mg), bis(pinacolato)diboron (1.03 g), and [1,1'-bis(diphenylphosphino)ferrocene]dichloropalladium(II) (247 mg) was added 1,4-dioxane (15 mL), and the mixture was stirred at 85° C. for 18 hours. The mixture was cooled to room temperature and diluted with EtOAc (100 mL) and H$_2$O (100 mL). The biphasic mixture was filtered through a pad of Celite, and the layers were separated. The aqueous phase was extracted with EtOAc (100 mL). The combined organic extracts were washed with brine, dried over Na$_2$SO$_4$, and concentrated to a crude solid. The solid was suspended in CH$_2$Cl$_2$ (5 mL), triturated, and aged at room temperature for 15 min. The precipitate was collected to give 4,4-dimethyl-6-(4,4,5,5-tetramethyl-1,3,2-dioxaborolan-2-yl)-2H-spiro[isoquinoline-1,3'-oxetan]-3(4H)-one (721 mg) as a solid.

Preparation Example 27

To a mixture of 3-(2,6-dichloropyridin-3-yl)oxetan-3-amine monohydrochloride (31.0 g) and DMF (300 mL) were added 2-(tert-butoxycarbonyl)butanoic acid (27.4 g), WSC/HCl (34.9 g), HOBt (24.6 g), and triethylamine (42 mL) at room temperature. Then the mixture was stirred at the same temperature for 3 hours. To the mixture was added H$_2$O, and extracted with EtOAc. The organic layer was washed with brine, and dried over MgSO$_4$, filtered, and concentrated under reduced pressure. The residue was purified by silica gel column chromatography (EtOAc/hexanes) to give tert-butyl 2-{[3-(2,6-dichloropyridin-3-yl)oxetan-3-yl]carbamoyl}butanoate (42.9 g) as a solid.

Preparation Example 28

To a mixture of 2-chloro-8,8-diethyl-6H-spiro[1,6-naphthyridine-5,3'-oxetan]-7(8H)-one (1.18 g), Pd$_2$(dba)$_3$ (200 mg), 4,5-bis(diphenylphosphino)-9,9-dimethylxanthene (XantPhos, 245 mg), and 1,4-dioxane (24 mL) were added 2-ethylhexyl 3-sulfanylpropanoate (1.35 mL) and DIPEA (2.20 mL). The mixture was stirred at 90° C. for 15 hours under Ar atmosphere. After the mixture was cooled to room temperature, the solid was removed by filtration and the filtrate was concentrated under reduced pressure. The residue was purified by silica gel chromatography (EtOAc/hexanes) to give 2-ethylhexyl 3-[(8,8-diethyl-7-oxo-7,8-dihydro-6H-spiro[1,6-naphthyridine-5,3'-oxetan]-2-yl)sulfanyl]propanoate (1.78 g) as an oil.

Preparation Example 29

To a mixture of 8-(2-{[tert-butyl(dimethyl)silyl]oxy}ethyl)-2-chloro-8-ethyl-6H-spiro[1,6-naphthyridine-5,3'-oxetan]-7(8H)-one (20.94 g) and toluene (200 mL) were added $Cs_2CO_3$ (33.2 g), 4,5-bis(diphenylphosphino)-9,9-dimethylxanthene (XantPhos, 1.18 g), palladium(II) diacetate (230 mg), benzyl alcohol (10.55 mL) in this order, and then the mixture was stirred at 110° C. for 30 min under Ar atmosphere. The mixture was cooled to room temperature. The mixture was filtered through a pad of Celite, and the filter cake was washed with EtOAc. The filtrate was washed with brine, dried over $MgSO_4$, filtered, and concentrated under reduced pressure. The residue was purified by silica gel column chromatography (EtOAc/hexanes) to give 2-(benzyloxy)-8-(2-{[tert-butyl(dimethyl)silyl]oxy}ethyl)-8-ethyl-6H-spiro[1,6-naphthyridine-5,3'-oxetan]-7(8H)-one (23.89 g) as a solid.

Preparation Example 30

A mixture of 2-(benzyl oxy)-8-(2-{[tert-butyl (dimethyl)silyl]oxy}ethyl)-8-ethyl-6H-spiro[1,6-naphthyridine-5,3'-oxetan]-7(8H)-one (23.87 g), 10% palladium on carbon (50% wet, 2 g), and EtOH (240 mL) was stirred at room temperature for 2 hours under a hydrogen atmosphere (1 atm). After the mixture was filtered through a pad of Celite, the filter cake was washed with $CHCl_3$. The filtrate was concentrated under reduced pressure. The residue in 50% IPE/hexane (200 mL) was stirred at reflux, and then cooled to room temperature. The precipitate was collected to give 8-(2-{[tert-butyl(dimethyl)silyl]oxy}ethyl)-8-ethyl-2-hydroxy-6H-spiro[1,6-naphthyridine-5,3'-oxetan]-7(8H)-one (14.15 g) as a solid.

Preparation Example 31

To a mixture of 2-hydroxy-8,8-dimethyl-6-{[2-(trimethylsilyl)ethoxy]methyl}-6H-spiro[1,6-naphthyridine-5,3'-oxetan]-7(8H)-one (1.44 g), NMP (15 mL), and $H_2O$ (1.5 mL) were added $Cs_2CO_3$ (2.59 g) and sodium chloro(difluoro)acetate (1.52 g) under Ar atmosphere, then the mixture was stirred at 100° C. for 2 hours. The mixture was cooled to room temperature, and $Cs_2CO_3$ (2.59 g) and sodium chloro(difluoro)acetate (1.52 g) were added to the mixture. The mixture was stirred at 100° C. for 1.5 hours. The mixture was cooled to room temperature, and $Cs_2CO_3$ (2.59 g) and sodium chloro(difluoro)acetate (1.52 g) were added to the mixture. The mixture was stirred at 100° C. for 1 hour. The mixture was cooled to room temperature, then diluted with $H_2O$ and extracted with EtOAc. The organic layer was washed with $H_2O$ and brine, dried over $MgSO_4$, filtered and concentrated under reduced pressure. The residue was purified by silica gel chromatography (EtOAc/hexanes) to give 2-(difluoromethoxy)-8,8-dimethyl-6-{[2-(trimethylsilyl)ethoxy]methyl}-6H-spiro[1,6-naphthyridine-5,3'-oxetan]-7(8H)-one (1.48 g) as a solid.

Preparation Example 32

A mixture of 2-(5-chloro-3-fluoropyridin-2-yl)-2-methylpropanamide (2.16 g), [bis(trifluoroacetoxy)iodo]benzene (5.16 g), MeCN (48 mL), and $H_2O$ (24 mL) was stirred overnight. The reaction was then diluted with EtOAc (200 mL), washed with $H_2O$ (100 mL), brine (100 mL), dried over $Na_2SO_4$, and concentrated to give 5-chloro-3-fluoro-2-(2-isocyanatopropan-2-yl)pyridine (1.9 g) as a solid.

Preparation Example 33

To a mixture of 8-(2-{[tert-butyl(dimethyl)silyl]oxy}ethyl)-8-ethyl-2-hydroxy-6H-spiro[1,6-naphthyridine-5,3'-oxetan]-7(8H)-one (14.69 g) and MeCN (75 mL) was added a mixture of KOH (21.0 g) and $H_2O$ (75 mL). To the mixture was added diethyl [bromo(difluoro)methyl]phosphonate (13.0 g) under ice bath cooling, and then the mixture was stirred at the same temperature for 30 min. The mixture was extracted with EtOAc three times, and combined organic layers were washed with sat. aq. $NaHCO_3$ and brine, and dried over $MgSO_4$, filtered, and concentrated under reduced pressure. The residue in EtOAc (30 mL) and hexane (100 mL) was stirred at reflux, and then cooled to room temperature. The precipitate was collected to give 8-(2-{[tert-butyl(dimethyl)silyl]oxy}ethyl)-2-(difluoromethoxy)-8-ethyl-6H-spiro[1,6-naphthyridine-5,3'-oxetan]-7(8H)-one (11.46 g) as a solid.

Preparation Example 34

To a mixture of 8-(2-{[tert-butyl(dimethyl)silyl]oxy}ethyl)-2-(difluoromethoxy)-8-methyl-6-{[2-(trimethylsilyl)ethoxy]methyl}-6H-spiro[1,6-naphthyridine-5,3'-oxetan]-7(8H)-one (1.80 g) and THF (36 mL) was added TBAF (1.0 M in THF, 3.5 mL) under ice bath cooling, and then the mixture was stirred for 1 hour at the same temperature, and then stirred at room temperature overnight. The mixture was poured into sat. aq. $NaHCO_3$, and extracted with EtOAc. The organic layer was washed with brine, dried over $MgSO_4$, and concentrated under reduced pressure. The residue was purified by silica gel chromatography (EtOAc/hexanes) to give 2-(difluoromethoxy)-8-(2-hydroxyethyl)-8-methyl-6-{[2-(trimethylsilyl)ethoxy]methyl}-6H-spiro[1,6-naphthyridine-5,3'-oxetan]-7(8H)-one (1.43 g) as an oil.

Preparation Example 35

A mixture of 5-chloro-3-fluoro-2-(2-isocyanatopropan-2-yl)pyridine (1.7 g), MeOH (8 mL), and trimethylamine (2 mL) was stirred for 1 hour and then partially concentrated. The resultant solid was filtered, and the filtrate was concentrated to give methyl [2-(5-chloro-3-fluoropyridin-2-yl)propan-2-yl]carbamate that was used directly in the next step.

Preparation Example 36

To a mixture of 4-bromo-1-iodo-2-methylbenzene (87.5 g) and THF (400 mL) was added dropwise n-BuLi (1.55 M in hexane, 200 mL) over 50 min with dry ice-acetone bath cooling under Ar atmosphere. Then the mixture was stirred at the same temperature for 10 min. To the mixture was added a mixture of 2-methyl-N-(oxetan-3-ylidene)propane-2-sulfinamide (56.8 g) and THF (40 mL) dropwise over 30 min at the same temperature. Then the mixture was stirred at the same temperature for 1 hour. The mixture was diluted with sat. aq. $NH_4Cl$ (200 mL) at the same temperature, and brine (100 mL) was added, and stirred at room temperature for 30 min. Then organic layer was separated, concentrated, and diluted with EtOAc (300 mL). Aqueous layer was extracted with EtOAc (300 mL), and combined organic layers were washed with brine twice, and dried over MgSO$_4$, filtered, and concentrated under reduced pressure. To the residue was added IPE (150 mL), and the mixture was stirred at room temperature for 15 min and under ice bath cooling for 30 min. The precipitate was collected, and washed with IPE to give N-[3-(4-bromo-2-methylphenyl)oxetan-3-yl]-2-methylpropane-2-sulfinamide (48.07 g) as a solid.

Preparation Example 37

To a mixture of 2,2,6,6-tetramethylpiperidine (81 mL) and THF (95 mL) was added n-BuLi (1.55 M in hexane, 300 mL) dropwise over 8 min with dry ice-acetone bath cooling under Ar atmosphere. Then the mixture was stirred under ice bath cooling for 30 min. To the mixture was added a mixture of N-[3-(4-bromo-2-methylphenyl)oxetan-3-yl]-2-methylpropane-2-sulfinamide (48.06 g), diethyl carbonate (33.7 mL), and THF (220 mL) dropwise over 30 min under dry ice-acetone bath cooling. Then the mixture was warmed to −40° C. over 30 min, and stirred at the same temperature for 10 min. The mixture was diluted with sat. aq. NH$_4$Cl (700 mL) at the same temperature, and brine (100 mL) was added. Then organic layer was separated, concentrated, and diluted with EtOAc (500 mL). Aqueous layer was extracted with EtOAc (500 mL), and combined organic layers were washed with brine, and dried over MgSO$_4$, filtered, and concentrated under reduced pressure to give ethyl (5-bromo-2-{3-[(tert-butylsulfinyl)amino]oxetan-3-yl}phenyl)acetate (63.78 g) as a solid.

Preparation Example 38

To a mixture of HCl (4 M in EtOAc, 115 mL), EtOAc (250 mL), and a piece of seed solid of desired compound (ethyl [2-(3-aminooxetan-3-yl)-5-bromophenyl]acetate monohydrochloride) was added a mixture of ethyl (5-bromo-2-{3-[(tert-butylsulfinyl)amino]oxetan-3-yl}phenyl)acetate (63.77 g) and EtOAc (250 mL) dropwise at room temperature over 20 min. Then the mixture was stirred at the same temperature for 20 min. The precipitate was collected and washed with EtOAc (100 mL) and 50% EtOAc/hexane (200 mL) to give ethyl [2-(3-aminooxetan-3-yl)-5-bromophenyl]acetate monohydrochloride (48.68 g) as a solid.

The seed solid described above was prepared by the same procedure without seed solid on small scale experiment.

Preparation Example 39

To a mixture of NaHCO$_3$ (15.2 g) and H$_2$O (700 mL) was added ethyl [2-(3-aminooxetan-3-yl)-5-bromophenyl]acetate monohydrochloride (48.67 g) portionwise at room temperature. Then the mixture was stirred at the same temperature for 40 min. The precipitate was collected and washed with H$_2$O (100 mL) twice and MeOH (100 mL) twice to give 6-bromo-2H-spiro[isoquinoline-1,3'-oxetan]-3(4H)-one (32.35 g) as a solid.

Preparation Example 40

To a mixture of (2,6-dichloropyridin-3-yl)acetonitrile (3.86 g) and THF (120 mL) was added NaH (55% dispersion in mineral oil, 2.00 g) with ice bath cooling under Ar atmosphere. Then the mixture was stirred at the same temperature for 10 min. To the mixture was added MeI (3.25 mL) with ice bath cooling under Ar atmosphere. Then the mixture was stirred at the same temperature for 2 hours. The mixture was diluted with sat. aq. NH$_4$Cl at the same temperature. H$_2$O and EtOAc were added to the mixture, and the phases were separated. Aqueous layer was extracted with EtOAc, and combined organic layers were washed with brine, and dried over Na$_2$SO$_4$, filtered, and concentrated under reduced pressure. The residue was purified by silica gel column chromatography (EtOAc/hexanes) to give 2-(2,6-dichloropyridin-3-yl)-2-methylpropanenitrile (4.39 g) as a solid.

Preparation Example 41

A mixture of methyl (2-(5-chloro-3-fluoropyridin-2-yl)propan-2-yl)carbamate (900 mg), EtOH (12 mL), and NaOH (3 M in H$_2$O, 4 mL) was heated in a microwave reactor at 150° C. for 30 min. The reaction was then concentrated and extracted with EtOAc (100 mL). The organic layer was washed with brine, dried over Na$_2$SO$_4$, and concentrated to give 2-(5-chloro-3-fluoropyridin-2-yl)propan-2-amine (520 mg).

Preparation Example 42 (42a and 42b)

8-(2-{[tert-Butyl(dimethyl)silyl]oxy}ethyl)-2-(difluoromethoxy)-8-ethyl-6H-spiro[1,6-naphthyridine-5,3'-oxetan]-7(8H)-one (14.42 g) was resolved with chiral column chromatography (CHIRALFLASH (trademark) IA, eluent; Hexane/EtOAc 80/20-0/100, flow rate; 12-20 mL/min) to give 8-(2-{[tert-butyl(dimethyl)silyl]oxy}ethyl)-2-(difluoromethoxy)-8-ethyl-6H-spiro[1,6-naphthyridine-5,3'-oxetan]-7(8H)-one (6.93 g, one enantiomer with shorter retention time) as a solid, and 8-(2-{[tert-butyl(dimethyl)silyl]oxy}ethyl)-2-(difluoromethoxy)-8-ethyl-6H-spiro[1,6-naphthyridine-5,3'-oxetan]-7(8H)-one (6.78 g: one enantiomer with longer retention time) as a solid.

Preparation Example 83

To a mixture of 1-bromo-4-chloro-2-methylbenzene (73.28 g) and THF (250 mL) was added dropwise n-BuLi (1.55 M in hexane, 220 mL) over 90 min with dry ice-acetone bath cooling under N$_2$ atmosphere. Then the mixture was stirred at the same temperature for 10 min. To the mixture was added a mixture of 2-methyl-N-(oxetan-3-ylidene)propane-2-sulfinamide (50.00 g) and THF (100 mL) dropwise over 60 min at the same temperature. Then the mixture was stirred at the same temperature for 20 min. The mixture was diluted with sat. aq. NH$_4$Cl at the same temperature and warmed up to room temperature. The mixture was partially concentrated under reduced pressure, and then the mixture was diluted with H$_2$O, and extracted with EtOAc twice. The combined organic layers were washed with brine, and dried over MgSO$_4$, filtered, and concentrated under reduced pressure. The combined aqueous layers were filtered through a pad of Celite and the cake was washed with EtOAc three times. The filtrate was extracted with EtOAc, and the organic layer was washed with brine, and dried over MgSO$_4$, filtered, and concentrated under reduced pressure. The combined residues were diluted with WE and then concentrated under reduced pressure. To the residue was added WE and stood at room temperature overnight. The solid was collected, and washed with 50% IPE/hexanes to give N-[3-(4-chloro-2-methylphenyl)oxetan-3-yl]-2-methylpropane-2-sulfinamide (57.00 g) as a solid.

Preparation Example 84

To a mixture of 2,2,6,6-tetramethylpiperidine (109 mL) and THF (114 mL) was added n-BuLi (1.55 M in hexane, 400 mL) dropwise over 40 min with dry ice-MeCN bath cooling under N$_2$ atmosphere. To the mixture was added a mixture of N-[3-(4-chloro-2-methylphenyl)oxetan-3-yl]-2-methylpropane-2-sulfinamide (57.0 g), diethyl carbonate (45.0 mL), and THF (256 mL) dropwise over 90 min under dry ice-MeCN bath cooling. Then the mixture was stirred at the same temperature for 30 min. The mixture was diluted with sat. aq. NH$_4$Cl at the same temperature. The mixture was partially concentrated under reduced pressure, and the mixture was extracted with EtOAc twice. The combined organic layers were washed with 50% brine/H$_2$O twice, and dried over MgSO$_4$, filtered, and concentrated under reduced pressure to give ethyl (2-{3-[(tert-butylsulfinyl)amino]oxetan-3-yl}-5-chlorophenyl)acetate (70.6 g) as an oil.

Preparation Example 85

To a mixture of HCl (4 M in EtOAc, 285 mL) and EtOAc (850 mL) was added a mixture of ethyl (2-{3-[(tert-butylsulfinyl)amino]oxetan-3-yl}-5-chlorophenyl)acetate (142.46 g) and EtOAc (800 mL) dropwise at room temperature over 25 min. Then the mixture was stirred at the same temperature for 25 min. The precipitate was collected and washed with 50% EtOAc/hexanes three times to give ethyl [2-(3-aminooxetan-3-yl)-5-chlorophenyl]acetate monohydrochloride (116.70 g) as a solid.

Preparation Example 86

To a mixture of NaHCO$_3$ (42.0 g) and H$_2$O (1170 mL) was added ethyl [2-(3-aminooxetan-3-yl)-5-chlorophenyl]acetate monohydrochloride (116.7 g) portionwise at room temperature. Then the mixture was stirred at the same temperature for 1 hour. The precipitate was collected and washed with H$_2$O twice and EtOAc twice to give 6-chloro-2H-spiro[isoquinoline-1,3'-oxetan]-3(4H)-one (62.9 g) as a solid.

Preparation Example 95

To a mixture of 2-(3,5-dichloropyrazin-2-yl)-2-methylpropanamide (2.5 g), H$_2$O (11 mL), MeCN (11 mL), and sulfuric acid (11 mL) was added sodium nitrite (3.7 g) under ice bath cooling. The mixture was stirred at the same temperature for 5 min and then warmed to room temperature and stirred for 2 hours. The resultant solid was collected and washed with H$_2$O to give 2-(3,5-dichloropyrazin-2-yl)-2-methylpropanoic acid (2.5 g) as a solid.

Preparation Example 96

A mixture of 2-(3,5-dichloropyrazin-2-yl)-2-methylpropanoic acid (2.2 g), toluene (45 mL), triethylamine (1.7 mL) and diphenylphosphorylazide (3.1 g) was stirred at reflux for 2.5 hours. The mixture was then cooled to room temperature, and 4-methoxybenzyl alcohol (5.2 g) and triethylamine (7.8 mL) were added. The mixture was stirred at room temperature for 2 hours and then concentrated. The crude product was dissolved in CH$_2$Cl$_2$ (10 mL), followed by the addition of TFA (10 mL). The mixture was stirred at room temperature for 3 hours and then concentrated. To the crude solid was added HCl (4 M in 1,4-dioxane, 10 mL) at room temperature, and then concentrated to give 2-(3,5-dichloropyrazin-2-yl)propan-2-amine monohydrochloride (1.4 g) as a solid.

Preparation Example 100

To a mixture of 2-bromo-4-fluoro-1-iodobenzene (3.12 g) and THF (25 mL) was added n-BuLi (1.6 M in hexane, 6.5 mL) dropwise at −100° C. under a nitrogen atmosphere. The resulting mixture was stirred at the same temperature for 30 min, and then 2-methyl-N-(oxetan-3-ylidene)propane-2-sulfinamide (2.0 g) in TI-IF (5 mL) was slowly added dropwise while maintaining the internal temperature between −90 and −100° C. The resulting solution was stirred at the same temperature for 30 min. The mixture was diluted with sat. aq. NH$_4$Cl (50 mL) and H$_2$O (50 mL), and extracted with EtOAc (2×100 mL). Combined organic layers were washed with brine, dried over Na$_2$SO$_4$, filtered, concentrated, and then purified by silica gel column chromatography (EtOAc/hexanes) to give N-[3-(2-bromo-4-fluorophenyl)oxetan-3-yl]-2-methylpropane-2-sulfinamide (1.29 g) as a solid.

Preparation Example 101

A 200-mL round bottom flask was charged with N-[3-(2-bromo-4-fluorophenyl)oxetan-3-yl]-2-methylpropane-2-sulfinamide (1.05 g), Pd$_2$(dba)$_3$ (137 mg), and 2-dicyclohexylphosphino-2',4',6'-triisopropylbiphenyl (Xphos, 143 mg). The flask was evacuated and back-filled with nitrogen 3 times, and anhydrous degassed THF (15 mL) was added via syringe, followed by tert-butoxy-2-oxoethylzinc chloride (0.5 M in Et$_2$O, 15 mL). The resulting mixture was stirred at 55° C. for 1 hour and then cooled to room temperature and diluted with EtOAc (100 mL) and H$_2$O (50 mL). The mixture was filtered through a pad of Celite. The phases were separated, and the aqueous phase was extracted with EtOAc (50 mL). Combined organic layers were washed with brine, dried over Na$_2$SO$_4$, and concentrated to give a brown solid. To a mixture of the crude solid and CH$_2$Cl$_2$ (50 mL) was added TFA (10 mL). The resulting mixture was stirred at room temperature for 1.5 hours. The solvents were evaporated, and the remaining residue was partitioned between sat. aq. NaHCO$_3$ (50 mL) and EtOAc (50 mL). The layers were separated and the aqueous phase was washed with EtOAc (50 mL). The aqueous phase was then acidified to a pH of 5 with formic acid and extracted with EtOAc (2×50 mL). The combined organic extracts were dried over Na$_2$SO$_4$, and concentrated to give (2-{3-[(tert-butylsulfinyl)amino]oxetan-3-yl}-5-fluorophenyl)acetic acid (0.52 g) as a solid.

Preparation Example 102

To a mixture of (2-{3-[(tert-butylsulfinyl)amino]oxetan-3-yl}-5-fluorophenyl)acetic acid (491 mg) and 1,4-dioxane (4 mL) was added HCl (4 M in 1,4-dioxane, 0.45 mL) under ice bath cooling. The reaction mixture was warmed to room temperature and stirred for 1 hour. The precipitate was filtered to give a crude solid (150 mg), and used directly in the next step. A mixture of the crude solid (150 mg), DMF (2 mL), O-(benzotriazol-1-yl)-N,N,N',N'-tetramethyluronium hexafluorophosphate (HBTU, 326 mg), HOBt (116 mg), and trimethylamine (0.24 mL) was stirred at room temperature for 1 hour. The reaction was then poured into H$_2$O (25 mL) and EtOAc (25 mL). The organic layer was separated, washed with brine, dried over Na$_2$SO$_4$, filtered, and concentrated. The resultant solid was washed by 25% CH$_2$Cl$_2$/hexanes to give 6-fluoro-2H-spiro[isoquinoline-1,3'-oxetan]-3(4H)-one (85 mg) as a solid.

Preparation Example 104

To a mixture of (2-{3-[(tert-butylsulfinyl)amino]oxetan-3-yl}-5-chloropyridin-3-yl)acetic acid (4.84 g) and MeCN (112 mL) was added thionyl chloride (2.1 mL) under ice bath cooling. The reaction mixture was stirred at the same temperature for 90 min. To the mixture was added sat. aq. NaHCO₃ (40 mL), and then the mixture was concentrated to a volume of about 80 mL, and the resultant solid was filtered and washed with H₂O (15 mL), Et₂O (30 mL), and EtOAc (10 mL). The resultant solid was then triturated with a 10% MeOH/hexane to give 3-chloro-5H-spiro[1,7-naphthyridine-8,3'-oxetan]-6(7H)-one (1.12 g) as a solid.

Example 1

A 1000 mL 3-necked flask was charged with 6-bromo-2H-spiro[isoquinoline-1,3'-oxetan]-3(4H)-one (17.35 g) and DMF (160 mL). The flask was evacuated and back-filled with Ar twice, and NaH (55% dispersion in mineral oil, 6.50 g) was added portionwise under ice bath cooling, and then the mixture was stirred at room temperature for 30 min. To the mixture was added a mixture of MeI (8.1 mL) and DMF (35 mL) dropwise under ice bath cooling over 1 hour. Additional MeI (0.5 mL) was added under ice bath cooling, and the mixture was stirred at the same temperature for 10 min. The mixture was diluted with H₂O (250 mL) and sat. aq. NH₄Cl (150 mL), and stirred at room temperature for 1 hour. The precipitate was collected, and a mixture of the solid and 40% toluene/hexane (200 mL) was stirred at reflux for 1 hour, and then cooled to room temperature. The mixture was stirred at room temperature for 30 min, and the precipitate was collected to give 6-bromo-4,4-dimethyl-2H-spiro[isoquinoline-1,3'-oxetan]-3(4H)-one (14.47 g) as a solid.

Example 2

To a solid of P₂O₅ (20.00 g) was added H₃PO₄ (12 mL), and the mixture was stirred at 140° C. for 1 hour. To the mixture were added 2-(3-methylphenyl)butanamide (3.00 g) and acetone (2.70 mL) at 100° C., and stirred at the same temperature for 2 hours. To the mixture was added acetone (2.70 mL) at 120° C., and stirred at the same temperature for 2 hours. The mixture was poured into iced water, and diluted with EtOAc, and separated. The organic layer was washed with brine and dried over Na₂SO₄, filtered, and concentrated under reduced pressure. The residue was washed with EtOAc/hexanes to give 4-ethyl-1,1,6-trimethyl-1,4-dihydroisoquinolin-3(2H)-one (2.83 g) as a solid.

Example 3

A mixture of 4-ethyl-1,1,6-trimethyl-1,4-dihydroisoquinolin-3(2H)-one (600 mg), NaH (60% dispersion in mineral oil, 167 mg) and DMF (6.0 mL) was stirred under ice bath cooling for 30 min. To the mixture was added 2-(3-bromopropoxy)tetrahydro-2H-pyran (924 mg) at the same temperature and stirred at room temperature overnight. To the mixture were added EtOAc and brine, and the phases were separated. The organic layer was washed with H₂O, and brine, and dried over Na₂SO₄, and concentrated under reduced pressure. The residue was purified by silica gel column chromatography (EtOAc/hexanes). To the residue were added HCl (1 M aq., 5.0 mL) and THF (5.0 mL), and stirred at 70° C. for 2 hours. To the mixture were added EtOAc and brine, and the phases were separated. The organic layer was washed with H₂O, and brine, and dried over Na₂SO₄, and concentrated under reduced pressure. The residue was purified by silica gel column chromatography (EtOAc/hexanes to CHCl₃/MeOH). The residue was washed with hexane to give 4-ethyl-4-(3-hydroxypropyl)-1,1,6-trimethyl-1,4-dihydroisoquinolin-3(2H)-one (84 mg) as a solid.

Example 4

A 500 mL flask was charged with 6-bromo-4,4-diethyl-1,1-dimethyl-1,4-dihydroisoquinolin-3(2H)-one (15.0 g), palladium(II) bis(trifluoroacetate) (1.62 g), Zn (1.27 g), di-tert-butyl(2',4',6'-triisopropylbiphenyl-2-yl)phosphine (tBuXPhos, 4.11 g), and degassed DMAc (prepared by Ar bubbling for 5 min, 150 mL). The flask was evacuated and back-filled with Ar three times, and Zn(CN)₂ (7.39 g) was added at room temperature. The mixture was stirred at 80° C. for 6 hours. After cooling to room temperature, to the mixture was added EtOAc (300 mL). Then insoluble matter was filtered through a pad of Celite, and washed with EtOAc (300 mL). The filtrate was washed with H₂O (150 mL) twice and brine, dried over Na₂SO₄, filtered, and concentrated under reduced pressure. To the residue was added 50% hexane/EtOAc (240 mL), and stirred at 80° C. for 30 min and room temperature for 30 min. The precipitate was collected, and washed with 50% hexane/EtOAc (80 mL) to give 4,4-diethyl-1,1-dimethyl-3-oxo-1,2,3,4-tetrahydroisoquinoline-6-carbonitrile (6.18 g) as a solid.

Example 5

To a mixture of 4,6-dibromo-1,1-dimethyl-1,4-dihydroisoquinolin-3(2H)-one (150 mg) and THF (3.0 mL) was added N-methylcyclohexylamine (153 mg). Then the mixture was stirred at room temperature for 15 hours. The mixture was poured into the sat. aq. NaHCO₃, and extracted with EtOAc. The organic layer was washed with brine, dried over MgSO₄, filtered, and concentrated under reduced pressure. The residue was purified by silica gel column chromatography (EtOAc/hexanes) to give 6-bromo-4-[cyclohexyl(methyl)amino]-1,1-dimethyl-1,4-dihydroisoquinolin-3(2H)-one (118 mg) as a solid.

Example 6

To a mixture of 2-chloro-8-ethyl-6H-spiro[1,6-naphthyridine-5,3'-oxetan]-7(8H)-one (6.0 g) and DMF (150 mL) was added NaH (55% dispersion in mineral oil, 1.13 g) with ice bath cooling under Ar atmosphere. After 10 min, EtI (2.0 mL) was added and the mixture was stirred at room temperature for 1 hour. Sat. aq. NH₄Cl and EtOAc were added and the organic layer was separated, washed with H₂O twice and brine, dried over Na₂SO₄, filtered and concentrated under reduced pressure. The residue was purified by silica gel column chromatography (EtOAc/hexanes) to give 2-chloro-8,8-diethyl-6H-spiro[1,6-naphthyridine-5,3'-oxetan]-7(8H)-one (6.19 g) as a solid.

Example 7

To a mixture of methyl 4-[(6-bromo-4-ethyl-1,1-dimethyl-3-oxo-1,2,3,4-tetrahydroisoquinolin-4-yl)methyl]benzoate (300 mg), THF (6.0 mL), and MeOH (6.0 mL) was added NaOH (1 M aq., 1.4 mL) at room temperature, and stirred at the same temperature for 72 hours. The mixture was neutralized to pH7-8 with 1 M aq. HCl and H₂O under ice bath cooling. To the mixture was added EtOAc, and the phases were separated. The aqueous layer was extracted with EtOAc, and the combined organic layers were washed with brine, dried over Na₂SO₄, filtered, and concentrated under reduced pressure. The residue was purified by silica gel column chromatography (CHCl$_3$/MeOH) to give a solid. The obtained solid was washed with EtOAc to give 4-[(6-bromo-4-ethyl-1,1-dimethyl-3-oxo-1,2,3,4-tetrahydroisoquinolin-4-yl)methyl]benzoic acid (212 mg) as a solid.

Example 8

To a mixture of (6-bromo-4-ethyl-1,1-dimethyl-3-oxo-1,2,3,4-tetrahydroisoquinolin-4-yl)acetic acid (170 mg) and DMF (2 mL) were added HOBt (101 mg), WSC/HCl (144 mg), dimethylamine monohydrochloride (122 mg), and DIPEA (260 µL), and the mixture was stirred at room temperature for 15 hours. The mixture was diluted with H$_2$O and extracted with EtOAc. The organic layer was washed with H$_2$O and brine, dried over MgSO$_4$, filtered, and concentrated under reduced pressure to give 2-(6-bromo-4-ethyl-1,1-dimethyl-3-oxo-1,2,3,4-tetrahydroisoquinolin-4-yl)-N,N-dimethylacetamide (128 mg) as a solid.

Example 9

6-Bromo-4-ethyl-4-(2-hydroxyethyl)-1,1-dimethyl-1,4-dihydroisoquinolin-3(2H)-one (210 mg) was resolved by chiral supercritical fluid chromatography (SFC) (CHIRALPAK® IC, elute CO$_2$:MeOH=65:35, flow rate; 15 mL/min, back pressure; 100 bar, column temperature; 40° C.). One enantiomer with shorter retention time was washed with hexane to give (+)-6-bromo-4-ethyl-4-(2-hydroxyethyl)-1,1-dimethyl-1,4-dihydroisoquinolin-3(2H)-one (82 mg) as a solid. The other enantiomer with longer retention time was washed with hexane to give (−)-6-bromo-4-ethyl-4-(2-hydroxyethyl)-1,1-dimethyl-1,4-dihydroisoquinolin-3(2H)-one (82 mg) as a solid.

Example 10

To a mixture of 2-chloro-8,8-diethyl-6H-spiro[1,6-naphthyridine-5,3'-oxetan]-7(8H)-one (1.65 g), 1,4-dioxane (40 mL), and H$_2$O (4 mL) (which were bubbled with Ar gas prior to use) were added trimethylboroxine (1.64 mL), [1,1'-bis(diphenylphosphino)ferrocene]dichloropalladium(II) (430 mg), and K$_2$CO$_3$ (3.0 g). Then the mixture was stirred at 110° C. for 4 hours. The mixture was diluted with EtOAc and H$_2$O, and filtered through a pad of Celite. The organic layer was separated, washed with brine, dried over Na$_2$SO$_4$, filtered, and concentrated under reduced pressure. The residue was purified sequentially by silica gel column chromatography (EtOAc/hexanes), by amino-silica gel column chromatography (EtOAc/hexanes), and then by silica gel column chromatography (CHCl$_3$/MeOH). The residue was solidified with 9% IPE/hexane (10 mL) to give 8,8-diethyl-2-methyl-6H-spiro[1,6-naphthyridine-5,3'-oxetan]-7(8H)-one (1.3 g) as a solid.

Example 11

A mixture of 2-chloro-8,8-diethyl-6H-spiro[1,6-naphthyridine-5,3'-oxetan]-7(8H)-one (0.75 g), 2,2,2-trifluoroethanol (1.90 mL), Cs$_2$CO$_3$ (1.75 g), palladium(II) diacetate (60 mg), di-tert-butyl(2',4',6'-triisopropylbiphenyl-2-yl)phosphine (tBuXphos, 225 mg), and degassed toluene (15 mL) was heated in the microwave reactor at 150° C. for 90 min. An additional batch (total two batches) was performed with the same procedure as above. The mixture in 2 vials were diluted with H$_2$O and EtOAc, and filtered through a pad of Celite. The organic layer was separated, dried over Na$_2$SO$_4$, filtered, and concentrated under reduced pressure. The residue was purified by silica gel column chromatography (EtOAc/hexanes). The residue was solidified with 6% IPE/hexane (10 mL), and collected to give 8,8-diethyl-2-(2,2,2-trifluoroethoxy)-6H-spiro[1,6-naphthyridine-5,3'-oxetan]-7(8H)-one (1.56 g) as a solid.

Example 12

To a mixture of 2-chloro-8,8-diethyl-6H-spiro[1,6-naphthyridine-5,3'-oxetan]-7(8H)-one (500 mg) and EtOH (17 mL) were added triethylamine (500 µL) and 10% palladium on carbon (50% wet, 100 mg) under a positive flow of Ar. The mixture was stirred at room temperature under a hydrogen atmosphere overnight. The mixture was filtered, and the filtrate was concentrated under reduced pressure. To the residue was added H$_2$O, and the mixture was extracted with CHCl$_3$. The organic layer was dried over Na$_2$SO$_4$, filtered, and concentrated under reduced pressure to give 8,8-diethyl-6H-spiro[1,6-naphthyridine-5,3'-oxetan]-7(8H)-one (385 mg) as a solid.

Example 13

To a mixture of 8,8-diethyl-6H-spiro[1,6-naphthyridine-5,3'-oxetan]-7(8H)-one (100 mg), zinc bis(difluoromethanesulfinate) (253 mg), TFA (31 µL), CH$_2$Cl$_2$ (2.1 mL), and H$_2$O (0.6 mL) was added t-butyl hydroperoxide (70% aq., 177 µL) under ice bath cooling. Then the mixture was stirred at room temperature for 22 hours. The mixture was diluted with 50% sat. aq. Na$_2$S$_2$O$_3$/sat. aq. NaHCO$_3$. The mixture was extracted with CHCl$_3$. The organic layer was dried over Na$_2$SO$_4$, filtered, and concentrated under reduced pressure. The residue was purified by silica gel column chromatography (EtOAc/hexanes) to give 2-(difluoromethyl)-8,8-diethyl-6H-spiro[1,6-naphthyridine-5,3'-oxetan]-7(8H)-one (62 mg).

Example 14

To a mixture of 8,8-diethyl-2-(methoxymethyl)-6-{[2-(trimethylsilyl)ethoxy]methyl}-6H-spiro[1,6-naphthyridine-5,3'-oxetan]-7(8H)-one (299 mg) and DMF (9 mL) was added TBAF (550 mg). Then the mixture was stirred at 100° C. for 8 hours. H$_2$O and EtOAc were added to the mixture, and the phases were separated. The organic layer was washed with H$_2$O twice and brine, dried over Na$_2$SO$_4$, filtered, and concentrated under reduced pressure. The residue was purified by silica gel column chromatography (EtOAc/hexanes). The residue was washed with 5% IPE/hexane (2 mL) to give 8,8-diethyl-2-(methoxymethyl)-6H-spiro[1,6-naphthyridine-5,3'-oxetan]-7(8H)-one (100 mg) as a solid.

Example 15

To a mixture of 8-(2-{[tert-butyl(dimethyl)silyl]oxy}ethyl)-2-(difluoromethoxy)-8-ethyl-6H-spiro[1,6-naphthyridine-5,3'-oxetan]-7(8H)-one (8260 mg, one enantiomer with shorter retention time) and THF (80 mL) was added HCl (1M aq., 25 mL) under water bath, and then the mixture was stirred for 10 min at room temperature. The mixture was diluted with sat. aq. NaHCO$_3$, and concentrated under reduced pressure, and the mixture was extracted with CHCl$_3$ three times. The combined organic layers were dried over MgSO$_4$, filtered, and concentrated under reduced pressure. The residue was purified by silica gel column chromatography (CHCl$_3$/MeOH). The residue in IPE (20 mL) was heated. After the mixture was cooled to room temperature, the precipitate was collected to give (−)-2-(difluoromethoxy)-8-ethyl-8-(2-hydroxyethyl)-6H-spiro[1,6-naphthyridine-5,3'-oxetan]-7(8H)-one (5.73 g) as a solid.

Example 16

A mixture of 2-chloro-8,8-diethyl-6H-spiro[1,6-naphthyridine-5,3'-oxetan]-7(8H)-one (118 mg), Zn(CN)$_2$ (150 mg), Zn (12 mg), palladium(II) bis(trifluoroacetate) (15 mg), di-tert-butyl(2',4',6'-triisopropylbiphenyl-2-yl)phosphine (tBuXphos, 38 mg) and DMAc (4 mL) was heated in the microwave reactor at 130 (C for 1 hour. After cooling, the mixture was diluted with EtOAc and H$_2$O, and then filtered through a pad of Celite. The organic layer was separated, washed with H$_2$O and brine, dried over Na$_2$SO$_4$, filtered and concentrated under reduced pressure. The residue was purified by silica gel column chromatography (EtOAc/hexanes) to give 8,8-diethyl-7-oxo-7,8-dihydro-6H-spiro[1,6-naphthyridine-5,3'-oxetane]-2-carbonitrile (78 mg) as a solid.

Example 17

To a mixture of 2-ethylhexyl 3-[(8,8-diethyl-7-oxo-7,8-dihydro-6H-spiro[1,6-naphthyridine-5,3'-oxetan]-2-yl)sulfanyl]propanoate (625 mg), THF (6.3 mL), and MeOH (6.3 mL) was added KOtBu (168 mg) under ice bath cooling, and the mixture was stirred at room temperature for 1 hour and at 60° C. for 20 hours under Ar atmosphere. After cooled to room temperature, to the mixture was added MeI (110 μL) and the mixture was stirred at room temperature for 1 hour. Solvents were evaporated under reduced pressure. The residue was purified by silica gel chromatography (EtOAc/hexanes) and amino-silica gel chromatography (EtOAc/hexanes). To the residue was added IPE (2 mL), and the mixture was sonicated. After hexane (10 mL) was added, the mixture was stirred at room temperature for 10 min. The precipitate was collected to give 8,8-diethyl-2-(methylsulfanyl)-6H-spiro[1,6-naphthyridine-5,3'-oxetan]-7(8H)-one (225 mg) as a solid.

Example 18

To a mixture of 2-(difluoromethoxy)-8,8-dimethyl-6-{[2-(trimethylsilyl)ethoxy]methyl}-6H-spiro[1,6-naphthyridine-5,3'-oxetan]-7(8H)-one (1.40 g) and NMP (25 mL) was added TBAF hydrate (2.90 g), and the mixture was stirred at 100° C. for 3 hours. The mixture was cooled to room temperature, then diluted with H$_2$O and extracted with EtOAc. The organic layer was washed with brine, dried over MgSO$_4$, filtered and concentrated under reduced pressure. The residue was purified by silica gel column chromatography (EtOAc/hexanes) to give a solid. The obtained solid was diluted with IPE (3 mL) and hexane (15 mL), and the mixture was stirred at room temperature for 10 min. The solid was collected to give a crude solid. The solid obtained above (crude, 483 mg) was dissolved with MeCN (6 mL) and MeOH (4 mL). Then the solution was purified by HPLC [column: YMC-Pack ODS-A, S-15 μm, 12 nm, 250×50, flow rate: 80 mL/min, detection: ELSD (evaporative light scattering detector) (and UV=210 nm), eluent: MeCN/0.1% HCO$_2$H aq.] to give 2-(difluoromethoxy)-8,8-dimethyl-6H-spiro[1,6-naphthyridine-5,3'-oxetan]-7(8H)-one (406 mg) as a solid.

Example 19

To a mixture of 2-(difluoromethoxy)-8-(2-hydroxyethyl)-8-methyl-6-{[2-(trimethylsilyl)ethoxy]methyl}-6H-spiro[1, 6-naphthyridine-5,3'-oxetan]-7(8H)-one (343 mg) and CH$_2$Cl$_2$ (7 mL) was added TFA (0.3 mL) under ice bath cooling, and then the mixture was stirred for 3 hours at the same temperature. To the mixture was added TFA (0.3 mL) under ice bath cooling and then the mixture was stirred for additional 1 hour. The mixture was concentrated, and the residue was diluted with CHCl$_3$ (4 mL) and MeCN (4 mL). To the mixture was added ethylenediamine (1 mL), and then the mixture was stirred at room temperature overnight. The mixture was concentrated, and the residue was purified by silica gel chromatography (CHCl$_3$/MeOH) to give a solid (132 mg). The residue was solidified with MeOH and IPE to give 2-(difluoromethoxy)-8-(2-hydroxyethyl)-8-methyl-6H-spiro[1,6-naphthyridine-5,3'-oxetan]-7(8H)-one (93 mg) as a solid.

Example 20

To a mixture of 6-bromo-4,4-dimethyl-2H-spiro[isoquinoline-1,3'-oxetan]-3(4H)-one (24.9 g) and degassed DMF (prepared by Ar bubbling for 10 min) were added Zn(CN)$_2$ (9.9 g), Zn (2.75 g), Pd$_2$(dba)$_3$ (770 mg), and 1,1'-bis(diphenylphosphino)ferrocene (932 mg). Then the mixture was stirred at 80° C. for 14 hours. To the mixture was added EtOAc (500 mL) and stirred for 10 min. Then insoluble matter was filtered through a pad of Celite, and washed with EtOAc (500 mL). The filtrate was washed with H$_2$O (50 mL), 28% aq. ammonia (100 mL), and brine (50 mL) twice, and combined aqueous layers were extracted with EtOAc (250 mL) twice. Combined organic layers were washed with brine, dried over MgSO$_4$, filtered, and concentrated under reduced pressure. The residue was dissolved in THF (750 mL) under heating condition, and after cooling to room temperature, ammonium pyrrolidine-1-carbodithioate (1.22 g) was added. Then the mixture was stirred at room temperature for 1 hour. The mixture was filtered through a pad of Celite, and filtrate was concentrated under reduced pressure. The residue was solidified with EtOAc (200 mL), and collected. The solid was purified by amino-silica gel column chromatography (CHCl$_3$/hexane) to give 4,4-dimethyl-3-oxo-3,4-dihydro-2H-spiro[isoquinoline-1,3'-oxetane]-6-carbonitrile (18.87 g) as a solid.

Example 21

To a mixture of 7-chloro-4,4-diethyl-1,1-dimethyl-3-oxo-1,2,3,4-tetrahydroisoquinoline-6-carbonitrile (80 mg) and 1,4-dioxane (800 μL) were added MeOH (56 μL) and KOtBu (38 mg) at room temperature. The mixture was heated in the microwave reactor at 120° C. for 30 min. To the mixture was added sat. aq. NH$_4$Cl, and extracted with CHCl$_3$. The organic layer was concentrated under reduced pressure. The residue was purified by amino-silica gel column chromatography (EtOAc/hexanes). To the obtained solid was added 50% hexane/EtOAc (2 mL), and then the mixture was stirred at room temperature for 10 min. The precipitate was collected, washed with 50% hexane/EtOAc (1 mL) to give 4,4-diethyl-7-methoxy-1,1-dimethyl-3-oxo-1,2,3,4-tetrahydroisoquinoline-6-carbonitrile (14 mg) as a solid.

Example 22

6-Chloro-4-(2-hydroxyethyl)-4-methyl-2H-spiro[isoquinoline-1,3'-oxetan]-3(4H)-one (130.00 g) was resolved with chiral column chromatography (CHIRALPAK(trademark) IC, eluent; 100% MeOH) to give (+)-6-chloro-4-(2-hydroxyethyl)-4-methyl-2H-spiro[isoquinoline-1,3'-oxetan]-3 (4H)-one (58.4 g: >99% ee, shorter retention time) as a solid, and (−)-6-chloro-4-(2-hydroxyethyl)-4-methyl-2H-spiro [isoquinoline-1,3'-oxetan]-3(4H)-one (58.3 g: 99% ee, longer retention time) as a solid.

Example 23

To a mixture of 4,4-dimethyl-3-oxo-3,4-dihydro-2H-spiro [isoquinoline-1,3'-oxetane]-6-carbaldehyde (150 mg) and $CH_2Cl_2$ (4 mL) was added bis(2-methoxyethyl)aminosulfur trifluoride (2.70 g). The mixture was stirred at room temperature for 48 hours. To the mixture were added $CH_2Cl_2$ (25 mL) and sat. aq. $NaHCO_3$ (25 mL). The layers were separated, and the aqueous phase was extracted with additional $CH_2Cl_2$ (20 mL). The combined organic phases were dried over $Na_2SO_4$, filtered, and concentrated. The residue was purified by reverse phase HPLC with a gradient from 10% to 100% $MeCN/H_2O$ with 0.1% formic acid over 40 min (Phenomenex Gemini, 5 micron C18) to give 6-(difluoromethyl)-4,4-dimethyl-2H-spiro[isoquinoline-1,3'-oxetan]-3 (4H)-one (38 mg) as a solid.

Example 24

To a mixture of 6-hydroxy-4,4-dimethyl-2H-spiro[isoquinoline-1,3'-oxetan]-3(4H)-one (475 mg) and DMF (4 mL) were added $Cs_2CO_3$ (1.20 g) and sodium chlorodifluoroacetate (700 mg), and the mixture was stirred at 90° C. for 18 hours. The mixture was cooled to room temperature, and EtOAc (100 mL) and $H_2O$ (100 mL) were added. The layers were separated and the aqueous phase was extracted with EtOAc (50 mL). The combined organic phases were dried over $Na_2SO_4$ and concentrated. The residue was purified by reverse phase HPLC with a gradient from 10% to 100% $MeCN/H_2O$ with 0.1% formic acid over 40 min (Phenomenex Gemini, 5 micron C18) to give 6-(difluoromethoxy)-4,4-dimethyl-2H-spiro[isoquinoline-1,3'-oxetan]-3(4H)-one (107 mg) as a solid.

Example 25

To a mixture of DMF (0.5 mL), 2,2,2-trifluoroethanol (0.5 mL), and NaH (60% dispersion in mineral oil, 28 mg) was added 2'-chloro-8',8'-diethyl-6'H-spiro[oxetane-3,5'-pyrido [3,4-b]pyrazin]-7'(8'H)-one (20 mg). The mixture was stirred at 100° C. for 1 hour. The mixture was cooled to room temperature and diluted with sat. aq. $NH_4Cl$ (10 mL). EtOAc (30 mL) and $H_2O$ (20 mL) were then added, and the resultant organic layer was separated, washed with brine, dried over $Na_2SO_4$, and purified by reverse phase HPLC (20-100% $MeCN/H_2O$, 0.1% formic acid buffer) over 40 min to give 8',8'-diethyl-2'-(2,2,2-trifluoroethoxy)-6'H-spiro[oxetane-3, 5'-pyrido[3,4-b]pyrazin]-7'(8'H)-one (15 mg) as a solid.

Example 26

A mixture of bis(cyclopentadienyl)zirconium(IV) dichloride (20 mg) and sodium bis(2-methoxyethoxy)aluminum hydride (Red-Al, 3.4 M in toluene, 1.8 g) was stirred for 10 min and then cooled with ice bath. To the mixture was then added 2'-chloro-8',8'-diethyl-6'H-spiro[oxetane-3,5'-pyrido [3,4-b]pyrazin]-7'(8'H)-one (200 mg), and the mixture was stirred for 30 min. The mixture was warmed to room temperature and diluted with sat. aq. $NaHCO_3$ (10 mL). EtOAc (30 mL) and $H_2O$ (20 mL) were then added, and the organic layer was separated, washed with brine, dried over $Na_2SO_4$, and purified by reverse phase HPLC (20-100% $MeCN/H_2O$, 0.1% formic acid buffer) over 40 min to give 8',8'-diethyl-6'H-spiro[oxetane-3,5'-pyrido[3,4-b]pyrazin]-7'(8'H)-one (150 mg) as a solid.

Example 27

A mixture of 2-chloro-8,8-diethyl-5,5-dimethyl-5,8-dihydropyrido[3,4-b]pyrazin-7(6H)-one (100 mg) and sodium ethoxide (25% solution in EtOH, 5 mL) was heated in the microwave reactor at 190° C. for 30 min. EtOAc (100 mL) and $H_2O$ (50 mL) were added to the mixture, and the organic layer was then separated. The organic layer was then washed with $H_2O$ (50 mL), dried over $Na_2SO_4$, concentrated under reduced pressure, and purified by silica gel column chromatography (EtOAc/hexanes) to give 2-ethoxy-8,8-diethyl-5,5-dimethyl-5,8-dihydropyrido[3,4-b]pyrazin-7(6H)-one (45 mg) as a solid.

Example 28

A mixture of 8',8'-diethyl-2'-vinyl-6'H-spiro[oxetane-3,5'-pyrido[3,4-b]pyrazin]-7'(8'H)-one (6 mg), 10% palladium on carbon (12 mg), and MeOH (2 mL) was stirred under a hydrogen atmosphere (20 psi) for 2 hours. The mixture was then filtered through a pad of Celite, and the filtrate was concentrated. The residue was purified by reverse phase HPLC (20-100% $MeCN/H_2O$, 0.1% formic acid buffer) over 40 min to give 2',8',8'-triethyl-6'H-spiro[oxetane-3,5'-pyrido [3,4-b]pyrazin]-7'(8'H)-one (4 mg) as a solid.

Example 29

To a mixture of 5-({[tert-butyl(dimethyl)silyl] oxy}methyl)-2-chloro-8,8-diethyl-5-methyl-5,8-dihydropyrido[3,4-b]pyrazin-7(6H)-one (20 mg) and anhydrous THF (1 mL) was added TBAF (1 M in THF, 0.070 mL) under ice bath cooling, and the mixture was stirred for 5 min under ice bath cooling, followed by 15 min at room temperature. The mixture was diluted with sat. aq. $NaHCO_3$ (5 mL), and extracted with EtOAc (2×20 mL). The combined organic extracts were washed with brine and dried over $Na_2SO_4$, and concentrated under reduced pressure. The residue was purified by silica gel chromatography (EtOAc/hexanes) to give 2-chloro-8,8-diethyl-5-(hydroxymethyl)-5-methyl-5,8-dihydropyrido[3,4-b]pyrazin-7(6H)-one (11 mg) as a solid.

Example 30

A mixture of 2'-chloro-8',8'-diethyl-6'H-spiro[oxetane-3, 5'-pyrido[3,4-b]pyrazin]-7'(8'H)-one (28 mg) and $Me_2NH$ (2 M in THF, 1 mL) was heated in the microwave reactor at 130° C. for 1 hour. The reaction was cooled and purified directly by reverse phase HPLC (20-100% $MeCN/H_2O$, 0.1% formic acid buffer) over 40 min to give 2'-(dimethylamino)-8',8'-diethyl-6'H-spiro[oxetane-3,5'-pyrido[3,4-b] pyrazin]-7'(8'H)-one (10 mg) as a solid.

Example 31 (31a and 31b)

A mixture of 5-allyl-2-chloro-8,8-diethyl-5-methyl-5,8-dihydro-1,6-naphthyridin-7(6H)-one (100 mg), 1-methyl-4-vinyl-1H-pyrazole (74 mg), Grubbs second generation catalyst (6 mg), and $CH_2Cl_2$ (1 mL) was stirred at 40° C. for 4 days, and more catalyst (6 mg) was added at the beginning of days 2 and 3. The reaction was directly purified by reverse phase HPLC (20-100% MeCN/H₂O, 0.1% formic acid buffer) over 40 min to give the cis and trans isomers of 2-chloro-8,8-diethyl-5-methyl-5-[3-(1-methyl-1H-pyrazol-4-yl)prop-2-en-1-yl]-5,8-dihydro-1,6-naphthyridin-7(6H)-one as solids (isomer with shorter retention time, 2 mg; isomer with longer retention time, 7 mg).

Example 32

To a mixture of methyl (6-chloro-4-ethyl-3-oxo-3,4-dihydro-2H-spiro[isoquinoline-1,3'-oxetan]-4-yl)acetate (389 mg) and anhydrous THF (5 mL) was added lithium aluminum hydride (1.0 M in THF, 1.32 mL) dropwise under ice bath cooling. The mixture was stirred at under ice bath cooling for 20 min and then H₂O (0.050 mL), NaOH (3M aq., 0.050 mL), and H₂O (0.150 mL) were added. The mixture was filtered through a pad of Celite, and the filtered solids were washed with excess THF (200 mL). The filtrate was dried over Na₂SO₄ and concentrated. The residue was purified by silica gel chromatography (EtOAc/hexanes) to give foam. The foam was triturated and sonicated in Et₂O and filtered to give 6-chloro-4-ethyl-4-(2-hydroxyethyl)-2H-spiro[isoquinoline-1,3'-oxetan]-3(4H)-one (235 mg) as a solid.

Example 33

To a mixture of 5,5,8-trimethyl-7-oxo-8-({1-[(trimethylsilyl)methyl]-1H-1,2,3-triazol-4-yl}methyl)-5,6,7,8-tetrahydro-1,6-naphthyridine-2-carbonitrile (27 mg) and THF (2 mL) were added H₂O (20 μL) and TBAF (1M in THF, 100 μL). The mixture was stirred at room temperature for 24 hours. The mixture was concentrated and partitioned between EtOAc (10 mL) and H₂O. The organic layer was separated, and the aqueous phase was extracted with EtOAc (3×10 mL). The combined organic layers were dried over Na₂SO₄, filtered, and concentrated. The residue was purified by reverse phase HPLC (5 to 100% MeCN, 0.1% formic acid) to give 5,5,8-trimethyl-8-[(1-methyl-1H-1,2,3-triazol-4-yl)methyl]-7-oxo-5,6,7,8-tetrahydro-1,6-naphthyridine-2-carbonitrile (11 mg) as a solid.

Example 34

To a mixture of 4,4-diethyl-1,1-dimethyl-3-oxo-1,2,3,4-tetrahydroisoquinoline-6-carbonitrile (1.00 g) and DCE (15 mL) were added N-chlorosuccinimide (690 mg), palladium(II) diacetate (45 mg), and p-toluenesulfonic acid monohydrate (378 mg) at room temperature. Then the mixture was stirred at 70° C. for 16 hours. To the mixture was added N-chlorosuccinimide (676 mg) at room temperature. Then the mixture was stirred at 70° C. for 7 hours. To the mixture were added N-chlorosuccinimide (676 mg), palladium(II) diacetate (47 mg), and p-toluenesulfonic acid monohydrate (375 mg) at room temperature. Then the mixture was stirred at 70° C. for 1 day. After cooling to room temperature, the mixture was directly purified by silica gel column chromatography (EtOAc/hexanes). To the obtained residue was added 50% hexane/EtOAc, and then the mixture was stirred at 80° C. for 10 min and room temperature for 1 hour. The precipitate was collected to give 7-chloro-4,4-diethyl-1,1-dimethyl-3-oxo-1,2,3,4-tetrahydroisoquinoline-6-carbonitrile (140 mg) as a solid.

Example 35

To a mixture of 4-(2-{[tert-butyl(dimethyl)silyl]oxy}ethyl)-6-chloro-4-methyl-2H-spiro[isoquinoline-1,3'-oxetan]-3(4H)-one (49.98 g) and THF (350 mL) was added HCl (1 M aq., 164 mL) under ice bath cooling. The mixture was stirred at room temperature for 30 min. A mixture of NaHCO₃ (16.0 g) and H₂O (200 mL) was added under ice bath cooling, and then THF was evaporated under reduced pressure. To the mixture was added EtOAc (200 mL), and stirred at room temperature for 15 min. Then hexane (400 mL) was added and stirred at room temperature for 2 hours. The precipitate was collected, rinsed with H₂O (100 mL), 33% EtOAc/hexanes (50 mL) to give 6-chloro-4-(2-hydroxyethyl)-4-methyl-2H-spiro[isoquinoline-1,3'-oxetan]-3(4H)-one (31.56 g) as a solid.

Example 36

To a mixture of tert-butyl 2-{[3-(2,6-dichloropyridin-3-yl)oxetan-3-yl]carbamoyl}butanoate (42.9 g) and THF (500 mL) was added NaHMDS (1.1 M in THF, 250 mL) dropwise with ice bath cooling under Ar atmosphere. Then the mixture was stirred at the same temperature for 2 hours. To the mixture was added H₂O and extracted with EtOAc. The organic layer was washed with H₂O and brine, and dried over MgSO₄, filtered, and concentrated under reduced pressure. The residue was purified by silica gel column chromatography (CHCl₃/MeOH). The residue was washed with hexane to give tert-butyl 2-chloro-8-ethyl-7-oxo-7,8-dihydro-6H-spiro[1,6-naphthyridine-5,3'-oxetane]-8-carboxylate (27.7 g) as a solid.

Example 37

A mixture of ethyl 2-chloro-6-(2,4-dimethoxybenzyl)-8-ethyl-5,5-dimethyl-7-oxo-5,6,7,8-tetrahydro-1,6-naphthyridine-8-carboxylate (8.36 g), anisole (6 mL), and TFA (25 mL) was stirred at 80° C. for 4 hours. After cooling, solvent was evaporated under reduced pressure. The residue was basified to pH 7-8 with sat. aq. NaHCO₃ under ice bath cooling, and extracted with EtOAc. The organic layer was washed with brine, and dried over Na₂SO₄, filtered, and concentrated under reduced pressure. The residue was purified by silica gel column chromatography (EtOAc/hexanes) to give ethyl 2-chloro-8-ethyl-5,5-dimethyl-7-oxo-5,6,7,8-tetrahydro-1,6-naphthyridine-8-carboxylate (5.56 g) as a solid.

Example 38

A mixture of ethyl 2-chloro-8-ethyl-5,5-dimethyl-7-oxo-5,6,7,8-tetrahydro-1,6-naphthyridine-8-carboxylate (5.60 g) and H₂SO₄ (12 M aq., 60 mL) was stirred at 50° C. for 8 hours. After cooling, the mixture was poured into iced water, and basified with 28% aq. ammonia. EtOAc and H₂O were added to the mixture, and the phases were separated. Aqueous layer was extracted with EtOAc, and combined organic layers were washed with brine, and dried over Na₂SO₄, filtered, and concentrated under reduced pressure to give 2-chloro-8-ethyl-5,5-dimethyl-5,8-dihydro-1,6-naphthyridin-7(6H)-one (4.25 g) as a solid.

Example 39

To a mixture of tert-butyl 2-chloro-8-ethyl-7-oxo-7,8-dihydro-6H-spiro[1,6-naphthyridine-5,3'-oxetane]-8-carboxylate (27.7 g) and DCE (300 mL) was added TFA (30 mL). Then the mixture was stirred at 50° C. for 4 hours. The mixture was concentrated. To the residue was added H₂O and 1 M aq. NaOH under ice bath cooling, and extracted with a mixture of EtOAc and THF. The organic layer was washed with brine, and dried over $MgSO_4$, filtered, and concentrated under reduced pressure. To the residue was added IPE, and sonicated. The precipitate was collected to give 2-chloro-8-ethyl-6H-spiro[1,6-naphthyridine-5,3'-oxetan]-7(8H)-one (17.1 g) as a solid.

Example 40

A mixture of 6-chloro-2H-spiro[isoquinoline-1,3'-oxetan]-3(4H)-one (4.0 g), pentamethylcyclopentadienyliridium(III) dichloride dimer (73 mg), KOH (123 mg), and MeOH (16 mL) was sonicated for degassing under Ar atmosphere. The mixture was heated in the microwave reactor at 130° C. for 90 min. Then the mixture was stirred under ice bath cooling for 15 min. Additional nine batches (total ten batches) were performed with the same procedure as above. The precipitate in all vials were collected on the same funnel, rinsed with EtOH to give 6-chloro-4-methyl-2H-spiro[isoquinoline-1,3'-oxetan]-3(4H)-one (34.31 g) as a solid.

Example 41

To a mixture of 4,4-dimethyl-6-(4,4,5,5-tetramethyl-1,3,2-dioxaborolan-2-yl)-2H-spiro[isoquinoline-1,3'-oxetan]-3(4H)-one (700 mg) and THF (20 mL) were added KOH (1 M aq., 6.12 mL) and $H_2O_2$ (35% aq., 0.56 mL). The mixture was stirred at room temperature for 15 min. The mixture was neutralized to pH 7 using 1 M aq. HCl. EtOAc (100 mL) was added, and the layers were separated. The aqueous phase was extracted with EtOAc (75 mL). The combined organic extracts were combined, washed with brine, and dried over $Na_2SO_4$, filtered, and concentration under reduced pressure to give 6-hydroxy-4,4-dimethyl-2H-spiro[isoquinoline-1,3'-oxetan]-3(4H)-one (475 mg) as a solid.

Example 42

To a mixture of 6-bromo-2H-spiro[isoquinoline-1,3'-oxetan]-3(4H)-one (3.00 g) and DMF (75 mL, degassed with nitrogen) was added NaH (60% dispersion in mineral oil, 895 mg). The reaction flask was evacuated and back-filled with nitrogen three times, and the reaction was stirred at room temperature under nitrogen for 30 min. To the mixture was added a mixture of EtI (3.49 g) and DMF (2 mL) dropwise under ice bath cooling, and the mixture was stirred at the room temperature for 30 min. To the mixture was carefully added $H_2O$ under ice bath cooling, and the mixture was diluted with EtOAc, and the phases were separated. The aqueous phase was extracted with EtOAc, and the combined organic layers were washed with brine, dried over $Na_2SO_4$, filtered, and concentrated under reduced pressure. The residue was purified by silica gel column chromatography (EtOAc/hexanes) to give 6-bromo-4,4-diethyl-2H-spiro[isoquinoline-1,3'-oxetan]-3(4H)-one (2.59 g) as a solid.

Example 52

A 1000 mL 3-necked flask was charged with 6-chloro-2H-spiro[isoquinoline-1,3'-oxetan]-3(4H)-one (30.00 g), NMP (75 mL) and DMI (75 mL). The flask was evacuated and back-filled with Ar twice, and NaH (55% dispersion in mineral oil, 13.48 g) was added portionwise over 10 min under ice bath cooling, and then the mixture was stirred at the same temperature for 10 min. To the mixture was added a mixture of MeI (17.5 mL) and NMP (30 mL) dropwise under ice bath cooling over 100 min. The mixture was stirred at the same temperature for 20 min. Additional MeI (0.25 mL) was added under ice bath cooling, and the mixture was stirred at the same temperature for 1 hour. The mixture was diluted with $H_2O$ under ice bath cooling and then stirred at the same temperature for 30 min. The precipitate was collected, and washed with $H_2O$ and EtOAc/hexanes (⅓) to give a crude solid. To the solid was added EtOAc, and the mixture was warmed to 90° C., and then stirred at room temperature overnight. The precipitate was collected to give a crude solid. The solid was purified by silica gel chromatography (EtOAc/hexanes) to give 6-chloro-4,4-dimethyl-2H-spiro[isoquinoline-1,3'-oxetan]-3(4H)-one (10.88 g) as a solid.

Example 55

A 250 mL round bottom flask was charged with 6-bromo-4,4-diethyl-2H-spiro[isoquinoline-1,3'-oxetan]-3(4H)-one (2.70 g), 1,1'-bis(diphenylphosphino)ferrocene (462 mg), $Pd_2(dba)_3$ (381 mg), $Zn(CN)_2$ (1.27 g), Zn (218 mg). To the solids was added DMAc (30 mL, degassed with nitrogen for 45 min prior to use). The flask was evacuated and backfilled with nitrogen three times and then stirred at 80° C. for 18 hours. The mixture was cooled to room temperature and diluted with $H_2O$ and EtOAc. The biphasic mixture was filtered through a pad of Celite and the layers were separated. The aqueous phase was extracted with additional EtOAc three times, and the combined organic layers were washed with brine, dried over $Na_2SO_4$, filtered and concentrated under reduced pressure. The residue was purified by silica gel chromatography (MeOH/$CH_2Cl_2$) to give a solid. The solid was washed with EtOH to give 4,4-diethyl-3-oxo-3,4-dihydro-2H-spiro[isoquinoline-1,3'-oxetane]-6-carbonitrile (1.55 g) as a solid.

Example 137

To a mixture of methyl (6-chloro-4-methyl-3-oxo-3,4-dihydro-2H-spiro[isoquinoline-1,3'-oxetan]-4-yl)acetate (60 mg) and anhydrous THF (2 mL) was added methylmagnesium bromide (3 M in $Et_2O$, 0.323 mL). The mixture was stirred at room temperature for 15 min. The mixture was diluted with sat. aq. $NH_4Cl$ (1 mL) and $H_2O$ (5 mL). The mixture was extracted with EtOAc (2×35 mL), and combined organic layers were dried over $Na_2SO_4$, filtered, and concentrated. The residue was purified by reverse phase HPLC using a gradient from 10-100% MeCN/$H_2O$ over 50 min with 0.1% formic acid (Phenomenex Gemini, 5 micron C18). The residue was solidified with $Et_2O$ to give 6-chloro-4-(2-hydroxy-2-methylpropyl)-4-methyl-2H-spiro[isoquinoline-1,3'-oxetan]-3(4H)-one (38 mg) as a solid.

Example 143

To a mixture of 8,8-diethyl-2-(hydroxymethyl)-6-{[2-(trimethylsilyl)ethoxy]methyl}-6H-spiro[1,6-naphthyridine-5,3'-oxetan]-7(8H)-one (283 mg), CuI (47 mg), and MeCN (12 mL) was added difluoro(fluorosulfonyl)acetic acid (0.14 mL) at 80° C. After 1 hour, to the mixture was added difluoro(fluorosulfonyl)acetic acid (0.14 mL) at the same temperature. After 2 hour, to the mixture were added CuI (106 mg) and difluoro(fluorosulfonyl)acetic acid (0.14 mL) at the same temperature. Then the mixture was stirred at the same temperature for 1 hour. After cooling to room temperature, sat. aq. $NaHCO_3$ was added, and extracted with EtOAc. The organic layer was dried over $Na_2SO_4$, filtered, and concentrated under reduced pressure. The residue was purified by silica gel chromatography (EtOAc/hexanes) twice to give 2-[(difluoromethoxy)methyl]-8,8-diethyl-6H-spiro[1,6-naphthyridine-5,3'-oxetan]-7(8H)-one (14 mg) as a solid.

Example 148

To a mixture of 4,4-dimethyl-3-oxo-3,4-dihydro-2H-spiro[isoquinoline-1,3'-oxetane]-6-carbonitrile (59.22 g) and EtOH (1260 mL) was added $H_2O$ (540 mL). The mixture was stirred at 75° C. for 20 min and 78° C. for 15 min. To the mixture was added $H_2O$ (1.8 L), and stirred at 65° C. for 80 min, and cooled to 20° C. over 1 hour, and then, stirred at 20° C. for 2 hours. The precipitate was collected, washed with 35% aq. EtOH to give 4,4-dimethyl-3-oxo-3,4-dihydro-2H-spiro[isoquinoline-1,3'-oxetane]-6-carbonitrile (54.43 g) as crystal.

As a result obtained by subjecting the crystals to powder X-ray diffraction measurement using Cu as a tube, a chart including peaks at 2θ (°)=8.3, 12.1, 15.6, 16.6, 17.3, 20.5, 21.4, 23.4, 24.0 and 25.7 was obtained.

Example 149

6-Chloro-4-(2-hydroxyethyl)-4-methyl-2H-spiro[isoquinoline-1,3'-oxetan]-3(4H)-one (21.59 g) was resolved with chiral column chromatography (CHIRALFLASH(trademark) IC, eluent; 40-100% EtOH/hexanes then 100% MeOH) to give (−)-6-chloro-4-(2-hydroxyethyl)-4-methyl-2H-spiro[isoquinoline-1,3'-oxetan]-3(4H)-one (longer retention time). Then, the compound was purified by silica gel column chromatography ($CHCl_3$/MeOH). The residue was co-evaporated with EtOAc, then, EtOAc (30 mL) was added, and sonicated. To the mixture were added EtOAc (10 mL) and hexane (80 mL), and then sonicated again. The mixture was stirred at room temperature for 15 min. The precipitate was collected and dried at 50° C. under reduced pressure to give (−)-6-chloro-4-(2-hydroxyethyl)-4-methyl-2H-spiro[isoquinoline-1,3'-oxetan]-3(4H)-one (8.99 g) as crystal.

As a result obtained by subjecting the crystals to powder X-ray diffraction measurement using Cu as a tube, a chart including peaks at 2θ(°)=6.7, 11.1, 12.2, 13.7, 15.5, 16.2, 17.0, 18.3, 21.7 and 22.7 was obtained.

Example 154

To a liquid of polyphosphoric acid (20 g) was added tert-butyl 4-(3-chlorophenyl)-4-cyanopiperidine-1-carboxylate (4.5 g) at 140° C., and stirred for 5 min. To the mixture was added acetone (2.3 g) dropwise over 2 hour. The mixture was then stirred at 100° C. for 1 hour. The mixture was cooled to room temperature and poured slowly into a mixture of ice (ca 100 g) and EtOAc (300 mL). The organic layer was separated. The aqueous layer was treated with $K_2CO_3$ until the pH of the mixture was 10, followed by extraction twice with EtOAc (400 mL). The combined organic layers were washed with sat. aq. $NaHCO_3$, dried over $MgSO_4$, filtered, and concentrated to give 6-chloro-1,1-dimethyl-1,2-dihydro-3H-spiro[isoquinoline-4,4'-piperidin]-3-one (1.5 g) as a solid.

Example 155

A mixture of 6-chloro-1,1-dimethyl-1,2-dihydro-3H-spiro[isoquinoline-4,4'-piperidin]-3-one (56 mg), $CH_2Cl_2$ (2 mL), DIPEA (0.070 mL), and methanesulfonyl chloride (0.017 mL) was stirred at room temperature for 30 min and then purified directly using reverse phase HPLC (20-100% MeCN/$H_2O$, 0.1% formic acid buffer) over 40 min to give 6-chloro-1,1-dimethyl-1'-(methylsulfonyl)-1,2-dihydro-3H-spiro[isoquinoline-4,4'-piperidin]-3-one (34 mg) as a solid.

Reference Example 166

To a mixture of 6-chloro-4-(2-hydroxyethyl)-4-methyl-2H-spiro[isoquinoline-1,3'-oxetan]-3(4H)-one (259 mg) and $CH_2Cl_2$ (7 mL) was added 1,1,1-triacetoxy-1,1-dihydro-1,2-benziodoxol-3(1H)-one (Dess-Martin periodinane) (585 mg), and the mixture was stirred at room temperature for 30 min. To the mixture was added $CH_2Cl_2$, and washed twice with sat. aq. $NaHCO_3$. The organic layer was then dried over $Na_2SO_4$, filtered, and concentrated to give (6-chloro-4-methyl-3-oxo-3,4-dihydro-2H-spiro[isoquinoline-1,3'-oxetan]-4-yl)acetaldehyde (514 mg) as a solid.

Example 167 (167a and 167b)

To a mixture of (6-chloro-4-methyl-3-oxo-3,4-dihydro-2H-spiro[isoquinoline-1,3'-oxetan]-4-yl)acetaldehyde (514 mg, crude from previous reaction) and THF (8 mL) was added methylmagnesium bromide (3 M in $Et_2O$, 0.9 mL) under ice bath cooling, and the resulting mixture was stirred under ice bath cooling for 30 min. The mixture was diluted with sat. aq. $NH_4Cl$ (5 mL) and $H_2O$ (30 mL), followed by extraction twice with EtOAc (75 mL). Combined organic layers were washed with brine, and concentrated to a crude solid. The crude solid was purified by reverse phase HPLC (Phenomenex Gemini, 5 micron C18, 10-100% MeCN/$H_2O$ with 0.1% formic acid over 50 minutes) to give both diastereomers as solids. As a result of a measurement of single-crystal x-ray structure analysis, the first diastereomer to elute from the column was rac-(4R)-6-chloro-4-[(2R)-2-hydroxypropyl]-4-methyl-2H-spiro[isoquinoline-1,3'-oxetan]-3(4H)-one (65 mg) and the second diastereomer to elute from the column was rac-(4R)-6-chloro-4-[(2S)-2-hydroxypropyl]-4-methyl-2H-spiro[isoquinoline-1,3'-oxetan]-3(4H)-one (69 mg).

The compounds of Preparation Examples, Reference Examples and Examples shown in Tables below were produced in the same or a similar manner as the methods in Preparation Examples, Reference Examples or Examples as described above. In Table 4, "Ex. Cmpd." denotes Example Compound. In Table 4, "Reference Ex. Cmpd. 166" denotes Reference Example Compound 166. In Table 5, "Ex. Cmpd." denotes the Example Compound with reference to the structures provided in Table 4. In Table 5, "Reference Ex. Cmpd. 166" denotes the Reference Example Compound 166 with reference to the structure of Reference Example Compound 166 provided in Table 4. Furthermore, each Example Compound and Reference Example Compound listed in Table 5 were prepared by a procedure described in or analogous to the procedure described in the corresponding indicated Example or Reference Example, denoted by "Syn". For instance, the first entry of Table 5 pertains to Example Compound 1, having the structure shown in the first entry of Table 4. This Example Compound was prepared in accordance with the procedure described in Example 1 herein, and the data for this Example Compound is as provided in the first entry of Table 5. In Table 6, "Prep. Ex. Cmpd." denotes Preparation Example Compound. In Table 7, "Prep. Ex. Cmpd." denotes the Preparation Example Compound with reference to the structures provided in Table 6. Furthermore, each Preparation Example Compound listed in Table 7 was prepared by a procedure described in or analogous to the procedure described in the corresponding indicated Preparation Example, denoted by "PSyn". For instance, the first entry of Table 7 pertains to Preparation Example Compound 1a, having the structure shown in the first entry of Table 6. This Preparation Example Compound was prepared in accordance with the procedure described in Preparation Example 1 herein, and the data for this Preparation Example Compound is as provided in the first entry of Table 7.

TABLE 4

| Ex. Cmpd. | Str |
|---|---|
| 1 | |
| 2 | # |
| 3 | # |
| 4 | |
| 5 | # |
| 6 | |
| 7 | # |
| 8 | # |
| 9a | * |
| 9b | * |
| 10 | |

TABLE 4-continued

| Ex. Cmpd. | Str |
|---|---|
| 11 | 7-(2,2,2-trifluoroethoxy)-spiro[oxetane-3,4'-[1,6]naphthyridin]-8,8-diethyl-2'-one |
| 12 | 8,8-diethyl-spiro[oxetane-3,4'-[1,6]naphthyridin]-2'-one |
| 13 | 7-(difluoromethyl)-8,8-diethyl-spiro[oxetane-3,4'-[1,6]naphthyridin]-2'-one |
| 14 | 7-(methoxymethyl)-8,8-diethyl-spiro[oxetane-3,4'-[1,6]naphthyridin]-2'-one |
| 15 | * 7-(difluoromethoxy)-8-ethyl-8-(2-hydroxyethyl)-spiro[oxetane-3,4'-[1,6]naphthyridin]-2'-one |
| 16 | 7-cyano-8,8-diethyl-spiro[oxetane-3,4'-[1,6]naphthyridin]-2'-one |
| 17 | 7-(methylthio)-8,8-diethyl-spiro[oxetane-3,4'-[1,6]naphthyridin]-2'-one |
| 18 | 7-(difluoromethoxy)-8,8-dimethyl-spiro[oxetane-3,4'-[1,6]naphthyridin]-2'-one |
| 19 | # |
| 20 | 7-(difluoromethoxy)-8-methyl-8-(2-hydroxyethyl)-spiro[oxetane-3,4'-[1,6]naphthyridin]-2'-one |
| 20 | 7-cyano-8,8-dimethyl-spiro[oxetane-3,4'-[1,6]naphthyridin]-2'-one |
| 21 | 7-methoxy-6-cyano-1,1-dimethyl-4,4-diethyl-isoquinolin-3-one |
| 22a | * 6-chloro-4-methyl-4-(2-hydroxyethyl)-spiro[oxetane-3,1'-isoquinolin]-3'-one |
| 22b | * 6-chloro-4-methyl-4-(2-hydroxyethyl)-spiro[oxetane-3,1'-isoquinolin]-3'-one |

TABLE 4-continued

| Ex. Cmpd. | Str |
|---|---|
| 23 | (structure) |
| 24 | (structure) |
| 25 | (structure) |
| 26 | (structure) |
| 27 | (structure) |
| 28 | (structure) |
| 29 | (structure) # |
| 30 | (structure) |
| 31a | (structure) # |
| 31b | (structure) # |
| 32 | (structure) # |
| 33 | (structure) # |

TABLE 4-continued

| Ex. Cmpd. | Str |
|---|---|
| 34 | [structure] |
| 35 | [structure] |
| 36 | [structure] |
| 37 | [structure] |
| 38 | [structure] |
| 39 | [structure] |
| 40 | [structure] |
| 41 | [structure] |
| 42 | [structure] |
| 43 | [structure] |
| 44 | [structure] |
| 45 | [structure] |
| 46 | [structure] |

TABLE 4-continued

| Ex. Cmpd. | Str |
|---|---|
| 47 | 8-bromo-1,1-dimethyl-4,4-diethyl-3,4-dihydroisoquinolin-3(2H)-one |
| 48 | 6-chloro-1,1-dimethyl-4,4-diethyl-3,4-dihydroisoquinolin-3(2H)-one |
| 49 | 7-bromo-1,1-dimethyl-4,4-diethyl-3,4-dihydroisoquinolin-3(2H)-one |
| 50 | 6,8-dimethoxy-1,1-dimethyl-4,4-diethyl-3,4-dihydroisoquinolin-3(2H)-one |
| 51 | 7-bromo-1,1,4,4-tetramethyl-3,4-dihydroisoquinolin-3(2H)-one |
| 52 | 6-chloro-4,4-dimethyl-spiro[oxetane-3,1'-isoquinolin]-3'(2'H)-one |
| 53 | # 7-bromo-1,1-dimethyl-4-ethyl-3,4-dihydroisoquinolin-3(2H)-one |
| 54 | # 7-bromo-1,1-dimethyl-4-ethyl-4-(3-hydroxypropyl)-3,4-dihydroisoquinolin-3(2H)-one |
| 55 | 6-cyano-4,4-diethyl-spiro[oxetane-3,1'-isoquinolin]-3'(2'H)-one |
| 56 | # 6-cyano-4-methyl-4-(2-hydroxyethyl)-spiro[oxetane-3,1'-isoquinolin]-3'(2'H)-one |
| 57 | 1,1,4,4-tetramethyl derivative with pyridine and CN |
| 58 | pyridine-fused analog with Me, Me, Me, Me and CN |
| 59 | # 1-methyl-1-(difluoromethyl)-4,4-diethyl-6-cyano-3,4-dihydroisoquinolin-3(2H)-one |
| 60 | # naphthyridine analog with Me groups, CN, and allyl substituent |
| 61 | 1,1,4,4-tetramethyl-6-cyano-3,4-dihydroisoquinolin-3(2H)-one |

TABLE 4-continued

| Ex. Cmpd. | Str |
|---|---|
| 62 | (structure) |
| 63 | (structure) |
| 64 | (structure) |
| 65 | # (structure) |
| 66 | # (structure) |
| 67 | # (structure) |
| 68 | (structure) |
| 69 | (structure) |
| 70 | # (structure) |
| 71 | # (structure) |
| 72 | (structure) |
| 73 | (structure) |
| 74 | (structure) |
| 75 | # (structure) |

TABLE 4-continued

| Ex. Cmpd. | Str |
|---|---|
| 76 | (6-chloro-1,4-dihydro-1,1,4-trimethyl-4-allyl-1,6-naphthyridin-3(2H)-one) # |
| 77 | (6-chloro-1,4-dihydro-4,4-diethyl-1-methyl-1-allyl-1,6-naphthyridin-3(2H)-one) # |
| 78 | (6'-bromo-1'H-spiro[oxetane-3,1'-isoquinolin]-3'(4'H)-one, 4'-methyl-4'-(methoxycarbonylmethyl)) # |
| 79 | (6-bromo-1,1-dimethyl-4-ethyl-4-(2-chlorobenzyl)-3,4-dihydroisoquinolin-3(2H)-one) # |
| 80 | (6-bromo-1,1-dimethyl-4-ethyl-4-(3-chlorobenzyl)-3,4-dihydroisoquinolin-3(2H)-one) # |

TABLE 4-continued

| Ex. Cmpd. | Str |
|---|---|
| 81 | (6-bromo-1,1-dimethyl-4-ethyl-4-(2-fluoroethyl)-3,4-dihydroisoquinolin-3(2H)-one) # |
| 82 | (6-bromo-1,1-dimethyl-4-ethyl-4-(4-chlorobenzyl)-3,4-dihydroisoquinolin-3(2H)-one) # |
| 83 | (6-bromo-1,1-dimethyl-4-ethyl-4-(2,2-difluoroethyl)-3,4-dihydroisoquinolin-3(2H)-one) # |
| 84 | (6-chloro-1,1-dimethyl-4,4-diethyl-1,6-naphthyridin-3(2H)-one) |
| 85 | (6-bromo-1,1-dimethyl-4-ethyl-4-(4-methoxycarbonylbenzyl)-3,4-dihydroisoquinolin-3(2H)-one) # |

TABLE 4-continued

| Ex. Cmpd. | Str |
|---|---|
| 86 | (structure) |
| 87 | (structure) |
| 88 | (structure) |
| 89 | (structure) |
| 90 | (structure) |
| 91 | (structure) |
| 92a | (structure) |
| 92b | (structure) |
| 93 | (structure) |
| 94 | (structure) |
| 95 | (structure) |
| 96 | (structure) |

TABLE 4-continued

| Ex. Cmpd. | Str |
|---|---|
| 97 | |
| 98 | |
| 99 | |
| 100 | |
| 101 | |
| 102 | |
| 103 | |
| 104 | |
| 105 | |
| 106 | |
| 107 | |
| 108 | |

TABLE 4-continued

| Ex. Cmpd. | Str |
|---|---|
| 109 | (structure) |
| 110 | (structure) |
| 111 | (structure) |
| 112 | (structure) |
| 113 | (structure) |
| 114 | (structure) |
| 115 | (structure) |
| 116 | (structure) |
| 117 | (structure) |
| 118 | (structure) |
| 119 | (structure) |

TABLE 4-continued

| Ex. Cmpd. | Str |
|---|---|
| 120 | (structure) # |
| 121 | (structure) $ |
| 122 | (structure) # |
| 123 | (structure) # |
| 124 | (structure) # |
| 125 | (structure) # |
| 126 | (structure) # |
| 127 | (structure) # |
| 128 | (structure) # |
| 129 | (structure) # |
| 130 | (structure) $ |
| 131 | (structure) # |

TABLE 4-continued
| Ex. Cmpd. | Str |
|---|---|
| 132 | 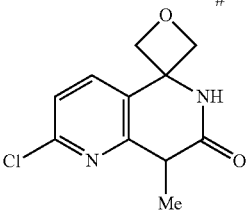 # |
| 133 | 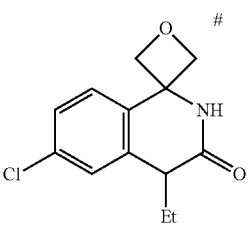 [SMILES: CCC1C(=O)NC2(COC2)c2ccc(Cl)cc21] # |
| 134a | 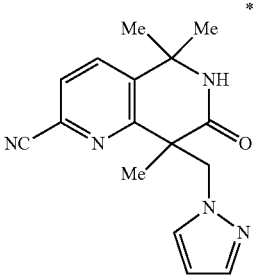 [SMILES: CC1(C)NC(=O)C(C)(Cn2cccn2)c2nc(C#N)ccc21] * |
| 134b | 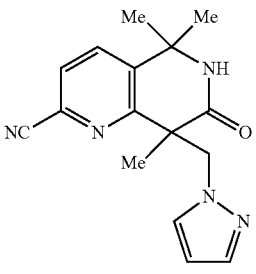 * |
| 135 | 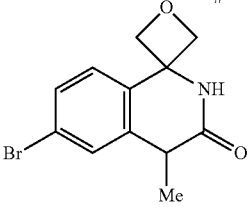 # |
| 136 | 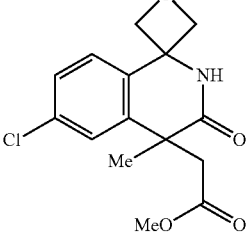 # |
| 137 | 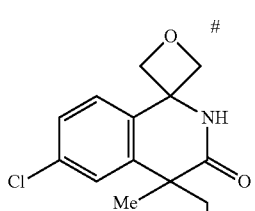 # |
| 138 | 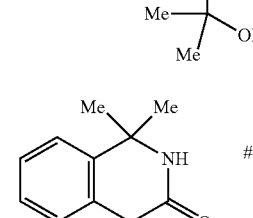 # |
| 139 | 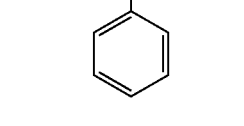 # |
| 140 | 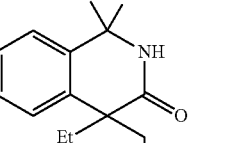 |
| 141 | 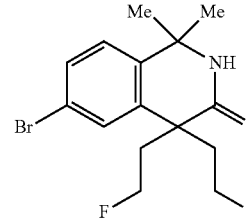 |
| 142 | 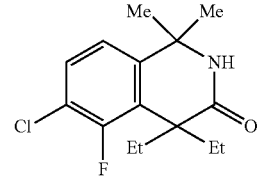 [SMILES: CCC1(CC)C(=O)NC(C)(C)c2ccc(Cl)c(F)c21] |

TABLE 4-continued

| Ex. Cmpd. | Str |
|---|---|
| 143 | (structure) |
| 144 | (structure) # |
| 145 | (structure) # |
| 146 | (structure) # |
| 147 | (structure) |
| 148 | (structure) |
| 149 | (structure) * |
| 150 | (structure) # |
| 151 | (structure) # |
| 152 | (structure) |
| 153 | (structure) |
| 154 | (structure) |

TABLE 4-continued

| Ex. Cmpd. | Str |
|---|---|
| 155 | 6-chloro-1,1-dimethyl-4-(1-(methylsulfonyl)piperidin-4-yl)spiro structure |
| 156 | 6-chloro-1,1-dimethyl spiro piperidine with N-C(=O)OMe |
| 157 | 6-fluoro-4,4-dimethyl-spiro[isoquinoline-1,3'-oxetan]-3(4H)-one |
| 158 | # chloro-pyridine fused spiro with Me, Me, Me, CH2C(=O)OMe |
| 159 | # chloro-pyridine fused with Me, Me, Me, CH2CH2OH |
| 160 | chloro-pyridine fused spiro[oxetane] with Et, Et |
| 161 | cyano-pyridine fused spiro[oxetane] with Et, Et |
| 162 | # 6-bromo spiro[oxetane] with Et |
| 163 | # 6-bromo spiro[oxetane] with Et, CH2C(=O)OMe |
| 164 | # 6-bromo spiro[oxetane] with Et, CH2CH2OH |
| 165 | cyano spiro[oxetane] with Et, CH2CH2OH |
| Reference Ex. Cmpd. 166 | # chloro spiro[oxetane] with Me, CH2CHO |

TABLE 4-continued

| Ex. Cmpd. | Str |
|---|---|
| 167a | Mixture of [structure: 6-chloro-isoquinolinone with spiro-oxetane, Me, and CH2-CH(OH)-Me with (R)-OH stereochemistry] and [structure: same with different stereochemistry at Me] |
| 167b | Mixture of [structure: 6-chloro-isoquinolinone with spiro-oxetane, Me, and CH2-CH(OH)-Me] and [structure: same with different stereochemistry] |

TABLE 4-continued

| Ex. Cmpd. | Str |
|---|---|
| 168 | [structure: naphthyridinone with spiro-oxetane and gem-dimethyl] |
| 169 | [structure: 2-(difluoromethyl)-naphthyridinone with spiro-oxetane and gem-dimethyl] |
| 170 | [structure: 2-chloro-naphthyridinone with spiro-oxetane, Me, Et] # |

TABLE 5

| Ex. Cmpd. | Syn | DAT |
|---|---|---|
| 1 | 1 | ESI+; 298; |
| 2 | 2 | ESI+; 218 |
| 3 | 3 | ESI+; 276 |
| 4 | 4 | ESI+; 257 $^1$H-NMR(DMSO-d$_6$)δ: 8.29 (s, 1H), 7.89 (d, J = 1.6 Hz, 1H), 7.71 (dd, J = 8.3, 1.6 Hz, 1H), 7.66 (d, 8.3 Hz, 1H), 2.09-1.98 (m, 2H), 1.81-1.71 (m, 2H), 1.50 (s, 6H), 0.45 (t, J = 7.4 Hz, 6H). |
| 5 | 5 | ESI+; 365, 367 |
| 6 | 6 | ESI+; 281 |
| 7 | 7 | ESI+; 416, 418 |
| 8 | 8 | ESI+; 367, 369 |

TABLE 5-continued

| Ex. Cmpd. | Syn | DAT |
|---|---|---|
| 9a | 9 | ESI+; 326, 328<br>$^1$H-NMR(DMSO-d$_6$)δ: 8.15(s, 1H), 7.54(d, J = 2.0 Hz, 1H), 7.43 (dd, J = 8.5, 2.1 Hz, 1H), 7.36 (d, J = 8.5 Hz, 1H), 4.30 (t, J = 5.1 Hz, 1H), 3.13-3.04 (m, 1H), 2.88-2.79 (m, 1H), 2.27-2.19 (m, 1H), 2.08-1.98 (m, 1H), 1.93-1.85 (m, 1H), 1.77-1.67 (m, 1H), 1.46 (s, 3H), 1.45 (s, 3H), 0.45 (t, J = 7.3 Hz, 3H)<br>optical rotation (EtOH): (+) |
| 9b | 9 | ESI+; 326, 328<br>$^1$H-NMR(DMSO-d$_6$)δ: 8.15(s, 1H), 7.54(d, J = 2.0 Hz, 1H), 7.43 (dd, J = 8.5, 2.1 Hz, 1H), 7.36 (d, J = 8.5 Hz, 1H), 4.30 (t, J = 5.1 Hz, 1H), 3.13-3.04 (m, 1H), 2.88-2.79 (m, 1H), 2.27-2.19 (m, 1H), 2.08-1.98 (m, 1H), 1.93-1.85 (m, 1H), 1.87-1.67 (m, 1H), 1.46 (s, 3H), 1.45 (s, 3H), 0.45 (t, J = 7.3 Hz, 3H)<br>optical rotation (EtOH): (−) |
| 10 | 10 | ESI+; 261 |
| 11 | 11 | ESI+; 345 |
| 12 | 12 | ESI+; 247 |
| 13 | 13 | ESI+; 297<br>$^1$H-NMR(DMSO-d$_6$) δ: 9.26 (s, 1H), 8.53 (d, J = 8.2 Hz, 1H), 7.79 (d, J = 8.2 Hz, 1H), 6.98 (t, J = 54.9 Hz, 1H), 4.96 (d, J = 6.7 Hz, 2H), 4.65 (d, J = 6.7 Hz, 2H), 1.98-1.87 (m, 4H), 0.38 (t, J = 7.4 Hz, 6H) |
| 14 | 14 | ESI+; 291 |
| 15 | 15 | ESI+; 329<br>$^1$H-NMR(DMSO-d$_6$)δ: 9.07 (s, 1H), 8.37 (d, J = 8.6 Hz, 1H), 7.76 (t, J = 72.7 Hz, 1H), 7.14 (d, J = 8.6 Hz, 1H), 4.92 (d, J = 6.4 Hz, 1H), 4.89 (d, J = 6.4 Hz, 1H), 4.63 (d, J = 6.3 Hz, 1H), 4.55 (d, J = 6.4 Hz, 1H), 4.15 (t, J = 5.1 Hz, 1H), 2.98-2.87 (m, 2H), 2.12-2.01 (m, 2H), 1.98-1.82 (m, 2H), 0.37 (t, J = 7.3 Hz, 3H),<br>optical rotation (EtOH): (−) |
| 16 | 16 | ESI+; 272<br>$^1$H-NMR(DMSO-d$_6$)δ: 9.32 (s, 1H), 8.56 (d, J = 8.2 Hz, 1H), 8.13 (d, J = 8.2 Hz, 1H), 4.96 (d, J = 6.8 Hz, 2H), 4.66 (d, J = 6.8 Hz, 2H), 1.99-1.83 (m, 4H), 0.39 (t, J = 7.3 Hz, 6H) |
| 17 | 17 | ESI+; 293 |
| 18 | 18 | ESI+; 285<br>$^1$H-NMR(DMSO-d$_6$)δ: 8.97 (s, 1H), 8.38 (d, J = 8.6 Hz, 1H), 7.79 (t, J = 72.7 Hz, 1H), 7.15 (d, J = 8.6 Hz, 1H), 4.95 (d, J = 6.8 Hz, 2H), 4.64 (d, J = 6.8 Hz, 2H), 1.36 (s, 6H) |
| 19 | 19 | ESI+; 315 |
| 20 | 20 | ESI+; 243<br>$^1$H-NMR(DMSO-d$_6$)δ: 8.99 (s, 1H), 8.10 (d, J = 8.2 Hz, 1H), 7.99 (d, J = 1.6 Hz, 1H), 7.90 (dd, J = 8.2, 1.7 Hz, 1H), 4.97 (d, J = 6.9 Hz, 2H), 4.69 (d, J = 6.8 Hz, 2H), 1.37 (s, 6H) |
| 21 | 21 | ESI+; 287 |
| 22a | 22 | ESI+; 282, 284<br>$^1$H-NMR(DMSO-d$_6$)δ: 8.91 (s, 1H), 7.95-7.90 (m, 1H), 7.52-7.47 (m, 2H), 4.94 (d, J = 6.4 Hz, 1H), 4.89 (d, J = 6.2 Hz, 1H), 4.68 (d, J = 6.4 Hz, 1H), 4.53 (d, J = 6.2 Hz, 1H), 4.27 (t, J = 5.0 Hz, 1H), 2.97-2.88 (m, 2H), 2.19-2.09 (m, 1H), 1.87-1.78 (m, 1H), 1.39 (s, 3H)<br>optical rotation (EtOH): (+) |
| 22b | 22 | ESI+; 282, 284<br>$^1$H-NMR(DMSO-d$_6$)δ: 8.91 (s, 1H), 7.95-7.90 (m, 1H), 7.52-7.47 (m, 2H), 4.94 (d, J = 6.4 Hz, 1H), 4.89 (d, J = 6.2 Hz, 1H), 4.68 (d, J = 6.4 Hz, 1H), 4.53 (d, J = 6.2 Hz, 1H), 4.27 (t, J = 5.0 Hz, 1H), 2.97-2.88 (m, 2H), 2.19-2.09 (m, 1H), 1.87-1.78 (m, 1H), 1.39 (s, 3H)<br>optical rotation (EtOH): (−) |
| 23 | 23 | APCI; 268<br>$^1$H NMR (DMSO-d$_6$)δ: 8.96 (s, 1H), 8.06 (d, J = 8.4 Hz, 1H), 7.68-7.62 (m, 2H), 7.07 (t, J = 56 Hz, 1H), 4.97 (d, J = 6.7 Hz, 2H), 4.70 (d, J = 6.7 Hz, 2H), 1.37 (s, 6H) |
| 24 | 24 | APCI; 284<br>$^1$H NMR (DMSO-d$_6$)δ: 8.92 (s, 1H), 7.95 (d, J = 8.6 Hz, 1H), 7.32 (t, J = 74 Hz, 1H), 7.28-7.22 (m, 2H), 4.95 (d, J = 6.7 Hz, 2H), 4.67 (d, J = 6.6 Hz, 2H), 1.35 (s, 6H) |
| 25 | 25 | APCI; 346<br>$^1$H NMR (CDCl$_3$)δ: 8.45 (s, 1H), 6.99 (s, 1H), 5.19 (d, J = 6.6 Hz, 2H), 4.88-4.79 (m, 4H), 2.14 (dq, J = 13.3, 7.4 Hz, 2H), 1.99 (dq, J = 13.3, 7.4 Hz, 2H), 0.55 (t, J = 7.4 Hz, 6H) |
| 26 | 26 | APCI; 248<br>$^1$H NMR (CDCl$_3$)δ: 8.72 (d, J = 2.3 Hz, 1H), 8.69 (d, J = 2.3 Hz, 1H), 7.09 (s, 1H), 5.21 (d, J = 6.5 Hz, 2H), 4.85 (d, J = 6.5 Hz, 2H), 2.23-2.01 (m, 4H), 0.54 (t, J = 7.4 Hz, 6H) |

TABLE 5-continued

| Ex. Cmpd. | Syn | DAT |
|---|---|---|
| 27 | 27 | APCI; 278<br>$^1$H NMR (DMSO-$d_6$) δ: 8.38 (s, 1H), 8.19 (s, 1H), 4.36 (q, J = 7.0 Hz, 2H), 1.91 (qd, J = 7.4, 4.7 Hz, 4H), 1.48 (s, 6H), 1.34 (t, J = 7.0 Hz, 3H), 0.49 (t, J = 7.4 Hz, 6H) |
| 28 | 28 | APCI; 276<br>$^1$H NMR (CDCl$_3$)δ: 8.44 (s, 1H), 6.97 (s, 1H), 5.11 (d, J = 6.5 Hz, 2H), 4.73 (d, J = 6.5 Hz, 2H), 2.84 (q, J = 7.6 Hz, 2H), 2.02 (q, J = 7.4 Hz, 4H), 1.28 (t, J = 7.6 Hz, 3H), 0.43 (t, J = 7.4 Hz, 6H) |
| 29 | 29 | APCI; 284<br>$^1$H NMR (DMSO-$d_6$)δ: 8.73 (s, 1H), 8.15 (s, 1H), 4.87 (t, J = 6.0 Hz, 1H), 3.78-3.68 (m, 1H), 3.53-3.46 (m, 1H), 2.03-1.87 (m, 3H), 1.79-1.71 (m, 1H), 1.39 (s, 3H), 0.58 (t, J = 7.4 Hz, 3H), 0.49 (t, J = 7.4 Hz, 3H) |
| 30 | 30 | APCI; 291<br>$^1$H NMR (CDCl$_3$)δ: 8.09 (s, 1H), 7.31 (s, 1H), 5.15 (d, J = 6.3 Hz, 2H), 4.78 (d, J = 6.4 Hz, 2H), 3.18 (s, 6H), 2.04 (q, J = 7.4 Hz, 4H), 0.54 (t, J = 7.4 Hz, 6H). |
| 31a | 31 | APCI; 373<br>shorter retention time in a reverse phase HPLC (20-100% MeCN/H$_2$O, 0.1% formic acid buffer) |
| 31b | 31 | APCI; 373<br>longer retention time in a reverse phase HPLC (20-100% MeCN/H$_2$O, 0.1% formic acid buffer) |
| 32 | 32 | APCI; 296<br>$^1$H NMR (DMSO-$d_6$)δ: 9.02 (s, 1H), 7.94 (d, J = 8.6 Hz, 1H), 7.53-7.42 (m, 2H), 4.90 (t, J = 6.6 Hz, 2H), 4.61 (d, J = 6.2 Hz, 1H), 4.55 (d, J = 6.2 Hz, 1H), 4.25 (t, J = 5.1 Hz, 1H), 2.95-2.82 (m, 2H), 2.24-2.15 (m, 1H), 2.04-1.93 (m, 1H), 1.93-1.83 (m, 1H), 1.78-1.68 (m, 1H), 0.38 (t, J = 7.3 Hz, 3H) |
| 33 | 33 | APCI; 311<br>$^1$H NMR (CD$_3$OD)δ: 7.94 (d, J = 8.2 Hz, 1H), 7.75 (d, J = 8.2 Hz, 1H), 7.38 (s, 1H), 3.94 (s, 3H), 3.56 (d, J = 13.9 Hz, 1H), 3.46 (d, J = 13.9 Hz, 1H), 1.70 (s, 3H), 1.55 (s, 3H), 1.13 (s, 3H) |
| 34 | 34 | ESI+; 291 |
| 35 | 35 | ESI+; 282 |
| 36 | 36 | ESI+; 253, 255 [M + H − Boc]$^+$<br>$^1$H-NMR(DMSO-$d_6$)δ: 9.49 (s, 1H), 8.42 (d, J = 8.5 Hz, 1H), 7.67 (d, J = 8.5 Hz, 1H), 4.99 (d, J = 6.4 Hz, 1H), 4.95 (d, J = 6.5 Hz, 1H), 4.69 (d, J = 6.4 Hz, 1H), 4.65 (d, J = 6.4 Hz, 1H), 2.28-2.07 (m, 2H), 1.20 (s, 9H), 0.41 (t, J = 7.5 Hz, 3H) |
| 37 | 37 | ESI+; 311, 313 |
| 38 | 38 | ESI+; 239, 241 |
| 39 | 39 | ESI+; 253 |
| 40 | 40 | ESI+; 238 |
| 41 | 41 | APCI; 234 |
| 42 | 1 or 42 | APCI; 324 |
| 43 | 1 | APCI; 280<br>$^1$H NMR (DMSO-$d_6$)δ: 9.15 (s, 1H), 7.97 (d, J = 8.5 Hz, 1H), 7.53 (dd, J = 8.5, 2.2 Hz, 1H), 7.44 (d, J = 2.2 Hz, 1H), 4.93 (d, J = 6.4 Hz, 2H), 4.66-4.57 (m, 2H), 1.98 (dq, J = 13.4, 7.3 Hz, 2H), 1.71 (dq, J = 14.5, 7.4 Hz, 2H), 0.40 (t, J = 7.4 Hz, 6H) |
| 44 | 1 | APCI; 324 |
| 45 | 1 | APCI; 302 |
| 46 | 1 | ESI+; 246 |
| 47 | 1 | ESI+; 310, 312 |
| 48 | 1 | ESI+; 288, 290 [M + Na]$^+$ |
| 49 | 1 | ESI+; 310, 312 |
| 50 | 1 | ESI+; 292 |
| 51 | 1 | ESI+; 282 |
| 52 | 1 or 52 | ESI+; 252, 254<br>$^1$H-NMR(DMSO-$d_6$)δ: 8.92 (s, 1H), 7.93-7.90 (m, 1H), 7.51-7.48 (m, 2H), 4.94 (d, J = 6.7 Hz, 2H), 4.66 (d, J = 6.7 Hz, 2H), 1.35 (s, 6H) |
| 53 | 2 | ESI+; 282, 284 |
| 54 | 3 | ESI+; 340, 342 |
| 55 | 20 or 55 | APCI; 271<br>1H NMR (400 MHz, DMSO-$d_6$)δ: 8.28 (dd, J = 8.3, 1.5 Hz, 1H), 7.85 (dt, J = 8.3, 1.5 Hz, 1H), 7.81 (d, J = 1.6 Hz, 1H), 5.10-5.02 (m, 2H), 4.83-4.77 (m, 2H), 2.16 (dt, J = 13.7, 7.4 Hz, 2H), 1.90-1.76 (m, 2H), 0.52 (td, J = 7.4, 1.2 Hz, 6H) |
| 56 | 20 | APCI; 273<br>$^1$H NMR (DMSO-$d_6$)δ: 8.97 (s, 1H), 8.10 (d, J = 8.2 Hz, 1H), 8.00 (d, J = 1.6 Hz, 1H), 7.89 (dd, J = 8.2, 1.7 Hz, 1H), 4.97 (d, J = 6.5 Hz, 1H), 4.90 (d, J = 6.3 Hz, 1H), 4.72 (d, J = 6.4 Hz, 1H), 4.55 (d, J = 6.3 Hz, 1H), 4.25 (t, J = 5.0 Hz, 1H), 2.97-2.86 (m, 2H), 2.22-2.11 (m, 1H), 1.94-1.81 (m, 1H), 1.42 (s, 3H) |

TABLE 5-continued

| Ex. Cmpd. | Syn | DAT |
|---|---|---|
| 57 | 16 | ESI+; 258<br>¹H NMR (CDCl₃)δ: 8.71 (d, J = 2.0 Hz, 1H), 7.76 (d, J = 2.0 Hz, 1H), 6.32 (s, 1H), 2.26 (dq, J = 13.7, 7.4 Hz, 2H), 1.60 (dq, J = 13.7, 7.4 Hz, 2H), 1.58 (s, 6H), 0.56 (t, J = 7.4 Hz, 6H) |
| 58 | 16 | APCI; 230<br>¹H NMR (CD₃OD)δ: 8.83 (d, J = 1.9 Hz, 1H), 8.34 (d, J = 1.9 Hz, 1H), 1.64 (s, 6H), 1.57 (s, 6H) |
| 59 | 16 | APCI; 293 |
| 60 | 16 | APCI; 256 |
| 61 | 16 | APCI; 229 |
| 62 | 16 | APCI; 271 |
| 63 | 4 | ESI+; 257 |
| 64 | 4 | ESI+; 258<br>¹H-NMR (DMSO-d₆)δ: 8.42 (s, 1H), 8.21 (d, J = 8.2 Hz, 1H), 7.96 (d, J = 8.2 Hz, 1H), 2.01-1.86 (m, 4H), 1.52 (s, 6H), 0.45 (t, J = 7.4 Hz, 6H) |
| 65 | 5 | ESI+; 325, 327 |
| 66 | 5 | ESI+; 359, 361 |
| 67 | 6 | APCI; 324 |
| 68 | 6 | APCI; 282 |
| 69 | 6 | APCI; 268 |
| 70 | 6 | APCI; 305 |
| 71 | 6 | APCI; 253<br>¹H NMR (CD₃OD)δ: 7.83 (d, J = 8.4 Hz, 1H), 7.32 (d, J = 8.4 Hz, 1H), 2.20-1.98 (m, 2H), 1.59 (s, H), 1.56 (s, 3H), 1.49 (s, 3H), 0.56 (t, J = 7.4 Hz, 3H) |
| 72 | 6 | APCI; 267<br>¹H NMR (CDCl₃)δ: 8.49 (d, J = 2.0 Hz, 1H), 7.54 (d, J = 2.0 Hz, 1H), 6.32 (s, 1H), 2.31 (dq, J = 13.7, 7.4 Hz, 2H), 1.60 (dq, J = 13.7, 7.4 Hz, 2H), 1.58 (s, 6H), 0.66 (t, J = 7.4 Hz, 6H) |
| 73 | 6 | APCI; 239 |
| 74 | 6 | ESI+; 281<br>¹H NMR (CDCl₃)δ: 8.69 (d, J = 2.2 Hz, 1H), 7.92 (s, 1H), 7.56 (d, J = 2.2 Hz, 1H), 5.20 (d, J = 6.5 Hz, 2H), 4.85 (d, J = 6.5 Hz, 2H), 2.27 (dt, J = 14.8, 7.4 Hz, 2H), 1.67 (dq, J = 14.6, 7.4 Hz, 2H), 0.58 (t, J = 7.4 Hz, 6H) |
| 75 | 6 | APCI; 318 |
| 76 | 6 | APCI; 265 |
| 77 | 6 | APCI; 293 |
| 78 | 6 | APCI; 354 |
| 79 | 6 | ESI+: 406, 408 |
| 80 | 6 | ESI+; 406, 408 |
| 81 | 6 | ESI+; 350, 352 [M + Na]⁺ |
| 82 | 6 | ESI+; 428, 430 [M + Na]⁺ |
| 83 | 6 | ESI+; 368, 370 [M + Na]⁺ |
| 84 | 6 | ESI+; 267, 269 |
| 85 | 6 | ESI+; 430, 432 |
| 86 | 6 | ESI+; 368, 370 |
| 87 | 6 | ESI+; 333, 335 [M + Na]⁺ |
| 88 | 6 | ESI+; 333 |
| 89 | 6 | ESI+; 325, 327 [M + Na]⁺ |
| 90 | 6 | ESI+; 253 |
| 91 | 7 | ESI+; 340, 342 |
| 92a | 9 | ESI+; 283<br>shorter retention time in a chiral supercritical fluid chromatography (SFC) using CHIRALCEL ® OZ-H (elute CO2:MeOH = 80:20)<br>optical rotation (EtOH): (−) |
| 92b | 9 | ESI+; 283<br>longer retention time in a chiral supercritical fluid chromatography (SFC) using CHIRALCEL ® OZ-H (elute CO₂:MeOH = 80:20)<br>optical rotation (EtOH): (+) |
| 93 | 10 | APCI; 244 |
| 94 | 10 | APCI; 274 |
| 95 | 10 | ESI+; 283 |
| 96 | 10 | ESI+; 291 |
| 97 | 10 | ESI+; 271 |
| 98 | 10 | ESI+; 297 |
| 99 | 12 | ESI+; 219 |
| 100 | 13 | ESI+; 269 |
| 101 | 15 | ESI+; 288 |
| 102 | 15 | ESI+; 277 |
| 103 | 15 | ESI+; 313<br>¹H-NMR (DMSO-d₆)δ: 9.12 (s, 1H), 8.49 (d, J = 8.2 Hz, 1H), 7.77 (d, J = 8.2 Hz, 1H), 6.97 (t, J = 54.9 Hz, 1H), 4.96 (d, J = 6.4 Hz, 1H), 4.92 (d, J = 6.4 Hz, 1H), 4.68 (d, J = 6.4 Hz, 1H), 4.57 (d, J = 6.4 Hz, 1H), 4.19 (t, J = 4.8 Hz, 1H), 2.93-2.87 (m, 2H), 2.18-2.03 |

TABLE 5-continued

| Ex. Cmpd. | Syn | DAT |
|---|---|---|
| | | (m, 2H), 2.01-1.90 (m, 2H), 0.36 (t, J = 7.4 Hz, 3H) |
| | | optical rotation (EtOH): (−) |
| 104 | 15 | ESI+; 313 |
| | | optical rotation (EtOH): (+) |
| 105 | 15 | ESI+; 329 |
| | | optical rotation (EtOH): (+) |
| 106 | 16 | APCI; 273 |
| | | $^1$H NMR (CDCl$_3$)δ: 9.00 (s, 1H), 7.08 (s, 1H), 5.19 (d, J = 6.7 Hz, 2H), 4.87 (d, J = 6.7 Hz, 2H), 2.27-2.13 (m, 2H), 2.08 (dq, J = 14.6, 7.4 Hz, 2H), 0.55 (t, J = 7.4 Hz, 6H) |
| 107 | 16 | APCI; 296 |
| | | $^1$H NMR (DMSO-d$_6$)δ: 8.34 (s, 1H), 8.11 (d, J = 8.2 Hz, 1H), 7.99 (d, J = 8.2 Hz, 1H), 7.29 (d, J = 2.2 Hz, 1H), 7.18 (d, J = 1.8 Hz, 1H), 6.08 (t, J = 2.1 Hz, 1H), 4.77 (d, J = 13.2 Hz, 1H), 4.68 (d, J = 13.1 Hz, 1H), 1.59 (s, 3H), 1.50 (s, 3H), 1.09 (s, 3H) |
| 108 | 16 | APCI; 244 |
| | | $^1$H NMR (CD$_3$OD)δ: 8.06 (d, J = 8.2 Hz, 1H), 7.77 (d, J = 8.2 Hz, 1H), 2.28-2.03 (m, 2H), 1.64 (s, 3H), 1.60 (s, 3H), , 0.56 (t, J = 7.4 Hz, 3H) |
| 109 | 16 | APCI; 296 |
| 110 | 16 | APCI; 296 |
| | | $^1$H NMR (CD$_3$OD)δ: 7.91 (dd, J = 8.2, 0.5 Hz, 1H), 7.76 (dd, J = 8.1, 0.5 Hz, 1H), 6.86 (s, 2H), 3.27 (s, 2H), 1.66 (s, 3H), 1.49 (s, 3H), 0.97 (s, 3H) |
| 111 | 16 | APCI; 254 |
| 112 | 16 | ESI+; 302 |
| 113 | 19 | ESI+; 335 |
| 114 | 32 | APCI; 326 |
| 115 | 32 | ESI+; 326, 328 |
| 116 | 34 | ESI+; 335 |
| 117 | 36 | ESI+; 377 [M + Na]$^+$ |
| 118 | 36 | APCI; 240 [M + H − Boc]$^+$ |
| 119 | 36 | APCI; 239 [M + H − Boc]$^+$ |
| 120 | 36 | APCI; 253 [M + H − Boc]$^+$ |
| 121 | 36 | APCI; 265 [M + H − Boc]$^+$ |
| 122 | 36 | APCI; 269 [M + H − C$_4$H$_9$]$^+$ |
| 123 | 36 | ESI+; 361, 363 [M + Na]$^+$ |
| 124 | 37 | APCI; 297 |
| 125 | 38 | APCI; 225 |
| 126 | 39 | APCI; 254 |
| 127 | 39 | APCI; 240 |
| 128 | 39 | ESI+; 239 |
| 129 | 39 | ESI+; 253 |
| 130 | 39 | APCI; 265 |
| 131 | 39 | APCI; 225 |
| 132 | 39 | ESI+; 239 |
| 133 | 40 | APCI; 252 |
| 134a | 9 | APCI; 296 |
| | | longer retention time in a chiral supercritical fluid chromatography (SFC) using ChromegaChiral CC4 (elute CO$_2$:EtOH with 0.5% isopropylamine = 85:15), |
| | | optical rotation (CHCl$_3$): (+) |
| 134b | 9 | APCI; 296 |
| | | shorter retention time in a chiral supercritical fluid chromatography (SFC) using ChromegaChiral CC4 (elute CO$_2$:EtOH with 0.5% isopropylamine = 85:15), |
| | | optical rotation (CHCl$_3$): (−) |
| 135 | 40 | APCI; 282 |
| 136 | 6 | APCI; 310 |
| 137 | 137 | APCI; 310 |
| | | $^1$H NMR (DMSO-d$_6$)δ: 8.69 (s, 1H), 7.90 (d, J = 8.5 Hz, 1H), 7.54-7.35 (m, 2H), 4.96 (d, J = 6.4 Hz, 1H), 4.85 (d, J = 6.4 Hz, 1H), 4.72 (d, J = 6.4 Hz, 1H), 4.47 (d, J = 6.4 Hz, 1H), 3.89 (s, 1H), 2.33 (d, J = 14.1 Hz, 1H), 1.92 (d, J = 14.1 Hz, 1H), 1.36 (s, 3H), 0.83 (s, 3H), 0.51 (s, 3H). |
| 138 | 2 | ESI+; 252 |
| 139 | 8 | ESI+; 451, 453 [M + Na]$^+$ |
| 140 | 1 | ESI+; 368, 370 [M + Na]$^+$ |
| 141 | 1 | ESI+; 306, 308 [M + Na]$^+$ |
| 142 | 16 | ESI+; 244 |
| 143 | 143 | ESI+; 327 |
| 144 | 6 | ESI+; 339, 341 [M + Na]$^+$ |
| 145 | 11 | ESI+; 313 |
| 146 | 18 | ESI+; 299 |
| 147 | 11 | ESI+; 249 |
| 148 | 148 | ESI+; 243 |
| 149 | 149 | ESI+; 282 |

TABLE 5-continued

| Ex. Cmpd. | Syn | DAT |
|---|---|---|
| 150 | 37 | APCI; 298 |
| 151 | 38 | APCI; 226 |
| 152 | 6 | APCI; 240 |
| 153 | 16 | APCI; 231 |
| 154 | 154 | APCI; 279 |
| 155 | 155 | APCI; 357 $^1$H-NMR (CD$_3$OD)δ: 7.52 (s, 1H), 7.40 (d, J = 8.4 Hz, 1H), 7.31 (d, J = 8.5 Hz, 1H), 3.73-3.60 (m, 4H), 2.90 (s, 3H), 2.24-2.12 (m, 2H), 2.09-1.93 (m, 2H), 1.58 (s, 6H) |
| 156 | 155 | APCI; 337 |
| 157 | 1 | APCI; 236 |
| 158 | 6 | APCI; 297 |
| 159 | 32 | ESI+; 269 |
| 160 | 1 | APCI; 281 |
| 161 | 16 | ESI+; 272 |
| 162 | 40 | APCI; 296 |
| 163 | 6 | APCI; 368 |
| 164 | 32 | APCI; 340 |
| 165 | 20 | APCI; 287 |
| Reference Ex. Cmpd. 166 | Reference Example 166 | APCI; 280 |
| 167a | 167 | APCI; 296 $^1$H-NMR (DMSO-d$_6$) δ: 8.99 (s, 1H), 7.89 (d, J = 9.2 Hz, 1H), 7.50-7.39 (m, 2H), 4.95 (d, J = 6.4 Hz, 1H), 4.89 (d, J = 6.4 Hz, 1H), 4.71 (d, J = 6.4 Hz, 1H), 4.52 (d, J = 6.4 Hz, 1H), 4.05 (d, J = 4.9 Hz, 1H), 3.29-3.19 (m, 1H), 1.94 (dd, J = 13.8, 5.5 Hz, 1H), 1.86 (dd, J = 13.8, 7.0 Hz, 1H), 1.38 (s, 3H), 0.83 (d, J = 6.1 Hz, 3H) |
| 167b | 167 | APCI; 296 $^1$H-NMR (DMSO-d$_6$) δ: 8.59 (s, 1H), 7.92 (d, J = 8.5 Hz, 1H), 7.53-7.35 (m, 2H), 4.95 (d, J = 6.4 Hz, 1H), 4.81 (d, J = 6.4 Hz, 1H), 4.72 (d, J = 6.4 Hz, 1H), 4.43 (d, J = 6.4 Hz, 1H), 3.95 (d, J = 4.9 Hz, 1H), 2.93-2.83 (m, 1H), 2.13 (dd, J = 13.8, 10.3 Hz, 1H), 1.71 (dd, J = 13.8, 3.2 Hz, 1H), 1.38 (s, 3H), 0.84 (d, J = 6.1 Hz, 3H) |
| 168 | 12 | ESI+; 219 |
| 169 | 13 | ESI+; 269 |
| 170 | 6 | ESI+; 289, 291 [M + Na]$^+$ |

TABLE 6

| Prep. Ex. Cmpd. | Str |
|---|---|
| 1a | [Structure: 6-bromo-1,1-dimethyl-1,4-dihydroisoquinolin-3(2H)-one] |
| 1b | Mixture of [Structure: 6-bromo-1,1-dimethyl-1,4-dihydroisoquinolin-3(2H)-one] and [Structure: 8-bromo-1,1-dimethyl-1,4-dihydroisoquinolin-3(2H)-one] |
| 2 | [Structure: 6-bromo-4-bromo-1,1-dimethyl-1,4-dihydroisoquinolin-3(2H)-one] # |
| 3 | [Structure: 2-(3-bromophenyl)butanamide] # |

TABLE 6-continued

| Prep. Ex. Cmpd. | Str |
|---|---|
| 4 | (structure) |
| 5 | (structure) |
| 6 | (structure) |
| 7 | (structure) |
| 8 | (structure) |
| 9 | (structure) |
| 10 | (structure) |
| 11 | (structure) |
| 12 | (structure) |
| 13 | (structure) |
| 14 | (structure) |
| 15 | (structure) |
| 16 | (structure) |
| 17 | (structure) |

TABLE 6-continued

| Prep. Ex. Cmpd. | Str |
|---|---|
| 18 | (chloro-naphthyridinone with spiro-oxetane, N-SEM, gem-diethyl) |
| 19 | (vinyl-naphthyridinone with spiro-oxetane, N-SEM, gem-diethyl) |
| 20 | (formyl-naphthyridinone with spiro-oxetane, N-SEM, gem-diethyl) |
| 21 | (hydroxymethyl-naphthyridinone with spiro-oxetane, N-SEM, gem-diethyl) |
| 22 | (methoxymethyl-naphthyridinone with spiro-oxetane, N-SEM, gem-diethyl) |
| 23 | (cyano-naphthyridinone with spiro-oxetane, NH, Et, CH₂CH₂OTBDMS) # |
| 24 | (chloro-isoquinolinone with spiro-oxetane, NH, Me, CH₂CH₂OTBDMS) # |
| 25 | (chloro-pyrido-pyrazinone with CH₂OTBDMS, Me, Et) $ |
| 26 | (pinacol boronate isoquinolinone with spiro-oxetane, NH, gem-dimethyl) |
| 27 | (2,6-dichloropyridine with oxetane, NH-C(O)-CH(Et)-C(O)OtBu) # |
| 28 | (ester linker with ethyl/hexyl chain, thioether to pyridine-naphthyridinone with spiro-oxetane, Et₂, NH, C=O) # |

TABLE 6-continued
| Prep. Ex. Cmpd. | Str |
|---|---|
| 29 | 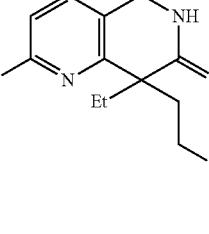 |
| 30 | 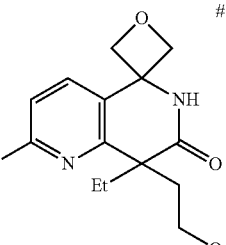 |
| 31 | 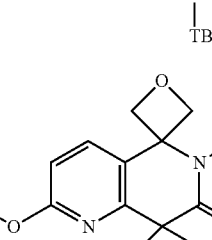 |
| 32 | 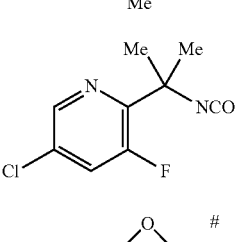 |
| 33 | 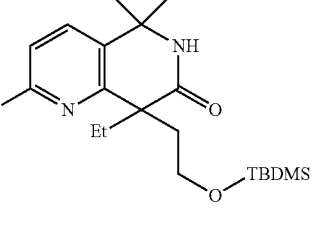 |
| 34 | 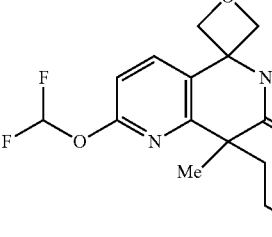 |
TABLE 6-continued
| Prep. Ex. Cmpd. | Str |
|---|---|
| 35 |  |
| 36 |  |
| 37 |  |
| 38 |  |
| 39 |  |
| 40 |  |
| 41 |  |

TABLE 6-continued
| Prep. Ex. Cmpd. | Str |
|---|---|
| 42a | 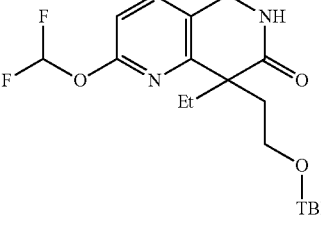 * |
| 42b | 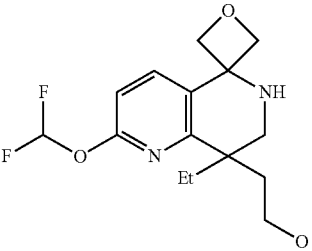 * |
| 43 | # 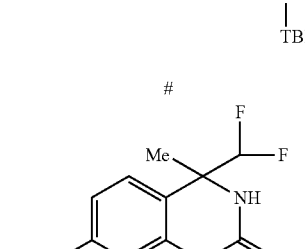 |
| 44 | 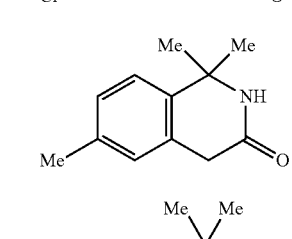 |
| 45 | 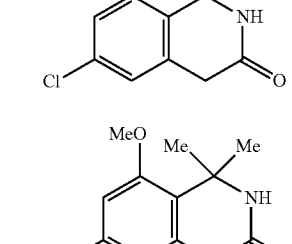 |
| 46 | 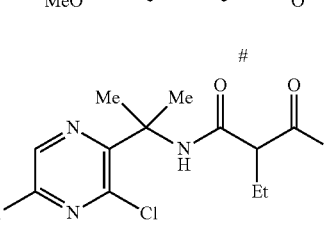 |
| 47 | #  |
| 48 | # |
| 49 | # |
| 50 | # |
| 51 | # |
| 52 | # |
| 53 | # |
| 54 | # |

TABLE 6-continued

| Prep. Ex. Cmpd. | Str |
|---|---|
| 55 | (structure) $ |
| 56 | (structure) |
| 57 | (structure) # |
| 58 | (structure) $ |
| 59 | (structure) # |
| 60 | (structure) # |
| 61 | (structure) |
| 62 | (structure) # |
| 63 | (structure) # |
| 64 | (structure) |
| 65 | (structure) # |
| 66 | (structure) # |

TABLE 6-continued
| Prep. Ex. Cmpd. | Str |
|---|---|
| 67 | 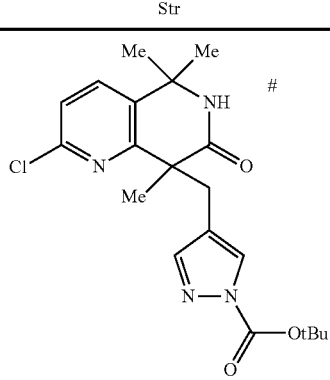 # |
| 68 | 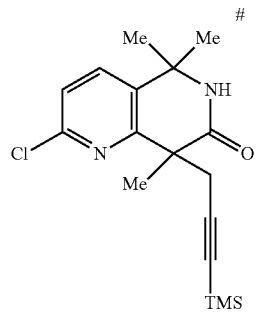 [SMILES: CC1(C)NC(=O)C(C)(CC#C[Si](C)(C)C)c2nc(Cl)ccc21] # |
| 69 | 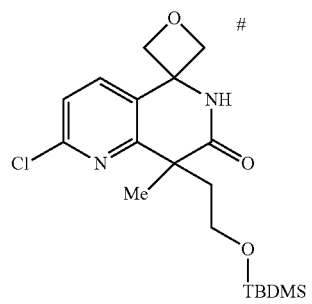 # |
| 70 | 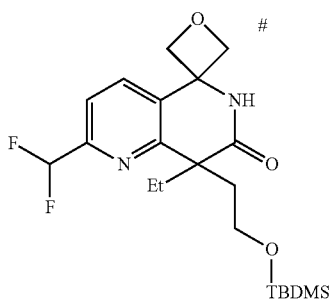 # |
| 71 | 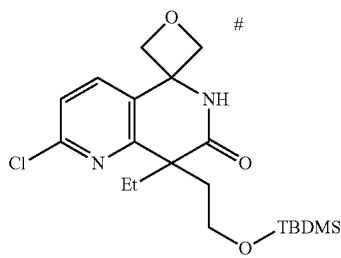 # |
| 72 | 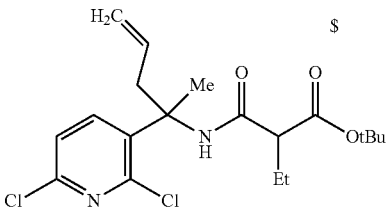 [SMILES: C=CCC(C)(NC(=O)C(CC)C(=O)OC(C)(C)C)c1ccc(Cl)nc1Cl] $ |
| 73 | 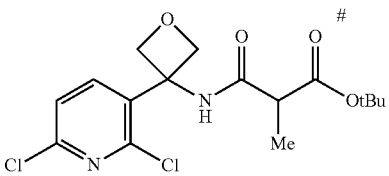 [SMILES: CC(C(=O)NC1(c2ccc(Cl)nc2Cl)COC1)C(=O)OC(C)(C)C] # |
| 74 | 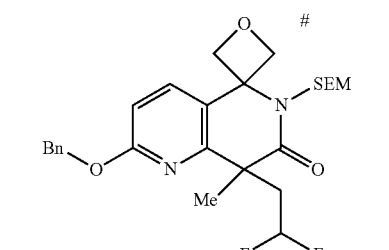 # |
| 75 | 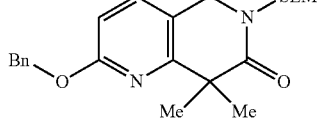 # |
| 76 | 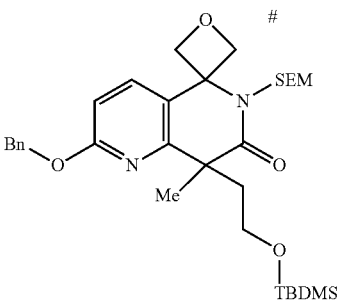 # |
| 77 | 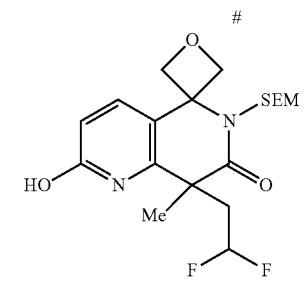 [SMILES: CC1(CC(F)F)C(=O)N(COCC[Si](C)(C)C)C2(COC2)c2ccc(O)nc21] # |

TABLE 6-continued
| Prep. Ex. Cmpd. | Str |
|---|---|
| 78 | 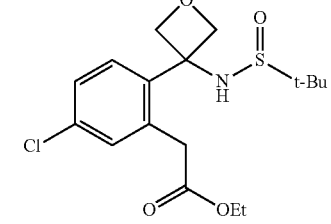 |
| 79 | 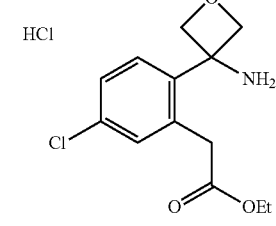 |
| 80 | 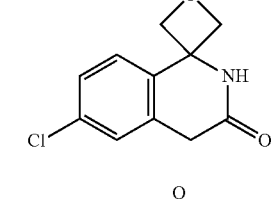 |
| 81 | 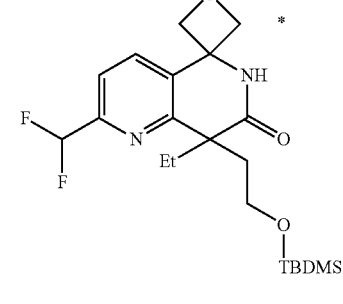 |
| 82 | 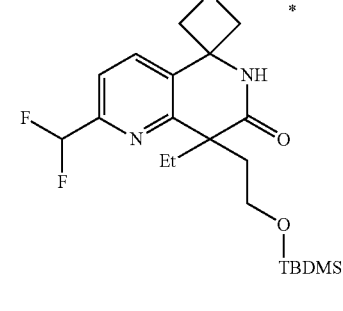 |
| 83 | 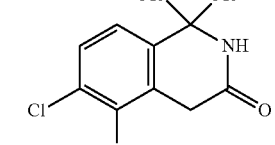 |
| 84 | |
| 85 | |
| 86 | |
| 87a | |
| 87b | |
| 88 | |

TABLE 6-continued
| Prep. Ex. Cmpd. | Str |
|---|---|
| 89 | 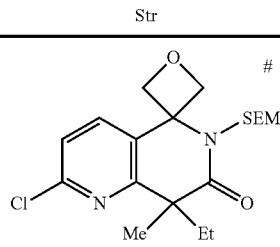 |
| 90 | 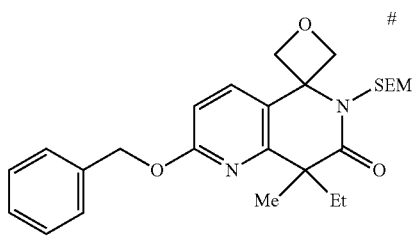 [SMILES: CCC1(C)C(=O)N(COCC[Si](C)(C)C)C2(COC2)c2ccc(OCc3ccccc3)nc21] |
| 91 | 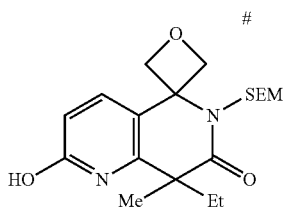 [SMILES: CCC1(C)C(=O)N(COCC[Si](C)(C)C)C2(COC2)c2ccc(O)nc21] |
| 92 | 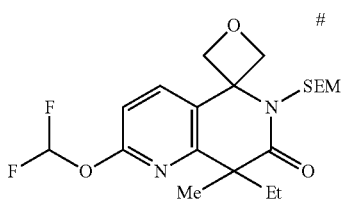 [SMILES: CCC1(C)C(=O)N(COCC[Si](C)(C)C)C2(COC2)c2ccc(OC(F)F)nc21] |
| 93 | 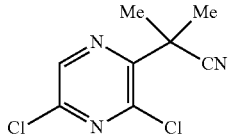 [SMILES: CC(C)(C#N)c1ncc(Cl)nc1Cl] |
| 94 | 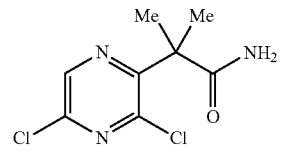 [SMILES: CC(C)(C(N)=O)c1ncc(Cl)nc1Cl] |
| 95 | 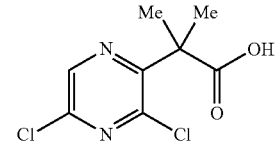 [SMILES: CC(C)(C(=O)O)c1ncc(Cl)nc1Cl] |
| 96 | 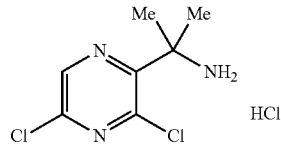 [SMILES: CC(C)(N)c1ncc(Cl)nc1Cl ; Cl] |
TABLE 6-continued
| Prep. Ex. Cmpd. | Str |
|---|---|
| 97 | 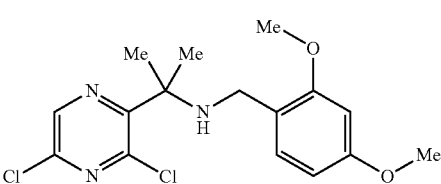 [SMILES: COc1ccc(CNC(C)(C)c2ncc(Cl)nc2Cl)c(OC)c1] |
| 98 | 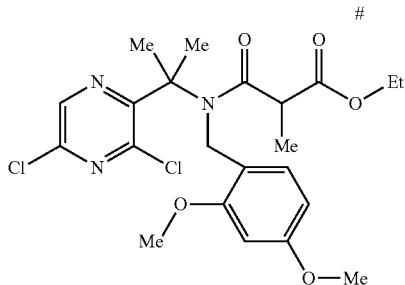 [SMILES: CCOC(=O)C(C)C(=O)N(Cc1ccc(OC)cc1OC)C(C)(C)c1ncc(Cl)nc1Cl] |
| 99 | 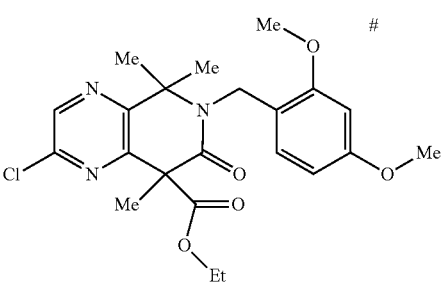 [SMILES: CCOC(=O)C1(C)C(=O)N(Cc2ccc(OC)cc2OC)C(C)(C)c2ncc(Cl)nc21] |
| 100 | 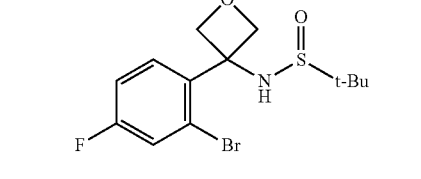 |
| 101 | 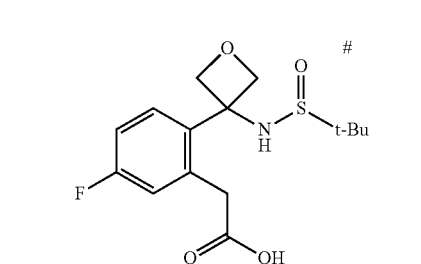 [SMILES: CC(C)(C)S(=O)NC1(c2ccc(F)cc2CC(=O)O)COC1] |
| 102 | 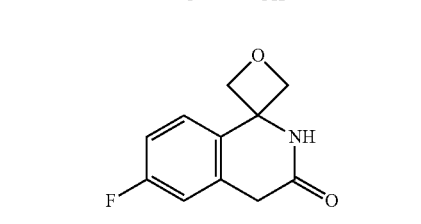 [SMILES: O=C1Cc2cc(F)ccc2C2(COC2)N1] |

TABLE 6-continued

| Prep. Ex. Cmpd. | Str |
|---|---|
| 103 | [Structure: 5-chloro-2-(3-(t-butylsulfinamido)oxetan-3-yl)pyridine with CH2COOH at 3-position] # |
| 104 | [Structure: chloro-pyridine fused spirocyclic oxetane with NH-C(=O)] |
| 105 | [Structure: 5-chloro-3-bromo-2-(3-(t-butylsulfinamido)oxetan-3-yl)pyridine] # |

TABLE 7

| Prep. Ex. Cmpd. | PSyn | DAT |
|---|---|---|
| 1a | 1 | ESI+; 254, 256 |
| 1b | 1 | 6-bromo-1,1-dimethyl-1,4-dihydroisoquinolin-3(2H)-one: $^1$H-NMR (DMSO-d$_6$)δ: 8.03(s, 1H), 7.45-7.39 (m, 2H), 7.34 (d, J = 8.3 Hz, 1H), 3.54 (s, 2H), 1.46 (s, 6H) 8-bromo-1,1-dimethyl-1,4-dihydroisoquinolin-3(2H)-one: $^1$H-NMR (DMSO-d$_6$)δ: 8.03(s, 1H), 7.55 (dd, J = 7.8, 1.6 Hz, 1H), 7.21-7.12 (m, 2H), 3.58 (s, 2H), 1.73 (s, 6H) |
| 2 | 2 | $^1$H-NMR (CDCl$_3$)δ: 7.55 (d, J = 2.0 Hz, 1H), 7.50 (dd, J = 8.5, 2.0 Hz, 1H), 7.19 (d, J = 8.5 Hz, 1H), 6.34 (s, 1H), 5.40 (s, 1H), 1.70 (s, 3H), 1.66 (s, 3H) |
| 3 | 3 | ESI+; 242, 244 |
| 4 | 4 | APCI; 293 |
| 5 | 5 | APCI; 336 |
| 6 | 6 | APCI; 199 |
| 7 | 7 | ESI+; 233, 235, 237 |
| 8 | 8 | ESI+; 205, 207 |
| 9 | 9 | ESI+; 355, 357 |
| 10 | 10 | ESI+; 497, 499, 501 |
| 11 | 11 | APCI; 370 [M + H − C$_4$H$_9$]$^+$ |
| 12 | 12 | APCI; 383 |
| 13 | 13 | $^1$H NMR (DMSO-d$_6$) δ: 3.12 (t, J = 7.5 Hz, 1H), 1.75-1.67(m, 2H), 1.40 (s, 9H), 0.88 (t, J = 7.4 Hz, 3H). |
| 14 | 14 | APCI; 217 |
| 15 | 15 | ESI+; 323, 325 |
| 16 | 16 | ESI+; 219, 221 |
| 17 | 17 | APCI; 390 |
| 18 | 18 | ESI+; 411 |
| 19 | 19 | ESI+; 403 |
| 20 | 20 | ESI+; 405 |
| 21 | 21 | ESI+; 407 |
| 22 | 22 | ESI+; 421 |
| 23 | 23 | ESI+; 402 |
| 24 | 24 | ESI+; 418, 420 [M + Na]$^+$ |
| 25 | 25 | APCI; 370 |
| 26 | 26 | APCI; 344 |
| 27 | 27 | ESI+; 389 |
| 28 | 28 | ESI+; 463 |

TABLE 7-continued

| Prep. Ex. Cmpd. | PSyn | DAT |
|---|---|---|
| 29 | 29 | ESI+; 483 |
| 30 | 30 | ESI+; 393 |
| 31 | 31 | ESI+; 437 [M + Na]$^+$ |
| 32 | 32 | APCI; 215 |
| 33 | 33 | ESI+; 443 |
| 34 | 34 | ESI+: 445 |
| 35 | 35 | APCI; 247 |
| 36 | 36 | ESI+; 346 |
| 37 | 37 | ESI+; 418 |
| 38 | 38 | ESI+; 314 |
| 39 | 39 | ESI+; 270 |
| 40 | 40 | ESI+; 215, 217 |
| 41 | 41 | APCI; 189 |
| 42a | 42 | ESI+; 443 shorter retention time in a chiral column chromatography using CHIRALFLASH(trademark) IA (elute Hexane/EtOAc 80/20-0/100) |
| 42b | 42 | ESI+; 443 longer retention time in a chiral column chromatography using CHIRALFLASH(trademark) IA (elute Hexane/EtOAc 80/20-0/100) |
| 43 | 1 | APCI; 246 |
| 44 | 1 | ESI+; 190 |
| 45 | 1 | $^1$H-NMR(CDCl$_3$)δ: 7.25-7.22 (m, 2H), 7.16-7.14 (m, 1H), 6.08 (s, 1H), 3.62 (s, 2H), 1.57 (s, 6H) |
| 46 | 1 | ESI+; 236 |
| 47 | 10 | APCI; 320 [M + H − C$_4$H$_9$]$^+$ |
| 48 | 10 | APCI; 483 |
| 49 | 10 | APCI; 259 [M + H − Boc]$^+$ |
| 50 | 10 | APCI; 289 [M + H − C$_4$H$_9$]$^+$ |
| 51 | 11 | APCI; 447 |
| 52 | 11 | ESI+; 461 |
| 53 | 15 | APCI; 324 |
| 54 | 15 | APCI; 310 |
| 55 | 15 | APCI; 440 |
| 56 | 16 | APCI; 206 |
| 57 | 16 | APCI; 231 |
| 58 | 17 | APCI; 506 |
| 59 | 17 | APCI; 373 |
| 60 | 18 | ESI+; 455, 457 [M + Na]$^+$ |
| 61 | 18 | ESI+; 405, 407 [M + Na]$^+$ |
| 62 | 18 | ESI+; 549, 551 [M + Na]$^+$ |
| 63 | 19 | ESI+; 391 |
| 64 | 20 | APCI; 276 |
| 65 | 24 | APCI; 398 |
| 66 | 24 | APCI; 405 |
| 67 | 24 | APCI; 305 [M + H − Boc]$^+$ |
| 68 | 24 | APCI; 335 |
| 69 | 24 | ESI+; 419, 421 [M + Na]$^+$ |
| 70 | 24 | APCI; 427 |
| 71 | 24 | ESI+; 433, 435 [M + Na]$^+$ |
| 72 | 27 | APCI; 399 [M − H]$^-$ |
| 73 | 27 | ESI+; 397, 399 [M + Na]$^+$ |
| 74 | 29 | ESI+; 505 |
| 75 | 29 | ESI+; 455 |
| 76 | 29 | ESI+; 599 |
| 77 | 30 | APCI/ESI+; 415 |
| 78 | 30 | ESI+; 365 |
| 79 | 30 | ESI+; 509 |
| 80 | 31 | ESI+; 487 [M + Na]$^+$ |
| 81 | 33 | ESI+; 559 |
| 82 | 36 | APCI; 307 |
| 83 | 36 or 83 | ESI+; 302 |
| 84 | 37 or 84 | ESI+; 374 |
| 85 | 38 or 85 | ESI+; 270, 272 |
| 86 | 39 or 86 | ESI+; 224 |
| 87a | 42 | ESI+; 427 shorter retention time in a chiral chromatography using CHIRALFLASH(trademark) IA, (eluent; Hexane/EtOAc 100/0-40/60) |

TABLE 7-continued

| Prep. Ex. Cmpd. | PSyn | DAT |
|---|---|---|
| 87b | 42 | ESI+; 427 longer retention time in a chiral chromatography using CHIRALFLASH(trademark) IA, (eluent; Hexane/EtOAc 100/0-40/60) |
| 88 | 1 | ESI+; 250, 252 [M + Na]+ |
| 89 | 18 | ESI+; 419, 421 [M + Na]+ |
| 90 | 29 | ESI+; 469 |
| 91 | 30 | ESI+; 379 |
| 92 | 31 | ESI+; 451 [M + Na]+ |
| 93 | 40 | APCI; 216 |
| 94 | 7 | APCI; 234 |
| 95 | 95 | APCI; 235 |
| 96 | 96 | APCI; 206 |
| 97 | 9 | APCI; 351 |
| 98 | 10 | APCI; 484 |
| 99 | 11 | APCI; 448 |
| 100 | 100 | APCI; 350 |
| 101 | 101 | APCI; 330 |
| 102 | 102 | APCI; 208 |
| 103 | 101 | APCI; 347 |
| 104 | 104 | APCI; 225 |
| 105 | 36 | APCI; 367 |

While the methods and compositions have been described in detail with reference to certain exemplary aspects thereof, it will be understood that modifications and variations are within the spirit and scope of that which is described and claimed.

INDUSTRIAL APPLICABILITY

The compounds of the formula (I) or the formula (I'), or a salt thereof modulate the contractility of the skeletal sarcomere, and thus are expected to be used as an agent for preventing or treating 1) neuromuscular disorders, 2) disorders of voluntary muscle, 3) CNS disorders in which muscle weakness, atrophy, and fatigue are prominent symptoms, 4) muscle symptoms stemming from systemic disorders, and 5) dysfunctions of pelvic floor and urethral/anal sphincter muscle.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

We claim the following:

1. A method for preventing or treating a disease or condition selected from the group consisting of stress urinary incontinence (SUI), mixed urinary incontinence (MUI), and fecal incontinence, comprising administering to a subject in need thereof an effective amount of a compound of formula (I) or a salt thereof:

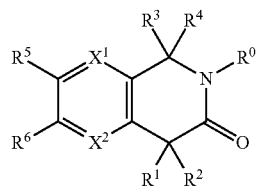

(I)

wherein,
$X^1$ is C—$R^{11}$ or N;
$X^2$ is C—$R^{12}$ or N;
$R^{11}$ is i) H, ii) halogen, iii) —CN, or iv) —O—$C_{1-6}$ alkyl;
$R^{12}$ is H or halogen;
$R^1$ is i) H, ii) $C_{1-6}$ alkyl which may be substituted with one or more substituent(s) selected from the group consisting of halogen(s), and pyrazolyl(s), iii) $C_{2-6}$ alkenyl, or iv) —$OR^0$;
$R^2$ is i) $C_{1-6}$ alkyl which may be substituted with one or more substituent(s) selected from the group consisting of —$OR^0$(s), halogen(s), —$COOR^0$(s), —$CONR^{21}R^{22}$(s), phenyl(s) which may be substituted with one or more substituent(s) selected from the $G^1$ group, and heteroaryl(s) which is selected from the group consisting of pyridyl, pyrazolyl, imidazolyl, thiazolyl, thiadiazolyl, thienyl, oxazolyl, isoxazolyl, and triazolyl, wherein, the heteroaryl may be substituted with one or more substituent(s) selected from the $G^2$ group, ii) $C_{2-6}$ alkenyl, iii) $C_{2-6}$ alkynyl, iv) —$OR^0$, v) —$NR^{23}R^{24}$, vi) —$COOR^0$, or vii) phenyl;
$R^{21}$ is H or $C_{1-6}$ alkyl;
$R^{22}$ is i) $C_{1-6}$ alkyl which may be substituted with one or more phenyl(s), or ii) phenyl;
$R^{23}$ is i) H, or ii) $C_{1-6}$ alkyl which may be substituted with one or more —OH(s);
$R^{24}$ is i) $C_{1-6}$ alkyl which may be substituted with one or more phenyl(s) which may be substituted with one or more halogen(s), ii) $C_{3-8}$ cycloalkyl which may be substituted with one or more $C_{1-6}$ alkyl(s), iii) phenyl which may be substituted with one or more halogen(s), or iv) tetrahydropyranyl; or
$R^1$, $R^2$, and a carbon atom bounded by $R^1$ and $R^2$ may interact to form a 4-piperidine ring or 4-tetrahydropyran ring, and the carbon atom bounded by $R^1$ and $R^2$ is a spiro atom and the 4-piperidine ring may be substituted with one or more substituent(s) selected from the group consisting of —$SO_2$—($C_{1-6}$ alkyl) and —$COOR^0$;
$R^3$ and $R^4$ are the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and heteroaryl(s) which is selected from the group consisting of pyrazolyl and thienyl, wherein the heteroaryl may be substituted with one or more $C_{1-6}$ alkyl(s), or,
$R^3$, $R^4$, and a carbon atom bounded by $R^3$ and $R^4$ may interact to form a 3-oxetane ring and the carbon atom bounded by $R^3$ and $R^4$ is a spiro atom;
$R^5$ is i) H, ii) $C_{1-6}$ alkyl which may be substituted with one or more —O—($C_{1-6}$ alkyl)(s), iii) —O—$C_{1-6}$ alkyl, iv) halogen, v) —COO—($C_{1-6}$ alkyl), or vi) $C_{3-8}$ cycloalkyl;

$R^6$ is i) H, ii) $C_{1-6}$ alkyl which may be substituted with one or more substituent(s) selected from the group consisting of —O—($C_{1-6}$ alkyl(s)) which may be substituted with one or more halogen(s)) and halogen(s), iii) —OH, iv) —O—($C_{1-6}$ alkyl which may be substituted with one or more halogen(s)), v) halogen, vi) —CN, vii) —S—($C_{1-6}$ alkyl), viii) $C_{3-8}$ cycloalkyl, ix) —NR⁰R⁰, or x) $C_{2-6}$ alkenyl;

$G^1$ group is i) halogen, ii) —COOR⁰, iii) —CONR⁰R⁰, iv) —OH, v) $C_{1-6}$ alkyl which may be substituted with one or more substituent(s) selected from the group consisting of —OH(s) and halogen, or vi) —O—($C_{1-6}$ alkyl which may be substituted with one or more substituent(s) selected from the group consisting of —OH(s) and halogen(s));

$G^2$ group is i) halogen, ii) $C_{1-6}$ alkyl which may be substituted with one or more substituent(s) selected from the group consisting of —OH(s) and halogen(s) or iii) —CONR⁰R⁰;

$R^0$ is the same or different each other, H or $C_{1-6}$ alkyl, provided that said compound is not methyl 1,1-diallyl-3-oxo-2,4-dihydroisoquinoline-4-carboxylate or a salt thereof.

2. The method according to claim 1, wherein
$R^1$ is i) H, or ii) $C_{1-6}$ alkyl;
$R^2$ is i) $C_{1-6}$ alkyl which may be substituted with one or more substituent(s) selected from the group consisting of —OR⁰(s), halogen(s), —CONR²¹R²²(s), phenyl(s) which may be substituted with one or more substituent(s) selected from the group consisting of halogen(s) and —COOR⁰(s), and heteroaryl(s) which is selected from the group consisting of pyrazolyl, and triazolyl, ii) $C_{2-6}$ alkenyl, iii) $C_{2-6}$ alkynyl, iv) —NR²³R²⁴, or v) —COOR⁰;
$R^{21}$ is $C_{1-6}$ alkyl;
$R^{22}$ is $C_{1-6}$ alkyl;
$R^{23}$ is $C_{1-6}$ alkyl; and
$R^{24}$ is i) $C_{3-8}$ cycloalkyl, or ii) phenyl; or
$R^1$, $R^2$, and a carbon atom bounded by $R^1$ and $R^2$ may interact to form a 4-tetrahydropyran ring, and the carbon atom bounded by $R^1$ and $R^2$ is a spiro atom.

3. The method according to claim 2, wherein
$R^3$ and $R^4$ are the same or different each other, i) $C_{1-3}$ alkyl which may be substituted with one or more substituent(s) selected from the group consisting of halogen(s) and —OH(s) or ii) $C_{2-6}$ alkenyl which may be substituted with one or more substituent(s) selected from the group consisting of —OH(s) and pyrazolyl(s) which may be substituted with one or more $C_{1-6}$ alkyl(s), or,
$R^3$, $R^4$, and a carbon atom bounded by $R^3$ and $R^4$ may interact to form a 3-oxetane ring and the carbon atom bounded by $R^3$ and $R^4$ is a Spiro atom.

4. The method according to claim 3, wherein
$R^5$ is i) H, ii) $C_{1-6}$ alkyl, iii) —O—$C_{1-6}$ alkyl, iv) halogen, or v) $C_{3-8}$ cycloalkyl; and
$R^6$ is i) H, ii) $C_{1-6}$ alkyl which may be substituted with one or more substituent(s) selected from the group consisting of —O—($C_{1-6}$ alkyl)(s) and halogen(s), iii) —OH, iv) —O—($C_{1-6}$ alkyl which may be substituted with one or more halogen(s)), v) halogen, vi) —CN, vii) —S—$C_{1-6}$ alkyl, viii) —NR⁰R⁰, or ix) $C_{2-6}$ alkenyl.

5. The method according to claim 4, wherein
$X^1$ is C—$R^{11}$ or N;
$X^2$ is C—$R^{12}$ or N;
$R^{11}$ is i) H, ii) halogen, iii) —CN, or iv) —O—$C_{1-6}$ alkyl; and
$R^{12}$ is H.

6. The method according to claim 5, wherein
$R^1$ is $C_{1-6}$ alkyl;
$R^2$ is $C_{1-6}$ alkyl which may be substituted with a —OR⁰;
$R^3$, $R^4$, and a carbon atom bounded by $R^3$ and $R^4$ interact to form a 3-oxetane ring and the carbon atom bounded by $R^3$ and $R^4$ is a spiro atom as represented by formula (II) below:

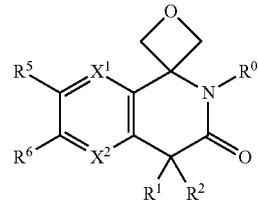

(II)

$R^5$ is H; and
$R^6$ is i) $C_{1-6}$ alkyl, ii) —O—$C_{1-6}$ alkyl which is substituted with one to three halogen(s), iii) halogen, or iv) —CN.

7. The method according to claim 6, wherein
$X^1$ is C—$R^{11}$;
$X^2$ is C—$R^{12}$;
$R^{11}$ is i) H, ii) halogen, iii) —CN, or iv) —O—$C_{1-6}$ alkyl; and
$R^{12}$ is H.

8. The method according to claim 1, which comprises administering a compound selected from the group consisting of
(−)-2-(difluoromethyl)-8-ethyl-8-(2-hydroxyethyl)-6H-spiro[1,6-naphthyridine-5,3'-oxetan]-7(8H)-one,
4,4-diethyl-1,1-dimethyl-3-oxo-1,2,3,4-tetrahydroisoquinoline-6-carbonitrile,
8,8-diethyl-5,5-dimethyl-7-oxo-5,6,7,8-tetrahydro-1,6-naphthyridine-2-carbonitrile,
(−)-6-bromo-4-ethyl-4-(2-hydroxyethyl)-1,1-dimethyl-1,4-dihydroisoquinolin-3(2H)-one,
(+)-6-bromo-4-ethyl-4-(2-hydroxyethyl)-1,1-dimethyl-1,4-dihydroisoquinolin-3(2H)-one,
8,8-diethyl-7-oxo-7,8-dihydro-6H-spiro[1,6-naphthyridine-5,3'-oxetane]-2-carbonitrile,
8',8'-diethyl-7'-oxo-7',8'-dihydro-6'H-spiro[oxetane-3,5'-pyrido[3,4-b]pyrazine]-2'-carbonitrile,
4,4-diethyl-3-oxo-3,4-dihydro-2H-spiro [isoquinoline-1,3'-oxetane]-6-carbonitrile,
6-chloro-4,4-dimethyl-2H-spiro[isoquinoline-1,3'-oxetan]-3(4H)-one,
4,4-dimethyl-3-oxo-3,4-dihydro-2H-spiro[isoquinoline-1,3'-oxetane]-6-carbonitrile,
2-(difluoromethoxy)-8,8-dimethyl-6H-spiro[1,6-naphthyridine-5,3'-oxetan]-7(8H)-one,
(+)-6-chloro-4-(2-hydroxyethyl)-4-methyl-2H-spiro[isoquinoline-1,3'-oxetan]-3(4H)-one,
(−)-6-chloro-4-(2-hydroxyethyl)-4-methyl-2H-spiro[isoquinoline-1,3'-oxetan]-3(4H)-one, and
(−)-2-(difluoromethoxy)-8-ethyl-8-(2-hydroxyethyl)-6H-spiro[1,6-naphthyridine-5,3'-oxetan]-7(8H)-one,
or a salt of said compound.

9. A method according to claim 1, which comprises administering a compound selected from the group consisting of
4,4-diethyl-3-oxo-3,4-dihydro-2H-spiro[isoquinoline-1,3'-oxetane]-6-carbonitrile,
6-chloro-4,4-dimethyl-2H-spiro[isoquinoline-1,3'-oxetan]-3(4H)-one, 4,4-dimethyl-3-oxo-3,4-dihydro-2H-spiro[isoquinoline-1,3'-oxetane]-6-carbonitrile,
(+)-6-chloro-4-(2-hydroxyethyl)-4-methyl-2H-spiro[isoquinoline-1,3'-oxetan]-3(4H)-one, and
(−)-6-chloro-4-(2-hydroxyethyl)-4-methyl-2H-spiro[isoquinoline-1,3'-oxetan]-3(4H)-one,
or a salt of said compound.

10. The method according to claim 1, which comprises administering 4,4-diethyl-3-oxo-3,4-dihydro-2H-spiro[isoquinoline-1,3'-oxetane]-6-carbonitrile,
or a salt thereof.

11. The method according to claim 1, which comprises administering 6-chloro-4,4-dimethyl-2H-spiro[isoquinoline-1,3'-oxetan]-3 (4H)-one,
or a salt thereof.

12. The method according to claim 1, which comprises administering 4,4-dimethyl-3-oxo-3,4-dihydro-2H-spiro[isoquinoline-1,3'-oxetane]-6-carbonitrile,
or a salt thereof.

13. The method according to claim 1, which comprises administering (+)-6-chloro-4-(2-hydroxyethyl)-4-methyl-2H-spiro[isoquinoline-1,3'-oxetan]-3(4H)-one,
or a salt thereof.

14. The method according to claim 1, which comprises administering (−)-6-chloro-4-(2-hydroxyethyl)-4-methyl-2H-spiro[isoquinoline-1,3'-oxetan]-3(4H)-one,
or a salt thereof.

* * * * *